(12) United States Patent
Han

(10) Patent No.: US 11,325,942 B2
(45) Date of Patent: May 10, 2022

(54) CHIRAL SPECIFIC BORON-CONTAINING COMPOUNDS AND THEIR USE IN TREATING CANCER OR AMYLOIDOSIS

(71) Applicant: BEIJING ARTIVILA BIOPHARMA CO. LTD., Beijing (CN)

(72) Inventor: Guoxia Han, Philadelphia, PA (US)

(73) Assignee: BEIJING ARTIVILA BIOPHARMA CO. LTD., Beijing (CN)

( * ) Notice: Subject to any disclaimer, the term of this patent is extended or adjusted under 35 U.S.C. 154(b) by 0 days.

(21) Appl. No.: 17/137,788

(22) Filed: Dec. 30, 2020

(65) Prior Publication Data

US 2021/0155658 A1 May 27, 2021

Related U.S. Application Data

(63) Continuation of application No. 16/204,066, filed on Nov. 29, 2018, now abandoned, which is a continuation of application No. 15/186,988, filed on Jun. 20, 2016, now Pat. No. 10,144,761.

(60) Provisional application No. 62/181,910, filed on Jun. 19, 2015.

(51) Int. Cl.
  *C07K 5/06* (2006.01)
  *C07K 5/078* (2006.01)
  *C07F 5/02* (2006.01)
  *A61K 38/00* (2006.01)

(52) U.S. Cl.
  CPC .......... *C07K 5/06139* (2013.01); *C07F 5/022* (2013.01); *C07F 5/025* (2013.01); *C07K 5/06191* (2013.01); *A61K 38/00* (2013.01)

(58) Field of Classification Search
  None
  See application file for complete search history.

(56) References Cited

U.S. PATENT DOCUMENTS

| | | | |
|---|---|---|---|
| 5,169,841 | A | 12/1992 | Kleeman et al. |
| 5,780,454 | A | 7/1998 | Adams et al. |
| 6,083,903 | A | 7/2000 | Adams et al. |
| 8,541,590 | B2 | 9/2013 | Roemmele |
| 8,785,418 | B2 | 7/2014 | Bricout et al. |
| 9,175,018 | B2 | 11/2015 | Elliott et al. |
| 9,340,559 | B2 | 5/2016 | Ruggeri et al. |
| 10,144,761 | B2 | 12/2018 | Han et al. |
| 2005/0282757 | A1 | 12/2005 | Combe-Marzelle et al. |
| 2009/0325903 | A1* | 12/2009 | Elliott ............. A61P 25/04 514/64 |
| 2014/0121182 | A1 | 5/2014 | Bakale et al. |
| 2016/0075736 | A1 | 3/2016 | Puppala et al. |
| 2019/0233470 | A1 | 8/2019 | Han |

FOREIGN PATENT DOCUMENTS

| | | |
|---|---|---|
| CN | 103897026 A | 7/2014 |
| CN | 103897027 A | 7/2014 |
| WO | 2009/020448 A1 | 2/2009 |
| WO | 2009/154737 A1 | 12/2009 |
| WO | 2010/114982 A2 | 10/2010 |
| WO | 2011/087822 A1 | 7/2011 |
| WO | 2012/119056 A1 | 9/2012 |
| WO | 2012/177835 A1 | 12/2012 |
| WO | 2014/161072 A1 | 10/2014 |
| WO | 2014/170628 A1 | 10/2014 |
| WO | 2015/117136 A1 | 8/2015 |

OTHER PUBLICATIONS

U.S. Appl. No. 15/186,988, filed Jun. 20, 2016, U.S. Pat. No. 10,144,761, Patented.
U.S. Appl. No. 16/204,066, filed Nov. 29, 2018, US-2019-0233470-A1, Published.
Achilli et al., Susceptibility to hydrolysis of phenylboronic pinacol esters at physiological pH. Central Europe Journal of Chemistry. Feb. 2013;11(2):137-139.
Ahn et al., General Methods for Synthesis of N-Methyliminodiacetic Acid Boronates from Unstable ortho-Phenolboronic Acids. Adv Synth Catal. May 26, 2014;356(8):1767-1772.
Berchet, Methyliminodiacetic Acid. Organic Synthesis Coll. 1943;2:397, 1938;18:56-57.
Bernardini et al., Stability of Boronic Esters to Hydrolysis: A Comparative Study. Chemistry Letters. 2009;38(7):750-751.
Charton et al., Imidazole-derived 2-[N-carbamoylmethyl-alkylamino]acetic acids, substrate-dependent modulators of insulin-degrading enzyme in amyloid-β hydrolysis. Eur J Med Chem. May 22, 2014;79:184-93.
Chase et al., The Synthesis of C-labelled Diethylcarbamazine, 1-Diethylcarbamyl-4-methylpiperazine ("hetrazan"). J Chem Soc. 1953;3874-3877.
Dick et al., General method for synthesis of 2-heterocyclic N-methyliminodiacetic acid boronates. Org Lett. May 21, 2010;12(10):2314-7.
Farfan et al., High-Yield Syntheses of N-(2-Hydroxyethyl)-N-alkylglycine Derivatives by Reaction of Ethanolamines with Glyoxal. Synthesis. 1987;1987(10):927-929.
Gillis et al., Multistep synthesis of complex boronic acids from simple MIDA boronates. J Am Chem Soc. Oct. 29, 2008;130(43):14084-5.
He et al., Boroalkyl group migration provides a versatile entry into a-aminoboronic acid derivatives. J Am Chem Soc. Jun. 20, 2012;134(24):9926-9.
Knapp et al., A general solution for unstable boronic acids: slow-release cross-coupling from air-stable MIDA boronates. J Am Chem Soc May 27, 2009;131(20):6961-3.
Lei et al., Pharmacophore modeling, docking studies, and synthesis of novel dipeptide proteasome inhibitors containing boron atoms. J Chem Inf Model. Sep. 2009;49(9):2092-100.

(Continued)

*Primary Examiner* — Fred H Reynolds
(74) *Attorney, Agent, or Firm* — McCarter & English, LLP; Steven G. Davis; Wei Song

(57) ABSTRACT

Useful chiral specific boron-containing compounds, such as boronate, boronate esters, boranamines, borane diamines, boranamine thioesters, and boronic mono/di-thioesters, have been prepared. These compounds and compositions containing them are useful as anti-cancer or anti-amyloidosis agents.

6 Claims, 1 Drawing Sheet

(56) References Cited

OTHER PUBLICATIONS

Mancilla et al., New bicyclic organylboronic esters derived from iminodiacetic acids. Journal of Organometallic Chemistry. Jun. 10, 1986:307(1):1-6.
Mancilla et al., Syntheses and characterization of (N?B)phenyl[N-arylaminodiacetate-O,O',N]boranes and N-arylaminodiacetic acids Heteroatom Chemistry. 1994;5(5-6):455-462.
Ram et al., Rapid Debenzylation of N-Benzylamino Derivatives to Amino-Derivatives Using Amonium Formate as Catalytic Hydrogen Transfer Agent. Tetrahedron Letters. 1987;28(5):515-516.
Reinemann et al., Vibrational spectroscopy of N-methyliminodiacetic acid (MIDA)-protected boronate ester: examination of the B-N dative bond. J Phys Chem A. Jun. 23, 2011;115(24):6426-31.
Roemmele et al., Development and Scale-Up of an Optimized Route to the Peptide Boronic Acid, CEP-18770. Org Process Res Dev. 2013;17(3):422-426.
Roy et al., A Comparative Study of the Relative Stability of Representative Chiral and Achiral Boronic Esters Employing Transesterification Monatshefte fur Chemie. Sep. 2007;138(9):879-887.
Stein et al., Alkyl Derivatives of Iminodiacetic Acid. J Am Chem Soc. 1955;77(1):191-192.
Wu et al., Degradation pathways of a peptide boronic acid derivative, 2-Pyz-(CO)-Phe-Leu-B(OH)(2). J Pharm Sci. Jun. 2000;89(6):758-65.
Zajdlik et al., Alpha-Boryl isocyanides enable facile preparation of bioactive boropeptides. Angew Chem Int Ed Engl. Aug. 5, 2013;52(32):8411-5.
Zajdlik et al., Efficient Preparation of alpha-Aminoboronic Acid Derivatives via Boroalkyl Group Migration. Synthesis. 2014;46(4):445-454.
Zhao et al., Clinical Characteristics and Treatment Outcome of Chinese Patients With Systemic Amyloid Light-Chain Amyloidosis: A Retrospective Single-Center Analysis. Clin Lymphoma Myeloma Leuk. Feb. 2016;16(2):104-10.
Zhu et al., 3D-QSAR studies of boron-containing dipeptides as proteasome inhibitors with CoMFA and CoMSIA methods. Eur J Med Chem Apr. 2009;44(4):1486-99.
The Drugs.com webpage on ammonia, https://www.drugs.com/inactive/ammonium-chloride-7.html, downloaded Oct. 3, 2019.
The sales literature for MLN2238, https://www.selleckchem.com/products/MLN-2238.html, version from Feb. 14, 2014.
Gillis, et al.; "A simple and modular strategy for small molecule synthesis: iterative suzuki-miyaura coupling of b-protected haloboronic acid building blocks." J. Am. Chem. Soc. (2007) 129 p. 6716-6717.

* cited by examiner

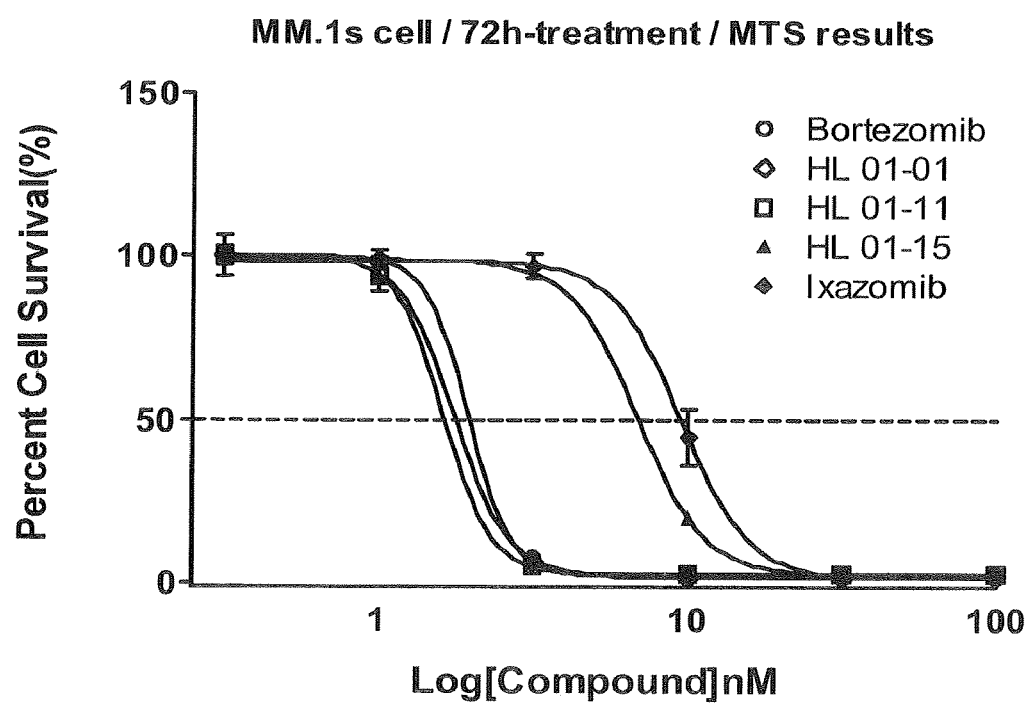

CHIRAL SPECIFIC BORON-CONTAINING COMPOUNDS AND THEIR USE IN TREATING CANCER OR AMYLOIDOSIS

CROSS-REFERENCE TO RELATED APPLICATION

This application is a continuation of U.S. patent application Ser. No. 16/204,066, filed Nov. 29, 2018, which is a continuation of U.S. patent application Ser. No. 15/186,988, filed Jun. 20, 2016 and now U.S. Pat. No. 10,144,761, which claims the benefit of U.S. Provisional Application Ser. No. 62/181,910, filed Jun. 19, 2015. The entire contents of each of the aforementioned applications are incorporated herein by reference.

FIELD OF THE INVENTION

The invention herein is directed to chiral specific boron-containing compounds, such as boronate, boronate esters, boranamines, boranediamines, boranamine thioesters, and boronic mono/di-thioesters, as anti-cancer or anti-amyloidosis agents, as well as their compositions, methods of preparation, and methods of treatment.

BACKGROUND OF THE INVENTION

It is known that some peptide boronic acid compounds are proteasome inhibitors, and they represent an important strategy in cancer therapy. Besides the marketed drug VELCADE® (Bortezomib or chemical name as [(1R)-3-methyl-1-[[(2S)-1-oxo-3-phenyl-2[(pyrazinylcarbonyl)amino]propyl]amino]butyl] boronic acid) for the treatment of multiple myeloma, other types of cancers, and amyloidosis. There are a number of structurally different peptide boronic acids at various stages of clinical trials. One major issue of this group of boronic acids as (active pharmaceutical ingredient (API) is that they are not very stable at ambient conditions. The drug VELCADE®, for example, needs to be stored at below ambient temperature and kept away from light. Partially related to its instability, the drug VELCADE® is formulated as an injection mixture, and patients must go to doctors' offices or hospitals for drug administration. Boronic acids are known to form many boronic acid derivatives, such as boronates and boronate esters. Boronates and boronate esters are able to be converted back to boronic acid under certain conditions.

The present invention describes a group of boron-containing compounds, such as boronate, boronate esters, boranamines, boranediamines, boranamine thioesters, and boronic mono/di-thioesters, that are stable at ambient conditions. They can be formulated as both liquid and solid drugs. Therefore, the bioactive component of the drug can be circulated longer in the human body and reach more areas unavailable to the direct injection into blood vessels.

DEFINITION OF TERMS

Unless otherwise explicitly stated, R is intended to refer an aliphatic or aromatic group.

Unless otherwise explicitly stated, the term "aliphatic" or "aliphatic group" is intended to refer a substituted or unsubstituted straight-chain, branched or cyclic $C_1$-$C_{12}$ hydrocarbon, which is completely saturated or which contains one or more units of unsaturation, but which is not aromatic. Aliphatic group also includes atoms other than C in the backbone, such as, but not limited to, N, S, and O. Aliphatic group also includes one or more functional groups attached to the backbone, such as, but not limited to, —OH, —SH, —CO—OH, —CO—OR (ester), —NH$_2$, —NHR, —CO—R (ketone), —O—SO$_2$ (sulfonate), —NH—SO$_2$ (sulfonamide) and —NR—SO$_2$ (sulfonamide).

Unless otherwise explicitly stated, the term "aromatic" or "aromatic group" is intended to refer a substituted or unsubstituted planar unsaturated ring of atoms that is stabilized by an interaction of the bonds forming the ring. Atoms forming an aromatic group include, but are not limited to, C, O, S, and N.

Unless otherwise explicitly stated, the term "peptide" is intended to refer to a short chain of amino acid monomers linked by amide (—NH—CO— or —NR—CO—) bonds. R represents an aliphatic or aromatic group. Each C atom in the amino acid monomer may have one or two substitution groups, and the substitution groups are aliphatic, aromatic or both aliphatic and aromatic. The covalent chemical bonds are formed when the carboxyl group of one amino acid reacts with the amino group of another.

Unless otherwise explicitly stated, the term "backbone" is intended to refer to the longest hydrocarbon chain in a molecule or a group. It also refers to the longest hydrocarbon chain with other atoms in the chain, such as, but not limited to, O, S, and N, in a molecule or a group.

Boronate, boronate esters, boranamines, boranediamines, boranamine thioesters and boronic mono/di-thioesters are illustrated by the corresponding general structures showed below.

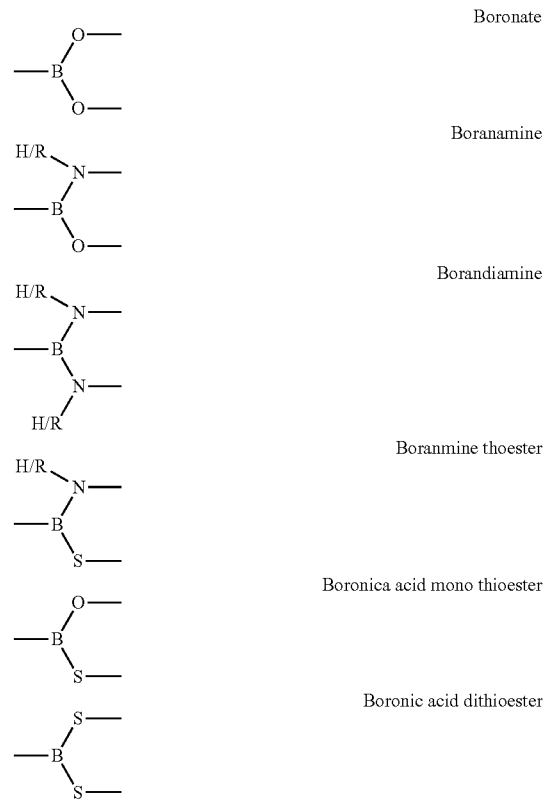

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also, unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

SUMMARY OF THE INVENTION

The present invention provides novel boron-containing compounds and stable pharmaceutically acceptable compositions comprising them. These compounds are useful in treatment of diseases, such as cancers, cancerous conditions, plaque, or a plaque-forming condition such as amyloidosis, in a human or warm-blooded animal or mammal.

In one aspect of the invention, compounds of the general formula (I), or pharmaceutically acceptable salts thereof, are provided:

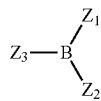

Formula (I)

wherein:

$Z_3$ is a peptide containing 1-20 amide bonds and the boron atom in formula (I) attaches to a C atom, not an N atom nor —C=O;

$Z_1$ and $Z_2$ are structurally the same or different side chains attached to boron atom in the formula (I);

$Z_1$ and $Z_2$ are each represented by the formula:

—X—$R_1$    Formula (II)

wherein:

X is O, S, NH, NR, —O—CO, —NH—CO, —NR—CO, —SO$_2$, —NH—SO$_2$, or —NR—SO$_2$, R being an aliphatic or aromatic substitution group; and $R_1$ is an aliphatic chain with $C_1$-$C_{20}$ hydrocarbon; $R_1$ also represents an aliphatic chain with $C_1$-$C_{20}$ hydrocarbon which has one or more X in the backbone; $R_1$ also represents an aliphatic chain with $C_1$-$C_{20}$ hydrocarbon which has one or more aliphatic, aromatic, or both aliphatic and aromatic substitution groups on the backbone.

In another aspect of the invention, compounds of the general formula (III), or pharmaceutically acceptable salts thereof, are provided:

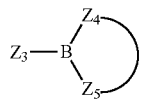

Formula (III)

wherein:

$Z_3$ is a peptide containing 1-20 amide bonds and the boron atom attaches in formula (III) to a C atom, not an N atom nor —C=O;

$Z_4$ and $Z_5$ each attach to the boron atom in the formula (III) and also join together on the other end to form a ring;

the ring formed by joining $Z_4$ and $Z_5$ together with boron is represented by formula (IV):

the ring size counting all atoms on the backbone of the ring in formula (IV) is 4-20 atoms; and the backbone of the compound in formula (IV) constructed with atoms such as, but not limited to, B, C, O, S, and N:

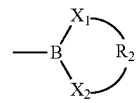

Formula (IV)

wherein:

$X_1$ and $X_2$ in formula (IV) are atoms or links or linkers, and they are the same or different;

$X_1$ is O, S, NH, NR, —O—CO, —NH—CO, —NR—CO, —O—SO$_2$, —NH—SO$_2$, or —NR—SO$_2$;

$X_2$ is O, S, NH, NR, —O—CO, —NH—CO, —NR—CO, —O—SO$_2$, —NH—SO$_2$, or —NR—SO$_2$;

R is an aliphatic or aromatic substitution group; and $R_2$ in formula (IV) represents the rest of the backbone of the ring besides B, $X_1$, and $X_2$: $R_2$ also represents an aliphatic chain with $C_1$-$C_{20}$ hydrocarbon which has one or more $X_1$ or $X_2$ in the backbone; $R_2$ also represents an aliphatic chain with $C_1$-$C_{20}$ hydrocarbon which has one or more aliphatic, aromatic, or both aliphatic and aromatic substitution groups on the backbone.

In some cases, two substitutions on the backbone of $R_2$ also form another ring A which is illustrated by formula (V):

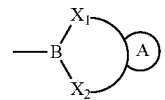

Formula (V)

wherein:

the size of ring A in formula (V) is 3-10 atoms; and

Ring A in formula (V) is constructed by atoms such as, but not limited to, C, O, S, or N.

In another aspect of the invention, compounds of the general formula (VI), or pharmaceutically acceptable salts thereof, are provided:

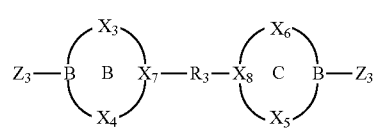

Formula (VI)

wherein:

$Z_3$ is a peptide containing 1-20 amide bonds and each boron atom attaches to a C atom, not an N atom nor —C=O;

Rings B and C are the same or different;

Rings B and C have the same descriptions as compounds represented by formula (III);

$X_3$ is O, S, NH, NR, —O—CO, —NH—CO, —NR—CO, —O—SO$_2$, —NH—SO$_2$, or —NR—SO$_2$;

$X_4$ is O, S, NH, NR, O—CO, —NH—CO, —NR—CO, —O—SO$_2$, —NH—SO$_2$, or —NR—SO$_2$;

$X_5$ is O, S, NH, NR, —O—CO, —NH—CO, —NR—CO, —O—SO$_2$, —NH—SO$_2$, or —NR—SO$_2$;

$X_6$ is O, S, NH, NR, —O—CO, —NH—CO, —NR—CO, —O—SO$_2$, —NH—SO$_2$, or —NR—SO$_2$;

R is an aliphatic or aromatic substitution group;

Rings B and C in compounds represented by formula (VI) are connected by link or linker $R_3$;

In compounds represented by formula (VI), link or linker $R_3$ connects with $X_7$ in ring B and $X_8$ in ring C;

In compounds represented by formula (VI), $X_7$ is C, N, or other atoms or groups that can form three bonds; $X_8$ is C, N, or other atoms or group that can form three bonds; and In compounds represented by formula (VI), $R_3$ represents an aliphatic chain with $C_1$-$C_{10}$ hydrocarbon; $R_3$ also represents an aliphatic chain with $C_1$-$C_{10}$ hydrocarbon which has one or more other atoms such as, but not limited to, O, S, or N in the backbone; $R_3$ also represents an aliphatic chain with $C_1$-$C_{10}$ hydrocarbon which has one or more aliphatic, aromatic, or both aliphatic and aromatic substitution groups on the backbone.

In another aspect of the invention, compounds of the general formula (VII), or pharmaceutically acceptable salts thereof, are provided:

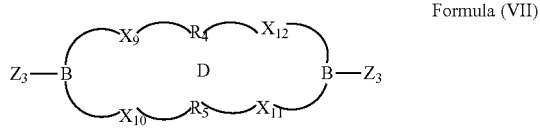

Formula (VII)

wherein:

$Z_3$ is a peptide containing 1-20 amide bonds and boron atom attaches to a C atom, not N atom nor —C═O;

Ring D in formula (VII) has two boron atoms;

the size of ring D counting for all atoms in the backbone of the ring in formula (VII) is 6-20 atoms;

$X_9$, $X_{10}$, $X_{11}$, and $X_{12}$ in formula (VII) are the same or different;

$X_9$ is O, S, NH, NR, —O—CO, —NH—CO, —NR—CO, —O—SO$_2$, —NH—SO$_2$, or —NR—SO$_2$;

$X_{10}$ is O, S, NH, NR, —O—CO, —NH—CO, —NR—CO, —O—SO$_2$, —NH—SO$_2$, or —NR—SO$_2$;

$X_{11}$ is O, S, NH, NR, —O—CO, —NH—CO, —NR—CO, —O—SO$_2$, —NH—SO$_2$, or —NR—SO$_2$;

$X_{12}$ is O, S, NH, NR, —O—CO, —NH—CO, —NR—CO, —O—SO$_2$, —NH—SO$_2$, or —NR—SO$_2$;

R is an aliphatic or aromatic substitution group;

$R_4$ and $R_5$ in formula (VII) are the same or different;

In compounds represented by formula (VII), $R_4$ represents an aliphatic chain with $C_1$-$C_{10}$ hydrocarbon; $R_4$ also represents an aliphatic chain with $C_1$-$C_{10}$ hydrocarbon which has one or more other atoms such as, but not limited to, O, S, or N in the backbone; $R_4$ also represents an aliphatic chain with $C_1$-$C_{10}$ hydrocarbon which has one or more aliphatic, aromatic, or both aliphatic and aromatic substitution groups on the backbone; and In compounds represented by formula (VII), $R_5$ represents an aliphatic chain with $C_1$-$C_{10}$ hydrocarbon; $R_5$ also represents an aliphatic chain with $C_1$-$C_{10}$ hydrocarbon which has one or more other atoms such as, but not limited to, O, S, or N in the backbone; $R_5$ also represents an aliphatic chain with $C_1$-$C_{10}$ hydrocarbon which has one or more aliphatic, aromatic, or both aliphatic and aromatic substitution groups on the backbone.

In another aspect of the invention, compounds of the general formula (VIII), or pharmaceutically acceptable salts or thereof, are provided:

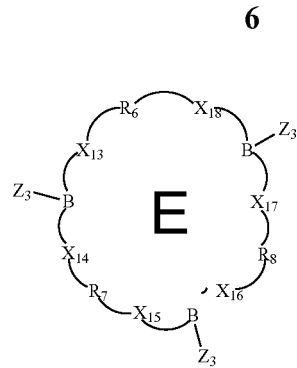

Formula (VIII)

wherein:

$Z_3$ is a peptide containing 1-20 amide bonds and each boron atom attaches to a C atom, not an N atom nor —C═O;

Ring E in formula (VIII) has three boron atoms;

the size of ring E counting for all atoms in the backbone of the ring in formula (VII) is 9-20 atoms;

$X_{13}$, $X_{14}$, $X_{15}$, $X_{16}$, $X_{17}$, and $X_{18}$ in formula (VII) are the same or different;

$X_{13}$ is O, S, NH, NR, —O—CO, —NH—CO, —NR—CO, —O—SO$_2$, —NH—SO$_2$, or —NR—S$_2$;

$X_{14}$ is O, S, NH, NR, —O—CO, —NH—CO, —NR—CO, —O—SO$_2$, —NH—SO$_2$, or —NR—SO$_2$;

$X_{15}$ is O, S, NH, NR, —O—CO, —NH—CO, —NR—CO, —O—SO$_2$, —NH—SO$_2$, or —NR—SO$_2$;

$X_{16}$ is O, S, NH, NR, —O—CO, —NH—CO, —NR—CO, —O—SO$_2$, —NH—SO$_2$, or —NR—SO$_2$;

$X_{17}$ is O, S, NH, NR, —O—CO, —NH—CO, —NR—CO, —O—SO$_2$, —NH—SO$_2$, or —NR—SO$_2$;

$X_{18}$ is O, S, NH, NR, —O—CO, —NH—CO, —NR—CO, —O—SO$_2$, —NH—SO$_2$, or —NR—SO$_2$;

R is an aliphatic or aromatic substitution group;

$R_6$, $R_7$, and $R_8$ in formula (VIII) are the same or different;

In compounds represented by formula (VIII), $R_6$ represents an aliphatic chain with $C_1$-$C_{10}$ hydrocarbon; $R_6$ also represents an aliphatic chain with $C_1$-$C_{10}$ hydrocarbon which has one or more other atoms such as, but not limited to, O, S, or N in the backbone; $R_6$ also represents an aliphatic chain with $C_1$-$C_{10}$ hydrocarbon which has one or more aliphatic, aromatic, or both aliphatic and aromatic substitution groups on the backbone;

In compounds represented by formula (VIII), $R_7$ represents an aliphatic chain with $C_1$-$C_{10}$ hydrocarbon; $R_7$ also represents an aliphatic chain with $C_1$-$C_{10}$ hydrocarbon which has one or more other atoms such as, but not limited to, O, S, or N in the backbone; $R_7$ also represents an aliphatic chain with $C_1$-$C_{10}$ hydrocarbon which has one or more aliphatic, aromatic, or both aliphatic and aromatic substitution groups on the backbone; and In compounds represented by formula (VIII), $R_8$ represents an aliphatic chain with $C_1$-$C_{10}$ hydrocarbon; $R_8$ also represents an aliphatic chain with $C_1$-$C_{10}$ hydrocarbon which has one or more other atoms such as, but not limited to, O, S, or N in the backbone; $R_8$ also represents an aliphatic chain with $C_1$-$C_{10}$ hydrocarbon which has one or more aliphatic, aromatic, or both aliphatic and aromatic substitution groups on the backbone.

In another aspect of the invention, compounds of the general formula (IX), or pharmaceutically acceptable salts thereof, are provided:

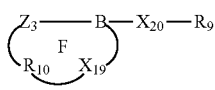

Formula (IX)

wherein:

$Z_3$ is a peptide containing 1-20 amide bonds and the boron atom attaches to a C atom, not an N atom nor —C=O;

$R_{10}$ is a substitution branch on backbone of $Z_3$;

$R_{10}$ forms ring F with boron in formula (IX);

the size of ring F counting all atoms on the ring is 4-10 atoms;

$X_{19}$ is directly attached to boron in ring F;

$X_{19}$ is O, S, NH, NR, —O—CO, —NH—CO, —NR—CO, —O—SO$_2$, —NH—SO$_2$, or —NR—SO$_2$; R is an aliphatic or aromatic substitution group;

In compounds represented by formula (IX), $R_{10}$ represents an aliphatic chain with $C_1$-$C_{10}$ hydrocarbon; $R_{10}$ also represents an aliphatic chain with $C_{10}$ hydrocarbon which has one or more other atoms such as, but not limited to, O, S, or N in the backbone; $R_{10}$ also represents an aliphatic chain with $C_1$-$C_{10}$ hydrocarbon which has one or more aliphatic, aromatic, or both aliphatic and aromatic substitution groups on the backbone;

In compounds represented by formula (IX), $X_2O$ is directly attached to boron and is not in ring F;

$X_{20}$ is O, S, NH, NR, —O—CO, —NH—CO, —NR—CO, —O—SO$_2$, —NH—SO$_2$, or —NR—SO$_2$;

R is an aliphatic or aromatic substitution group;

In compounds represented by formula (IX), $R_9$ attaches to $X_{20}$; and $R_9$ represents an aliphatic chain with $C_{1-10}$ hydrocarbon; $R_9$ also represents an aliphatic chain with $C_1$-$C_{10}$ hydrocarbon which has one or more other atoms such as, but not limited to, O, S, or N in the backbone; $R_9$ also represents an aliphatic chain with $C_1$-$C_{10}$ hydrocarbon which has one or more aliphatic, aromatic, or both aliphatic and aromatic substitution groups on the backbone.

In another aspect of the invention, a pharmaceutical composition comprises a compound of formula (I), (III), (IV), (V), (VI), (VII), (VIII), or (IX), or a pharmaceutically acceptable crystalline form thereof, suitable for the production of a drug in solid and/or liquid formulation.

Another aspect of the invention is directed to methods for the use of a pharmaceutical composition comprising one or more of the compounds described above to treat a patient who has or is at risk to have proteasome-mediated diseases, including cancers, or amyloidosis.

Non-toxic, pharmacologically acceptable salts useful herein comprise acid addition salts formed with inorganic or organic acids. Examples of suitable such salts include hydrohalides such as hydrochlorides, sulfates, hydrogen sulfates, phosphates, hydrogen phosphates, tartrates, succinates, maleates, benzoates, acetates, propionates, lactates, ascorbinates, and the like.

The compounds of formulae (I), (III), (IV), (V), (VI), (VII), (VIII), and (IX) according to the invention can be converted into their non-toxic, pharmacologically acceptable acid addition salts in conventional manner. Acids suitable for salt formation include, for example, hydrochloric acid, hydrobromic acid, hydriodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicyclic acid, ascorbic acid, methanesulfonic acid, 8-chlorotheophyllin, and the like.

The compounds of formulae (I), (III), (IV), (V), (VI), (VII), (VIII), and (IX) and pharmaceutically acceptable salts thereof can be incorporated, optionally in combination with other active ingredients, into the usual pharmaceutical preparations such as tablets, coated tablets, capsules, powders, suppositories, or solutions. Such preparations may be produced with use of conventional pharmaceutical excipients, carriers, disintegrants, or lubricants or substances for obtaining delayed or sustained release. The single dose for adults is from about 0.1 to 80 mg (from about 0.0013 to 1.07 mg/kg), preferably, however, from about 1 to 30 mg (from about 0.013 to 0.40 mg/kg), 1 to 4 times daily.

Dependent upon the type and body weight of the patient to be treated, on the type and severity of the disease, on the type of preparation, and on the route of administration, which may be peroral, parenteral, or rectal, as well as on the period or interval over which the administration takes place, it may, however, be necessary to deviate from the above dosages. Thus, it may be sufficient in some cases to administer less than the above-mentioned amount of active ingredient or in some cases the amount may be exceeded.

The optimum dosage and route of administration of the active ingredients which are necessary in each case can easily be determined by one skilled in the art.

Another aspect of the invention is directed to a compound of the formula:

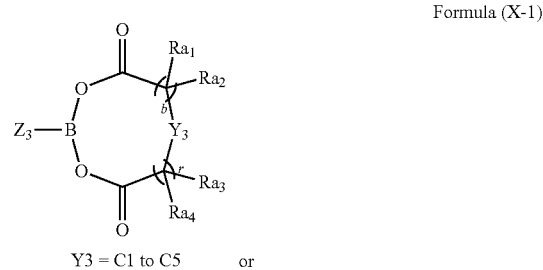

Formula (X-1)

$Y_3$ = C1 to C5 or

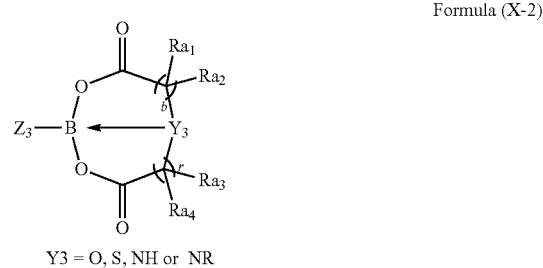

Formula (X-2)

$Y_3$ = O, S, NH or NR or a pharmaceutically acceptable salt, solvate, and/or hydrate, polymorph crystal or amorphous forms, thereof, wherein:

$Z_3$ is a peptide containing 1-20 amide bonds and boron atom attaches to a C atom, not an N atom nor —C=O;

$Y_3$ is $C_1$ to $C_5$, O, S, NH, or NR;

R represents an aliphatic or aromatic group with or without heteroatom or functional group, such as COOH, OH, or NH$_2$;

each Ra$_1$ and Ra$_2$ independently is H, aliphatic, or aromatic substitution group; each Ra$_3$ and Ra$_4$ independently is H, aliphatic, or aromatic substitution group;

q is 0, 1, or 2; and r is 0, 1, or 2.

In another aspect of the invention, Z$_3$ is characterized by the bare bones structure or its derivatives of formula (XI-1):

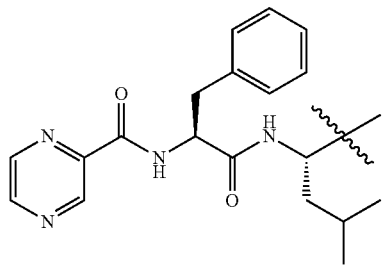

XI-1

In another aspect of the invention, Z$_3$ is characterized by the bare bones structure or its derivatives of formula (XI-2):

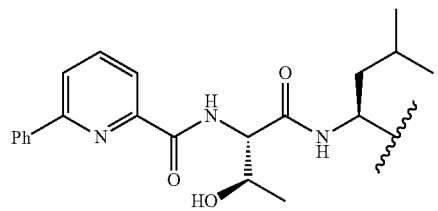

XI-2

In another aspect of the invention, Z$_3$ is characterized by the bare bones structure or its derivatives of formula (XI-3):

XI-3

In another aspect of the invention, the compound is one of:

HL01-08

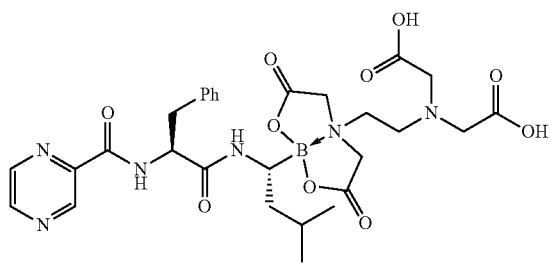

HL01-011

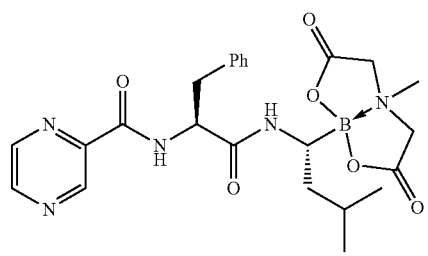

HL01-08-1

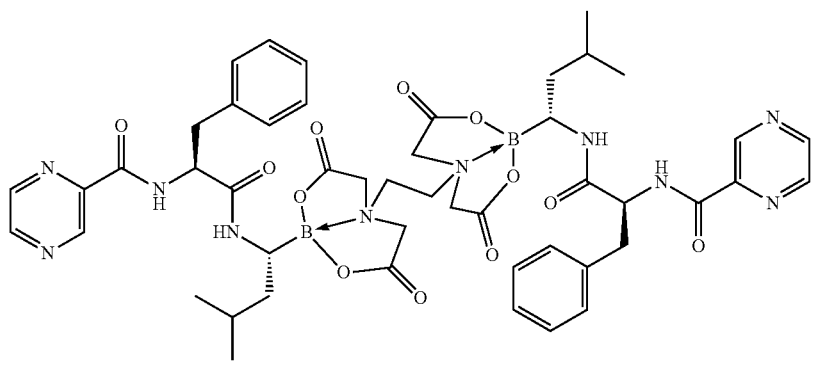

HL01-15

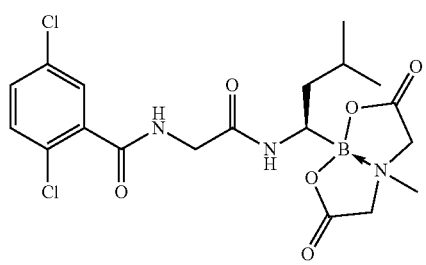

HL01-16

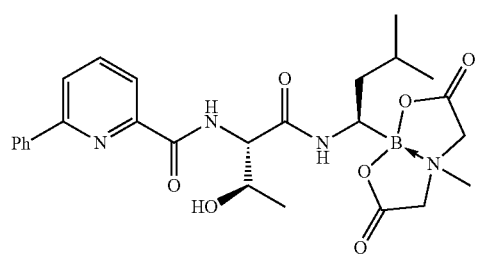

-continued

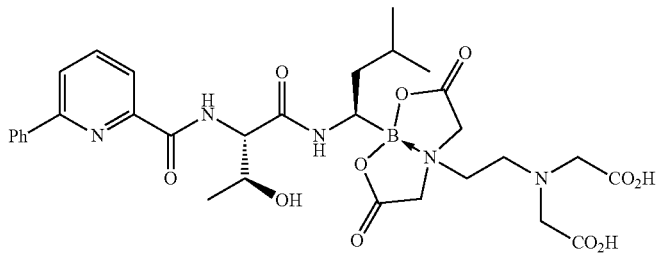
HL01-22-1

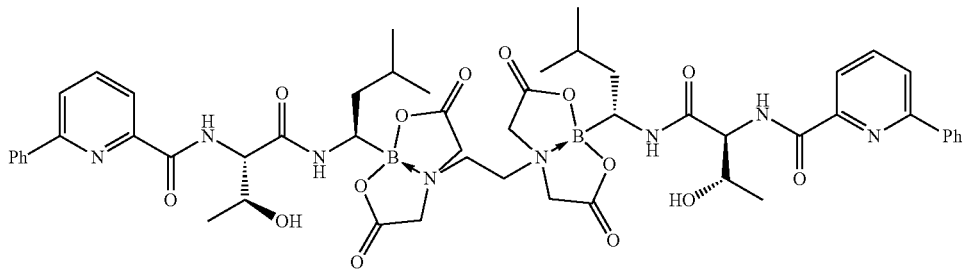
HL01-22-2

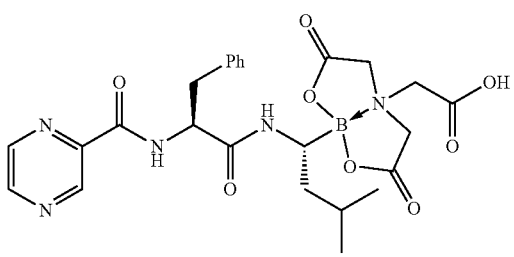
HL01-31

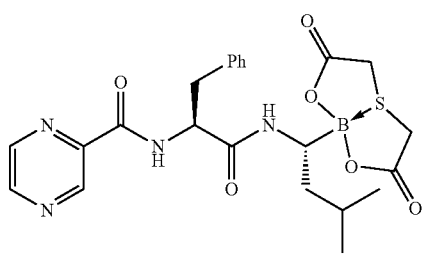
HL-385

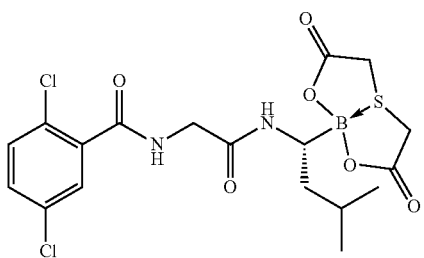
HL-386

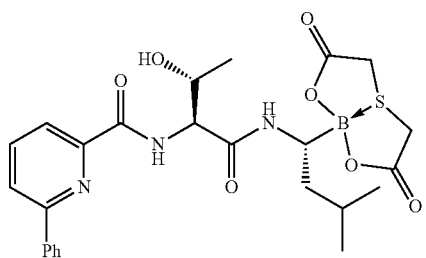
HL-387

Another aspect of the invention is directed to a compound of the formula:

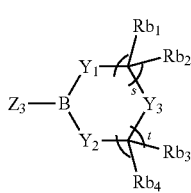

Formula (XII)

or a pharmaceutically acceptable salt, solvate, and/or hydrate, polymorph crystal or amorphous form thereof, wherein:

$Z_3$ is a peptide containing 1-20 amide bonds and boron atom attaches to a C atom, not an N atom or —C=O;

each of $Y_1$, $Y_2$, and $Y_3$ independently is O, S, NH, or NR; $Y_3$ can also be $C_1$ to $C_5$;

R represents an aliphatic or aromatic group with or without heteroatom or functional group, such as COOH, OH, or $NH_2$;

each $Rb_1$ and $Rb_2$ independently is H, aliphatic, or aromatic substitution group; $Rb_1$ and $Rb_2$ can also be a double bond, such as carbonyl group; each $Rb_3$ and $Rb_4$ independently is H, aliphatic, or aromatic substitution group;

s is 0, 1, or 2; and t is 0, 1, or 2.

Another aspect of the invention is directed to the compound characterized by the formula:

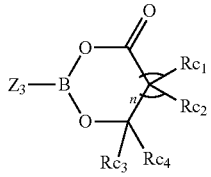

Formula (XIII)

or a pharmaceutically acceptable salt, solvate, and/or hydrate, polymorph crystal or amorphous form thereof, wherein:

$Z_3$ is a peptide containing 1-20 amide bonds and boron atom attaches to a C atom, not an N atom nor —C=O;

each $Rc_1$ and $Rc_2$ independently is H, aliphatic, or aromatic substitution group; each $Rc_3$ and $Rc_4$ independently is H, aliphatic, or aromatic substitution group, —(CH2)$_p$—COOH and —(CH2)$_p$—COOR wherein R is an aliphatic or aromatic group, with or without heteroatom or functional group, such as COOH, OH, or $NH_2$; and u is 0, 1, or 2.

In another aspect of the invention, the compound is characterized by the formula:

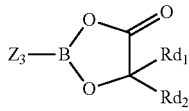

Formula (XIIa)

or a pharmaceutically acceptable salt, solvate, and/or hydrate, polymorph crystal or amorphous forms, thereof, wherein:

$Z_3$ is a peptide containing 1-20 amide bonds and boron atom attaches to a C atom, not an N atom nor —C=O; and each $Rd_1$ and $Rd_2$ independently is H, aliphatic, aromatic substitution group, —(CH2)$_p$-COOH and —(CH2)$_p$-COOR wherein R is an aliphatic or aromatic group with or without heteroatom or functional group, such as COOH, OH, or $NH_2$.

In another aspect of the invention, the compound is characterized by the formula:

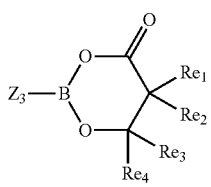

Formula (XIIb)

or a pharmaceutically acceptable salt, solvate, and/or hydrate, polymorph crystal or amorphous form thereof, wherein:

$Z_3$ is a peptide containing 1-20 amide bonds and boron atom attaches to a C atom, not an N atom nor —C=O;

each $Re_1$ and $Re_2$ independently is H, aliphatic, aromatic substitution group, —(CH2)$_p$-COOH and —(CH2)$_p$-COOR wherein R is an aliphatic or aromatic group with or without heteroatom or functional group, such as COOH, OH, or $NH_2$; and each $Re_3$ and $Re_4$ independently is H, aliphatic, aromatic substitution group, —(CH2)$_p$-COOH and —(CH2)$_p$-COOR wherein R is an aliphatic or aromatic group.

In another aspect of the invention, the compound is characterized by the formula:

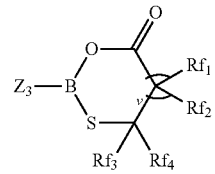

Formula (XIV)

or a pharmaceutically acceptable salt, solvate, and/or hydrate, polymorph crystal or amorphous form thereof, wherein:

$Z_3$ is a peptide containing 1-20 amide bonds and boron atom attaches to a C atom, not an N atom nor —C=O;

each $Rf_1$ and $Rf_2$ independently is H, aliphatic, aromatic substitution group;

each $Rf_3$ and $Rf_4$ independently is H, aliphatic, aromatic substitution group, —(CH$_2$)$_p$—COOH and —(CH$_2$)$_p$—COOR wherein R is an aliphatic or aromatic group with or without heteroatom or functional group, such as COOH, OH, or $NH_2$; and v is 0, 1, or 2.

In another aspect of the invention, the compound is characterized by the formula:

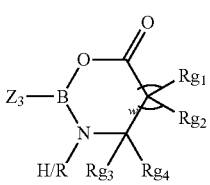

Formula (XV)

or a pharmaceutically acceptable salt, solvate, and/or hydrate, polymorph crystal or amorphous form thereof, wherein:

$Z_3$ is a peptide containing 1-20 amide bonds and boron atom attaches to a C atom, not an N atom nor —C=O;

R represents an aliphatic or aromatic group with or without heteroatom or functional group, such as COOH, OH, or $NH_2$;

each $Rg_1$ and $Rg_2$ independently is H, aliphatic, aromatic substitution group; each $Rg_3$ and $Rg_4$ independently is H, aliphatic, aromatic substitution group, —(CH$_2$)$_p$-COOH and —(CH2)$_p$-COOR wherein R is an aliphatic or aromatic group with or without heteroatom or functional group, such as COOH, OH, $NH_2$; and w is 0, 1, or 2.

In another aspect of the invention, the compound is one of the following:
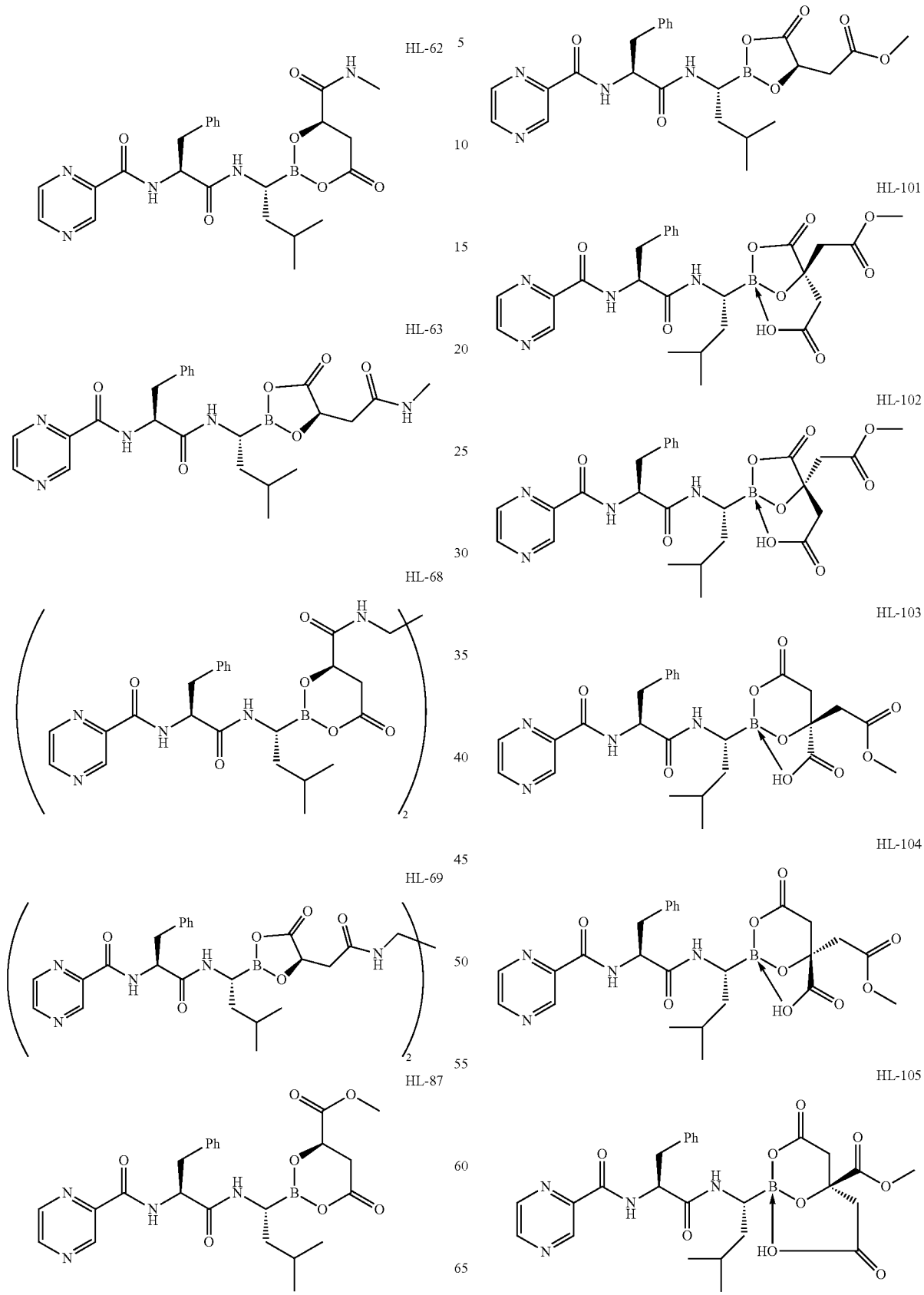

HL-106
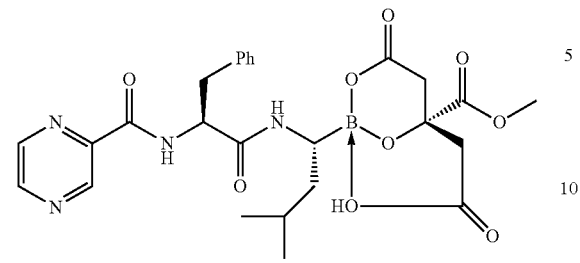
HL-131
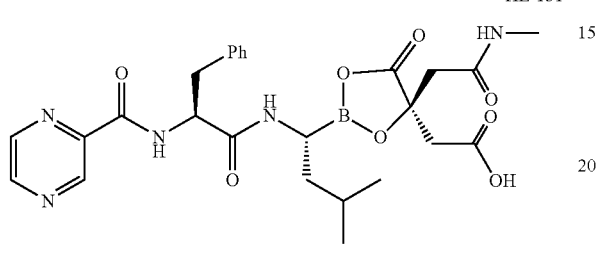
HL-132
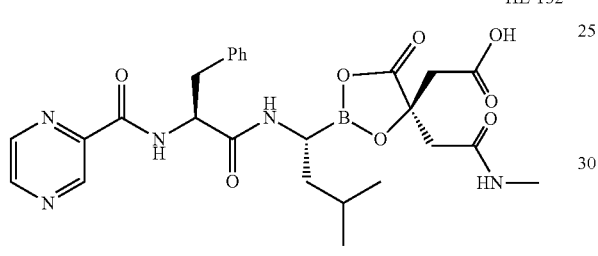
HL-133
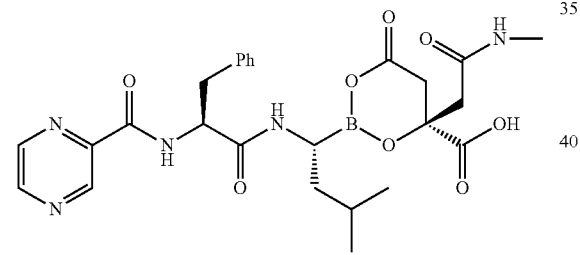
HL-134
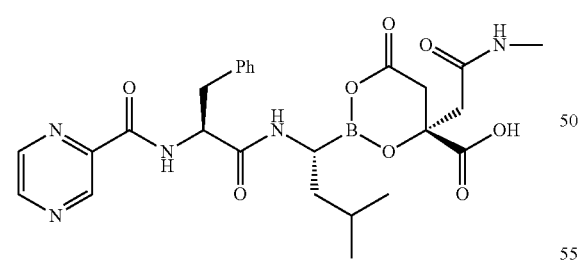
HL-135
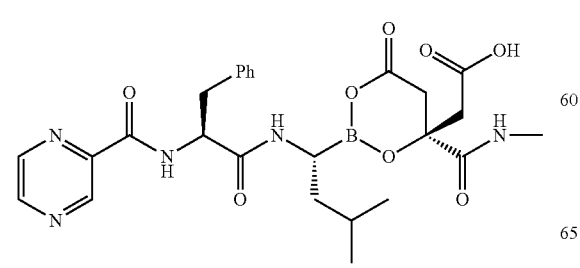
HL-136
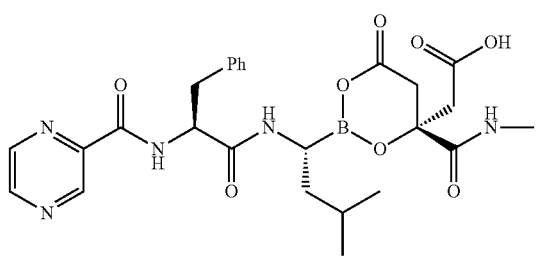
HL-238
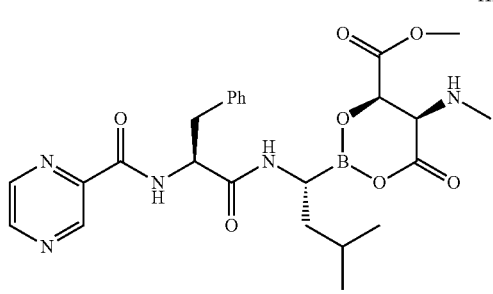
HL-239
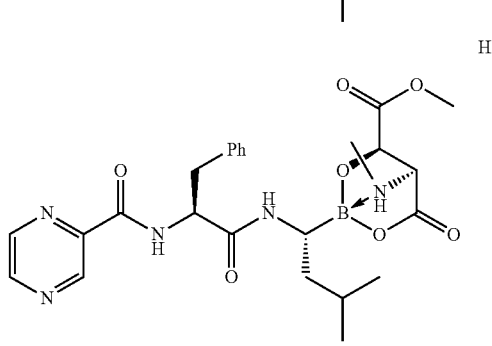
HL-240
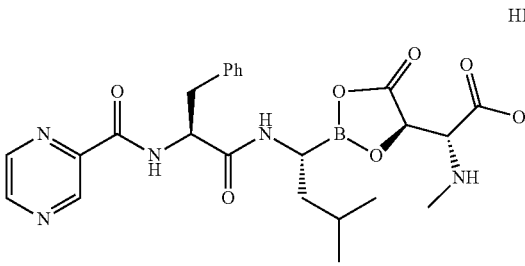
HL-241
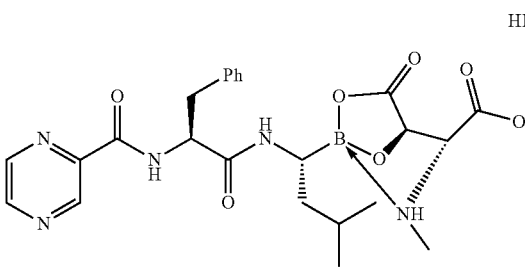
HL-448
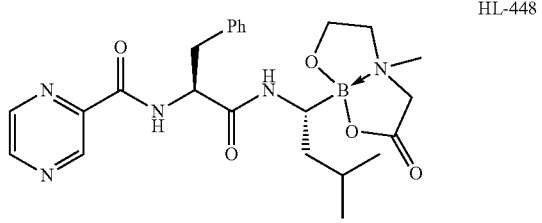

-continued

HL-451
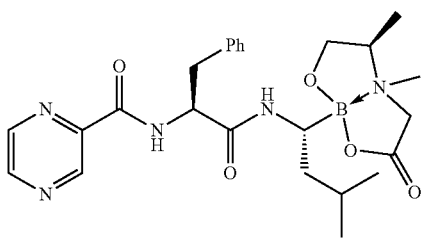

HL-466
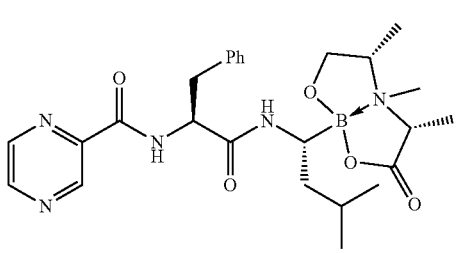

HL-478
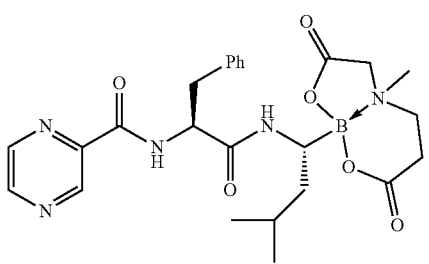

HL-481
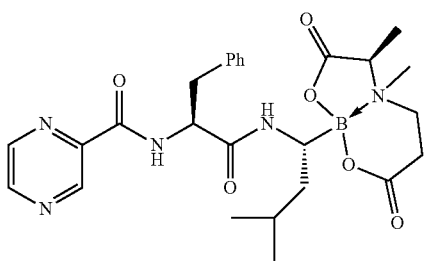

HL-484
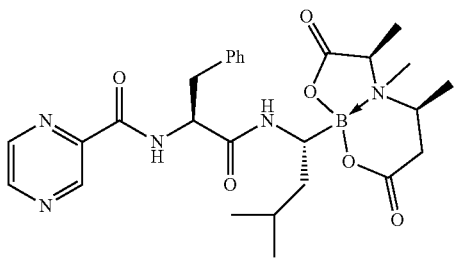

HL-493
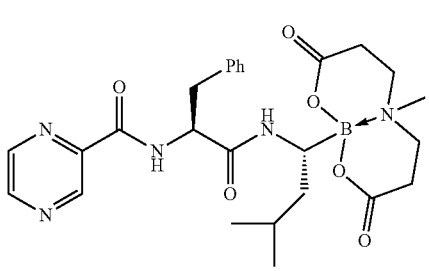

-continued

HL-505
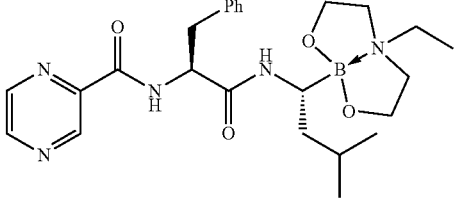

In another aspect of the invention, a medically useful composition comprises one or more of the compounds described herein in combination with pharmaceutically acceptable excipients, formulates as drugs in solid or liquid forms.

In another aspect of the medically useful compositions of the invention, the one or more compounds are present in an amount effective to treat cancer, a cancerous condition, such as multiple myeloma, or amyloidosis in a human or mammal.

Another aspect of the invention is directed a process for the preparation of compounds of the formula:

Formula X-1
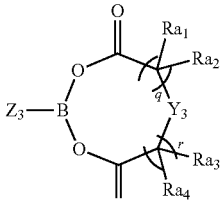

$Y_3 = C_1$ to $C_5$     or

Formula X-2
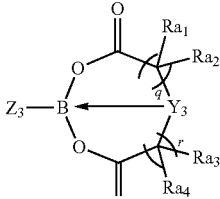

$Y_3 = O, S, NH$ or $NR$ or a pharmaceutically acceptable salt, solvate, and/or hydrate, polymorph crystal or amorphous form thereof, wherein:

$Z_3$ is a peptide containing 1-20 amide bonds and boron atom attaches to a C atom, not an N atom nor —C═O;

$Y_3$ is $C_1$ to $C_5$, O, S, NH, or NR; R represents an aliphatic or aromatic group with or without heteroatom or functional group, such as COOH, OH, or NH$_2$;

each $Ra_1$ and $Ra_2$ independently is H, aliphatic, aromatic substitution group;

each $Ra_3$ and $Ra_4$ independently is H, aliphatic, aromatic substitution group;

q is 0, 1, or 2; and r is 0, 1, or 2.

In another aspect of the invention, a compound of formula (XI-1) is reacted with N-methyliminodiacetic acid to form a compound of formula (X-2):

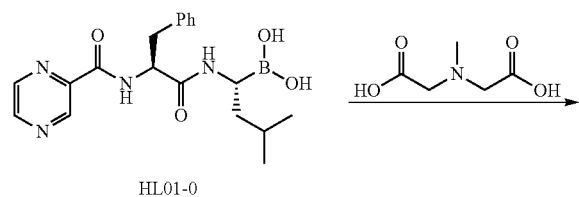
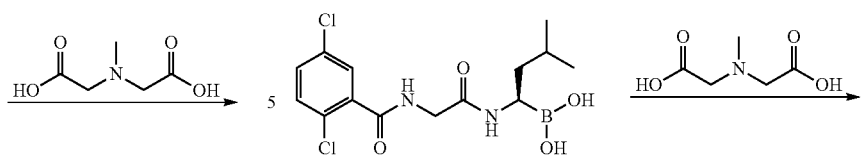
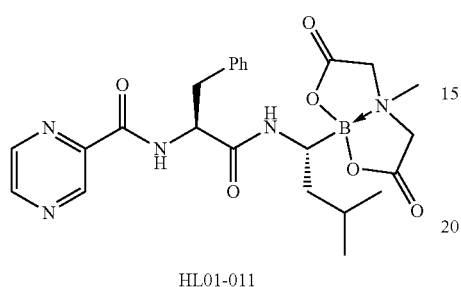
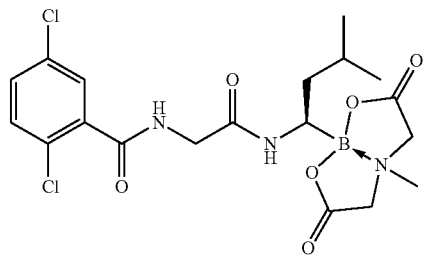
wherein, HL01-0 is XI-1 and HL01-011 is X-2.
In another aspect of the invention, a compound of formula (XI-3) is reacted with N-methyliminodiacetic acid to form a compound of formula (X-2):
wherein, HL01-00 is XI-3 and HL01-015 is X-2.
In another aspect of the invention, a compound of formula (XI-2) is reacted with N-methyliminodiacetic acid to form a compound of formula (X-2):
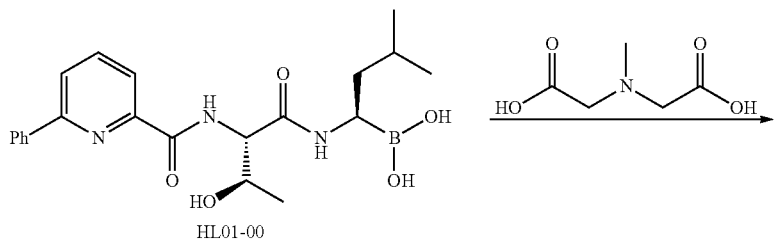
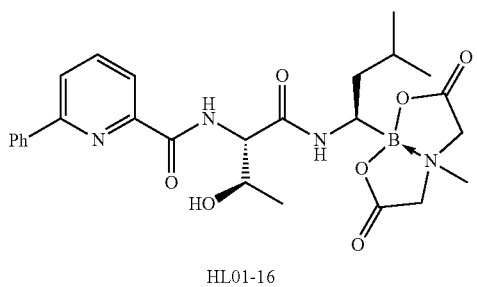

wherein, HL01-000 is XI-2 and HL01-016 is X-2.

In another aspect of the invention, a compound of formula (XI-1) is reacted with EDTA to form a compound of formula (X-2):

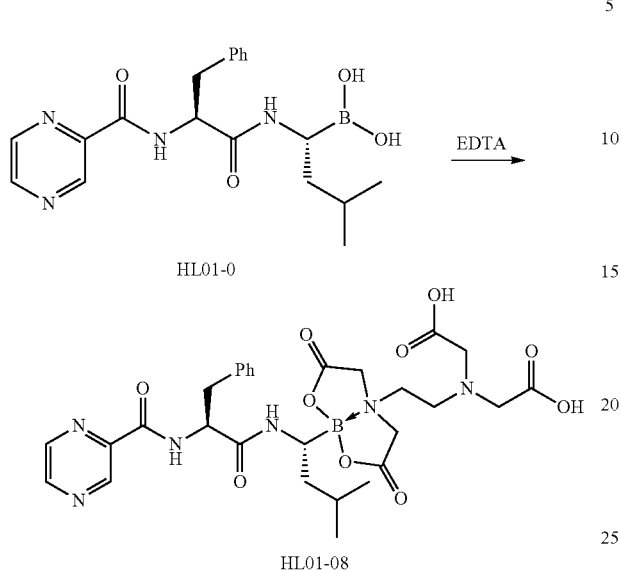

wherein, HL01-0 is XI-1 and HL01-08 is X-2.

In another aspect of the invention, a compound of formula (XI-1) is reacted with EDTA to form a compound of formula (X-2):

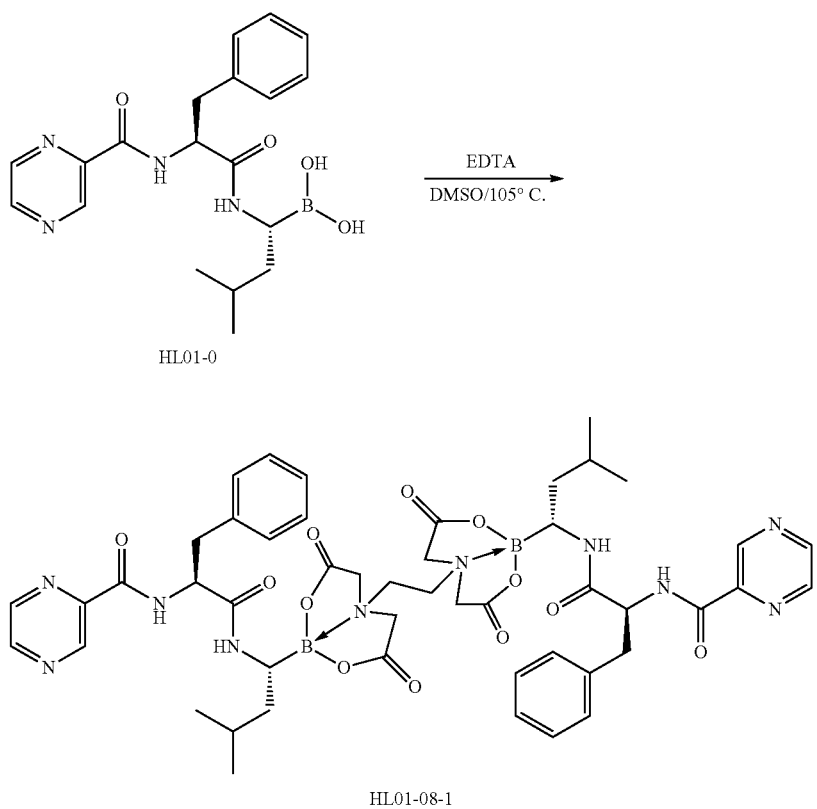

wherein, HL01-0 is XI-1 and HL01-08-1 is X-2.

In another aspect of the invention, a compound of formula (XI-1) is reacted with N-ethyl-iminodiacetic acid to form a compound of formula (X-2):

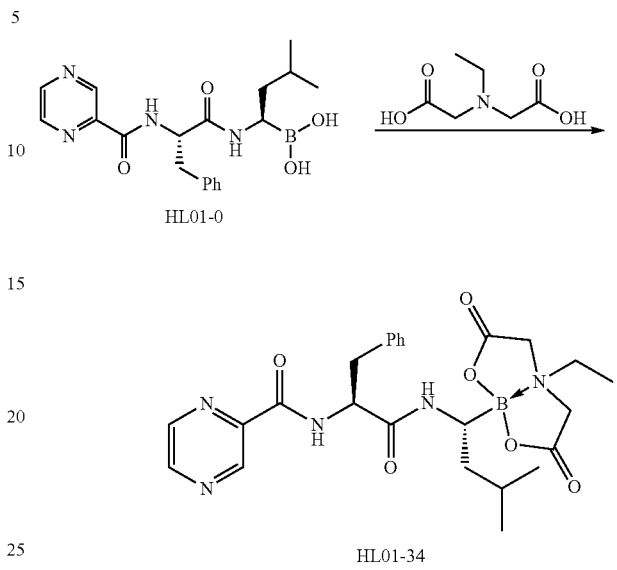

wherein, HL01-0 is XI-1 and HL01-34 is X-2.

In another aspect of the invention, a compound of formula (XI-1) is reacted with N-methyldiethanolamine to form a compound of formula (XII):

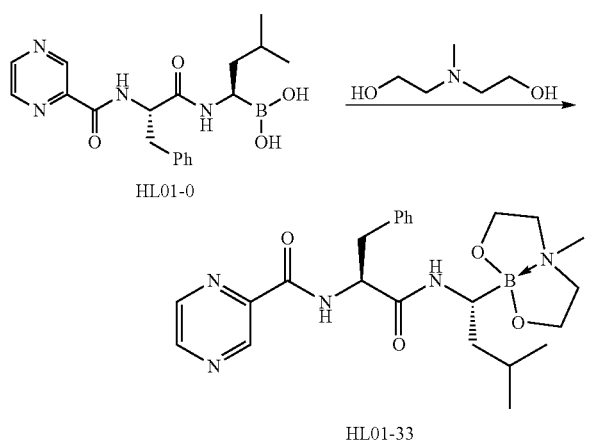

HL01-0

HL01-33 wherein, HL01-0 is XI-1 and HL01-33 is XII.

In another aspect of the invention, a compound of formula (XI-3) is coupled or reacted with an ester of amino substituted L-tartaric acid derivative to form a compound of formula (XI):

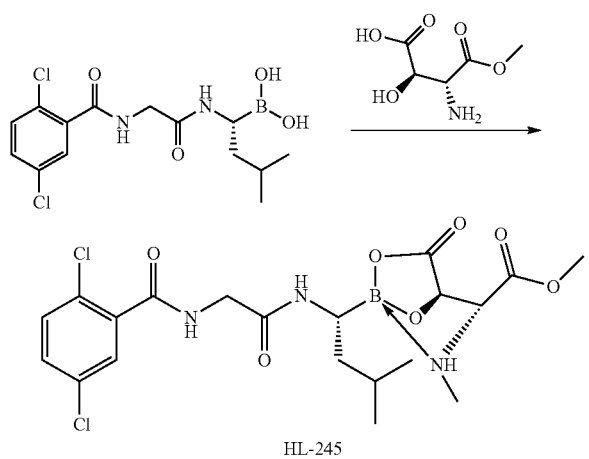

HL-245 wherein, HL01-00 is XI-3 and HL-245 is XI.

In another aspect of the invention, a compound of formula (XI-1) is reacted with N-methyliminodiacetic acid to form a compound of formula (XII):

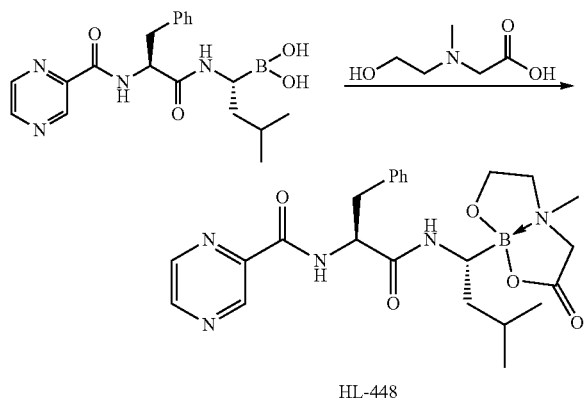

HL-448 wherein, HL01-0 is XI-1 and HL-448 is XII.

In another aspect of the invention, a compound of formula (XI-1) is coupled or reacted with N-ethyldiethanolamine to form a compound of formula (XII):

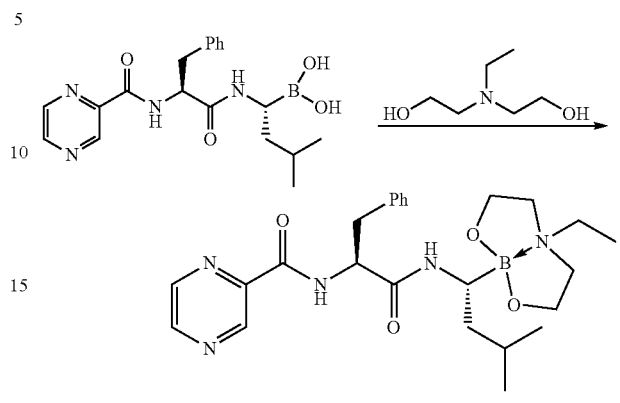

HL-505 wherein, HL01-0 is XI-1 and HL-505 is XII.

In another aspect of the invention, a composition for treating cancer, a cancerous condition, or amyloidosis in a human or mammal, comprises as active ingredient a pharmaceutically effective amount of a compound described herein, including, but not limited to, a compound of formulae (I), (III), (IV), (V), (VI), (VII), (VIII), and (IX) or a pharmaceutically acceptable acid addition salt thereof, in combination with pharmaceutically acceptable carriers, diluents, or excipients.

In another aspect of the invention, the composition comprises active ingredient in an amount effective to treat multiple myeloma or amyloidosis.

In another aspect of the invention, in a method of treating cancer, a cancerous condition, or amyloidosis in a human or mammal host in need of such treatment, the method comprises perorally, parentally, or rectally administering to said host an effective cancer, cancerous condition, or amyloidosis treatment amount of a compound of formula (I), (III), (IV), (V), (VI), (VII), (VIII), or (IX) or a pharmaceutically acceptable acid addition salt thereof.

BRIEF DESCRIPTION OF THE DRAWING

The FIGURE is a graph that represents the results of testing to demonstrate the cytotoxic effects of certain compounds, including compounds prepared according to the invention.

DETAILED DESCRIPTION OF THE INVENTION

The invention can perhaps be appreciated better from the description below, where compounds of the invention have been prepared and then some testing is described.

EXAMPLES

Boronic acid can readily form oligomeric anhydrides by dehydration of the boronic acid moiety. Hence, the monomeric structure form drawn below, such as HL01-0 drawn in the Example 1, is expressly intended to represent the free boronic acid, oligomeric anhydrides, including, but not limited to, dimers, trimers, and tetramers, and mixtures thereof.

Abbreviations: Bortezomib (HL01-0), Tetrahydrofuran (THF), Ethyl Acetate (EtOAc or EA), N,N-Dimethylsulfoxide (DMSO), Ethylenediaminetetraacetic Acid (EDTA), Hydrogen Chloride (HCl), room temperature (RT), Nuclear Magentci Resonance (NMR), Reverse Phase High Performance Liquid Chromatography (RP-HPLC), Liquid Chromatography-Mass Spectroscopy (LC-MS)

General Characterization Methods: $^1$H NMR, $^{13}$C NMR, HPLC, LCMS.

The product HL01-01 of Example 1, characterized by formula HL01-01-1, HL-01-01-2, HL-01-01-3, HL-01-01-4, HL-1-01-5, or a mixture thereof.

HL01-01-1
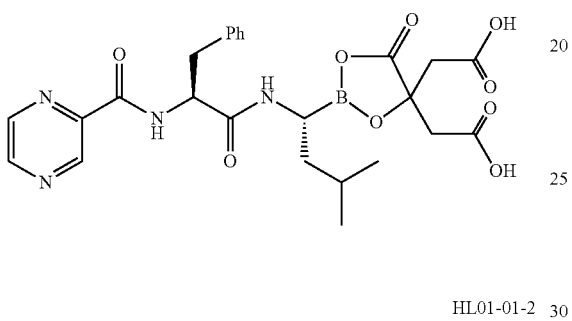

HL01-01-2
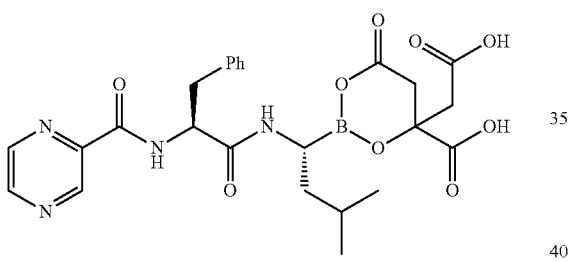

HL01-01-3
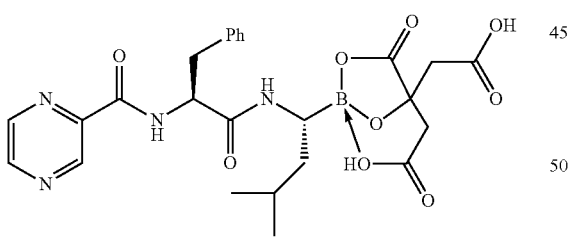

HL01-01-4
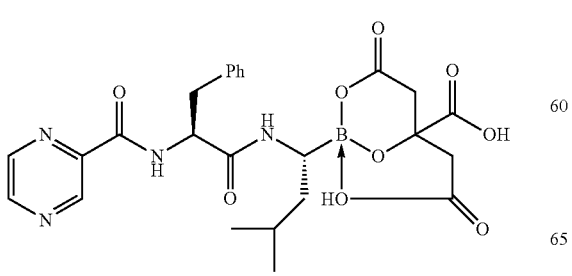

HL01-01-5
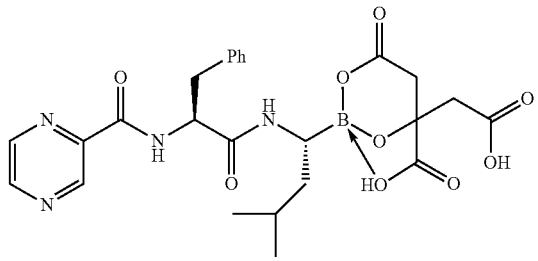

The product HL01-02 of Example 2, characterized by formula HL01-02-1, HL-01-02-2, HL-01-02-3, HL-01-02-4, or a mixture thereof.

HL01-02-1
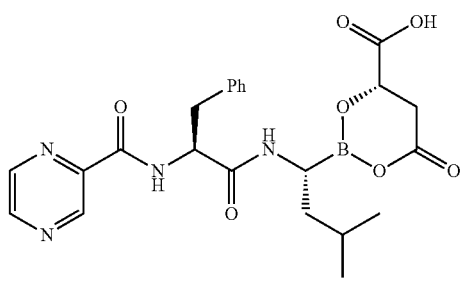

HL01-02-2
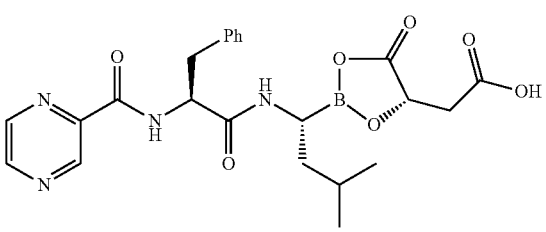

HL01-02-3
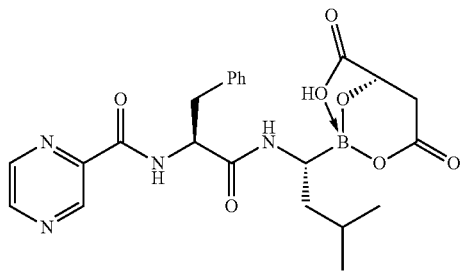

HL01-02-4
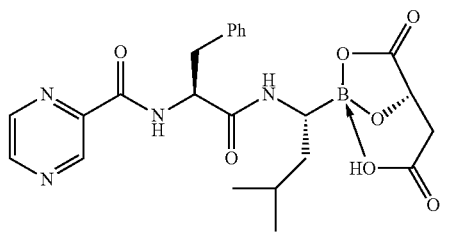

The product HL01-17 of Example 15, characterized by formula HL01-17-1, HL-01-17-2, HL-01-17-3, HL-01-17-4, HL-1-17-5, or a mixture thereof.

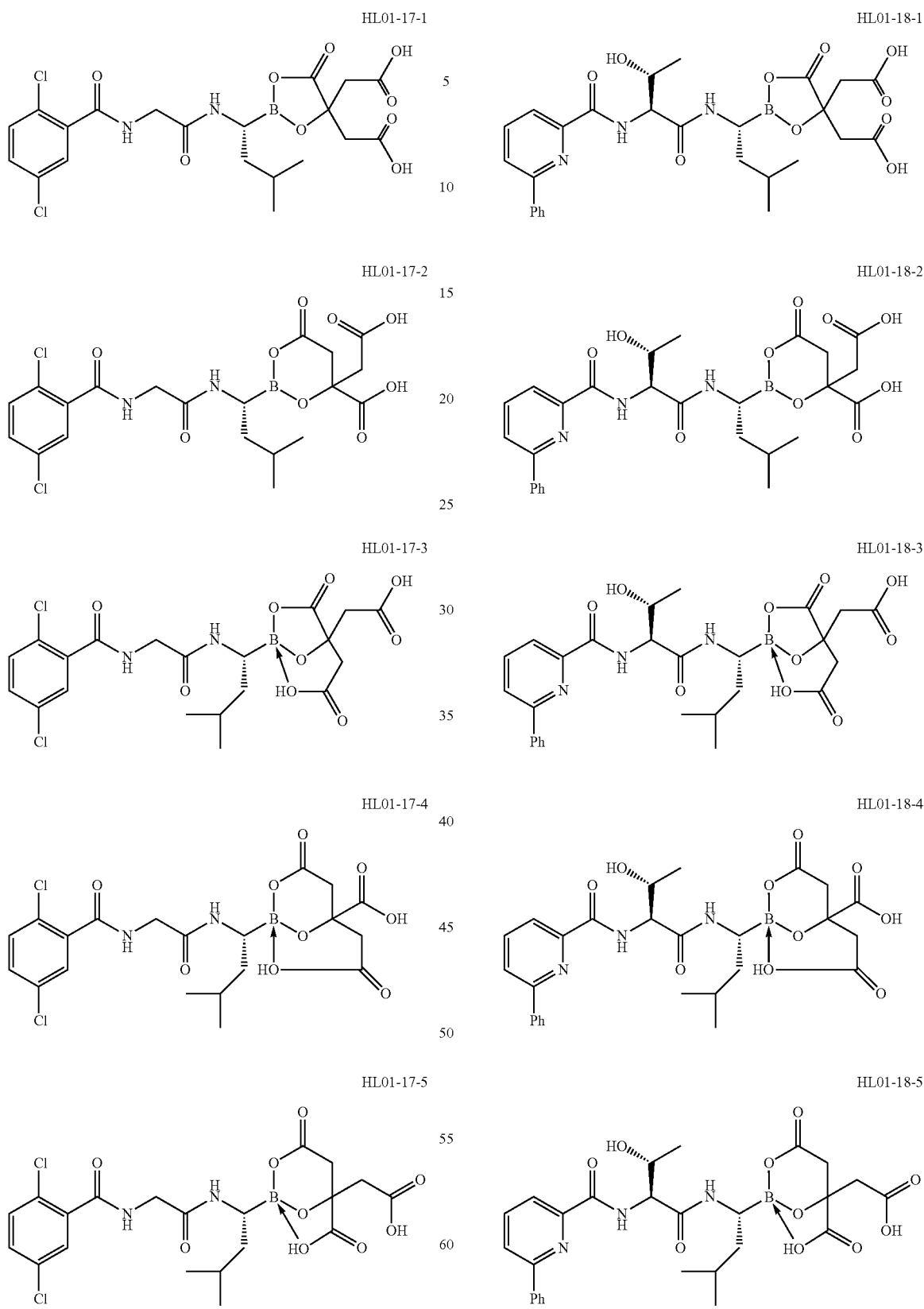
The product HL01-18 of Example 16, characterized by formula HL01-18-1, HL-01-18-2, HL-01-18-3, HL-01-18-4, HL-1-18-5, or a mixture thereof.
The product HL01-23 of Example 23, characterized by formula HL01-23-1, HL-01-23-2, HL-01-23-3, HL-01-23-4, or a mixture thereof.

HL01-23-1

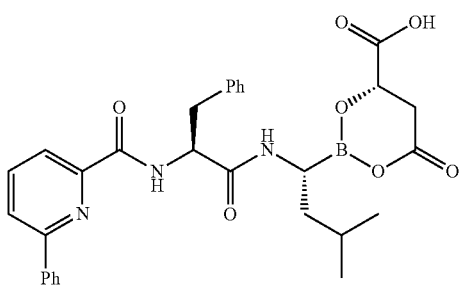

HL01-23-2

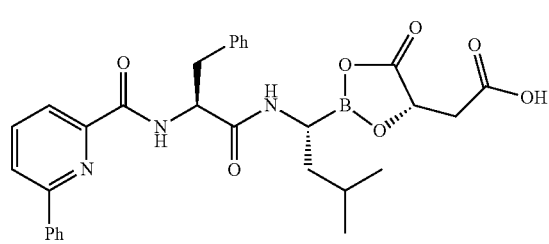

HL01-23-3

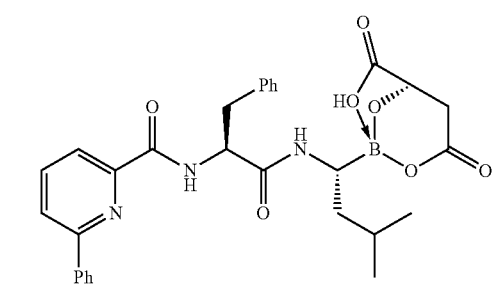

HL01-23-4

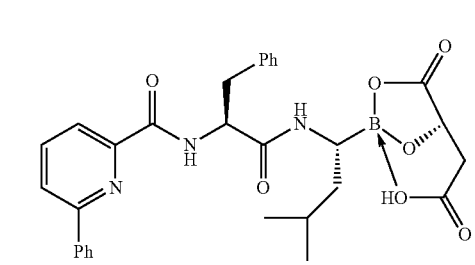

HL01-28-2

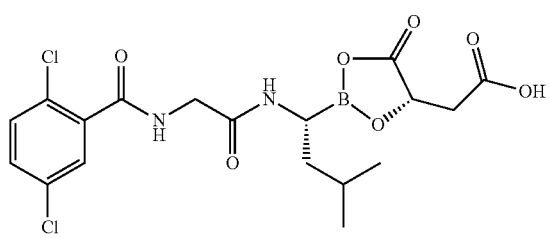

HL01-28-3

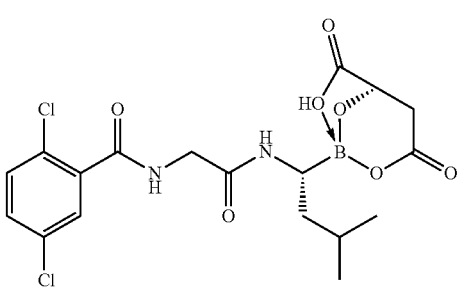

HL01-28-4

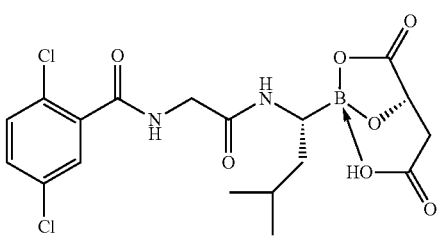

The product HL01-28 of Example 28, characterized by formula HL01-28-1, HL-01-28-2, HL-01-28-3, HL-01-28-4, or a mixture thereof.

HL01-28-1

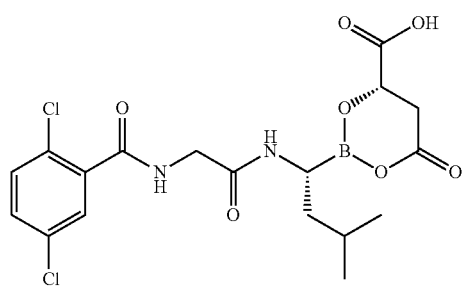

Example 1

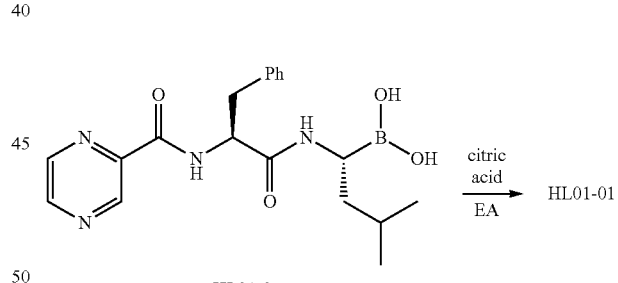

Bortezomib (HL01-0, 1.0 g) was dissolved in EA (80 mL) at 85° C., and citric acid (525 mg, 2.73 mmol) was added under inert gas. The reaction mixture was stirred at 85° C. for another 3.5 hrs, then cooled to room temperature (RT), and n-Hexane (24 mL) was added. The white precipitate was filtered and dried to get the white solid HL-01-01. $^1$H NMR (d$_6$-DMSO, 400 MHz) δ 12.08 (br, 1H), 10.62 (br, 1H), 9.19 (br, 1H), 9.18 (s, 1H), 8.89 (s, 1H), 8.77 (s, 1H), 7.28-7.19 (m, 5H), 5.06 (m, 1H), 3.25 (d, 2H, J=6.8 Hz), 2.85 (m, 1H), 2.72 (m, 2H), 2.57 (m, 2H), 1.45 (m, 1H), 1.10 (m, 1H), 0.97 (m, 1H), 0.78 (d, 6H, J=4.4 Hz). $^{13}$C NMR (d$_6$-DMSO, 400 MHz) δ 177.82, 170.73, 170.62, 163.28, 147.84, 143.98, 143.71, 143.39, 129.28, 128.31, 126.79, 76.24, 50.31, 36.25, 24.55, 23.51, 21.38.

Example 2

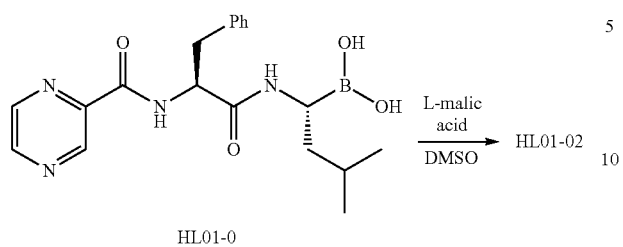

HL01-0 (100 mg) was dissolved in DMSO (2 mL), and L-malic acid (35 mg, 0.26 mmol) was added under inert gas. The reaction mixture was stirred at 95° C. for 6 hrs, then cooled to RT. The solvent was removed under reduced pressure, then EA/n-Hexane was added to the residue at −20° C. The white precipitate was filtered and dried to get the white solid, HL-01-02. $^1$H NMR (d$_6$-DMSO, 400 MHz) δ 12.30 (br, 1H), 10.72 (s, 1H), 9.33 (d, 1H, J=7.6 Hz), 9.13 (d, 1H, J=1.6 Hz), 8.89 (d, 1H, J=1.6 Hz), 8.78 (m, 1H), 7.28-7.21 (m, 5H), 5.07 (dd, 1H, J=15.2, 7.6 Hz), 4.37 (dd, 1H, J=7.2, 4.0 Hz), 3.46-3.42 (m, 1H), 3.29-3.20 (m, 2H), 2.63-2.28 (m, 2H), 1.46 (m, 1H), 1.17 (m, 2H), 0.81 (d, 6H, J=6.4 Hz). MS (m/z): [M+Na] calculated for C$_{23}$H$_{27}$BN$_4$NaO$_7$, 505.28; found, 505.19.

Example 3

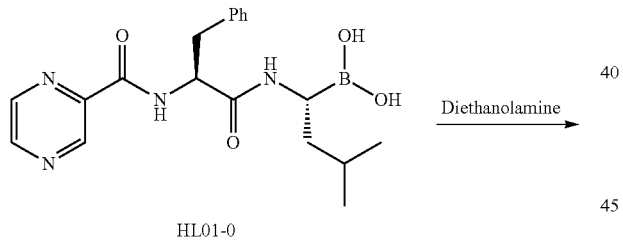

HL01-0 (200 mg) was dissolved in EA (8 mL) at 85° C., and diethanolamine (54.7 mg, 0.52 mmol) was added under inert gas. The reaction mixture was stirred at 85° C. for 6 hrs, then was cooled to RT. The white precipitate was collected and dried to get the white solid. (150 mg, 63. $^1$H NMR (d$_6$-DMSO, 400 MHz) δ 9.09 (s, 1H), 8.87 (d, 1H, J=2.4 Hz), 8.81 (d, 1H, J=8.8 Hz), 8.75 (s, 1H), 7.28-7.20 (m, 5H), 7.16-7.14 (m, 1H), 6.55 (br, 1H), 4.76 (td, 1H, J=9.2, 4.8 Hz), 3.69-3.61 (m, 2H), 3.28-3.23 (m, 1H), 3.48-3.41 (m, 1H), 3.16-3.04 (m, 3H), 2.85-2.77 (m, 1H), 2.74-2.67 (m, 2H), 1.63-1.53 (m, 1H), 1.37-1.30 (m, 1H), 1.22-1.16 (m, 1H), 0.80 (dd, 6H, J=12.8, 6.8 Hz).

Example 4

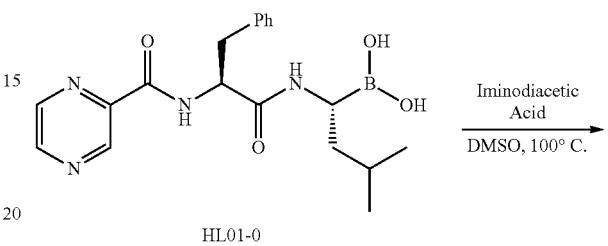

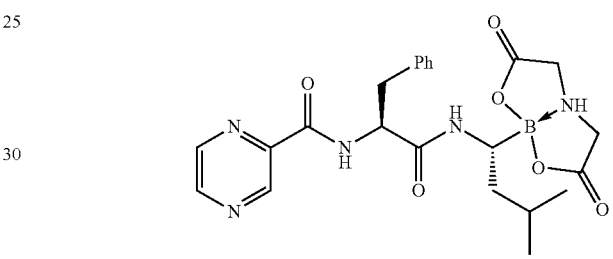

HL01-0 (384 mg) was dissolved in DMSO (3 mL) and EA (3 mL), and Iminodiacetic Acid (133 mg, 1 mmol) was added under inert gas. The reaction mixture was stirred at 85° C. for 6 hrs, then was cooled to RT. The white precipitate was collected under reduced pressure, washed by EtOH, and dried to get the white solid. $^1$H NMR (d$_6$-DMSO, 400 MHz) δ 9.09 (d, 1H, J=1.2 Hz), 8.87 (d, 1H, J=2.4 Hz), 8.73-8.72 (m, 1H), 8.70 (d, 1H, J=8.8 Hz), 8.16 (br, 1H), 7.76 (d, 1H, J=8 Hz), 7.26-7.13 (m, 5H), 4.72 (td, 1H, J=8.8, 5.6 Hz), 4.06 (dd, 1H, J=17.2, 8.4 Hz), 3.92 (dd, 1H, J=17.6, 8.4 Hz), 3.76 (dd, 1H, J=9.2, 3.2 Hz), 3.72 (dd, 1H, J=9.2, 3.2 Hz), 3.14-3.01 (m, 3H), 1.59-1.45 (m, 2H), 1.08-1.01 (m, 1H), 0.82 (dd, 6H, J=22.4, 6.8 Hz). MS (m/z): [M+H] calculated for C$_{23}$H$_{29}$BN$_5$O$_6$, 482.32; found, 482.15.

Example 5

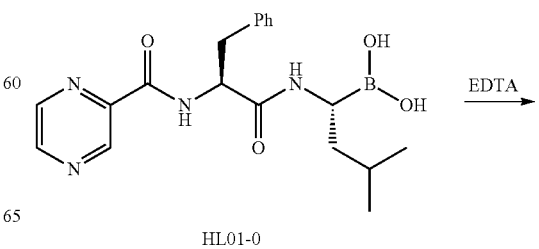

-continued

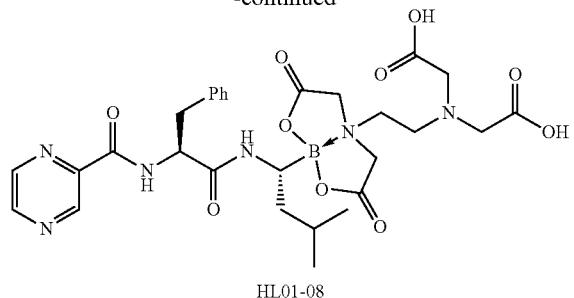

HL01-08

HL01-0 (19.2 mg) was dissolved in DMSO (1.5 mL), and EDTA (7.3 mg, 0.05 mmol) was added under inert gas. The reaction mixture was stirred at 100° C. for 3 hrs, then was cooled to RT. The white precipitate was collected under reduced pressure, and dried get the white solid. MS (m/z): [M+H] calculated for $C_{29}H_{38}BN_6O_{10}$, 641.46; found, 641.30.

Example 6

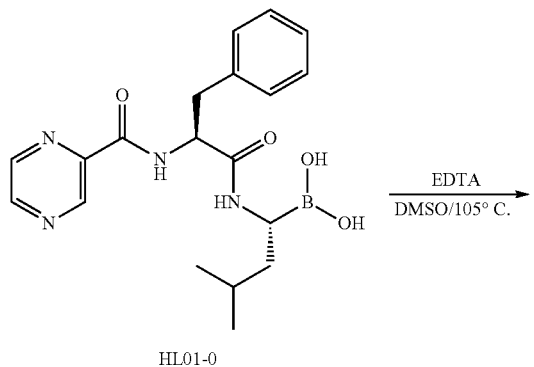

HL01-0

HL01-0 (50 mg) was dissolved in DMSO (2 mL), and EDTA (19 mg, 0.065 mmol) was added under inert gas. The reaction mixture was stirred at 105° C. for 4 hrs., then was cooled to RT. The white precipitate was collected under reduced pressure, purified by semi-prep RP-HPLC, and dried get the white solid. MS (m/z): [M+H] calculated for $C_{48}H_{59}B_2N_{10}O_{12}$, 989.67; found, 989.2.

Example 7

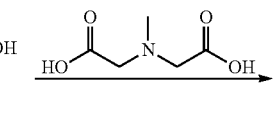

HL01-0

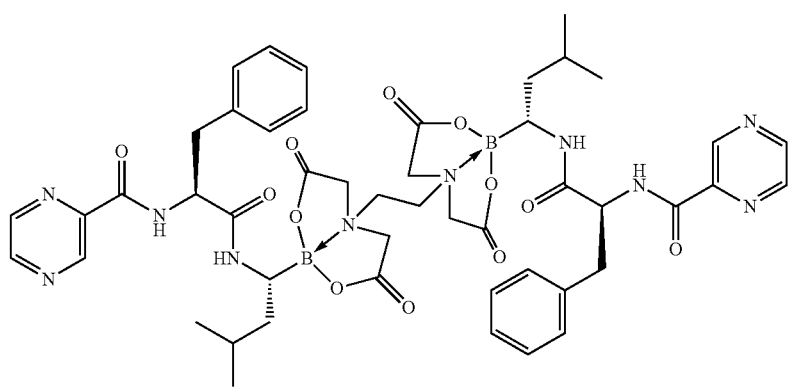

HL01-08-1

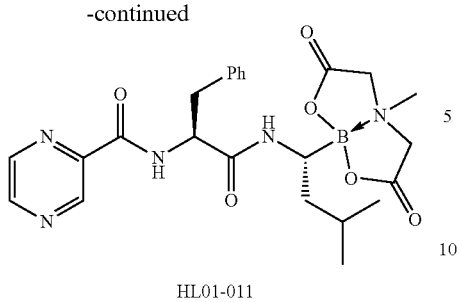

HL01-011

HL01-0 (200 mg) was dissolved in DMSO/EA (6 mL/6 mL), and N-methyliminodiacetic acid 133 mg, 0.52 mmol) as added under inert gas. The reaction mixture was stirred at 85° C. for 5 hrs, and then was cooled to RT. The white precipitate was collected under reduced pressure, and dried to get the white solid. $^1$H NMR (d$_6$-DMSO, 400 MHz) δ 9.07 (d, 1H, J=1.2 Hz), 8.92 (d, 1H, J=4.4 Hz), 8.87 (d, 1H, J=2.4 Hz), 8.74-8.73 (m, 1H), 7.30-7.23 (m, 5H), 7.20-7.15 (m, 1H), 4.70-4.64 (m, 1H), 4.22 (d, 1H, J=17.2 Hz), 4.07 (d, 1H, J=16.8 Hz), 3.98 (d, 1H, J=16.8 Hz), 3.57-3.51 (m, 2H), 3.09 (s, 1H), 3.07 (d, 1H, J=2.0 Hz), 2.82 (s, 3H), 1.59-1.53 (m, 1H), 1.43-1.36 (m, 1H), 1.22-1.16 (m, 1H), 0.84 (dd, 6H, J=11.2, 6.4 Hz). MS (m/z): [M+H] calculated for C$_{24}$H$_{31}$BN$_5$O$_6$, 496.34; found, 496.20.

Example 8

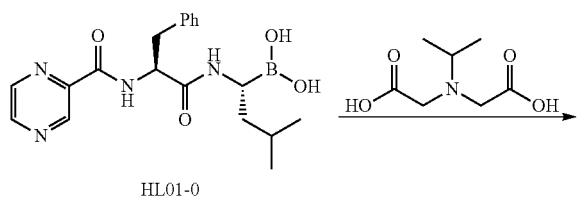

HL01-0

HL01-012

HL01-0 (150 mg) was dissolved in DMSO (5 mL), and N-isopropyl iminodiacetic acid (HL01-12-0, 69 mg, 0.39 mmol) as added under inert gas. The reaction mixture was stirred at 85° C. for 5 hrs, and then was cooled to RT. The solvent was removed under reduced pressure to get colorless oil. $^1$H NMR (d$_6$-DMSO, 400 MHz) δ 9.09 (d, 1H, J=1.6 Hz), 8.91 (d, 1H, J=8.4 Hz), 8.86 (d, 1H, J=2.4 Hz), 7.44 (d, 1H, J=9.6 Hz), 7.30-7.16 (m, 5H), 4.68-4.62 (m, 1H), 4.28 (d, 1H, J=18.0 Hz), 3.89 (dd, 2H, J=18.4, 5.2 Hz), 3.71-3.61 (m, 3H), 3.09 (s, 1H), 3.07 (d, 1H, J=2.8 Hz), 1.61-1.55 (m, 1H), 1.49-1.42 (m, 1H), 1.16 (dd, 6H, J=6.0, 2.0 Hz), 0.99 (d, 1H, J=6.8 Hz), 0.84 (dd, 6H, J=29.2, 6.8 Hz). MS (m/z): [M+H] calculated for C$_{26}$H$_{35}$BN$_5$O$_6$, 524.4; found, 524.30.

Example 9

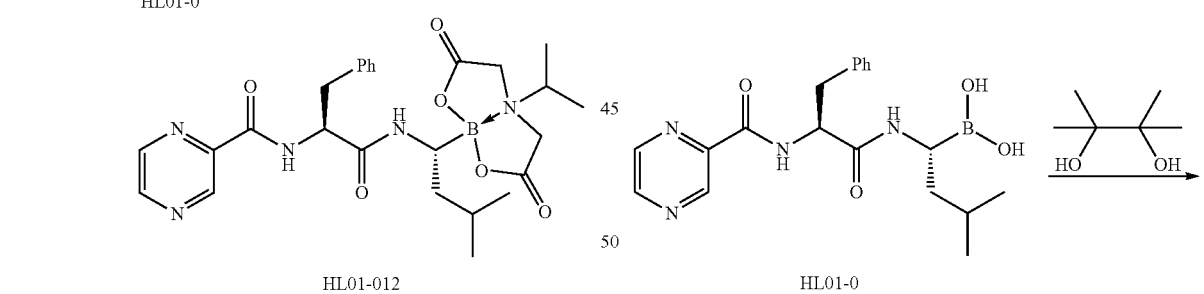

HL01-0

HL01-013

HL01-0 (200 mg) was dissolved in DMSO (3 mL), and N-benzyl iminodiacetic acid (HL01-13-0, 122 mg, 0.547 mmol) as added under inert gas. The reaction mixture was stirred at 85° C. for 2 hrs, then was cooled to RT. The solvent was removed under reduced pressure to get colorless oil. $^1$H NMR (d$_6$-DMSO, 400 MHz) δ 9.12 (d, 1H, J=1.6 Hz), 9.06 (d, 1H, J=8.0 Hz), 8.87 (d, 1H, J=2.0 Hz), 8.75 (dd, 1H, J=2.4, 1.6 Hz), 7.63-7.61 (m, 1H), 7.52-7.50 (m, 2H), 7.34-7.17 (m, 7H), 4.66-4.60 (m, 1H), 4.465 (d, 1H, J=13.2 Hz), 4.26 (d, 1H, J=13.2 Hz), 4.18 (d, 1H, J=17.2 Hz), 3.85-3.77 (m, 2H), 3.68-3.63 (m, 1H), 3.15-3.00 (m, 3H), 1.66-1.60 (m, 1H), 1.56-1.45 (m, 1H), 1.35-1.26 (m, 1H), 0.89 (dd, 6H, J=11.2, 6.8 Hz). MS (m/z): [M+H] calculated for C$_{30}$H$_{35}$BN$_5$O$_6$, 572.44; found, 572.30.

Example 10

HL01-14

HL01-0 (200 mg) was dissolved in EA (5 mL), and Pinacol (61.5 mg) was added under inert gas. The reaction mixture was stirred at 85° C. for 5 hrs, and then was cooled to RT, and the solvent was removed under reduced pressure to get the oil. ¹H NMR (d₆-DMSO, 400 MHz) δ 9.18 (d, 1H, J=1.2 Hz), 8.99-8.98 (m, 1H), 8.94 (d, 1H, J=2.8 Hz), 8.84 (d, 1H, 8.4 Hz), 8.91-8.80 (m, 1H), 7.33-7.23 (m, 5H), 4.96-4.91 (m, 1H), 3.19-3.17 (m, 2H), 2.70-2.66 (m, 1H), 1.65-1.56 (m, 1H), 1.37-1.31 (m, 1H), 1.27-1.23 (m, 1H), 1.18 (d, 12H, J=4.8 Hz), 0.88 (t, 6H, J=6.4 Hz). MS (m/z): [M+H] calculated for $C_{25}H_{36}BN_4O_4$, 467.28; found: 467.30.

Example 11

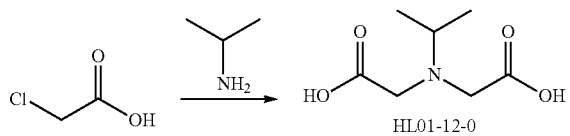

Chloroacetic acid (6 g, 0.0625 mol) was dissolved in water (20 mL) at 0° C., then neutralized with 5 N NaOH solution. Isopropylamine (1.85 g, 0.031 mol) was added to the solution and stirred at 50° C. overnight. $BaCl_2 \cdot 2H_2O$ (7.6 g, 0.031 mol) was dissolved in hot water (15 mL) and was added to the reaction mixture. The precipitate was filtered and dried at 60° C. for 2 hours. The solid was dissolved in the boiling water, and 5N $H_2SO_4$ was added. After removal of the precipitate, the filtrate was concentrated to give brown solid, HL01-12-0 (300 mg, 5.5%) H NMR (d6-DMSO, 400 MHz) δ 3.27 (s, 4H), 3.12 (s, 1H), 1.02 (s, 6H).

Example 12

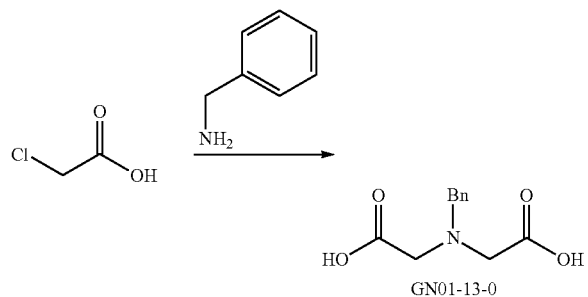

Chloroacetic acid (18.9 g, 0.2 mol) was dissolved in water (30 mL) at 0° C., then neutralized with 5 N NaOH solution. Benzylamine (10.7 g, 0.1 mol) was added to the solution and stirred at 60° C. overnight. $BaCl_2 \cdot 2H_2O$ (25.6 g, 0.105 mol) was dissolved in hot water (30 mL) and was added to the reaction mixture. The precipitate was filtered and dried at 80° C. for 4 hours. The solid was dissolved in the boiling water, and 5N $H_2SO_4$ was added. After removal of the precipitate, the filtrate was concentrated to give white solid, HL01-13-0 (8.0 g, 36%). ¹H NMR (d6-DMSO, 400 MHz) δ 7.33-7.24 (m, 5H), 3.82 (s, 2H), 3.38 (s, 4H).

Example 13

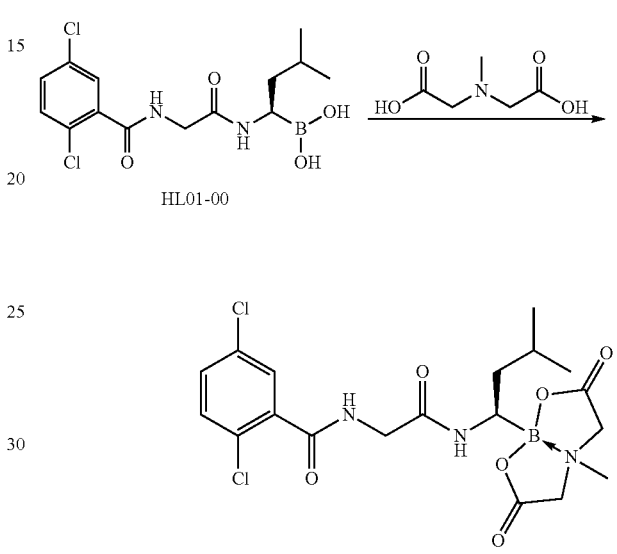

HL01-00 (30 mg, 0.083) was dissolved in DMSO (2 mL), and N-Methyl iminodiacetic acid (12.2 mg, 0.083 mmol) was added under inert gas. The reaction mixture was stirred at 85° C. for 2 hrs, then was cooled to RT. The solvent was removed under reduced pressure and the residue purified by Prep-HPLC to get the white solid, HL01-15 (15 mg, 38.5%) ¹H NMR (d6-DMSO, 400 MHz) δ 8.84 (s, 1H), 7.54-7.52 (m, 3H), 7.33 (d, 1H, J=8.8 Hz), 4.26-4.13 (m, 3H), 4.02-3.80 (m, 4H), 2.87 (s, 3H), 1.53-1.52 (m, 1H), 1.41-1.35 (m, 1H), 1.20-1.16 (m, 1H), 0.85 (m, 6H). MS (m/z): [M+H] calculated for $C_{19}H_{25}BCl_2N_3O_6$, 472.12; found, 472.00.

Example 14

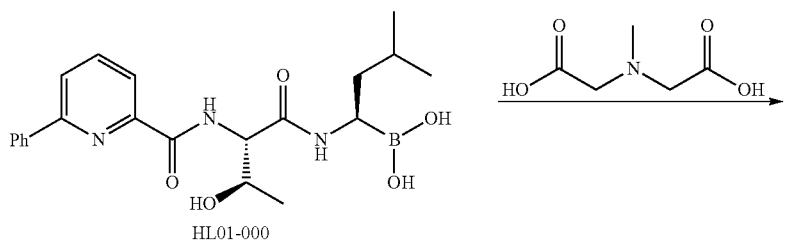

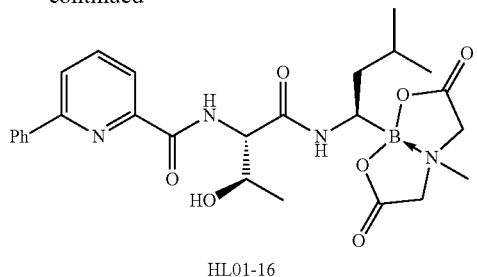
HL01-16

HL01-000 (30 mg) was dissolved in DMSO (2 mL), and N-Methyl iminodiacetic acid (10.7 mg, 0.073 mmol) was added under inert gas. The reaction mixture was stirred at 85° C. for 2 hrs, then was cooled to RT. The solvent was removed under reduced pressure and the residue was purified by Prep-HPLC to get the white solid, HL01-17 (10 mg, 36.3%). $^1$H NMR (d$_6$-DMSO, 400 MHz) δ 8.80 (d, 1H, J=8.4 Hz), 8.21-8.17 (m, 3H), 8.11 (t, 1H, J=8.0 Hz), 8.00 (d, 1H, J=6.8 Hz), 7.59-7.25 (m, 4H), 5.21-5.20 (m, 1H), 4.51 (dd, 1H, J=8.4, 3.6 Hz), 4.28 (d, 1H, J=17.6 Hz), 4.12 (d, 1H, J=16.8 Hz), 4.08 (br, 1H), 3.97 (d, 1H, J=17.2 Hz), 3.92 (d, 1H, J=16.4 Hz), 2.94 (s, 3H), 1.55-1.48 (m, 1H), 1.45-1.37 (m, 1H), 1.22-1.15 (m, 1H), 1.09 (d, 3H, J=6.0 Hz), 0.82 (dd, 6H, J=16.8, 6.8 Hz). MS (m/z): [M+H] calculated for C$_{26}$H$_{34}$BN$_4$O$_7$, 525.25; found, 525.30.

Example 15

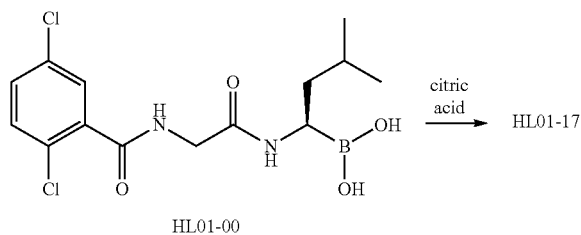 [SMILES: CC(C)C[C@H](NC(=O)CNC(=O)c1cc(Cl)ccc1Cl)B(O)O]
HL01-00

To a solution of HL01-00 (30 mg) in EA (2 mL) was added citric acid (16 mg, 0.083 mmol) at sealed tube. The reaction mixture was stirred at 85° C. for 1.5 hrs. The reaction mixture was cooled to RT, and the solid was filtered to get the product white solid, HL01-17. (~15 mg, 35.7%)$^1$H NMR (d$_6$-DMSO, 400 MHz) δ 12.18 (br, 1H), 10.72 (s, 1H), 9.13 (s, 1H), 7.66 (s, 1H), 7.57 (d, 2H, J=1.2 Hz), 4.27 (br, 2H), 2.92-2.88 (m, 1H), 2.78-2.74 (m, 1H), 2.67-2.63 (m, 1H), 2.53 (s, 1H), 1.68-1.67 (m, 1H), 1.29-1.77 (m, 3H), 0.87 (d, 6H, J=6.4 Hz).

Example 16

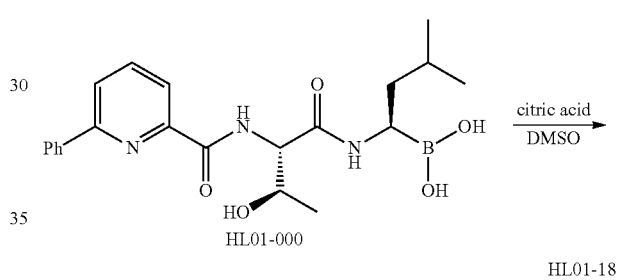
HL01-000 → HL01-18

HL01-000 (30 mg) was dissolved in DMSO (2 mL) at RT, and then citrate (14 mg, 0.073 mmol) was added. The reaction mixture was stirred at 85° C. under inert gas for another 4 hrs, then cooled to RT, The solvent was removed to get solid (15 mg). $^1$H NMR (d$_6$-DMSO, 400 MHz) δ 12.14 (s, 1H), 10.78 (s, 1H), 8.81-8.79 (d, 1H, J=8.4 Hz), 8.24-8.19 (m, 3H), 8.15-8.11 (t, 1H), 8.04-8.03 (d, 1H, J=7.2 Hz), 7.58-7.49 (m, 3H), 5.7 (s, 1H), 4.72-4.69 (dd, 1H), 4.27 (s, 1H), 2.90-2.67 (m, 4H), 1.62 (s, 1H), 1.30-1.14 (d, 5H), 0.83-0.82 (d, 6H, J=6.4 Hz)

Example 17

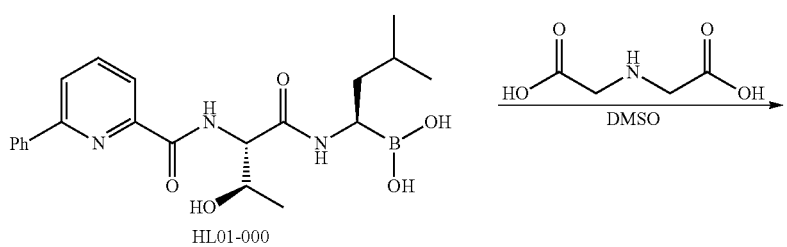
HL01-000

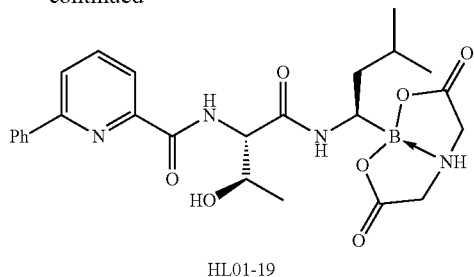

HL01-19

HL01-000 (30 mg) was dissolved in DMSO (2 mL) at RT, and then iminodiacetic acid (9.71 mg, 0.073 mmol) was added. The reaction mixture was stirred at 85° C. under inert gas for another 5 hrs, then cooled to RT. The solvent was removed to get white crystalline solid, HL01-19 (15 mg). $^1$H NMR (d$_6$-DMSO, 400 MHz) δ 8.78-8.76 (d, 1H, J=8.0 Hz), 8.21-8.16 (m, 3H), 8.12-8.08 (t, 2H), 8.02-8.00 (d, 1H), 7.74-7.73 (d, 1H, J=7.6 Hz), 7.58-7.49 (m, 3H), 5.16 (s, 1H), 4.41-4.38 (q, 1H), 4.15-4.07 (m, 3H), 3.79-3.72 (m, 2H), 3.19-3.13 (m, 1H), 1.65-1.62 (m, 1H), 1.56-1.48 (m, 1H), 1.11-1.04 (m, 3H), 0.86-0.85 (d, 3H=6.8 Hz), 0.80-0.78 (d, 3H, J=6.4 Hz). MS (m/z): [M+H] calculated for $C_{25}H_{32}BN_4O_7$, 511.35; found, 511.0.

Example 18

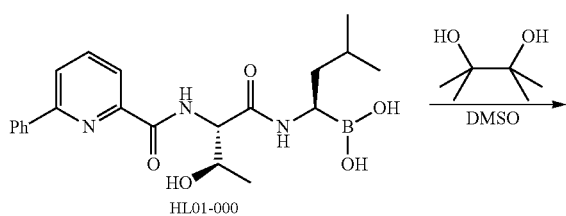

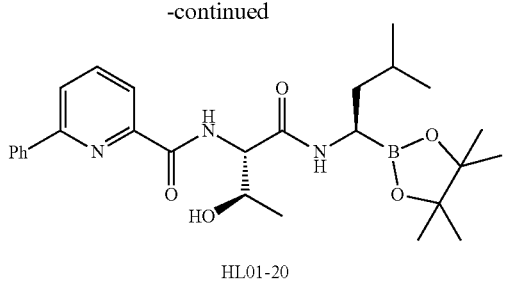

HL01-20

HL01-000 (30 mg) was dissolved in DMSO (2 mL) at RT, and Pinacol (8.61 mg, 0.073 mmol) was added. The reaction mixture was stirred at 85° C. under inert gas for another 5 hrs, then cooled to RT. The solvent was removed to get solid, HL01-20 (10 mg). $^1$H NMR (d$_6$-DMSO, 400 MHz) δ 9.11 (s, 1H), 8.78-8.76 (d, 1H, J=8.4 Hz), 8.23-8.19 (m, 3H), 8.13-8.10 (t, 1H), 8.03-8.01 (d, 1H, J=7.2 Hz), 7.57-7.50 (m, 4H), 5.32-5.31 (d, 1H, J=4.8 Hz), 4.55-4.51 (dd, 1H), 4.15-4.11 (dd, 1H), 1.68-1.64 (m, 1H), 1.29-1.20 (m, 2H), 1.14-1.09 (m, 12H), 0.85-0.83 (dd, 6H)

Example 19

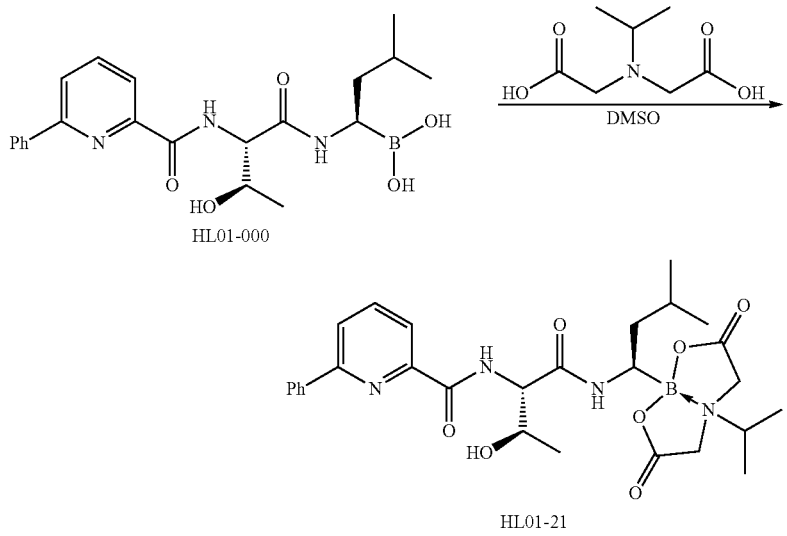

HL01-21

HL01-000 (30 mg) was dissolved in DMSO (2 mL) at RT, and N-isopropyl iminodiacetic (8.61 mg, 0.073 mmol) was added. The reaction mixture was stirred at 85° C. under inert gas for another 5 hrs, and then cooled to RT. The solvent was removed to get pale yellow sticky solid, HL01-21. $^1$H NMR (d$_6$-DMSO, 400 MHz) δ 8.76-8.74 (d, 1H, J=8.4 Hz), 8.18-8.16 (m, 3H), 8.12-8.08 (t, 1H), 8.02-8.00 (d, 1H), 7.59-7.51 (m, 4H), 5.17 (s, 1H), 4.56-4.53 (dd, 1H), 4.33-4.28 (d, 1H), 4.08 (s, 1H), 3.99-3.89 (d, 3H), 3.83-3.80 (t, 1H), 3.71-3.67 (t, 1H), 1.59-1.37 (m, 3H), 1.23-1.10 (dd, 6H), 0.86-0.79 (m, 6H) MS (m/z): [M+H] calculated for C$_{28}$H$_{38}$BN$_4$O$_7$, 553.43; found, 553.3.

Example 20

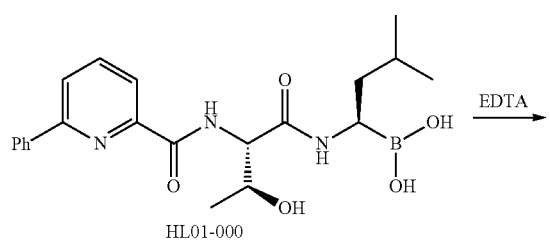

HL01-000

Example 21

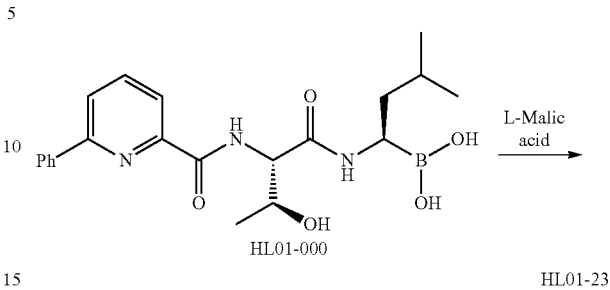

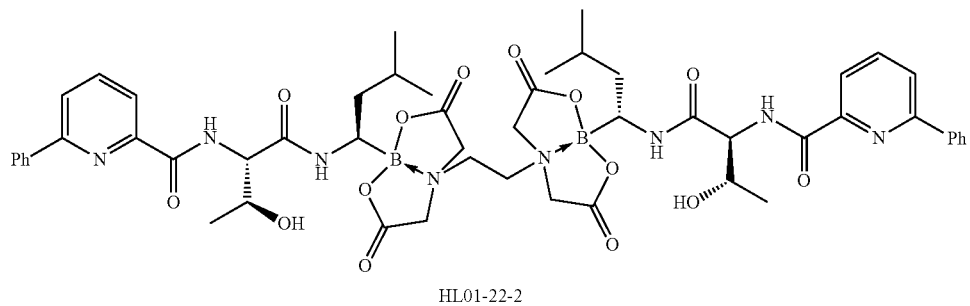

HL01-22-1

+

HL01-22-2

HL01-000 (30 mg) was dissolved in DMSO (2 mL) at RT, and EDTA (10.65 mg, 0.037 mmol) was added, the reaction mixture was stirred at 98° C. under inert gas for another 6 hrs, then cooled to RT. The solvent was removed to get solid which was purified by RP-HPLC to give HL01-220-1 and dimer HL01-22-2. HL01-22-1 MS (m/z): [M+H] calculated for C$_{31}$H$_{41}$BN$_5$O$_{14}$, 670.28; found, 670.2. HL01-22-2 MS (m/z): [M+H] calculated for C$_{52}$H$_{65}$B$_2$N$_8$O$_{14}$, 1047.47; found, 1047.1.

HL01-000 (30 mg) was dissolved in DMSO (2 mL) at RT, and L-malic acid (9.79 mg, 0.073 mmol) was added, the reaction mixture was stirred at 98° C. under inert gas for another 6 hrs, then cooled to RT. The solvent was removed to get solid. $^1$H NMR (d$_6$-DMSO, 400 MHz) δ 12.30 (s, 1H), 10.87 (s, 1H), 8.83-8.81 (d, 1H, J=8 Hz), 8.24-8.02 (m, 5H), 7.59-7.52 (m, 3H), 5.77-5.76 (d, 1H, J=5.2 Hz), 4.76-4.73 (m, 1H), 4.41-4.39 (m, 1H), 4.32-4.29 (m, 1H), 2.68-2.57 (m, 2H), 1.63-1.56 (m, 1H), 1.31-1.26 (t, 2H), 1.19-1.18 (d, 3H, J=6.4 Hz), 0.84-0.83 (m, 6H, J=6.4 Hz)

Example 22

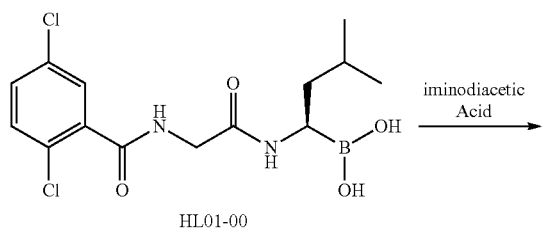

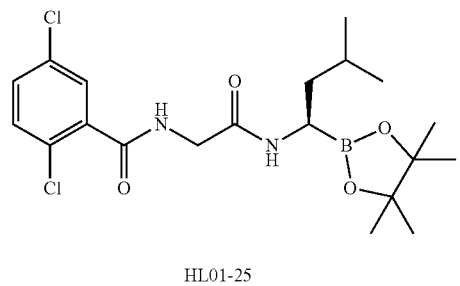

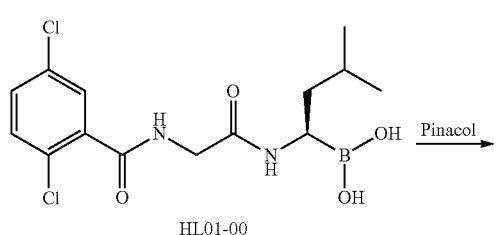

HL01-00 (30 mg) was dissolved in DMSO (2 mL) at RT, and Iminodiacetic Acid (11.03 mg, 0.083 mmol) was added. The reaction mixture was stirred at 85° C. under inert gas for another 5 hrs, then cooled to RT. The solvent was removed to get solid. $^1$H NMR (d6-DMSO, 400 MHz) δ 8.75-8.72 (t, 1H), 8.19 (s, 1H), 7.69-7.68 (m, 1H), 7.52-7.51 (d, 2H, J=1.2 Hz), 4.15-4.0 (m, 2H), 3.88-3.72 (m, 4H), 3.14-3.08 (m, 1H), 1.65-1.62 (m, 1H), 1.54-1.46 (m, 1H), 1.12-1.06 (m, 1H), 0.88-0.81 (dd, 6H, J=6.8, 21.6 Hz). MS (m/z): [M+H] calculated for C18H22BCl2N3O6, 458.09; found, 458.4.

Example 23

HL01-00 (30 mg) was dissolved in EA (2 mL) at RT, and pinacol (9.79 mg, 0.083 mmol) was added. The reaction mixture was stirred at 98° C. under inert gas for another 6 hrs, then cooled to RT. The solvent was removed to get solid. $^1$H NMR (d$_6$-DMSO, 400 MHz) δ 9.07 (s, 1H), 8.88-8.85 (t, 1H), 7.70 (s, 1H), 7.53 (s, 2H), 4.04-4.02 (d, 2H, J=6 Hz), 2.66-2.57 (m, 1H), 1.71-1.67 (m, 2H), 1.52-1.47 (m, 1H), 1.08 (s, 12H), 0.87-0.84 (t, 6H)

Example 24

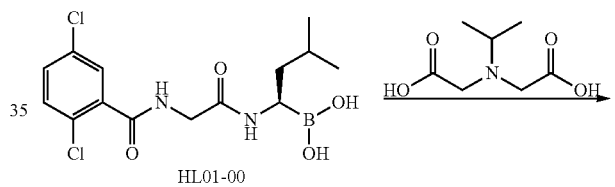

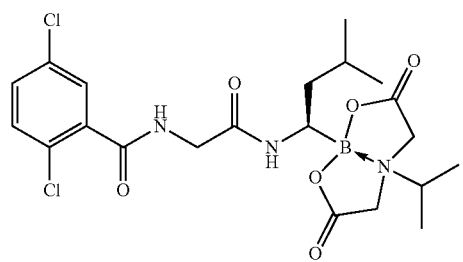

HL01-00 (30 mg) was dissolved in DMSO (1 mL) at RT, and N-isopropyl iminodiacetic acid (14.53 mg, 0.083 mmol) was added. The reaction mixture was stirred at 98° C. under inert gas for another 6 hrs, then cooled to RT. The solvent was removed to get solid. $^1$H NMR (d$_6$-DMSO, 400 MHz) δ 8.78 (s, 1H), 7.68 (s, 1H), 7.49-7.47 (d, 3H, J=8 Hz), 4.32-4.28 (d, 1H, J=16.8 Hz), 4.05-3.88 (m, 4H), 3.74-3.67 (m, 3H), 1.54 (s, 1H), 1.44-1.38 (t, 2H), 1.23-1.06 (m, 7H), 0.86-0.82 (d, 6H, J=15.2 Hz). MS (m/z): [M+H] calculated for C$_{21}$H$_{29}$BCl$_2$N$_3$O$_6$, 501.18; found, 502.1.

Example 25

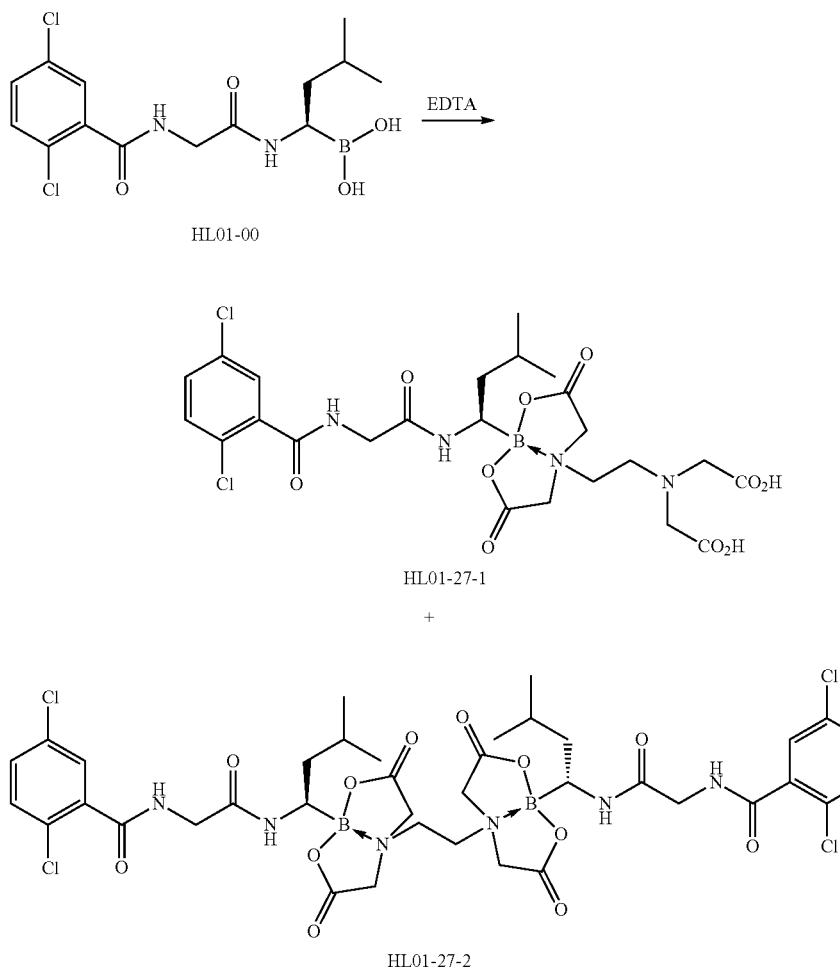

HL01-00 (30 mg) was dissolved in DMSO (1 mL) at RT, and EDTA (24.23 mg, 0.083 mmol) was added. The reaction mixture was stirred at 98° C. under inert gas for another 6 hrs, then cooled to RT. The solvent was removed to get solid which was purified by RP-HPLC to obtain HL01-27-1 and dimer HL01-27-2. HL01-27-1 MS (m/z): [M+H] calculated for $C_{24}H_{32}BCl_2N_4O_{10}$, 618.24; found, 618.4; HL01-27-2 MS (m/z): [M+H] calculated for $C_{38}H_{47}B_2Cl_4N_6O_2$, 943.24; found: 943.4.

HL01-00 (30 mg) was dissolved in DMSO (1 mL) at RT, and L-malic acid (11.12 mg, 0.083 mmol) was added. The reaction mixture was stirred at 98° C. under inert gas for another 6 hrs, then cooled to RT. The solvent was removed to get solid. $^1$H NMR (d$_4$-CD$_3$OD, 400 MHz) δ 7.59-7.56 (t, 2H), 7.46 (dd, 1H, J=2 Hz, 8.4 Hz), 4.591-4.565 (q, 1H), 4.37 (s, 2H), 2.87-2.78 (m, 2H), 2.61-2.58 (m, 1H), 1.74-1.64 (m, 1H), 1.47-1.43 (t, 2H), 0.96-0.94 (dd, 6H, J=2.8 Hz, 6.8 Hz)

Example 27

Example 26

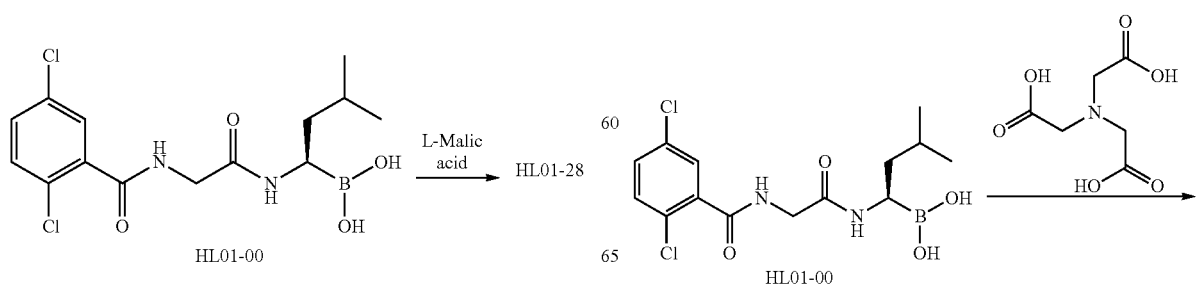

-continued

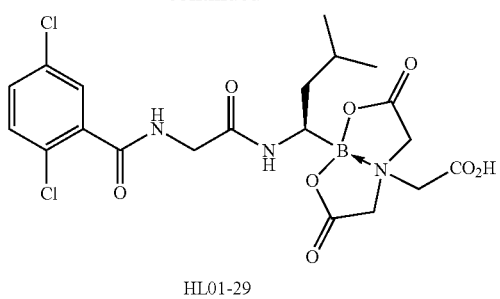

HL01-29

HL01-00 (30 mg) was dissolved in DMSO (1 mL) at RT, and Nitrilotriacetic acid (15.85 mg, 0.083 mmol) was added. The reaction mixture was stirred at 85° C. under inert gas for another 5 hrs, then cooled to RT. The solvent was removed to get solid. $^1$H NMR (d$_6$-DMSO, 400 MHz) δ 8.81-8.78 (t, 1H), 7.69-7.68 (t, 1H), 7.50-7.38 (m, 3H), 4.43-4.38 (d, 1H, J=20 Hz), 4.30-4.25 (d, 1H, J=16.8 Hz), 4.21-4.00 (m, 4H), 3.91-3.86 (dd, 1H, J=5.2 Hz, 15.6 Hz), 3.68-3.63 (dd, 1H, J=6.4 Hz, 16 Hz), 3.59-3.53 (m, 1H), 1.56-1.53 (m, 1H), 1.39-1.36 (m, 1H), 1.21-1.17 (m, 1H), 0.85 (dd, 6H, J=6.4 Hz, 14 Hz). MS (m/z): [M+H] calculated for C$_{20}$H$_{25}$BCl$_2$N$_3$O$_8$, 517.14; found, 517.3.

Example 28

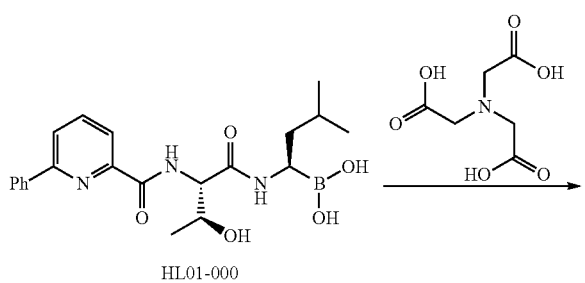

HL01-000 (30 mg) was dissolved in DMSO (1 mL) at RT, and Nitrilotriacetic acid (13.94 mg, 0.073 mmol) was added. The reaction mixture was stirred at 85° C. under inert gas for another 5 hrs, then cooled to RT. The solvent was removed to get solid. $^1$H NMR (d$_6$-DMSO, 400 MHz) δ 8.83-8.78 (t, 1H), 8.22-8.18 (t, 2H), 8.12-8.08 (t, 1H), 8.03-7.98 (t, 1H), 7.59-7.48 (m, 5H), 4.53-4.50 (m, 1H), 4.46-4.42 (d, 1H, J=17.6 Hz), 4.35-4.02 (m, 4H), 3.61-3.55 (m, 1H), 3.50 (s, 2H), 1.55-1.46 (m, 1H), 1.45-1.38 (m, 2H), 1.10-1.08 (d, 3H, J=6.4 Hz), 0.85-0.79 (m, 6H). MS (m/z): [M+H] calculated for C$_{27}$H$_{34}$BN$_4$O$_9$, 569.38; found, 569.5.

Example 29

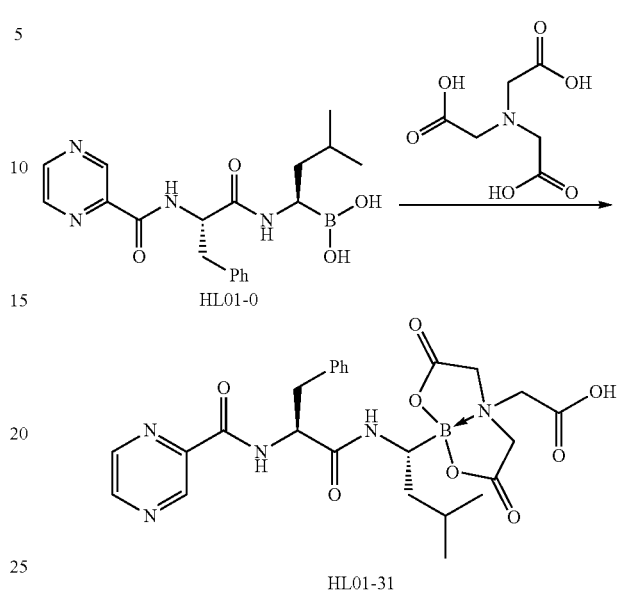

HL01-0 (30 mg) was dissolved in DMSO (1 mL) at RT, and Nitrilotriacetic acid (14.89 mg, 0.078 mmol) was added. The reaction mixture was stirred at 85° C. under inert gas for another 6 hrs, then cooled to RT. The solvent was removed to get solid. $^1$H NMR (d$_6$-DMSO, 400 MHz) δ 9.07-9.06 (d, 1H, J=1.2 Hz), 8.92-8.83 (m, 2H), 8.74-8.70 (m, 1H), 7.40-7.38 (d, 1H, J=10 Hz), 7.29-7.12 (m, 5H), 4.71-4.65 (m, 1H), 4.40-4.04 (m, 4H), 3.55-3.55 (m, 3H), 3.09-3.06 (m, 2H), 1.60-1.51 (m, 1H), 1.45-1.38 (m, 1H), 1.23-1.17 (m, 1H), 0.84 (dd, 6H, J=6.4 Hz, 18.4 Hz). MS (m/z): [M+H] calculated for C$_{25}$H$_{31}$BN$_5$O, 540.35; found, 540.3.

Example 30

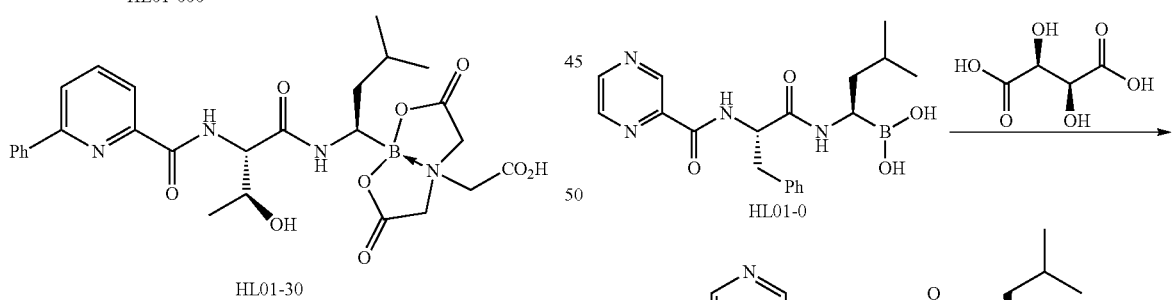

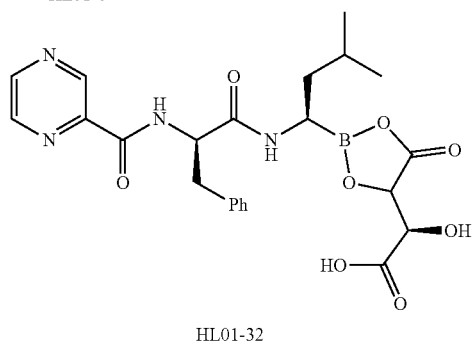

HL01-32

HL01-0 (30 mg) was dissolved in DMSO (1 mL) at RT, and L(+)-tartaric acid (11.70 mg, 0.078 mmol) was added, The reaction mixture was stirred at 85° C. under inert gas for another 5 hrs, then cooled to RT, The solvent was removed to get solid. $^1$H NMR (d$_6$-DMSO, 400 MHz) δ12.75 (bs, 1H), 10.77 (s, 1H), 9.38-9.35 (t, 1H), 9.12 (s, 1H), 8.90-8.89 (d, 1H, J=2.4 Hz), 8.78-8.77 (t, 1H), 7.29-7.18 (m, 5H), 5.12-5.07 (q, 1H), 4.49-4.21 (q, 2H), 3.32-3.21 (m, 2H), 2.68-2.57 (m, 1H), 1.55-1.37 (m, 1H), 1.23-1.06 (m, 2H), 0.86-0.79 (q, 6H).

Example 31

HL01-0 (30 mg) was dissolved in DMSO (1 mL) at RT, and N-ethyl-iminodiacetic acid (12.57 mg, 0.078 mmol) was added. The reaction mixture was stirred at 85° C. under inert gas for another 5 hrs, then cooled to RT. The solvent was removed to get solid. $^1$H NMR (d$_6$-DMSO, 400 MHz) δ 9.12-9.08 (m 1H), 8.93-8.84 (m, 2H), 8.74-8.66 (m, 1H), 7.35-7.12 (m, 5H), 4.93-4.87 (q, 1H), 4.81-4.75 (q, 1H), 4.71-4.65 (q, 1H), 4.18-3.93 (m, 4H), 3.30-3.24 (q, 1H), 3.14-3.03 (m, 2H), 1.56-1.49 (m, 1H), 1.41-1.25 (m, 2H), 1.22-1.13 (m, 3H), 0.86-0.74 (m, 6H).

Example 33

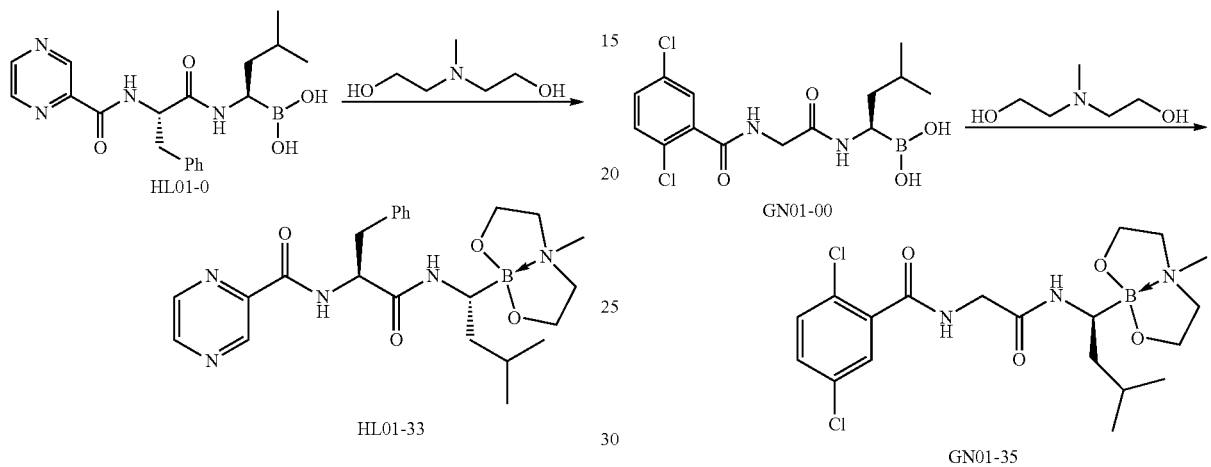

HL01-0 (60 mg) was dissolved in Ethyl acetate (1 mL) at RT, and N-methyldiethanolamine (18.56 mg, 0.156 mmol) was added. The reaction mixture was stirred at RT under inert gas for another 5 hrs, then solvent was removed to get solid. $^1$H NMR (d$_6$-DMSO, 400 MHz) δ 9.24-9.22 (d, 1H, J=8.4 Hz), 9.09-9.08 (d, 1H, J=1.2 Hz), 8.89-8.88 (d, 1H, J=2.4 Hz), 8.79-8.78 (m, 1H), 7.30-7.12 (m, 5H), 6.74-6.72 (d, 1H, J=10 Hz), 4.67-4.61 (m, 1H), 3.61-3.55 (m, 3H), 3.21-3.0 (m, 6H), 2.90-2.86 (m, 1H), 1.55-1.49 (m, 1H), 1.23-1.15 (m, 2H), 0.84-0.78 (dd, 6H, J=6.4, 16 Hz). 3H (N-Me) was contained in 2.5 (DMSO)

Example 32

HL01-00 (30 mg) was dissolved in ethyl acetate (1 mL) at RT, and N-methyldiethanolamine (9.87 mg, 0.083 mmol) was added, then the reaction mixture was stirred at RT under inert gas for another 5 hrs. The solvent was removed to get solid. $^1$H NMR (d$_6$-DMSO, 400 MHz) δ 8.94-8.91 (t, 1H), 7.72 (s, 1H), 7.56-7.45 (m, 1H), 6.51-6.48 (d, 1H, J=9.6 Hz), 3.77-3.62 (m, 6H), 3.20-3.11 (m, 3H), 2.94-2.91 (m, 1H), 2.85-2.81 (m, 1H), 2.59 (s, 3H), 1.49 (s, 1H), 1.22-1.17 (m, 2H), 0.84-0.79 (dd, 6H, J=6, 16.8 Hz). MS (m/z): [M+H] calculated for C$_{19}$H$_{29}$BCl$_2$N$_3$O$_4$, 445.16; found, 445.4.

Example 34

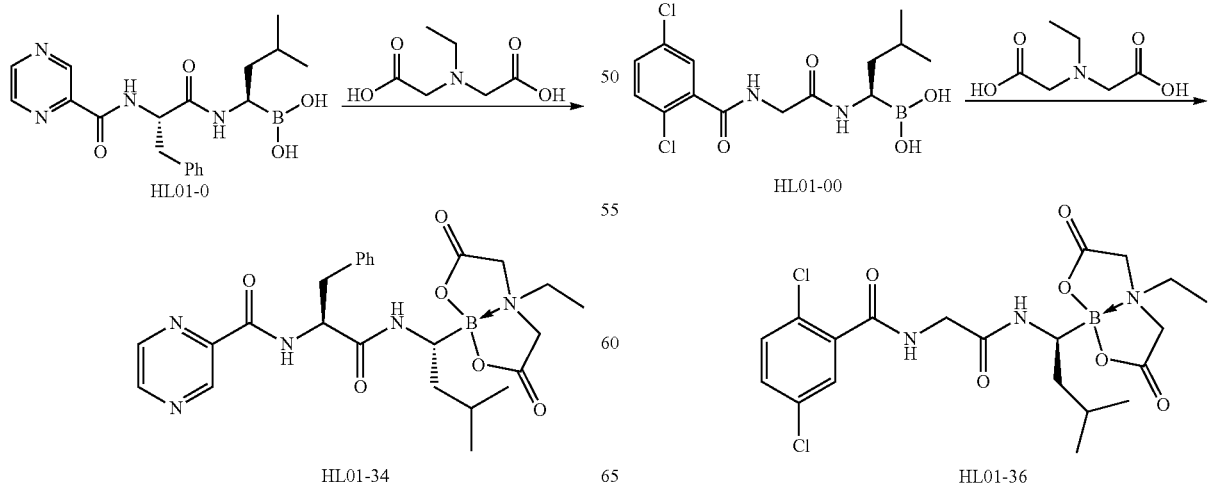

HL01-00 (30 mg, 0.078 mmol) was dissolved in DMSO (1 mL) at RT, and N-ethyl-iminodiacetic acid (12.57 mg, 0.078 mmol) was added. The reaction mixture was stirred at 85° C. under inert gas for another 5 hrs, then cooled to RT, The solvent was removed to get solid. ¹H NMR (d₆-DMSO, 400 MHz) δ8.78-8.66 (dt, 1H), 7.69 (s, 1H), 7.52-7.44 (m, 2H), 7.35-7.29 (m, 1H), 4.19-3.82 (m, 6H), 3.18-3.09 (m, 2H), 2.99 (s, 1H), 1.61-1.43 (m, 1H), 1.38-1.28 (m, 2H), 1.20-1.11 (m, 3H), 0.87-0.82 (m, 6H).

In addition to the foregoing, the above reaction schemes, and variations thereof, can be used to prepare the compounds set forth in the following table:

TABLE 1

| Serial # | Structure | Name |
| --- | --- | --- |
| HL-40 | 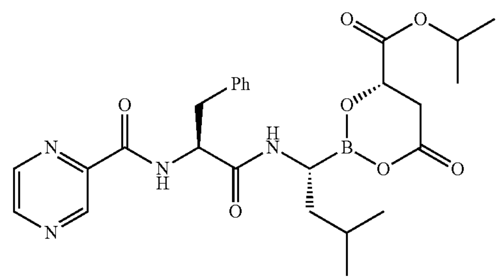 [SMILES: CC(C)C[C@H](NC(=O)[C@H](Cc1ccccc1)NC(=O)c1cnccn1)B1OC(=O)C[C@@H](C(=O)OC(C)C)O1] | isopropyl (S)-2-((R)-3-methyl-1-((S)-3-phenyl-2-(pyrazine-2-carboxamido)propanamido)butyl)-6-oxo-1,3,2-dioxaborinane-4-carboxylate |
| HL-41 | 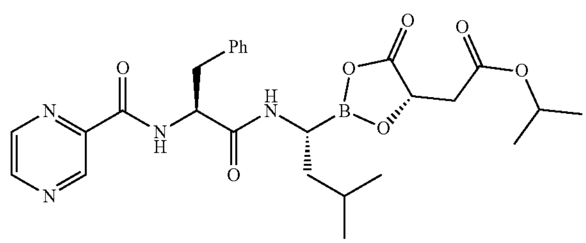 [SMILES: CC(C)C[C@H](NC(=O)[C@H](Cc1ccccc1)NC(=O)c1cnccn1)B1OC(=O)[C@H](CC(=O)OC(C)C)O1] | isopropyl 2-((S)-2-((R)-3-methyl-1-((S)-3-phenyl-2-(pyrazine-2-carboxamido)propanamido)butyl)-5-oxo-1,3,2-dioxaborolan-4-yl)acetate |
| HL-42 | 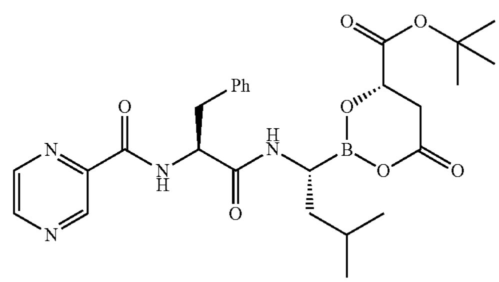 [SMILES: CC(C)C[C@H](NC(=O)[C@H](Cc1ccccc1)NC(=O)c1cnccn1)B1OC(=O)C[C@@H](C(=O)OC(C)(C)C)O1] | tert-butyl (S)-2-((R)-3-methyl-1-((S)-3-phenyl-2-(pyrazine-2-carboxamido)propanamido)butyl)-6-oxo-1,3,2-dioxaborinane-4-carboxylate |
| HL-43 | 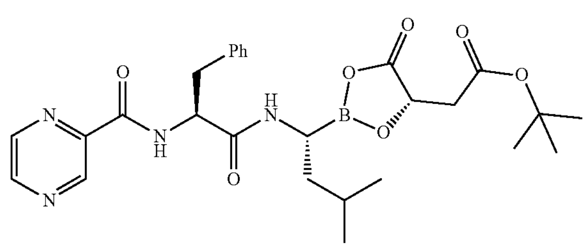 [SMILES: CC(C)C[C@H](NC(=O)[C@H](Cc1ccccc1)NC(=O)c1cnccn1)B1OC(=O)[C@H](CC(=O)OC(C)(C)C)O1] | tert-butyl 2-((S)-2-((R)-3-methyl-1-((S)-3-phenyl-2-(pyrazine-2-carboxamido)propanamido)butyl)-5-oxo-1,3,2-dioxaborolan-4-yl)acetate |
| HL-44 | 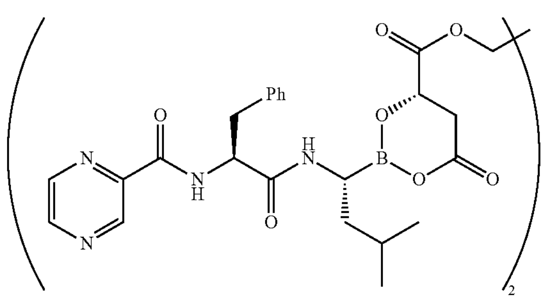 | ethane-1,2-diyl (4S,4'S)-bis(2-((R)-3-methyl-1-((S)-3-phenyl-2-(pyrazine-2-carboxamido)propanamido)butyl)-6-oxo-1,3,2-dioxaborinane-4-carboxylate) |

TABLE 1-continued

| Serial # | Structure | Name |
|---|---|---|
| HL-45 | 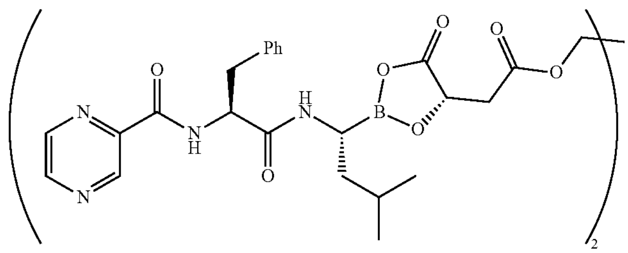 | ethane-1,2-diyl bis(2-((S)-2-((R)-3-methyl-1-((S)-3-phenyl-2-(pyrazine-2-carboxamido)propanamido)butyl)-5-oxo-1,3,2-dioxaborolan-4-yl)acetate) |
| HL-46 | 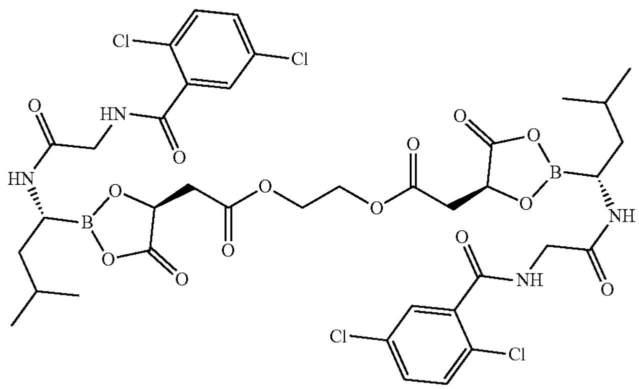 [SMILES: CC(C)C[C@H](NC(=O)CNC(=O)c1cc(Cl)ccc1Cl)B1OC(=O)[C@H](CC(=O)OCCOC(=O)C[C@@H]2OB([C@H](CC(C)C)NC(=O)CNC(=O)c3cc(Cl)ccc3Cl)OC2=O)O1] | ethane-1,2-diyl bis(2-((S)-2-((R)-1-(2-(2,5-dichlorobenzamido)acetamido)-3-methylbutyl)-5-oxo-1,3,2-dioxaborolan-4-yl)acetate) |
| HL-47 | 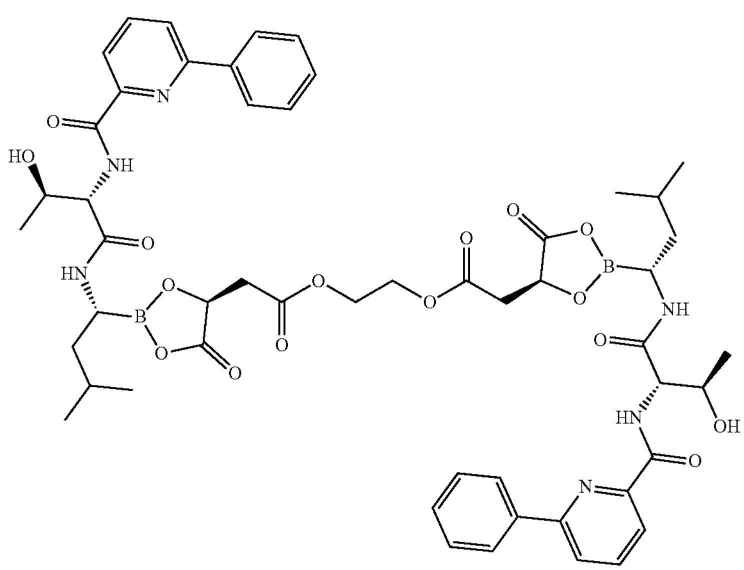 [SMILES: CC(C)C[C@H](NC(=O)[C@@H](NC(=O)c1cccc(-c2ccccc2)n1)[C@@H](C)O)B1OC(=O)[C@H](CC(=O)OCCOC(=O)C[C@@H]2OB([C@H](CC(C)C)NC(=O)[C@@H](NC(=O)c3cccc(-c4ccccc4)n3)[C@@H](C)O)OC2=O)O1] | ethane-1,2-diyl bis(2-((S)-2-((R)-1-((2S,3R)-3-hydroxy-2-(6-phenylpicolinamido)butanamido)-3-methylbutyl)-5-oxo-1,3,2-dioxaborolan-4-yl)acetate) |

TABLE 1-continued
| Serial # | Structure | Name |
|---|---|---|
| HL-48 | 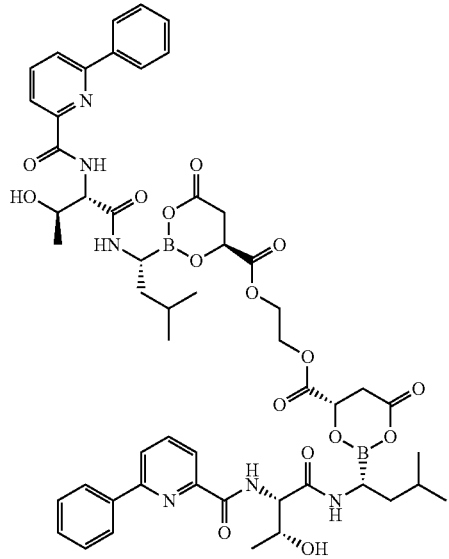 [SMILES: CC(C)C[C@H](NC(=O)[C@@H](NC(=O)c1cccc(-c2ccccc2)n1)[C@@H](C)O)B1OC(=O)C[C@@H](C(=O)OCCOC(=O)[C@@H]2CC(=O)OB([C@H](CC(C)C)NC(=O)[C@@H](NC(=O)c3cccc(-c4ccccc4)n3)[C@@H](C)O)O2)O1] | ethane-1,2-diyl(4S,4'S)-bis(2-((R)-1-((2S,3R)-3-hydroxy-2-(6-phenylpicolinamido)butanamido)-3-methylbutyl)-6-oxo-1,3,2-dioxaborinane-4-carboxylate) |
| HL-49 | 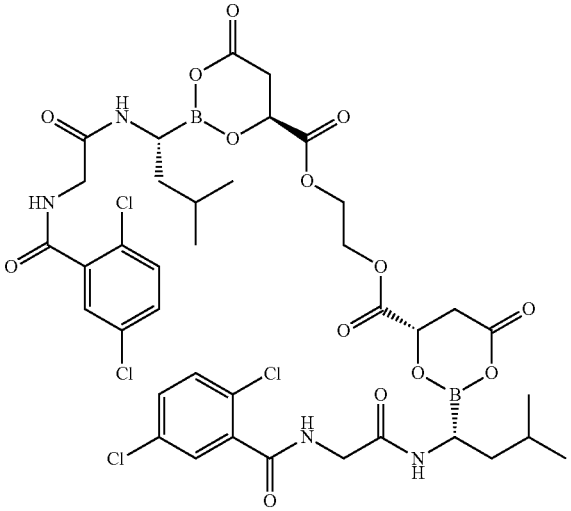 [SMILES: CC(C)C[C@H](NC(=O)CNC(=O)c1cc(Cl)ccc1Cl)B1OC(=O)C[C@@H](C(=O)OCCOC(=O)[C@@H]2CC(=O)OB([C@H](CC(C)C)NC(=O)CNC(=O)c3cc(Cl)ccc3Cl)O2)O1] | ethane-1,2-diyl (4S,4'S)-bis(2-((R)-1-(2-(2,5-dichlorobenzamido)acetamido)-3-methylbutyl)-6-oxo-1,3,2-dioxaborinane-4-carboxylate) |
| HL-50 | 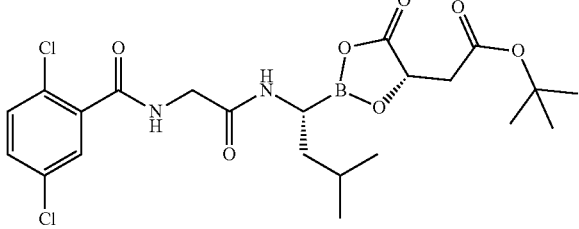 | tert-butyl 2-((S)-2-((R)-1-(2-(2,5-dichlorobenzamido)acetamido)-3-methylbutyl)-5-oxo-1,3,2-dioxaborolan-4-yl)acetate |

TABLE 1-continued

| Serial # | Structure | Name |
|---|---|---|
| HL-51 | 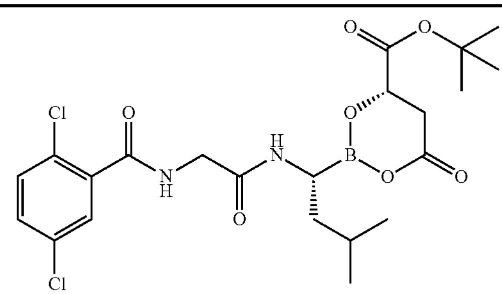 | (S)-tert-butyl 2-((R)-1-(2-(2,5-dichlorobenzamido)acetamido)-3-methylbutyl)-6-oxo-1,3,2-dioxaborinane-4-carboxylate |
| HL-52 | 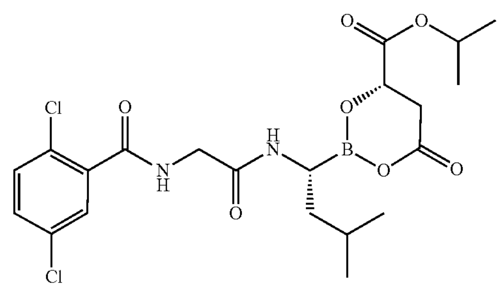 [SMILES: CC(C)C[C@H](NC(=O)CNC(=O)c1cc(Cl)ccc1Cl)B1OC(=O)C[C@@H](C(=O)OC(C)C)O1] | isopropyl (S)-2-((R)-1-(2-(2,5-dichlorobenzamido)acetamido)-3-methylbutyl)-6-oxo-1,3,2-dioxaborinane-4-carboxylate |
| HL-53 | 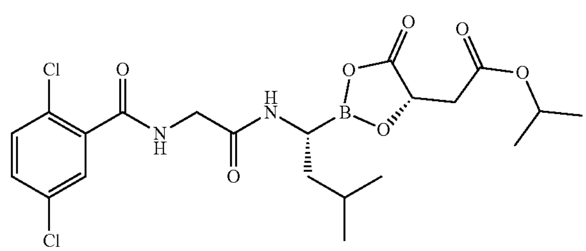 [SMILES: CC(C)C[C@H](NC(=O)CNC(=O)c1cc(Cl)ccc1Cl)B1OC(=O)[C@H](CC(=O)OC(C)C)O1] | isopropyl 2-((S)-2-((R)-1-(2-(2,5-dichlorobenzamido)acetamido)-3-methylbutyl)-5-oxo-1,3,2-dioxaborolan-4-yl)acetate |
| HL-54 | 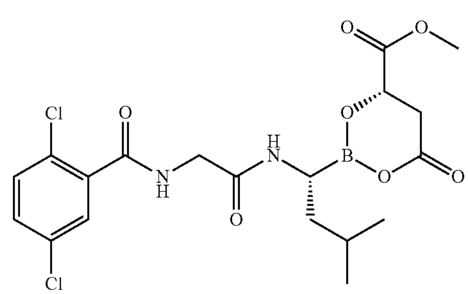 [SMILES: COC(=O)[C@@H]1CC(=O)OB([C@H](CC(C)C)NC(=O)CNC(=O)c2cc(Cl)ccc2Cl)O1] | (S)-methyl 2-((R)-1-(2-(2,5-dichlorobenzamido)acetamido)-3-methylbutyl)-6-oxo-1,3,2-dioxaborinane-4-carboxylate |
| HL-55 | 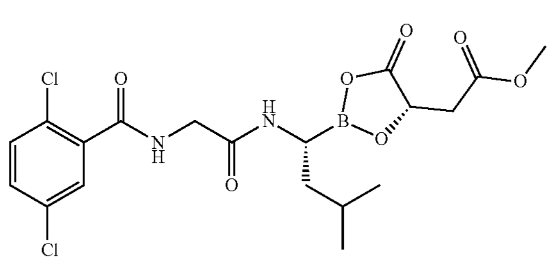 [SMILES: COC(=O)C[C@@H]1OB([C@H](CC(C)C)NC(=O)CNC(=O)c2cc(Cl)ccc2Cl)OC1=O] | methyl 2-((S)-2-((R)-1-(2-(2,5-dichlorobenzamido)acetamido)-3-methylbutyl)-5-oxo-1,3,2-dioxaborolan-4-yl)acetate |

TABLE 1-continued

| Serial # | Structure | Name |
|---|---|---|
| HL-56 | 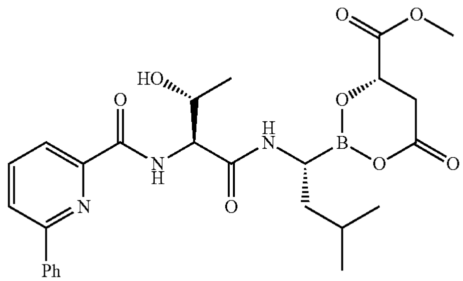 [SMILES: COC(=O)[C@@H]1CC(=O)OB([C@H](CC(C)C)NC(=O)[C@@H](NC(=O)c2cccc(-c3ccccc3)n2)[C@@H](C)O)O1] | (S)-methyl 2-((R)-1-((2S,3R)-3-hydroxy-2-(6-phenylpicolinamido)butanamido)-3-methylbutyl)-6-oxo-1,3,2-dioxaborinane-4-carboxylate |
| HL-57 | 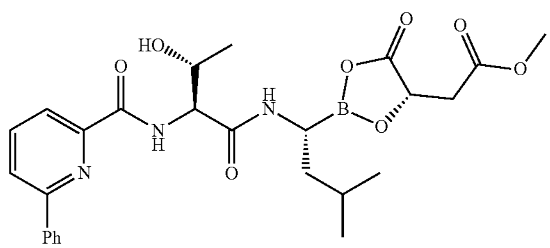 [SMILES: COC(=O)C[C@@H]1OB([C@H](CC(C)C)NC(=O)[C@@H](NC(=O)c2cccc(-c3ccccc3)n2)[C@@H](C)O)OC1=O] | methyl 2-((S)-2-((R)-1-((2S,3R)-3-hydroxy-2-(6-phenylpicolinamido)butanamido)-3-methylbutyl)-5-oxo-1,3,2-dioxaborolan-4-yl)acetate |
| HL-58 | 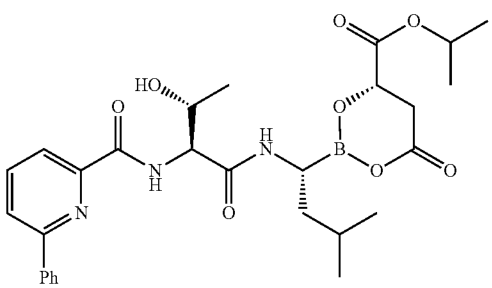 [SMILES: CC(C)C[C@H](NC(=O)[C@@H](NC(=O)c1cccc(-c2ccccc2)n1)[C@@H](C)O)B1OC(=O)C[C@@H](C(=O)OC(C)C)O1] | (S)-isopropyl 2-((R)-1-((2S,3R)-3-hydroxy-2-(6-phenylpicolinamido)butanamido)-3-methylbutyl)-6-oxo-1,3,2-dioxaborinane-4-carboxylate |
| HL-59 | 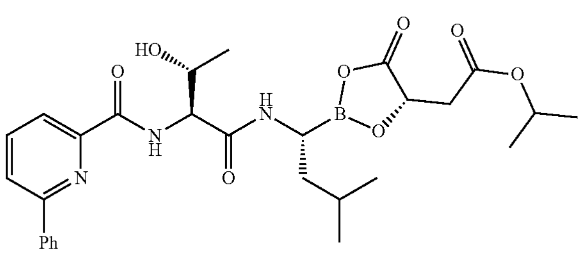 [SMILES: CC(C)C[C@H](NC(=O)[C@@H](NC(=O)c1cccc(-c2ccccc2)n1)[C@@H](C)O)B1OC(=O)[C@H](CC(=O)OC(C)C)O1] | isopropyl 2-((S)-2-((R)-1-((2S,3R)-3-hydroxy-2-(6-phenylpicolinamido)butanamido)-3-methylbutyl)-5-oxo-1,3,2-dioxaborolan-4-yl)acetate |
| HL-60 | 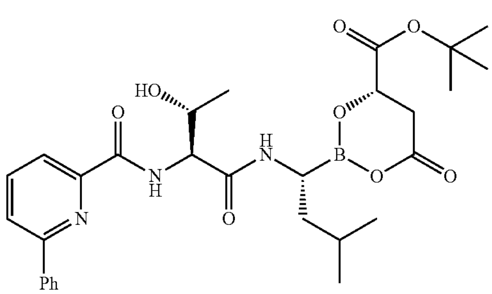 [SMILES: CC(C)C[C@H](NC(=O)[C@@H](NC(=O)c1cccc(-c2ccccc2)n1)[C@@H](C)O)B1OC(=O)C[C@@H](C(=O)OC(C)(C)C)O1] | (S)-tert-butyl 2-((R)-1-((2S,3R)-3-hydroxy-2-(6-phenylpicolinamido)butanamido)-3-methylbutyl)-6-oxo-1,3,2-dioxaborinane-4-carboxylate |

TABLE 1-continued

| Serial # | Structure | Name |
|---|---|---|
| HL-61 | 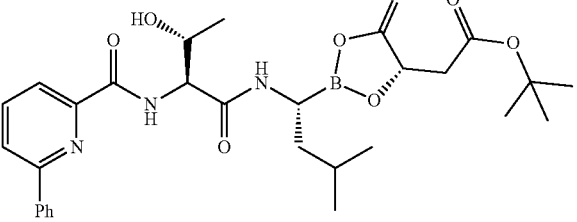 | tert-butyl 2-((S)-2-((R)-1-((2S,3R)-3-hydroxy-2-(6-phenylpicolinamido)butanamido)-3-methylbutyl)-5-oxo-1,3,2-dioxaborolan-4-yl)acetate |
| HL-62 | 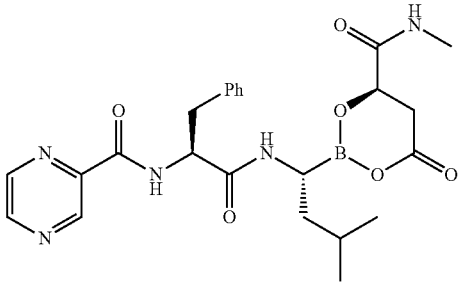 [SMILES: CNC(=O)[C@H]1CC(=O)OB([C@H](CC(C)C)NC(=O)[C@H](Cc2ccccc2)NC(=O)c2cnccn2)O1] | N-((S)-1-(((R)-3-methyl-1-((R)-4-(methylcarbamoyl)-6-oxo-1,3,2-dioxaborinan-2-yl)butyl)amino)-1-oxo-3-phenylpropan-2-yl)pyrazine-2-carboxamide |
| HL-63 | 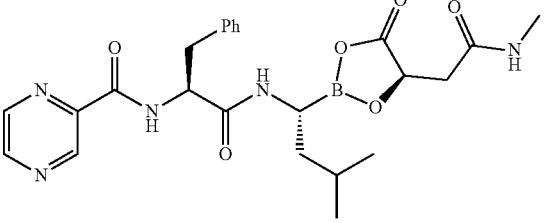 | N-((S)-1-(((R)-3-methyl-1-((R)-4-(2-(methylamino)-2-oxoethyl)-5-oxo-1,3,2-dioxaborolan-2-yl)butyl)amino)-1-oxo-3-phenylpropan-2-yl)pyrazine-2-carboxamide |
| HL-64 | 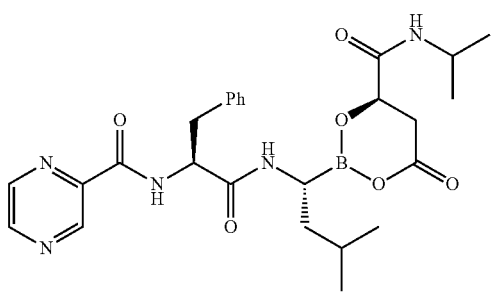 [SMILES: CC(C)C[C@H](NC(=O)[C@H](Cc1ccccc1)NC(=O)c1cnccn1)B1OC(=O)C[C@H](C(=O)NC(C)C)O1] | N-((S)-1-(((R)-1-((R)-4-(isopropylcarbamoyl)-6-oxo-1,3,2-dioxaborinan-2-yl)-3-methylbutyl)amino)-1-oxo-3-phenylpropan-2-yl)pyrazine-2-carboxamide |
| HL-65 | 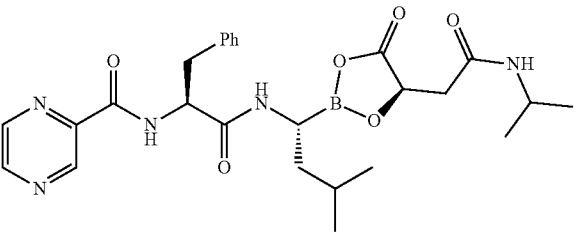 | N-((S)-1-(((R)-1-((R)-4-(2-(isopropylamino)-2-oxoethyl)-5-oxo-1,3,2-dioxaborolan-2-yl)-3-methylbutyl)amino)-1-oxo-3-phenylpropan-2-yl)pyrazine-2-carboxamide |

TABLE 1-continued

| Serial # | Structure | Name |
|---|---|---|
| HL-66 | 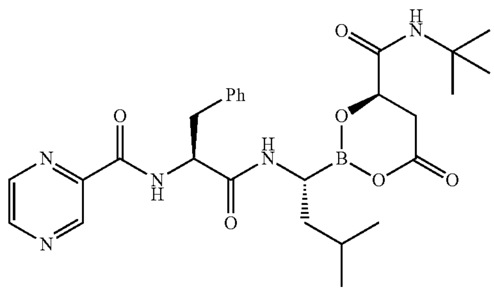 [SMILES: CC(C)C[C@H](NC(=O)[C@H](Cc1ccccc1)NC(=O)c1cnccn1)B1OC(=O)C[C@H](C(=O)NC(C)(C)C)O1] | N-((S)-1-(((R)-1-((R)-4-(tert-butylcarbamoyl)-6-oxo-1,3,2-dioxaborinan-2-yl)-3-methylbutyl)amino)-1-oxo-3-phenylpropan-2-yl)pyrazine-2-carboxamide |
| HL-67 | 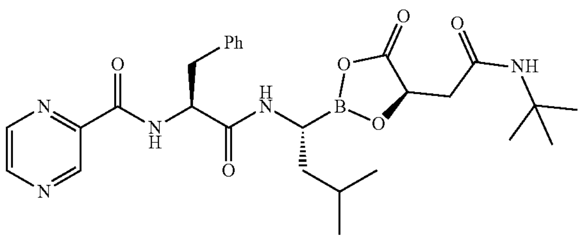 [SMILES: CC(C)C[C@H](NC(=O)[C@H](Cc1ccccc1)NC(=O)c1cnccn1)B1OC(=O)[C@@H](CC(=O)NC(C)(C)C)O1] | N-((S)-1-(((R)-1-((R)-4-(2-(tert-butylamino)-2-oxoethyl)-5-oxo-1,3,2-dioxaborolan-2-yl)-3-methylbutyl)amino)-1-oxo-3-phenylpropan-2-yl)pyrazine-2-carboxamide |
| HL-68 | 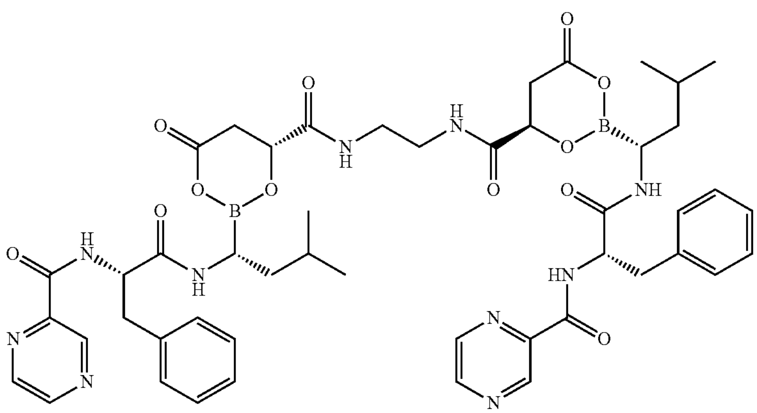 [SMILES: CC(C)C[C@H](NC(=O)[C@H](Cc1ccccc1)NC(=O)c1cnccn1)B1OC(=O)C[C@H](C(=O)NCCNC(=O)[C@H]2CC(=O)OB([C@H](CC(C)C)NC(=O)[C@H](Cc3ccccc3)NC(=O)c3cnccn3)O2)O1] | N,N-ethane-1,2-diyl (4R,4'R)-bis(2-((R)-3-methyl-1-((S)-3-phenyl-2-(pyrazine-2-carboxamido)propanamido)butyl)-6-oxo-1,3,2-dioxaborinane-4-carboxamide) |
| HL-69 | 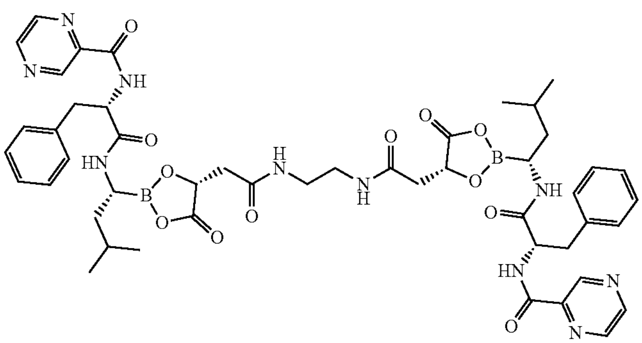 [SMILES: CC(C)C[C@H](NC(=O)[C@H](Cc1ccccc1)NC(=O)c1cnccn1)B1OC(=O)[C@@H](CC(=O)NCCNC(=O)C[C@H]2OB([C@H](CC(C)C)NC(=O)[C@H](Cc3ccccc3)NC(=O)c3cnccn3)OC2=O)O1] | N,N-ethane-1,2-diyl bis(2-((R)-2-((R)-3-methyl-1-((S)-3-phenyl-2-(pyrazine-2-carboxamido)propanamido)butyl)-5-oxo-1,3,2-dioxaborolan-4-yl)acetamide) |
| HL-70 | 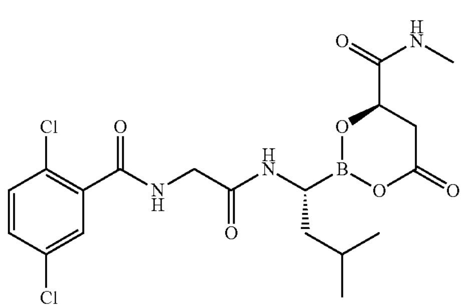 [SMILES: CNC(=O)[C@H]1CC(=O)OB([C@H](CC(C)C)NC(=O)CNC(=O)c2cc(Cl)ccc2Cl)O1] | (R)-2-((R)-1-(2-(2,5-dichlorobenzamido)acetamido)-3-methylbutyl)-N-methyl-6-oxo-1,3,2-dioxaborinane-4-carboxamide |

TABLE 1-continued

| Serial # | Structure | Name |
|---|---|---|
| HL-71 | 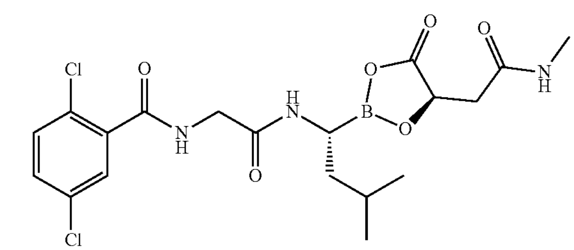 [SMILES: CNC(=O)C[C@H]1OB([C@H](CC(C)C)NC(=O)CNC(=O)c2cc(Cl)ccc2Cl)OC1=O] | 2,5-dichloro-N-(2-(((R)-3-methyl-1-((R)-4-(2-(methylamino)-2-oxoethyl)-5-oxo-1,3,2-dioxaborolan-2-yl)butyl)amino)-2-oxoethyl)benzamide |
| HL-72 | 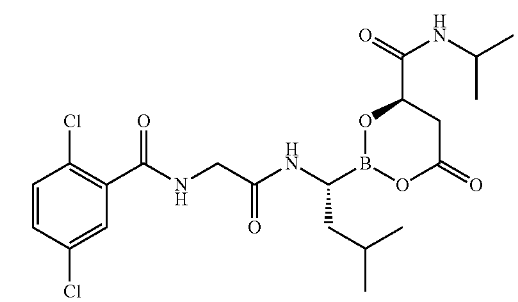 [SMILES: CC(C)C[C@H](NC(=O)CNC(=O)c1cc(Cl)ccc1Cl)B1OC(=O)C[C@H](C(=O)NC(C)C)O1] | (R)-2-((R)-1-(2-(2,5-dichlorobenzamido)acetamido)-3-methylbutyl)-N-isopropyl-6-oxo-1,3,2-dioxaborinane-4-carboxamide |
| HL-73 | 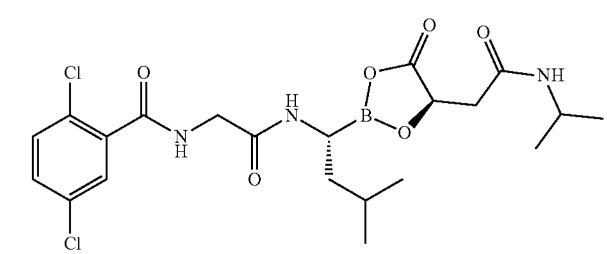 [SMILES: CC(C)C[C@H](NC(=O)CNC(=O)c1cc(Cl)ccc1Cl)B1OC(=O)[C@@H](CC(=O)NC(C)C)O1] | 2,5-dichloro-N-(2-(((R)-1-((R)-4-(2-(isopropylamino)-2-oxoethyl)-5-oxo-1,3,2-dioxaborolan-2-yl)-3-methylbutyl)amino)-2-oxoethyl)benzamide |
| HL-74 | 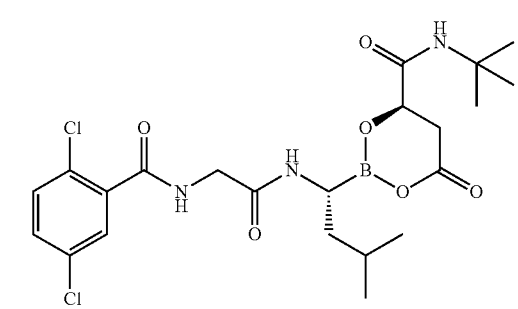 [SMILES: CC(C)C[C@H](NC(=O)CNC(=O)c1cc(Cl)ccc1Cl)B1OC(=O)C[C@H](C(=O)NC(C)(C)C)O1] | (R)-N-(tert-butyl)-2-((R)-1-(2-(2,5-dichlorobenzamido)acetamido)-3-methylbutyl)-6-oxo-1,3,2-dioxaborinane-4-carboxamide |
| HL-75 | 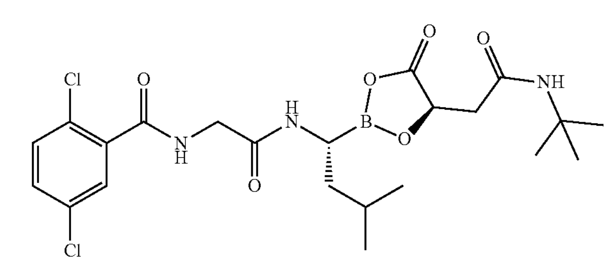 [SMILES: CC(C)C[C@H](NC(=O)CNC(=O)c1cc(Cl)ccc1Cl)B1OC(=O)[C@@H](CC(=O)NC(C)(C)C)O1] | N-(2-(((R)-1-((R)-4-(2-(tert-butylamino)-2-oxoethyl)-5-oxo-1,3,2-dioxaborolan-2-yl)-3-methylbutyl)amino)-2-oxoethyl)-2,5-dichlorobenzamide |

TABLE 1-continued

| Serial # | Structure | Name |
|---|---|---|
| HL-76 | 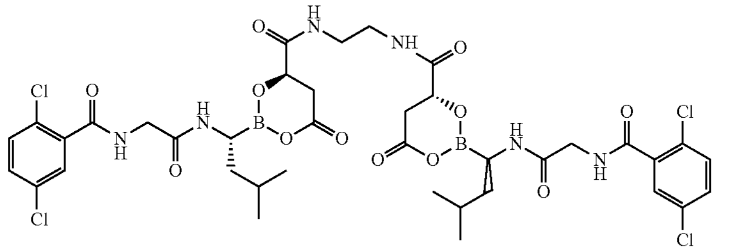 [SMILES: CC(C)C[C@H](NC(=O)CNC(=O)c1cc(Cl)ccc1Cl)B1OC(=O)C[C@H](C(=O)NCCNC(=O)[C@H]2CC(=O)OB([C@H](CC(C)C)NC(=O)CNC(=O)c3cc(Cl)ccc3Cl)O2)O1] | (4R,4'R)-N,N'-(ethane-1,2-diyl)bis(2-((R)-1-(2-(2,5-dichlorobenzamido)acetamido)-3-methylbutyl)-6-oxo-1,3,2-dioxaborinane-4-carboxamide) |
| HL-77 | 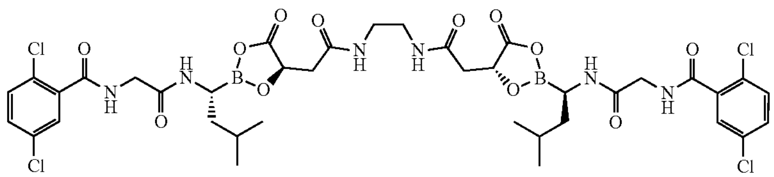 [SMILES: CC(C)C[C@H](NC(=O)CNC(=O)c1cc(Cl)ccc1Cl)B1OC(=O)[C@@H](CC(=O)NCCNC(=O)C[C@H]2OB([C@H](CC(C)C)NC(=O)CNC(=O)c3cc(Cl)ccc3Cl)OC2=O)O1] | N,N-ethane-1,2-diyl bis(2-((R)-2-((R)-1-(2-(2,5-dichlorobenzamido)acetamido)-3-methylbutyl)-5-oxo-1,3,2-dioxaborolan-4-yl)acetamide) |
| HL-78 | 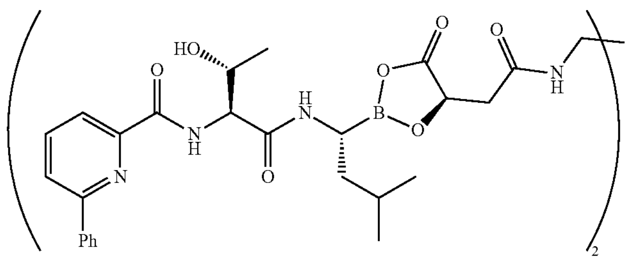 | N,N-ethane-1,2-diyl(4R,4'R)-bis(2-((R)-1-((2S,3R)-3-hydroxy-2-(6-phenylpicolinamido)butanamido)-3-methylbutyl)-6-oxo-1,3,2-dioxaborinane-4-carboxamide) |
| HL-79 | 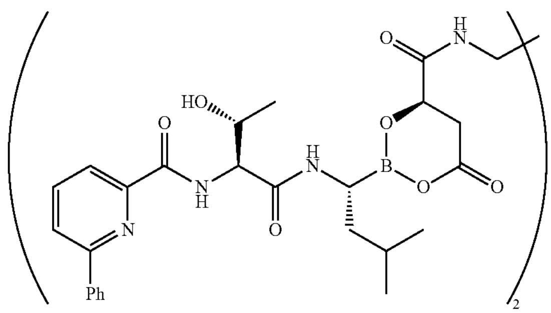 | N,N-ethane-1,2-diyl (4R,4'R)-bis(2-((R)-1-((2S,3R)-3-hydroxy-2-(6-phenylpicolinamido)butanamido)-3-methylbutyl)-6-oxo-1,3,2-dioxaborinane-4-carboxamide) |
| HL-80 | 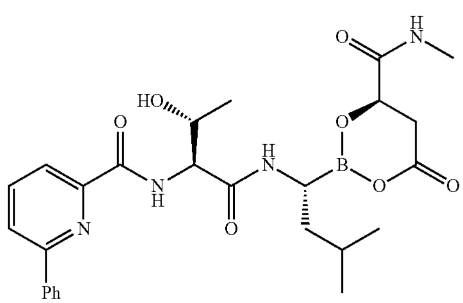 [SMILES: CNC(=O)[C@H]1CC(=O)OB([C@H](CC(C)C)NC(=O)[C@@H](NC(=O)c2cccc(-c3ccccc3)n2)[C@@H](C)O)O1] | N-((2S,3R)-3-hydroxy-1-(((R)-3-methyl-1-((R)-4-(methylcarbamoyl)-6-oxo-1,3,2-dioxaborinan-2-yl)butyl)amino)-1-oxobutan-2-yl)-6-phenylpicolinamide |
| HL-81 | 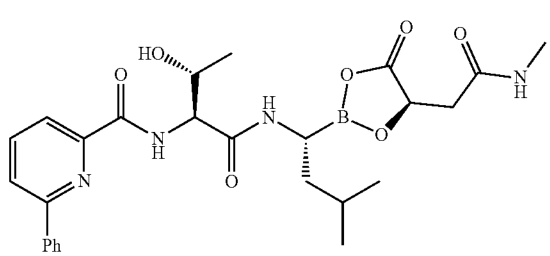 [SMILES: CNC(=O)C[C@H]1OB([C@H](CC(C)C)NC(=O)[C@@H](NC(=O)c2cccc(-c3ccccc3)n2)[C@@H](C)O)OC1=O] | N-((2S,3R)-3-hydroxy-1-(((R)-3-methyl-1-((R)-4-(2-(methylamino)-2-oxoethyl)-5-oxo-1,3,2-dioxaborolan-2-yl)butyl)amino)-1-oxobutan-2-yl)-6-phenylpicolinamide |

TABLE 1-continued

| Serial # | Structure | Name |
|---|---|---|
| HL-82 | 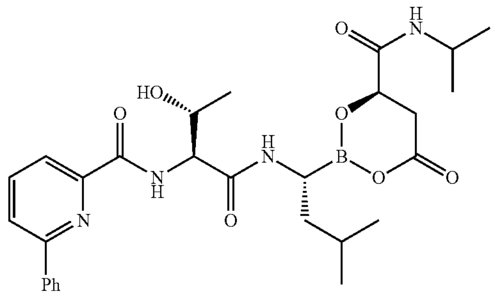 [SMILES: CC(C)C[C@H](NC(=O)[C@@H](NC(=O)c1cccc(-c2ccccc2)n1)[C@@H](C)O)B1OC(=O)C[C@H](C(=O)NC(C)C)O1] | N-((2S,3R)-3-hydroxy-1-(((R)-1-((R)-4-(isopropylcarbamoyl)-6-oxo-1,3,2-dioxaborinan-2-yl)-3-methylbutyl)amino)-1-oxobutan-2-yl)-6-phenylpicolinamide |
| HL-83 | 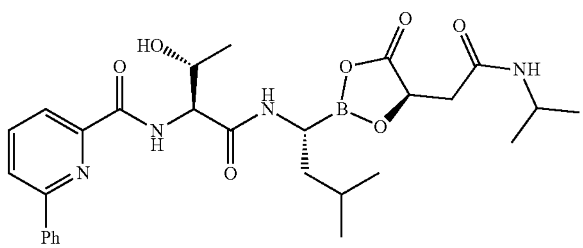 [SMILES: CC(C)C[C@H](NC(=O)[C@@H](NC(=O)c1cccc(-c2ccccc2)n1)[C@@H](C)O)B1OC(=O)[C@@H](CC(=O)NC(C)C)O1] | N-((2S,3R)-3-hydroxy-1-(((R)-1-((R)-4-(2-(isopropylamino)-2-oxoethyl)-5-oxo-1,3,2-dioxaborolan-2-yl)-3-methylbutyl)amino)-1-oxobutan-2-yl)-6-phenylpicolinamide |
| HL-84 | 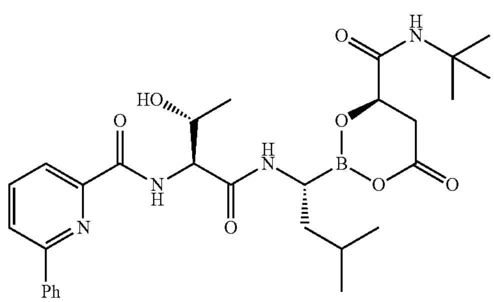 [SMILES: CC(C)C[C@H](NC(=O)[C@@H](NC(=O)c1cccc(-c2ccccc2)n1)[C@@H](C)O)B1OC(=O)C[C@H](C(=O)NC(C)(C)C)O1] | N-((2S,3R)-1-(((R)-1-((R)-4-(tert-butylcarbamoyl)-6-oxo-1,3,2-dioxaborinan-2-yl)-3-methylbutyl)amino)-3-hydroxy-1-oxobutan-2-yl)-6-phenylpicolinamide |
| HL-85 | 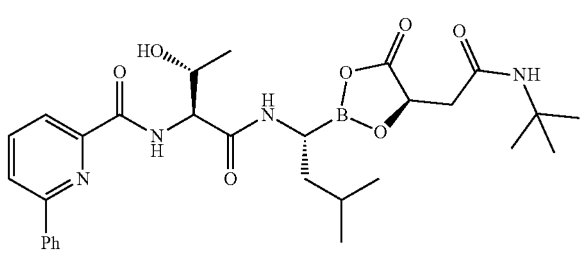 [SMILES: CC(C)C[C@H](NC(=O)[C@@H](NC(=O)c1cccc(-c2ccccc2)n1)[C@@H](C)O)B1OC(=O)[C@@H](CC(=O)NC(C)(C)C)O1] | N-((2S,3R)-1-(((R)-1-((R)-4-(2-(tert-butylamino)-2-oxoethyl)-5-oxo-1,3,2-dioxaborolan-2-yl)-3-methylbutyl)amino)-3-hydroxy-1-oxobutan-2-yl)-6-phenylpicolinamide |
| HL-86 | 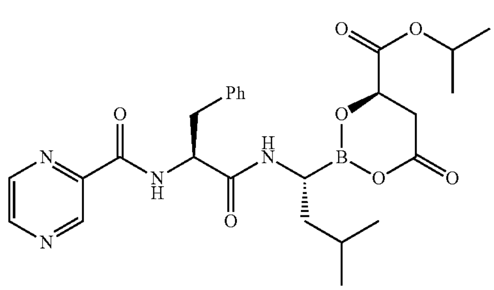 [SMILES: CC(C)C[C@H](NC(=O)[C@H](Cc1ccccc1)NC(=O)c1cnccn1)B1OC(=O)C[C@H](C(=O)OC(C)C)O1] | isopropyl (R)-2-((R)-3-methyl-1-((S)-3-phenyl-2-(pyrazine-2-carboxamido)propanamido)butyl)-6-oxo-1,3,2-dioxaborinane-4-carboxylate |

TABLE 1-continued

| Serial # | Structure | Name |
|---|---|---|
| HL-87 | 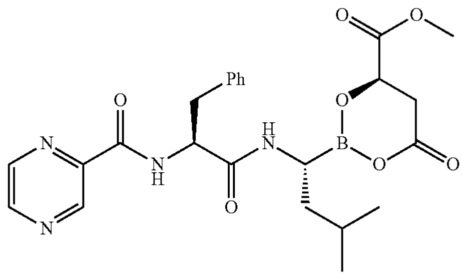 [SMILES: COC(=O)[C@H]1CC(=O)OB([C@H](CC(C)C)NC(=O)[C@H](Cc2ccccc2)NC(=O)c2cnccn2)O1] | methyl (R)-2-((R)-3-methyl-1-((S)-3-phenyl-2-(pyrazine-2-carboxamido)propanamido)butyl)-6-oxo-1,3,2-dioxaborinane-4-carboxylate |
| HL-88 | 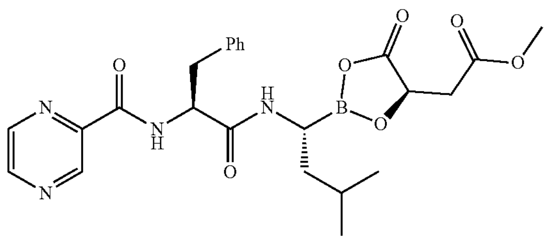 [SMILES: COC(=O)C[C@H]1OB([C@H](CC(C)C)NC(=O)[C@H](Cc2ccccc2)NC(=O)c2cnccn2)OC1=O] | methyl 2-((R)-2-((R)-3-methyl-1-((S)-3-phenyl-2-(pyrazine-2-carboxamido)propanamido)butyl)-5-oxo-1,3,2-dioxaborolan-4-yl)acetate |
| HL-89 | 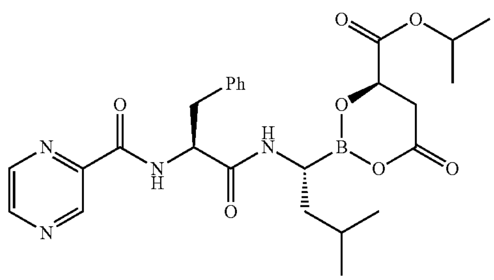 [SMILES: CC(C)C[C@H](NC(=O)[C@H](Cc1ccccc1)NC(=O)c1cnccn1)B1OC(=O)C[C@H](C(=O)OC(C)C)O1] | isopropyl (R)-2-((R)-3-methyl-1-((S)-3-phenyl-2-(pyrazine-2-carboxamido)propanamido)butyl)-6-oxo-1,3,2-dioxaborinane-4-carboxylate |
| HL-90 | 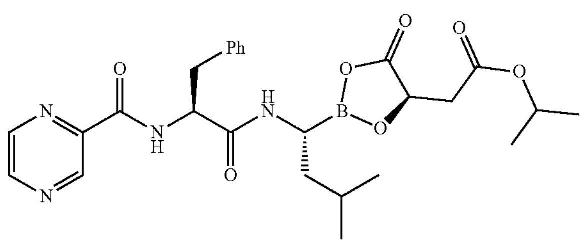 [SMILES: CC(C)C[C@H](NC(=O)[C@H](Cc1ccccc1)NC(=O)c1cnccn1)B1OC(=O)[C@@H](CC(=O)OC(C)C)O1] | isopropyl 2-((R)-2-((R)-3-methyl-1-((S)-3-phenyl-2-(pyrazine-2-carboxamido)propanamido)butyl)-5-oxo-1,3,2-dioxaborolan-4-yl)acetate |
| HL-91 | 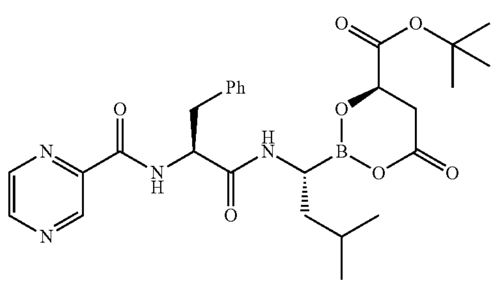 [SMILES: CC(C)C[C@H](NC(=O)[C@H](Cc1ccccc1)NC(=O)c1cnccn1)B1OC(=O)C[C@H](C(=O)OC(C)(C)C)O1] | tert-butyl (R)-2-(R)-3-methyl-1-((S)-3-phenyl-2-(pyrazine-2-carboxamido)propanamido)butyl)-6-oxo-1,3,2-dioxaborinane-4-carboxylate |
| HL-92 | 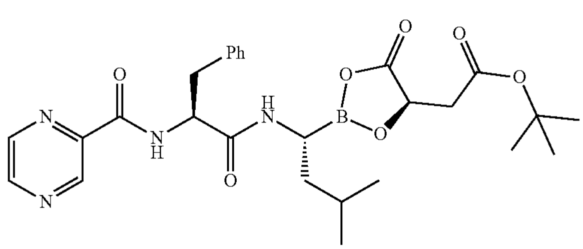 [SMILES: CC(C)C[C@H](NC(=O)[C@H](Cc1ccccc1)NC(=O)c1cnccn1)B1OC(=O)[C@@H](CC(=O)OC(C)(C)C)O1] | tert-butyl 2-((R)-2-((R)-3-methyl-1-((S)-3-phenyl-2-(pyrazine-2-carboxamido)propanamido)butyl)-5-oxo-1,3,2-dioxaborolan-4-yl)acetate |

TABLE 1-continued

| Serial # | Structure | Name |
|---|---|---|
| HL-93 | 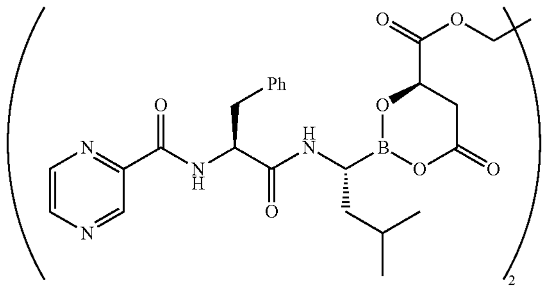 | ethane-1,2-diyl (4R,4'R)-bis(2-((R)-3-methyl-1-((S)-3-phenyl-2-(pyrazine-2-carboxamido)propanamido)butyl)-6-oxo-1,3,2-dioxaborinane-4-carboxylate) |
| HL-94 | 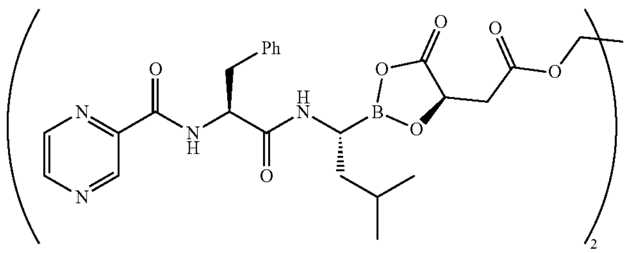 | ethane-1,2-diyl (4R,4'R)-bis(2-((R)-3-methyl-1-((S)-3-phenyl-2-(pyrazine-2-carboxamido)propanamido)butyl)-5-oxo-1,3,2-dioxaborolane-4-carboxylate) |
| HL-95 | 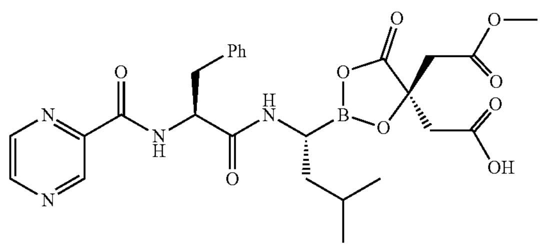 | 2-((R)-4-(2-methoxy-2-oxoethyl)-2-((R)-3-methyl-1-((S)-3-phenyl-2-(pyrazine-2-carboxamido)propanamido)butyl)-5-oxo-1,3,2-dioxaborolan-4-yl)acetic acid |
| HL-96 | 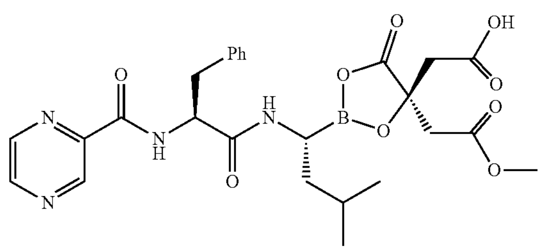 [SMILES: COC(=O)C[C@]1(CC(=O)O)OB([C@H](CC(C)C)NC(=O)[C@H](Cc2ccccc2)NC(=O)c2cnccn2)OC1=O] | 2-((S)-4-(2-methoxy-2-oxoethyl)-2-((R)-3-methyl-1-((S)-3-phenyl-2-(pyrazine-2-carboxamido)propanamido)butyl)-5-oxo-1,3,2-dioxaborolan-4-yl)acetic acid |
| HL-97 | 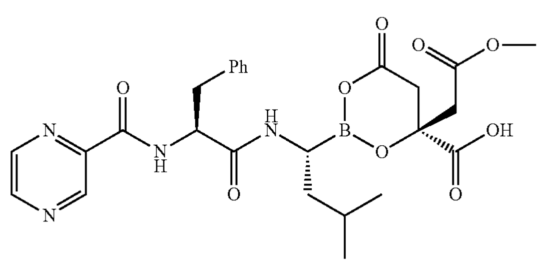 [SMILES: COC(=O)C[C@]1(C(=O)O)CC(=O)OB([C@H](CC(C)C)NC(=O)[C@H](Cc2ccccc2)NC(=O)c2cnccn2)O1] | (S)-4-(2-methoxy-2-oxoethyl)-2-((R)-3-methyl-1-((S)-3-phenyl-2-(pyrazine-2-carboxamido)propanamido)butyl)-6-oxo-1,3,2-dioxaborinane-4-carboxylic acid |
| HL-98 | 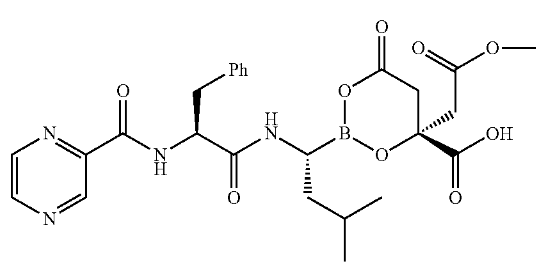 [SMILES: COC(=O)C[C@@]1(C(=O)O)CC(=O)OB([C@H](CC(C)C)NC(=O)[C@H](Cc2ccccc2)NC(=O)c2cnccn2)O1] | (R)-4-(2-methoxy-2-oxoethyl)-2-((R)-3-methyl-1-((S)-3-phenyl-2-(pyrazine-2-carboxamido)propanamido)butyl)-6-oxo-1,3,2-dioxaborinane-4-carboxylic acid |

TABLE 1-continued

| Serial # | Structure | Name |
|---|---|---|
| HL-99 | 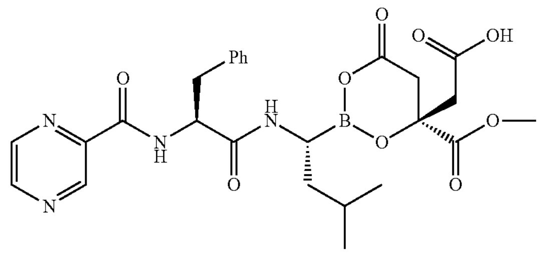 [SMILES: COC(=O)[C@@]1(CC(=O)O)CC(=O)OB([C@H](CC(C)C)NC(=O)[C@H](Cc2ccccc2)NC(=O)c2cnccn2)O1] | 2-((R)-4-(methoxycarbonyl)-2-((R)-3-methyl-1-((S)-3-phenyl-2-(pyrazine-2-carboxamido)propanamido)butyl)-6-oxo-1,3,2-dioxaborinan-4-yl)acetic acid |
| HL-100 | 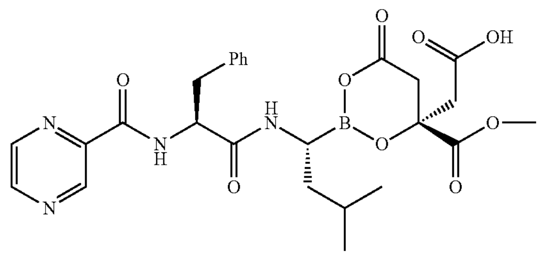 [SMILES: COC(=O)[C@]1(CC(=O)O)CC(=O)OB([C@H](CC(C)C)NC(=O)[C@H](Cc2ccccc2)NC(=O)c2cnccn2)O1] | 2-((S)-4-(methoxycarbonyl)-2-((R)-3-methyl-1-((S)-3-phenyl-2-(pyrazine-2-carboxamido)propanamido)butyl)-6-oxo-1,3,2-dioxaborinan-4-yl)acetic acid |
| HL-101 | 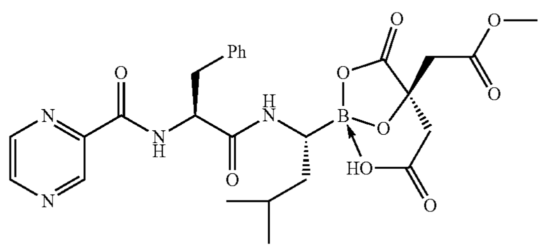 [SMILES: COC(=O)C[C@]12CC(=O)[OH+][B-]([C@H](CC(C)C)NC(=O)[C@H](Cc3ccccc3)NC(=O)c3cnccn3)(OC1=O)O2] | 2-((R)-4-(2-methoxy-2-oxoethyl)-2-((R)-3-methyl-1-((S)-3-phenyl-2-(pyrazine-2-carboxamido)propanamido)butyl)-5-oxo-1,3,2-dioxaborolan-4-yl)acetic acid |
| HL-102 | 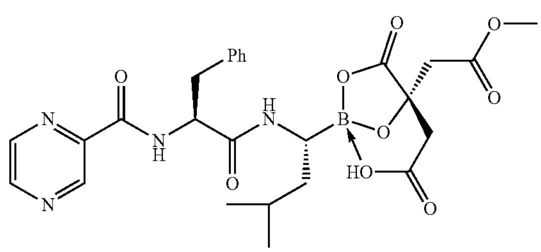 [SMILES: COC(=O)C[C@@]12CC(=O)[OH+][B-]([C@H](CC(C)C)NC(=O)[C@H](Cc3ccccc3)NC(=O)c3cnccn3)(OC1=O)O2] | 2-((S)-4-(2-methoxy-2-oxoethyl)-2-((R)-3-methyl-1-((S)-3-phenyl-2-(pyrazine-2-carboxamido)propanamido)butyl)-5-oxo-1,3,2-dioxaborolan-4-yl)acetic acid |
| HL-103 | 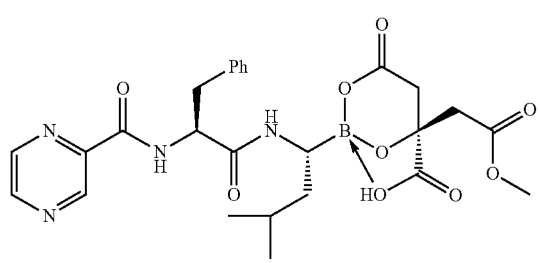 [SMILES: COC(=O)C[C@]12CC(=O)O[B-]([C@H](CC(C)C)NC(=O)[C@H](Cc3ccccc3)NC(=O)c3cnccn3)(O1)[OH+]C2=O] | (S)-4-(2-methoxy-2-oxoethyl)-2-((R)-3-methyl-1-((S)-3-phenyl-2-(pyrazine-2-carboxamido)propanamido)butyl)-6-oxo-1,3,2-dioxaborinane-4-carboxylic acid |
| HL-104 | 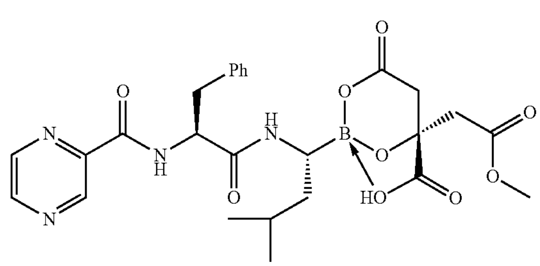 [SMILES: COC(=O)C[C@@]12CC(=O)O[B-]([C@H](CC(C)C)NC(=O)[C@H](Cc3ccccc3)NC(=O)c3cnccn3)(O1)[OH+]C2=O] | (R)-4-(2-methoxy-2-oxoethyl)-2-((R)-3-methyl-1-((S)-3-phenyl-2-(pyrazine-2-carboxamido)propanamido)butyl)-6-oxo-1,3,2-dioxaborinane-4-carboxylic acid |

TABLE 1-continued

| Serial # | Structure | Name |
|---|---|---|
| HL-105 | 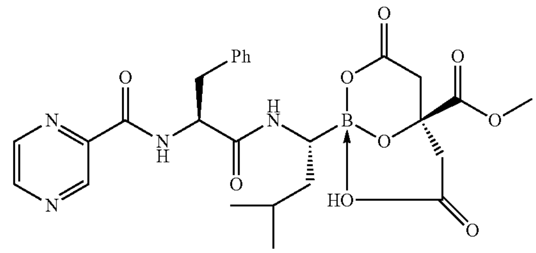 [SMILES: COC(=O)[C@]12CC(=O)O[B-]([C@H](CC(C)C)NC(=O)[C@H](Cc3ccccc3)NC(=O)c3cnccn3)(O1)[OH+]C(=O)C2] | 2-((S)-4-(methoxycarbonyl)-2-((R)-3-methyl-1-((S)-3-phenyl-2-(pyrazine-2-carboxamido)propanamido)butyl)-6-oxo-1,3,2-dioxaborinan-4-yl)acetic acid |
| HL-106 | 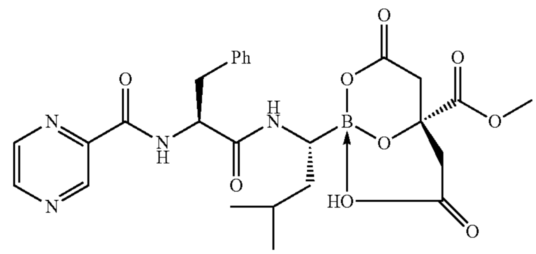 [SMILES: COC(=O)[C@@]12CC(=O)O[B-]([C@H](CC(C)C)NC(=O)[C@H](Cc3ccccc3)NC(=O)c3cnccn3)(O1)[OH+]C(=O)C2] | 2-((R)-4-(methoxycarbonyl)-2-((R)-3-methyl-1-((S)-3-phenyl-2-(pyrazine-2-carboxamido)propanamido)butyl)-6-oxo-1,3,2-dioxaborinan-4-yl)acetic acid |
| HL-107 | 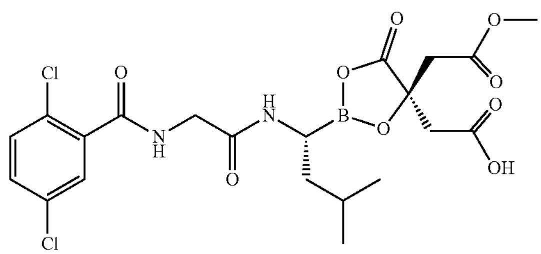 [SMILES: COC(=O)C[C@@]1(CC(=O)O)OB([C@H](CC(C)C)NC(=O)CNC(=O)c2cc(Cl)ccc2Cl)OC1=O] | 2-((R)-2-((R)-1-(2-(2,5-dichlorobenzamido)acetamido)-3-methylbutyl)-4-(2-methoxy-2-oxoethyl)-5-oxo-1,3,2-dioxaborolan-4-yl)acetic acid |
| HL-108 | 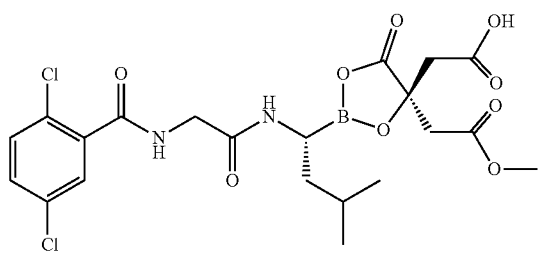 [SMILES: COC(=O)C[C@]1(CC(=O)O)OB([C@H](CC(C)C)NC(=O)CNC(=O)c2cc(Cl)ccc2Cl)OC1=O] | 2-((S)-2-((R)-1-(2-(2,5-dichlorobenzamido)acetamido)-3-methylbutyl)-4-(2-methoxy-2-oxoethyl)-5-oxo-1,3,2-dioxaborolan-4-yl)acetic acid |
| HL-109 | 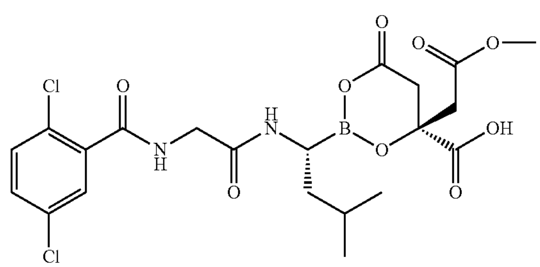 [SMILES: COC(=O)C[C@]1(C(=O)O)CC(=O)OB([C@H](CC(C)C)NC(=O)CNC(=O)c2cc(Cl)ccc2Cl)O1] | (S)-2-((R)-1-(2-(2,5-dichlorobenzamido)acetamido)-3-methylbutyl)-4-(2-methoxy-2-oxoethyl)-6-oxo-1,3,2-dioxaborinane-4-carboxylic acid |
| HL-110 | 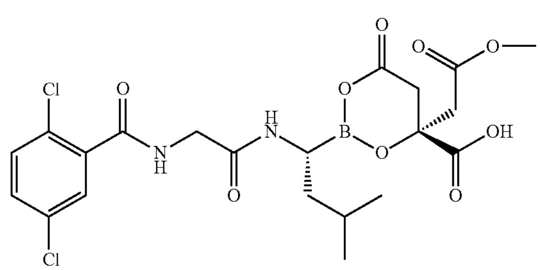 [SMILES: COC(=O)C[C@@]1(C(=O)O)CC(=O)OB([C@H](CC(C)C)NC(=O)CNC(=O)c2cc(Cl)ccc2Cl)O1] | (R)-2-((R)-1-(2-(2,5-dichlorobenzamido)acetamido)-3-methylbutyl)-4-(2-methoxy-2-oxoethyl)-6-oxo-1,3,2-dioxaborinane-4-carboxylic acid |

TABLE 1-continued

| Serial # | Structure | Name |
|---|---|---|
| HL-111 | 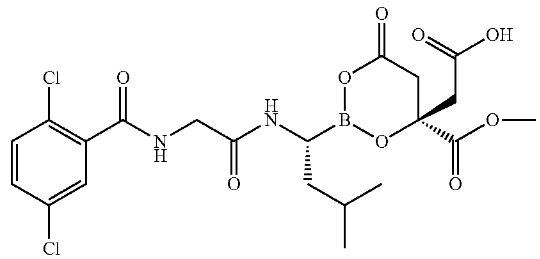 [SMILES: COC(=O)[C@@]1(CC(=O)O)CC(=O)OB([C@H](CC(C)C)NC(=O)CNC(=O)c2cc(Cl)ccc2Cl)O1] | 2-((R)-2-((R)-1-(2-(2,5-dichlorobenzamido)acetamido)-3-methylbutyl)-4-(methoxycarbonyl)-6-oxo-1,3,2-dioxaborinan-4-yl)acetic acid |
| HL-112 | 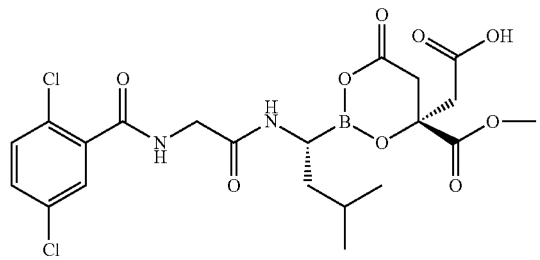 [SMILES: COC(=O)[C@]1(CC(=O)O)CC(=O)OB([C@H](CC(C)C)NC(=O)CNC(=O)c2cc(Cl)ccc2Cl)O1] | 2-((S)-2-((R)-1-(2-(2,5-dichlorobenzamido)acetamido)-3-methylbutyl)-4-(methoxycarbonyl)-6-oxo-1,3,2-dioxaborinan-4-yl)acetic acid |
| HL-113 | 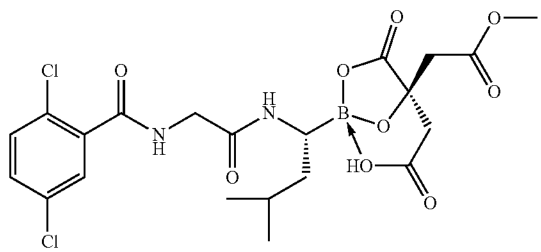 [SMILES: COC(=O)C[C@]12CC(=O)[OH+][B-]([C@H](CC(C)C)NC(=O)CNC(=O)c3cc(Cl)ccc3Cl)(OC1=O)O2] | 2-((R)-2-((R)-1-(2-(2,5-dichlorobenzamido)acetamido)-3-methylbutyl)-4-(2-methoxy-2-oxoethyl)-5-oxo-1,3,2-dioxaborolan-4-yl)acetic acid |
| HL-114 | 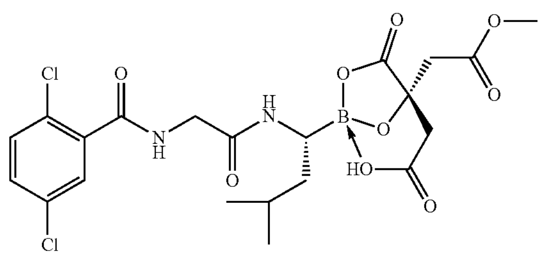 [SMILES: COC(=O)C[C@@]12CC(=O)[OH+][B-]([C@H](CC(C)C)NC(=O)CNC(=O)c3cc(Cl)ccc3Cl)(OC1=O)O2] | 2-((S)-2-((R)-1-(2-(2,5-dichlorobenzamido)acetamido)-3-methylbutyl)-4-(2-methoxy-2-oxoethyl)-5-oxo-1,3,2-dioxaborolan-4-yl)acetic acid |
| HL-115 | 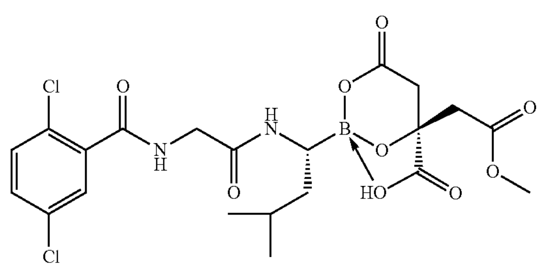 [SMILES: COC(=O)C[C@]12CC(=O)O[B-]([C@H](CC(C)C)NC(=O)CNC(=O)c3cc(Cl)ccc3Cl)(O1)[OH+]C2=O] | (S)-2-((R)-1-(2-(2,5-dichlorobenzamido)acetamido)-3-methylbutyl)-4-(2-methoxy-2-oxoethyl)-6-oxo-1,3,2-dioxaborinane-4-carboxylic acid |
| HL-116 | 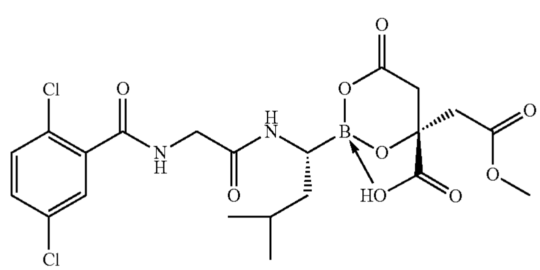 [SMILES: COC(=O)C[C@@]12CC(=O)O[B-]([C@H](CC(C)C)NC(=O)CNC(=O)c3cc(Cl)ccc3Cl)(O1)[OH+]C2=O] | (R)-2-((R)-1-(2-(2,5-dichlorobenzamido)acetamido)-3-methylbutyl)-4-(2-methoxy-2-oxoethyl)-6-oxo-1,3,2-dioxaborinane-4-carboxylic acid |

TABLE 1-continued

| Serial # | Structure | Name |
|---|---|---|
| HL-117 | 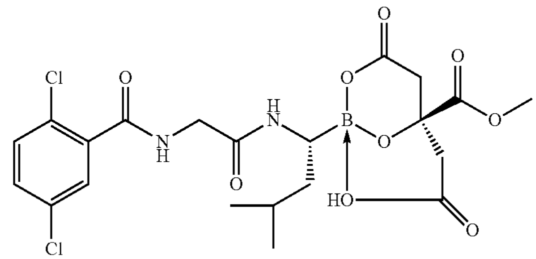 [SMILES: COC(=O)[C@]12CC(=O)O[B-]([C@H](CC(C)C)NC(=O)CNC(=O)c3cc(Cl)ccc3Cl)(O1)[OH+]C(=O)C2] | 2-((S)-2-((R)-1-(2-(2,5-dichlorobenzamido)acetamido)-3-methylbutyl)-4-(methoxycarbonyl)-6-oxo-1,3,2-dioxaborinan-4-yl)acetic acid |
| HL-118 | 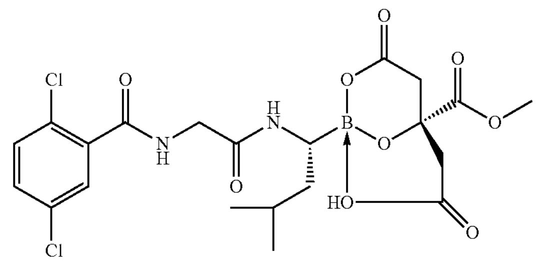 [SMILES: COC(=O)[C@@]12CC(=O)O[B-]([C@H](CC(C)C)NC(=O)CNC(=O)c3cc(Cl)ccc3Cl)(O1)[OH+]C(=O)C2] | 2-((R)-2-((R)-1-(2-(2,5-dichlorobenzamido)acetamido)-3-methylbutyl)-4-(methoxycarbonyl)-6-oxo-1,3,2-dioxaborinan-4-yl)acetic acid |
| HL-119 | 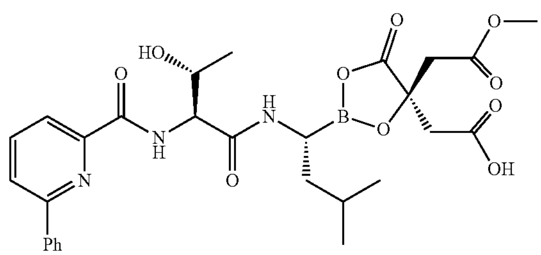 [SMILES: COC(=O)C[C@@]1(CC(=O)O)OB([C@H](CC(C)C)NC(=O)[C@@H](NC(=O)c2cccc(-c3ccccc3)n2)[C@@H](C)O)OC1=O] | 2-((R)-2-((R)-1-((2S,3R)-3-hydroxy-2-(6-phenylpicolinamido)butanamido)-3-methylbutyl)-4-(2-methoxy-2-oxoethyl)-5-oxo-1,3,2-dioxaborolan-4-yl)acetic acid |
| HL-120 | 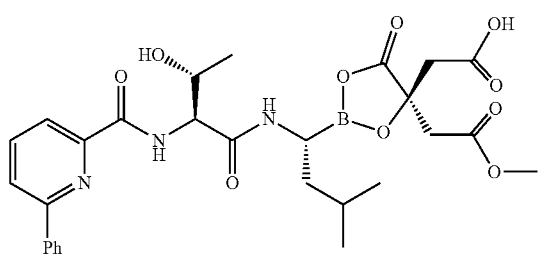 [SMILES: COC(=O)C[C@]1(CC(=O)O)OB([C@H](CC(C)C)NC(=O)[C@@H](NC(=O)c2cccc(-c3ccccc3)n2)[C@@H](C)O)OC1=O] | 2-((S)-2-((R)-1-((2S,3R)-3-hydroxy-2-(6-phenylpicolinamido)butanamido)-3-methylbutyl)-4-(2-methoxy-2-oxoethyl)-5-oxo-1,3,2-dioxaborolan-4-yl)acetic acid |
| HL-121 | 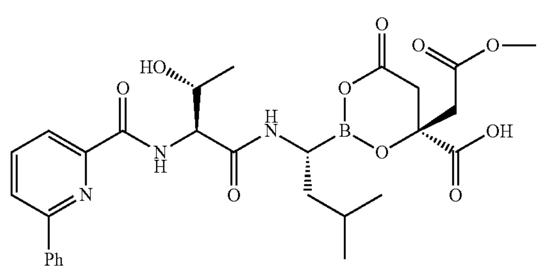 [SMILES: COC(=O)C[C@]1(C(=O)O)CC(=O)OB([C@H](CC(C)C)NC(=O)[C@@H](NC(=O)c2cccc(-c3ccccc3)n2)[C@@H](C)O)O1] | (S)-2-((R)-1-((2S,3R)-3-hydroxy-2-(6-phenylpicolinamido)butanamido)-3-methylbutyl)-4-(2-methoxy-2-oxoethyl)-6-oxo-1,3,2-dioxaborinane-4-carboxylic acid |
| HL-122 | 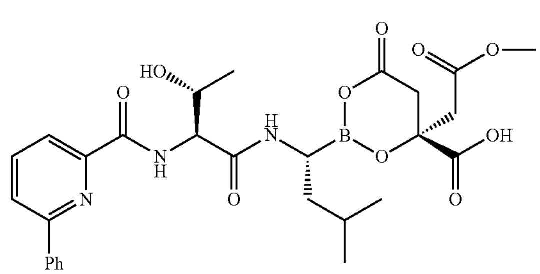 [SMILES: COC(=O)C[C@@]1(C(=O)O)CC(=O)OB([C@H](CC(C)C)NC(=O)[C@@H](NC(=O)c2cccc(-c3ccccc3)n2)[C@@H](C)O)O1] | (R)-2-((R)-1-((2S,3R)-3-hydroxy-2-(6-phenylpicolinamido)butanamido)-3-methylbutyl)-4-(2-methoxy-2-oxoethyl)-6-oxo-1,3,2-dioxaborinane-4-carboxylic acid |

TABLE 1-continued

| Serial # | Structure | Name |
|---|---|---|
| HL-123 | 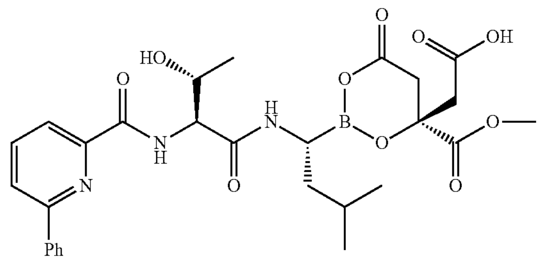 [SMILES: COC(=O)[C@@]1(CC(=O)O)CC(=O)OB([C@H](CC(C)C)NC(=O)[C@@H](NC(=O)c2cccc(-c3ccccc3)n2)[C@@H](C)O)O1] | 2-((R)-2-((R)-1-((2S,3R)-3-hydroxy-2-(6-phenylpicolinamido)butanamido)-3-methylbutyl)-4-(methoxycarbonyl)-6-oxo-1,3,2-dioxaborinan-4-yl)acetic acid |
| HL-124 | 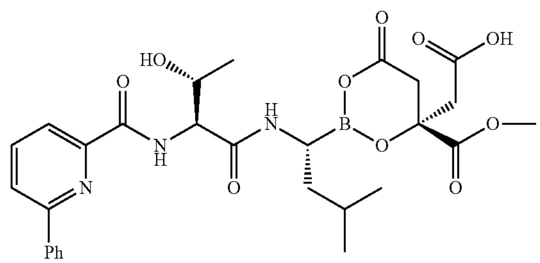 [SMILES: COC(=O)[C@]1(CC(=O)O)CC(=O)OB([C@H](CC(C)C)NC(=O)[C@@H](NC(=O)c2cccc(-c3ccccc3)n2)[C@@H](C)O)O1] | 2-((S)-2-((R)-1-((2S,3R)-3-hydroxy-2-(6-phenylpicolinamido)butanamido)-3-methylbutyl)-4-(methoxycarbonyl)-6-oxo-1,3,2-dioxaborinan-4-yl)acetic acid |
| HL-125 | 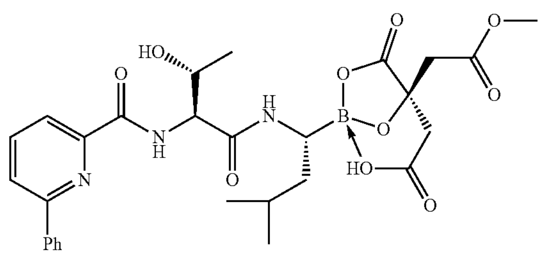 [SMILES: COC(=O)C[C@]12CC(=O)[OH+][B-]([C@H](CC(C)C)NC(=O)[C@@H](NC(=O)c3cccc(-c4ccccc4)n3)[C@@H](C)O)(OC1=O)O2] | 2-((R)-2-((R)-1-((2S,3R)-3-hydroxy-2-(6-phenylpicolinamido)butanamido)-3-methylbutyl)-4-(2-methoxy-2-oxoethyl)-5-oxo-1,3,2-dioxaborolan-4-yl)acetic acid |
| HL-126 | 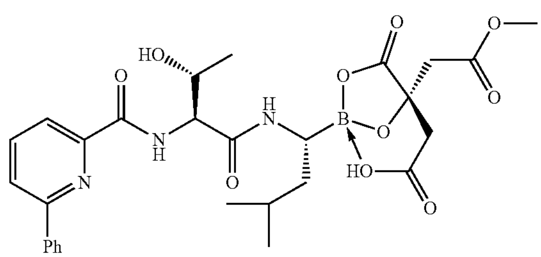 [SMILES: COC(=O)C[C@@]12CC(=O)[OH+][B-]([C@H](CC(C)C)NC(=O)[C@@H](NC(=O)c3cccc(-c4ccccc4)n3)[C@@H](C)O)(OC1=O)O2] | 2-((S)-2-((R)-1-((2S,3R)-3-hydroxy-2-(6-phenylpicolinamido)butanamido)-3-methylbutyl)-4-(2-methoxy-2-oxoethyl)-5-oxo-1,3,2-dioxaborolan-4-yl)acetic acid |
| HL-127 | 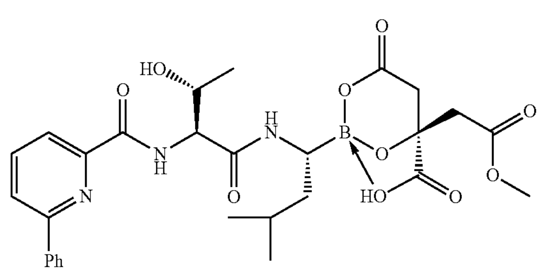 [SMILES: COC(=O)C[C@]12CC(=O)O[B-]([C@H](CC(C)C)NC(=O)[C@@H](NC(=O)c3cccc(-c4ccccc4)n3)[C@@H](C)O)(O1)[OH+]C2=O] | (S)-2-((R)-1-((2S,3R)-3-hydroxy-2-(6-phenylpicolinamido)butanamido)-3-methylbutyl)-4-(2-methoxy-2-oxoethyl)-6-oxo-1,3,2-dioxaborinane-4-carboxylic acid |
| HL-128 | 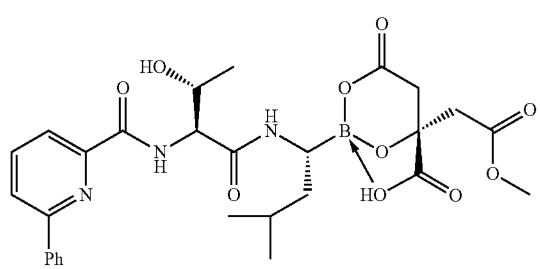 [SMILES: COC(=O)C[C@@]12CC(=O)O[B-]([C@H](CC(C)C)NC(=O)[C@@H](NC(=O)c3cccc(-c4ccccc4)n3)[C@@H](C)O)(O1)[OH+]C2=O] | (R)-2-((R)-1-((2S,3R)-3-hydroxy-2-(6-phenylpicolinamido)butanamido)-3-methylbutyl)-4-(2-methoxy-2-oxoethyl)-6-oxo-1,3,2-dioxaborinane-4-carboxylic acid |

TABLE 1-continued

| Serial # | Structure | Name |
|---|---|---|
| HL-129 | 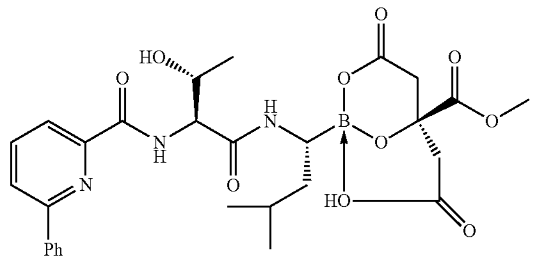 [SMILES: COC(=O)[C@]12CC(=O)O[B-]([C@H](CC(C)C)NC(=O)[C@@H](NC(=O)c3cccc(-c4ccccc4)n3)[C@@H](C)O)(O1)[OH+]C(=O)C2] | 2-((S)-2-((R)-1-((2S,3R)-3-hydroxy-2-(6-phenylpicolinamido)butanamido)-3-methylbutyl)-4-(methoxycarbonyl)-6-oxo-1,3,2-dioxaborinan-4-yl)acetic acid |
| HL-130 | 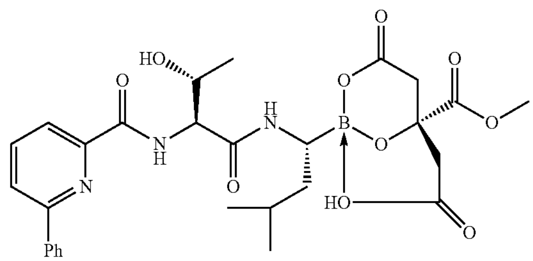 [SMILES: COC(=O)[C@@]12CC(=O)O[B-]([C@H](CC(C)C)NC(=O)[C@@H](NC(=O)c3cccc(-c4ccccc4)n3)[C@@H](C)O)(O1)[OH+]C(=O)C2] | 2-((R)-2-((R)-1-((2S,3R)-3-hydroxy-2-(6-phenylpicolinamido)butanamido)-3-methylbutyl)-4-(methoxycarbonyl)-6-oxo-1,3,2-dioxaborinan-4-yl)acetic acid |
| HL-131 | 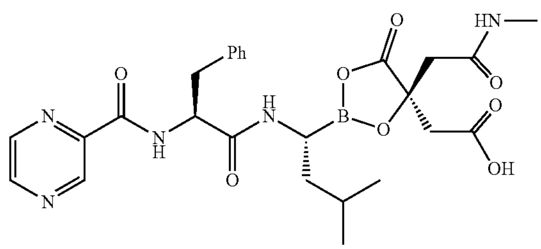 [SMILES: CNC(=O)C[C@@]1(CC(=O)O)OB([C@H](CC(C)C)NC(=O)[C@H](Cc2ccccc2)NC(=O)c2cnccn2)OC1=O] | 2-((S)-2-((R)-3-methyl-1-((S)-3-phenyl-2-(pyrazine-2-carboxamido)propanamido)butyl)-4-(2-(methylamino)-2-oxoethyl)-5-oxo-1,3,2-dioxaborolan-4-yl)acetic acid |
| HL-132 | 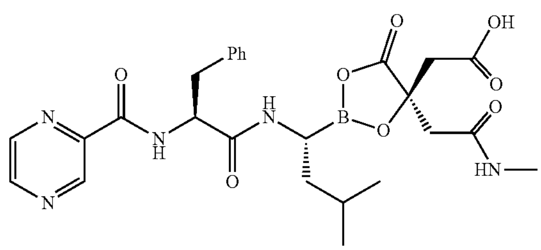 [SMILES: CNC(=O)C[C@]1(CC(=O)O)OB([C@H](CC(C)C)NC(=O)[C@H](Cc2ccccc2)NC(=O)c2cnccn2)OC1=O] | 2-((R)-2-((R)-3-methyl-1-((S)-3-phenyl-2-(pyrazine-2-carboxamido)propanamido)butyl)-4-(2-(methylamino)-2-oxoethyl)-5-oxo-1,3,2-dioxaborolan-4-yl)acetic acid |
| HL-133 | 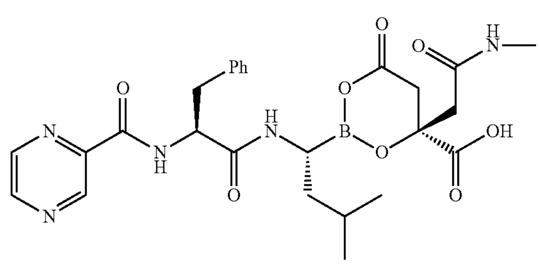 [SMILES: CNC(=O)C[C@]1(C(=O)O)CC(=O)OB([C@H](CC(C)C)NC(=O)[C@H](Cc2ccccc2)NC(=O)c2cnccn2)O1] | (R)-2-((R)-3-methyl-1-((S)-3-phenyl-2-(pyrazine-2-carboxamido)propanamido)butyl)-4-(2-(methylamino)-2-oxoethyl)-6-oxo-1,3,2-dioxaborinane-4-carboxylic acid |
| HL-134 | 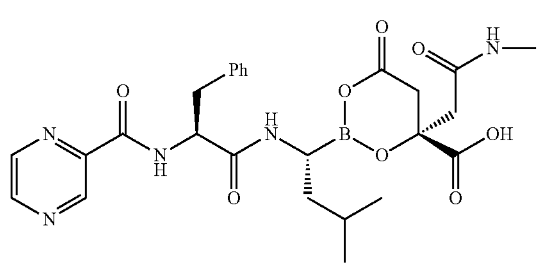 [SMILES: CNC(=O)C[C@@]1(C(=O)O)CC(=O)OB([C@H](CC(C)C)NC(=O)[C@H](Cc2ccccc2)NC(=O)c2cnccn2)O1] | (S)-2-((R)-3-methyl-1-((S)-3-phenyl-2-(pyrazine-2-carboxamido)propanamido)butyl)-4-(2-(methylamino)-2-oxoethyl)-6-oxo-1,3,2-dioxaborinane-4-carboxylic acid |

TABLE 1-continued

| Serial # | Structure | Name |
|---|---|---|
| HL-135 | 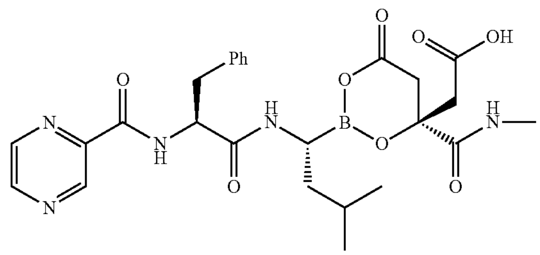 [SMILES: CNC(=O)[C@@]1(CC(=O)O)CC(=O)OB([C@H](CC(C)C)NC(=O)[C@H](Cc2ccccc2)NC(=O)c2cnccn2)O1] | 2-((R)-2-((R)-3-methyl-1-((S)-3-phenyl-2-(pyrazine-2-carboxamido)propanamido)butyl)-4-(methylcarbamoyl)-6-oxo-1,3,2-dioxaborinan-4-yl)acetic acid |
| HL-136 | 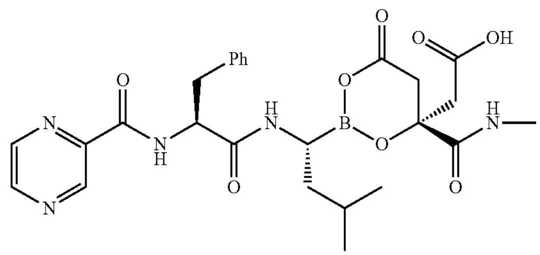 [SMILES: CNC(=O)[C@]1(CC(=O)O)CC(=O)OB([C@H](CC(C)C)NC(=O)[C@H](Cc2ccccc2)NC(=O)c2cnccn2)O1] | 2-((S)-2-((R)-3-methyl-1-((S)-3-phenyl-2-(pyrazine-2-carboxamido)propanamido)butyl)-4-(methylcarbamoyl)-6-oxo-1,3,2-dioxaborinan-4-yl)acetic acid |
| HL-137 | 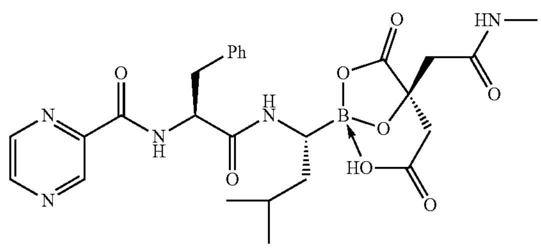 | 2-((S)-2-((R)-3-methyl-1-((S)-3-phenyl-2-(pyrazine-2-carboxamido)propanamido)butyl)-4-(2-(methylamino)-2-oxoethyl)-5-oxo-1,3,2-dioxaborolan-4-yl)acetic acid |
| HL-138 | 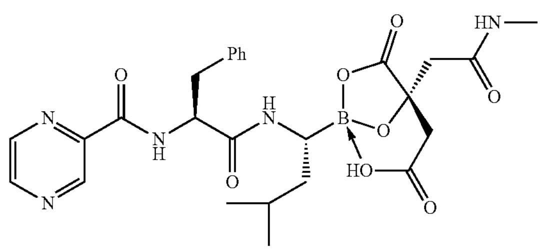 [SMILES: CNC(=O)C[C@@]12CC(=O)[OH+][B-]([C@H](CC(C)C)NC(=O)[C@H](Cc3ccccc3)NC(=O)c3cnccn3)(OC1=O)O2] | 2-((R)-2-((R)-3-methyl-1-((S)-3-phenyl-2-(pyrazine-2-carboxamido)propanamido)butyl)-4-(2-(methylamino)-2-oxoethyl)-5-oxo-1,3,2-dioxaborolan-4-yl)acetic acid |
| HL-139 | 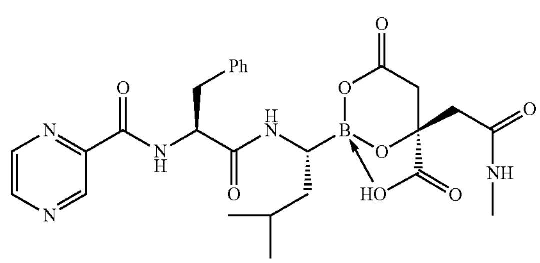 [SMILES: CNC(=O)C[C@]12CC(=O)O[B-]([C@H](CC(C)C)NC(=O)[C@H](Cc3ccccc3)NC(=O)c3cnccn3)(O1)[OH+]C2=O] | (R)-2-((R)-3-methyl-1-((S)-3-phenyl-2-(pyrazine-2-carboxamido)propanamido)butyl)-4-(2-(methylamino)-2-oxoethyl)-6-oxo-1,3,2-dioxaborinane-4-carboxylic acid |
| HL-140 | 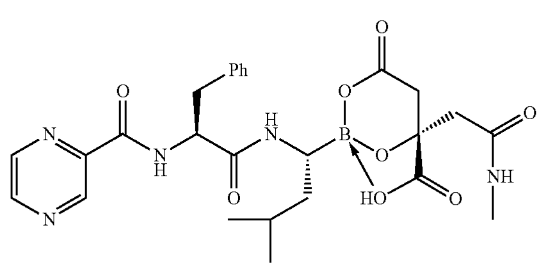 [SMILES: CNC(=O)C[C@@]12CC(=O)O[B-]([C@H](CC(C)C)NC(=O)[C@H](Cc3ccccc3)NC(=O)c3cnccn3)(O1)[OH+]C2=O] | (S)-2-((R)-3-methyl-1-((S)-3-phenyl-2-(pyrazine-2-carboxamido)propanamido)butyl)-4-(2-(methylamino)-2-oxoethyl)-6-oxo-1,3,2-dioxaborinane-4-carboxylic acid |

| Serial # | Structure | Name |
|---|---|---|
| HL-141 | 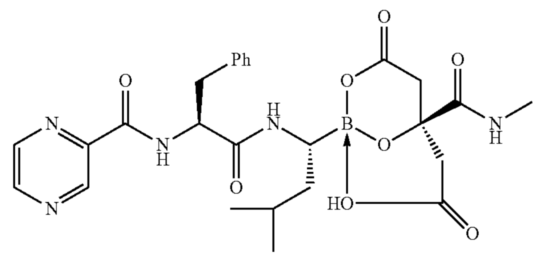 [SMILES: CNC(=O)[C@]12CC(=O)O[B-]([C@H](CC(C)C)NC(=O)[C@H](Cc3ccccc3)NC(=O)c3cnccn3)(O1)[OH+]C(=O)C2] | 2-((S)-2-((R)-3-methyl-1-((S)-3-phenyl-2-(pyrazine-2-carboxamido)propanamido)butyl)-4-(methylcarbamoyl)-6-oxo-1,3,2-dioxaborinan-4-yl)acetic acid |
| HL-142 | 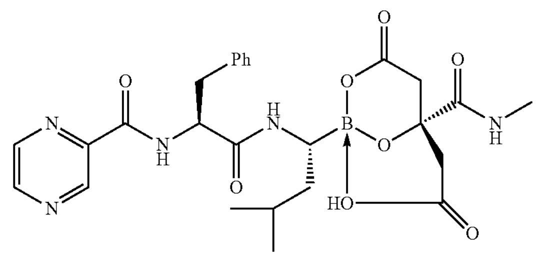 [SMILES: CNC(=O)[C@@]12CC(=O)O[B-]([C@H](CC(C)C)NC(=O)[C@H](Cc3ccccc3)NC(=O)c3cnccn3)(O1)[OH+]C(=O)C2] | 2-((R)-2-((R)-3-methyl-1-((S)-3-phenyl-2-(pyrazine-2-carboxamido)propanamido)butyl)-4-(methylcarbamoyl)-6-oxo-1,3,2-dioxaborinan-4-yl)acetic acid |
| HL-143 | 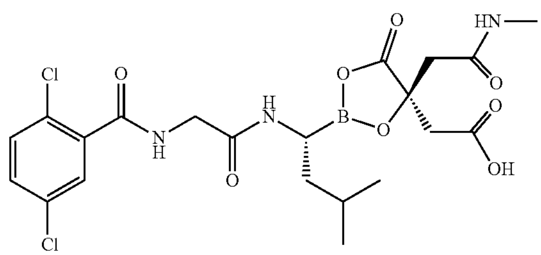 | 2-((S)-2-((R)-1-(2-(2,5-dichlorobenzamido)acetamido)-3-methylbutyl)-4-(2-(methylamino)-2-oxoethyl)-5-oxo-1,3,2-dioxaborolan-4-yl)acetic acid |
| HL-144 | 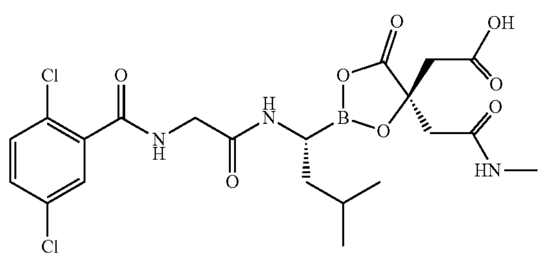 [SMILES: CNC(=O)C[C@]1(CC(=O)O)OB([C@H](CC(C)C)NC(=O)CNC(=O)c2cc(Cl)ccc2Cl)OC1=O] | 2-((R)-2-((R)-1-(2-(2,5-dichlorobenzamido)acetamido)-3-methylbutyl)-4-(2-(methylamino)-2-oxoethyl)-5-oxo-1,3,2-dioxaborolan-4-yl)acetic acid |
| HL-145 | 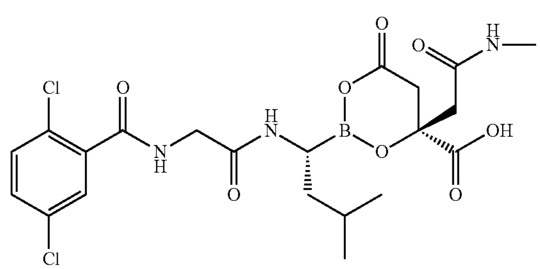 [SMILES: CNC(=O)C[C@]1(C(=O)O)CC(=O)OB([C@H](CC(C)C)NC(=O)CNC(=O)c2cc(Cl)ccc2Cl)O1] | (R)-2-((R)-1-(2-(2,5-dichlorobenzamido)acetamido)-3-methylbutyl)-4-(2-(methylamino)-2-oxoethyl)-6-oxo-1,3,2-dioxaborinane-4-carboxylic acid |
| HL-146 | 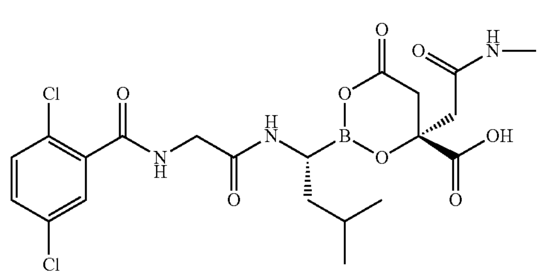 [SMILES: CNC(=O)C[C@@]1(C(=O)O)CC(=O)OB([C@H](CC(C)C)NC(=O)CNC(=O)c2cc(Cl)ccc2Cl)O1] | (S)-2-((R)-1-(2-(2,5-dichlorobenzamido)acetamido)-3-methylbutyl)-4-(2-(methylamino)-2-oxoethyl)-6-oxo-1,3,2-dioxaborinane-4-carboxylic acid |

TABLE 1-continued

| Serial # | Structure | Name |
|---|---|---|
| HL-147 | 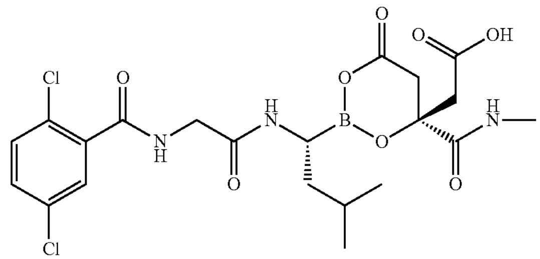 [SMILES: CNC(=O)[C@@]1(CC(=O)O)CC(=O)OB([C@H](CC(C)C)NC(=O)CNC(=O)c2cc(Cl)ccc2Cl)O1] | 2-((R)-2-((R)-1-(2-(2,5-dichlorobenzamido)acetamido)-3-methylbutyl)-4-(methylcarbamoyl)-6-oxo-1,3,2-dioxaborinan-4-yl)acetic acid |
| HL-148 | 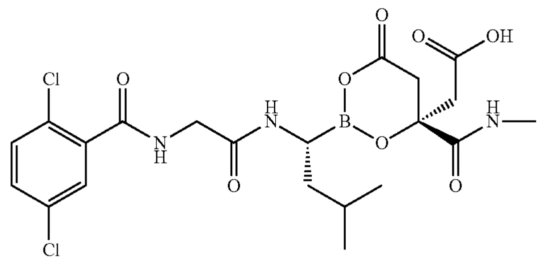 [SMILES: CNC(=O)[C@]1(CC(=O)O)CC(=O)OB([C@H](CC(C)C)NC(=O)CNC(=O)c2cc(Cl)ccc2Cl)O1] | 2-((S)-2-((R)-1-(2-(2,5-dichlorobenzamido)acetamido)-3-methylbutyl)-4-(methylcarbamoyl)-6-oxo-1,3,2-dioxaborinan-4-yl)acetic acid |
| HL-149 | 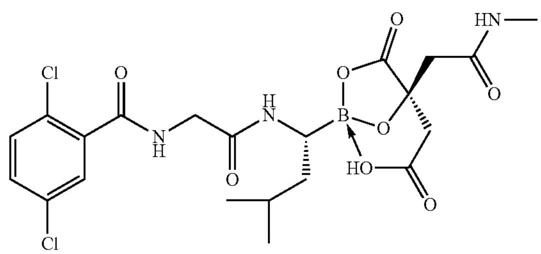 [SMILES: CNC(=O)C[C@]12CC(=O)[OH+][B-]([C@H](CC(C)C)NC(=O)CNC(=O)c3cc(Cl)ccc3Cl)(OC1=O)O2] | 2-((S)-2-((R)-1-(2-(2,5-dichlorobenzamido)acetamido)-3-methylbutyl)-4-(2-(methylamino)-2-oxoethyl)-5-oxo-1,3,2-dioxaborolan-4-yl)acetic acid |
| HL-150 | 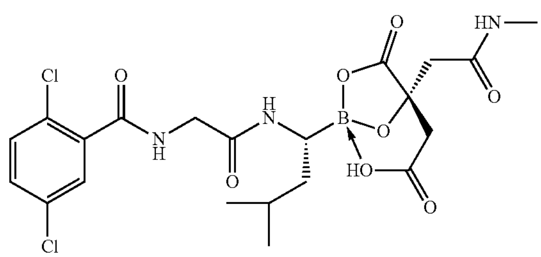 [SMILES: CNC(=O)C[C@@]12CC(=O)[OH+][B-]([C@H](CC(C)C)NC(=O)CNC(=O)c3cc(Cl)ccc3Cl)(OC1=O)O2] | 2-((R)-2-((R)-1-(2-(2,5-dichlorobenzamido)acetamido)-3-methylbutyl)-4-(2-(methylamino)-2-oxoethyl)-5-oxo-1,3,2-dioxaborolan-4-yl)acetic acid |
| HL-151 | 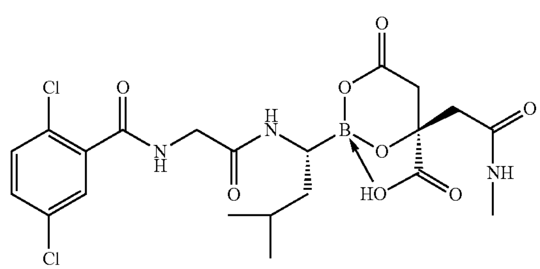 [SMILES: CNC(=O)C[C@]12CC(=O)O[B-]([C@H](CC(C)C)NC(=O)CNC(=O)c3cc(Cl)ccc3Cl)(O1)[OH+]C2=O] | (R)-2-((R)-1-(2-(2,5-dichlorobenzamido)acetamido)-3-methylbutyl)-4-(2-(methylamino)-2-oxoethyl)-6-oxo-1,3,2-dioxaborinane-4-carboxylic acid |
| HL-152 | 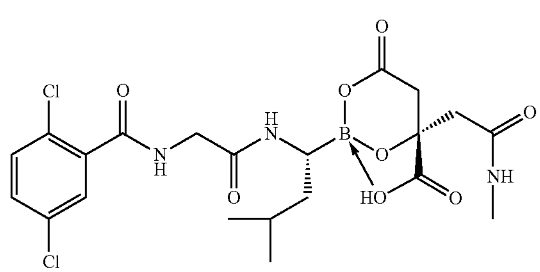 [SMILES: CNC(=O)C[C@@]12CC(=O)O[B-]([C@H](CC(C)C)NC(=O)CNC(=O)c3cc(Cl)ccc3Cl)(O1)[OH+]C2=O] | (S)-2-((R)-1-(2-(2,5-dichlorobenzamido)acetamido)-3-methylbutyl)-4-(2-(methylamino)-2-oxoethyl)-6-oxo-1,3,2-dioxaborinane-4-carboxylic acid |

TABLE 1-continued

| Serial # | Structure | Name |
|---|---|---|
| HL-153 | 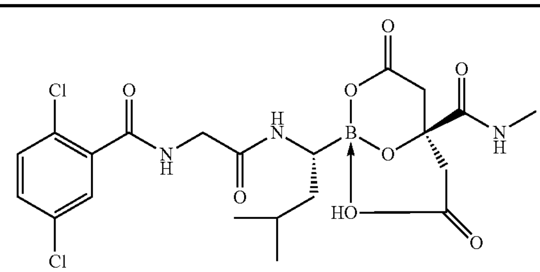 | 2-((S)-2-((R)-1-(2-(2,5-dichlorobenzamido)acetamido)-3-methylbutyl)-4-(methylcarbamoyl)-6-oxo-1,3,2-dioxaborinan-4-yl)acetic acid |
| HL-154 | 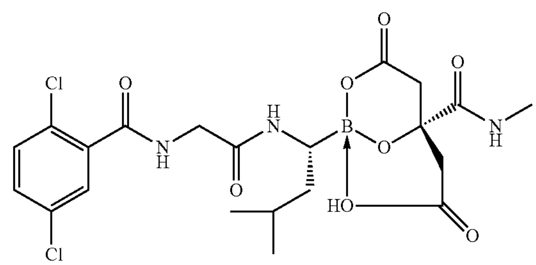 [SMILES: CNC(=O)[C@@]12CC(=O)O[B-]([C@H](CC(C)C)NC(=O)CNC(=O)c3cc(Cl)ccc3Cl)(O1)[OH+]C(=O)C2] | 2-((R)-2-((R)-1-(2-(2,5-dichlorobenzamido)acetamido)-3-methylbutyl)-4-(methylcarbamoyl)-6-oxo-1,3,2-dioxaborinan-4-yl)acetic acid |
| HL-155 | 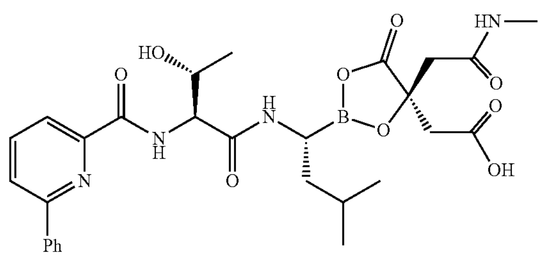 [SMILES: CNC(=O)C[C@@]1(CC(=O)O)OB([C@H](CC(C)C)NC(=O)[C@@H](NC(=O)c2cccc(-c3ccccc3)n2)[C@@H](C)O)OC1=O] | 2-((S)-2-((R)-1-((2S,3R)-3-hydroxy-2-(6-phenylpicolinamido)butanamido)-3-methylbutyl)-4-(2-(methylamino)-2-oxoethyl)-5-oxo-1,3,2-dioxaborolan-4-yl)acetic acid |
| HL-156 | 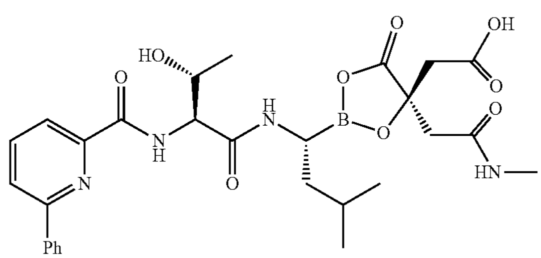 [SMILES: CNC(=O)C[C@]1(CC(=O)O)OB([C@H](CC(C)C)NC(=O)[C@@H](NC(=O)c2cccc(-c3ccccc3)n2)[C@@H](C)O)OC1=O] | 2-((R)-2-((R)-1-((2S,3R)-3-hydroxy-2-(6-phenylpicolinamido)butanamido)-3-methylbutyl)-4-(2-(methylamino)-2-oxoethyl)-5-oxo-1,3,2-dioxaborolan-4-yl)acetic acid |
| HL-157 | 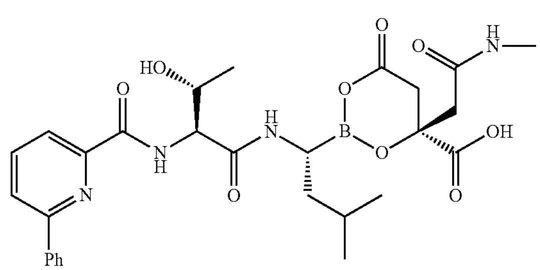 [SMILES: CNC(=O)C[C@]1(C(=O)O)CC(=O)OB([C@H](CC(C)C)NC(=O)[C@@H](NC(=O)c2cccc(-c3ccccc3)n2)[C@@H](C)O)O1] | (R)-2-((R)-1-((2S,3R)-3-hydroxy-2-(6-phenylpicolinamido)butanamido)-3-methylbutyl)-4-(2-(methylamino)-2-oxoethyl)-6-oxo-1,3,2-dioxaborinane-4-carboxylic acid |
| HL-158 | 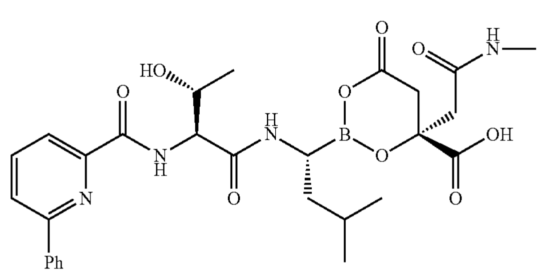 [SMILES: CNC(=O)C[C@@]1(C(=O)O)CC(=O)OB([C@H](CC(C)C)NC(=O)[C@@H](NC(=O)c2cccc(-c3ccccc3)n2)[C@@H](C)O)O1] | (S)-2-((R)-1-((2S,3R)-3-hydroxy-2-(6-phenylpicolinamido)butanamido)-3-methylbutyl)-4-(2-(methylamino)-2-oxoethyl)-6-oxo-1,3,2-dioxaborinane-4-carboxylic acid |

TABLE 1-continued

| Serial # | Structure | Name |
|---|---|---|
| HL-159 | 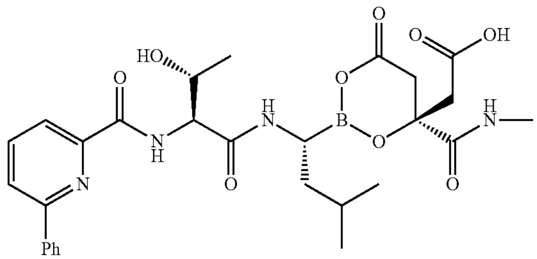 [SMILES: CNC(=O)[C@@]1(CC(=O)O)CC(=O)OB([C@H](CC(C)C)NC(=O)[C@@H](NC(=O)c2cccc(-c3ccccc3)n2)[C@@H](C)O)O1] | 2-((R)-2-((R)-1-((2S,3R)-3-hydroxy-2-(6-phenylpicolinamido)butanamido)-3-methylbutyl)-4-(methylcarbamoyl)-6-oxo-1,3,2-dioxaborinan-4-yl)acetic acid |
| HL-160 | 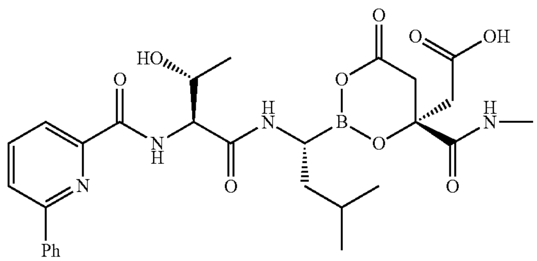 [SMILES: CNC(=O)[C@]1(CC(=O)O)CC(=O)OB([C@H](CC(C)C)NC(=O)[C@@H](NC(=O)c2cccc(-c3ccccc3)n2)[C@@H](C)O)O1] | 2-((S)-2-((R)-1-((2S,3R)-3-hydroxy-2-(6-phenylpicolinamido)butanamido)-3-methylbutyl)-4-(methylcarbamoyl)-6-oxo-1,3,2-dioxaborinan-4-yl)acetic acid |
| HL-161 | 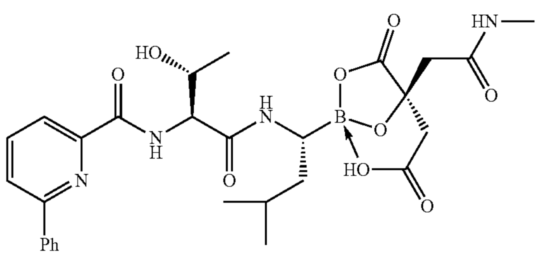 [SMILES: CNC(=O)C[C@]12CC(=O)[OH+][B-]([C@H](CC(C)C)NC(=O)[C@@H](NC(=O)c3cccc(-c4ccccc4)n3)[C@@H](C)O)(OC1=O)O2] | 2-((S)-2-((R)-1-((2S,3R)-3-hydroxy-2-(6-phenylpicolinamido)butanamido)-3-methylbutyl)-4-(2-(methylamino)-2-oxoethyl)-5-oxo-1,3,2-dioxaborolan-4-yl)acetic acid |
| HL-162 | 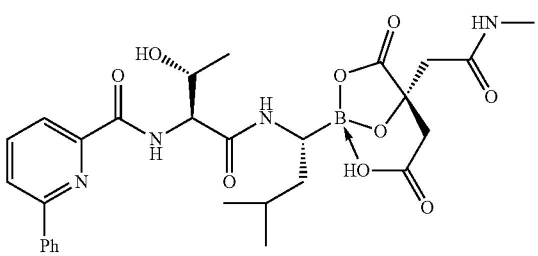 [SMILES: CNC(=O)C[C@@]12CC(=O)[OH+][B-]([C@H](CC(C)C)NC(=O)[C@@H](NC(=O)c3cccc(-c4ccccc4)n3)[C@@H](C)O)(OC1=O)O2] | 2-((R)-2-((R)-1-((2S,3R)-3-hydroxy-2-(6-phenylpicolinamido)butanamido)-3-methylbutyl)-4-(2-(methylamino)-2-oxoethyl)-5-oxo-1,3,2-dioxaborolan-4-yl)acetic acid |
| HL-163 | 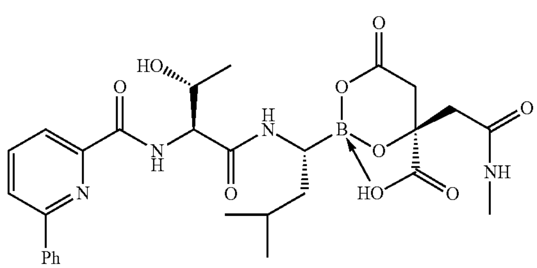 [SMILES: CNC(=O)C[C@]12CC(=O)O[B-]([C@H](CC(C)C)NC(=O)[C@@H](NC(=O)c3cccc(-c4ccccc4)n3)[C@@H](C)O)(O1)[OH+]C2=O] | (R)-2-((R)-1-((2S,3R)-3-hydroxy-2-(6-phenylpicolinamido)butanamido)-3-methylbutyl)-4-(2-(methylamino)-2-oxoethyl)-6-oxo-1,3,2-dioxaborinane-4-carboxylic acid |
| HL-164 | 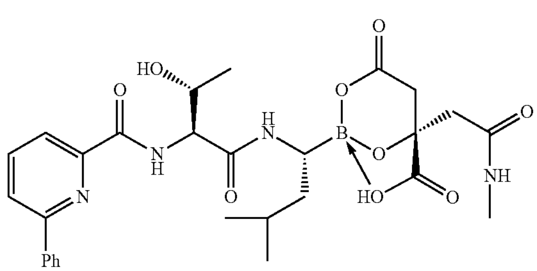 [SMILES: CNC(=O)C[C@@]12CC(=O)O[B-]([C@H](CC(C)C)NC(=O)[C@@H](NC(=O)c3cccc(-c4ccccc4)n3)[C@@H](C)O)(O1)[OH+]C2=O] | (S)-2-((R)-1-((2S,3R)-3-hydroxy-2-(6-phenylpicolinamido)butanamido)-3-methylbutyl)-4-(2-(methylamino)-2-oxoethyl)-6-oxo-1,3,2-dioxaborinane-4-carboxylic acid |

TABLE 1-continued

| Serial # | Structure | Name |
|---|---|---|
| HL-165 | 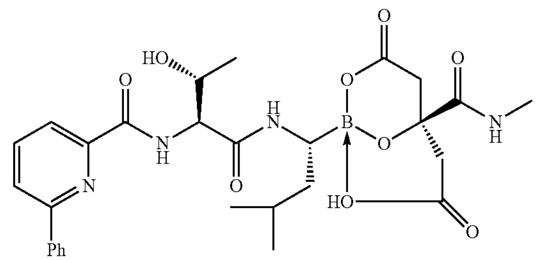 | 2-((S)-2-((R)-1-((2S,3R)-3-hydroxy-2-(6-phenylpicolinamido)butanamido)-3-methylbutyl)-4-(methylcarbamoyl)-6-oxo-1,3,2-dioxaborinan-4-yl)acetic acid |
| HL-166 | 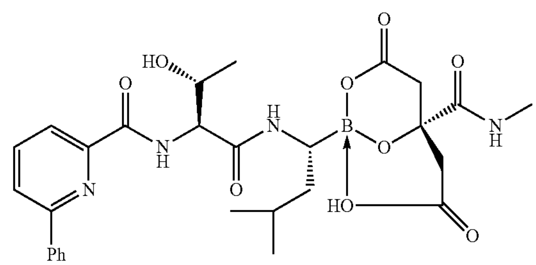 [SMILES: CNC(=O)[C@@]12CC(=O)O[B-]([C@H](CC(C)C)NC(=O)[C@@H](NC(=O)c3cccc(-c4ccccc4)n3)[C@@H](C)O)(O1)[OH+]C(=O)C2] | 2-((R)-2-((R)-1-((2S,3R)-3-hydroxy-2-(6-phenylpicolinamido)butanamido)-3-methylbutyl)-4-(methylcarbamoyl)-6-oxo-1,3,2-dioxaborinan-4-yl)acetic acid |
| HL-167 | 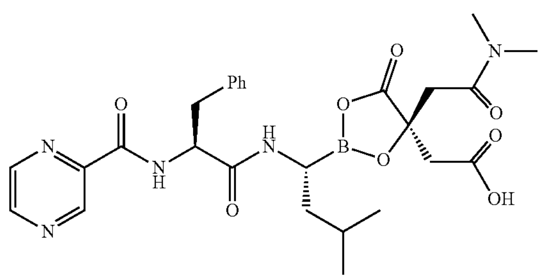 [SMILES: CC(C)C[C@H](NC(=O)[C@H](Cc1ccccc1)NC(=O)c1cnccn1)B1OC(=O)[C@@](CC(=O)O)(CC(=O)N(C)C)O1] | 2-((S)-4-(2-(dimethylamino)-2-oxoethyl)-2-((R)-3-methyl-1-((S)-3-phenyl-2-(pyrazine-2-carboxamido)propanamido)butyl)-5-oxo-1,3,2-dioxaborolan-4-yl)acetic acid |
| HL-168 | 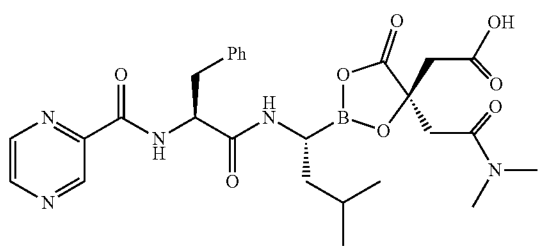 [SMILES: CC(C)C[C@H](NC(=O)[C@H](Cc1ccccc1)NC(=O)c1cnccn1)B1OC(=O)[C@](CC(=O)O)(CC(=O)N(C)C)O1] | 2-((R)-4-(2-(dimethylamino)-2-oxoethyl)-2-((R)-3-methyl-1-((S)-3-phenyl-2-(pyrazine-2-carboxamido)propanamido)butyl)-5-oxo-1,3,2-dioxaborolan-4-yl)acetic acid |
| HL-169 | 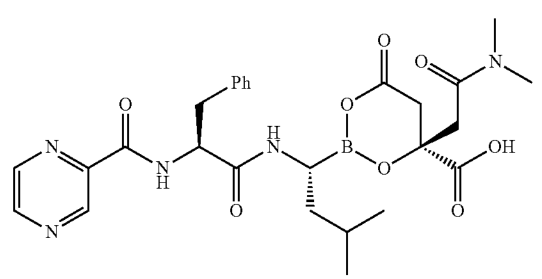 [SMILES: CC(C)C[C@H](NC(=O)[C@H](Cc1ccccc1)NC(=O)c1cnccn1)B1OC(=O)C[C@](CC(=O)N(C)C)(C(=O)O)O1] | (R)-4-(2-(dimethylamino)-2-oxoethyl)-2-((R)-3-methyl-1-((S)-3-phenyl-2-(pyrazine-2-carboxamido)propanamido)butyl)-6-oxo-1,3,2-dioxaborinane-4-carboxylic acid |

TABLE 1-continued

| Serial # | Structure | Name |
|---|---|---|
| HL-170 | 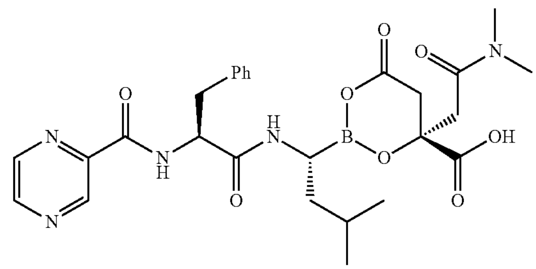 [SMILES: CC(C)C[C@H](NC(=O)[C@H](Cc1ccccc1)NC(=O)c1cnccn1)B1OC(=O)C[C@@](CC(=O)N(C)C)(C(=O)O)O1] | (S)-4-(2-(dimethylamino)-2-oxoethyl)-2-((R)-3-methyl-1-((S)-3-phenyl-2-(pyrazine-2-carboxamido)propanamido)butyl)-6-oxo-1,3,2-dioxaborinane-4-carboxylic acid |
| HL-171 | 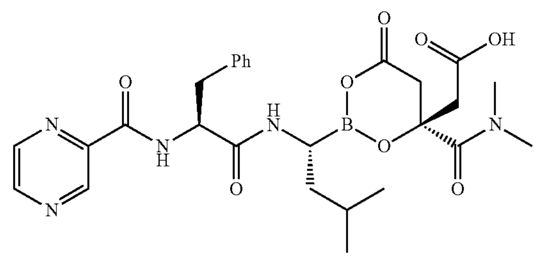 [SMILES: CC(C)C[C@H](NC(=O)[C@H](Cc1ccccc1)NC(=O)c1cnccn1)B1OC(=O)C[C@](CC(=O)O)(C(=O)N(C)C)O1] | 2-((R)-4-(dimethylcarbamoyl)-2-((R)-3-methyl-1-((S)-3-phenyl-2-(pyrazine-2-carboxamido)propanamido)butyl)-6-oxo-1,3,2-dioxaborinan-4-yl)acetic acid |
| HL-172 | 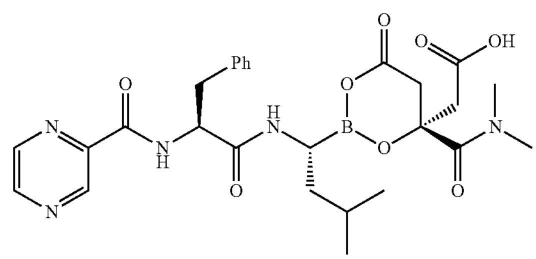 [SMILES: CC(C)C[C@H](NC(=O)[C@H](Cc1ccccc1)NC(=O)c1cnccn1)B1OC(=O)C[C@@](CC(=O)O)(C(=O)N(C)C)O1] | 2-((S)-4-(dimethylcarbamoyl)-2-((R)-3-methyl-1-((S)-3-phenyl-2-(pyrazine-2-carboxamido)propanamido)butyl)-6-oxo-1,3,2-dioxaborinan-4-yl)acetic acid |
| HL-173 | 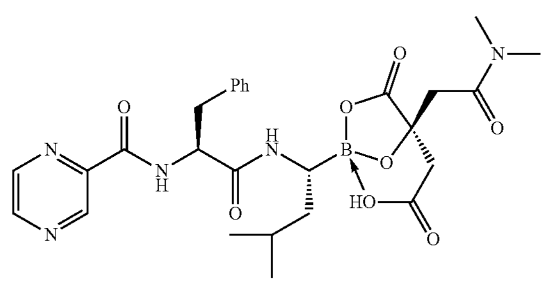 [SMILES: CC(C)C[C@H](NC(=O)[C@H](Cc1ccccc1)NC(=O)c1cnccn1)[B-]12OC(=O)[C@](CC(=O)N(C)C)(CC(=O)[OH+]1)O2] | 2-((S)-4-(2-(dimethylamino)-2-oxoethyl)-2-((R)-3-methyl-1-((S)-3-phenyl-2-(pyrazine-2-carboxamido)propanamido)butyl)-5-oxo-1,3,2-dioxaborolan-4-yl)acetic acid |
| HL-174 | 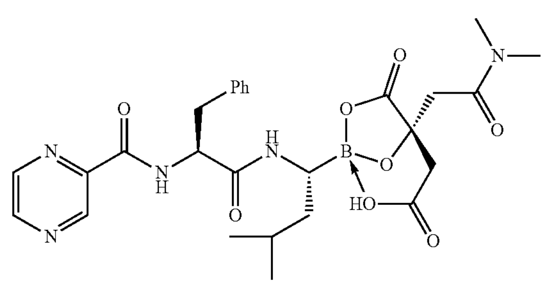 [SMILES: CC(C)C[C@H](NC(=O)[C@H](Cc1ccccc1)NC(=O)c1cnccn1)[B-]12OC(=O)[C@@](CC(=O)N(C)C)(CC(=O)[OH+]1)O2] | 2-((R)-4-(2-(dimethylamino)-2-oxoethyl)-2-((R)-3-methyl-1-((S)-3-phenyl-2-(pyrazine-2-carboxamido)propanamido)butyl)-5-oxo-1,3,2-dioxaborolan-4-yl)acetic acid |

TABLE 1-continued

| Serial # | Structure | Name |
|---|---|---|
| HL-175 | 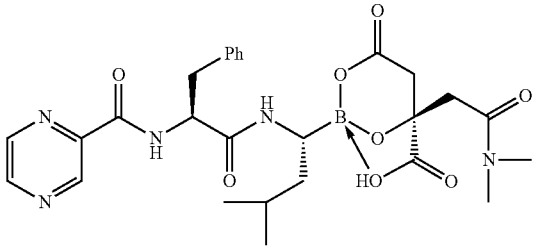 [SMILES: CC(C)C[C@H](NC(=O)[C@H](Cc1ccccc1)NC(=O)c1cnccn1)[B-]12OC(=O)C[C@@](CC(=O)N(C)C)(O1)C(=O)[OH+]2] | (R)-4-(2-(dimethylamino)-2-oxoethyl)-2-((R)-3-methyl-1-((S)-3-phenyl-2-(pyrazine-2-carboxamido)propanamido)butyl)-6-oxo-1,3,2-dioxaborinane-4-carboxylic acid |
| HL-176 | 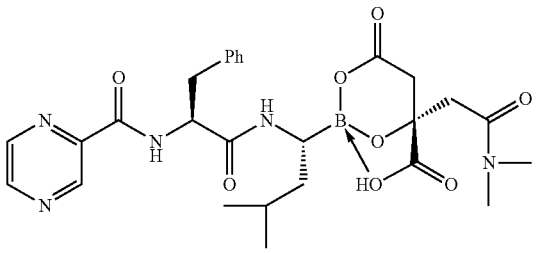 [SMILES: CC(C)C[C@H](NC(=O)[C@H](Cc1ccccc1)NC(=O)c1cnccn1)[B-]12OC(=O)C[C@](CC(=O)N(C)C)(O1)C(=O)[OH+]2] | (S)-4-(2-(dimethylamino)-2-oxoethyl)-2-((R)-3-methyl-1-((S)-3-phenyl-2-(pyrazine-2-carboxamido)propanamido)butyl)-6-oxo-1,3,2-dioxaborinane-4-carboxylic acid |
| HL-177 | 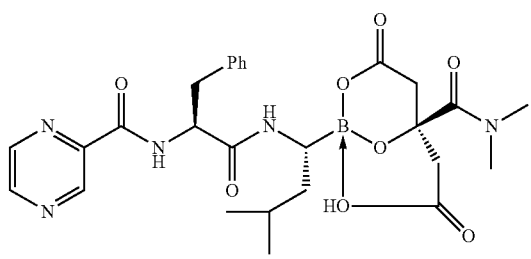 [SMILES: CC(C)C[C@H](NC(=O)[C@H](Cc1ccccc1)NC(=O)c1cnccn1)[B-]12OC(=O)C[C@](C(=O)N(C)C)(CC(=O)[OH+]1)O2] | 2-((S)-4-(dimethylcarbamoyl)-2-((R)-3-methyl-1-((S)-3-phenyl-2-(pyrazine-2-carboxamido)propanamido)butyl)-6-oxo-1,3,2-dioxaborinan-4-yl)acetic acid |
| HL-178 | 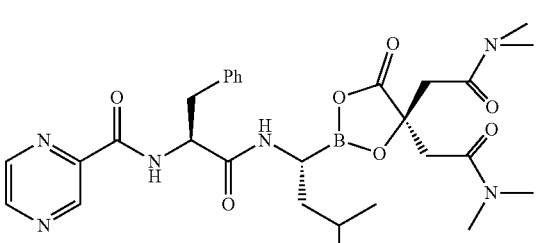 | 2,2'-(2-((R)-3-methyl-1-((S)-3-phenyl-2-(pyrazine-2-carboxamido)propanamido)butyl)-5-oxo-1,3,2-dioxaborolane-4,4-diyl)bis(N,N-dimethylacetamide) |
| HL-179 | 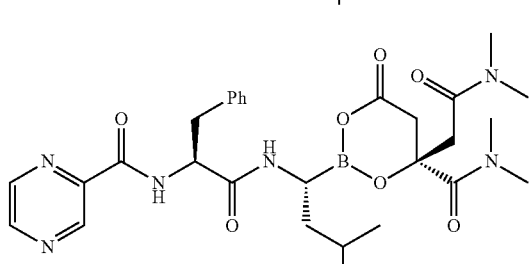 | N-((S)-1-(((R)-1-((R)-4-(2-(dimethylamino)-2-oxoethyl)-4-(dimethylcarbamoyl)-6-oxo-1,3,2-dioxaborinan-2-yl)-3-methylbutyl)amino)-1-oxo-3-phenylpropan-2-yl)pyrazine-2-carboxamide |
| HL-180 | 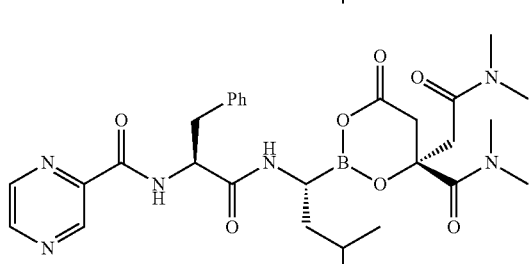 | N-((S)-1-(((R)-1-((S)-4-(2-(dimethylamino)-2-oxoethyl)-4-(dimethylcarbamoyl)-6-oxo-1,3,2-dioxaborinan-2-yl)-3-methylbutyl)amino)-1-oxo-3-phenylpropan-2-yl)pyrazine-2-carboxamide |

TABLE 1-continued

| Serial # | Structure | Name |
|---|---|---|
| HL-181 | 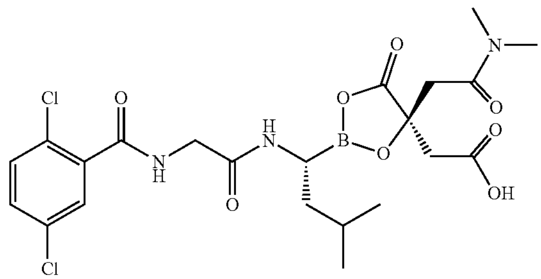 [SMILES: CC(C)C[C@H](NC(=O)CNC(=O)c1cc(Cl)ccc1Cl)B1OC(=O)[C@@](CC(=O)O)(CC(=O)N(C)C)O1] | 2-((S)-2-((R)-1-(2-(2,5-dichlorobenzamido)acetamido)-3-methylbutyl)-4-(2-(dimethylamino)-2-oxoethyl)-5-oxo-1,3,2-dioxaborolan-4-yl)acetic acid |
| HL-182 | 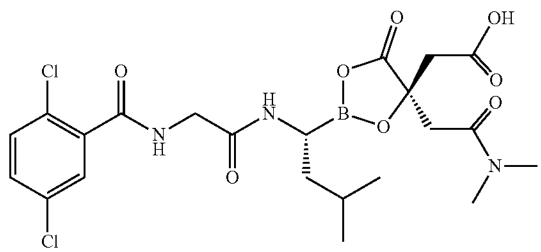 [SMILES: CC(C)C[C@H](NC(=O)CNC(=O)c1cc(Cl)ccc1Cl)B1OC(=O)[C@](CC(=O)O)(CC(=O)N(C)C)O1] | 2-((R)-2-((R)-1-(2-(2,5-dichlorobenzamido)acetamido)-3-methylbutyl)-4-(2-(dimethylamino)-2-oxoethyl)-5-oxo-1,3,2-dioxaborolan-4-yl)acetic acid |
| HL-183 | 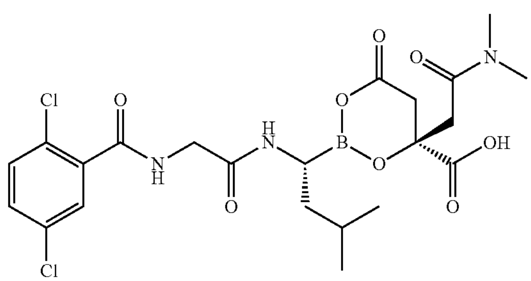 [SMILES: CC(C)C[C@H](NC(=O)CNC(=O)c1cc(Cl)ccc1Cl)B1OC(=O)C[C@](CC(=O)N(C)C)(C(=O)O)O1] | (R)-2-((R)-1-(2-(2,5-dichlorobenzamido)acetamido)-3-methylbutyl)-4-(2-(dimethylamino)-2-oxoethyl)-6-oxo-1,3,2-dioxaborinane-4-carboxylic acid |
| HL-184 | 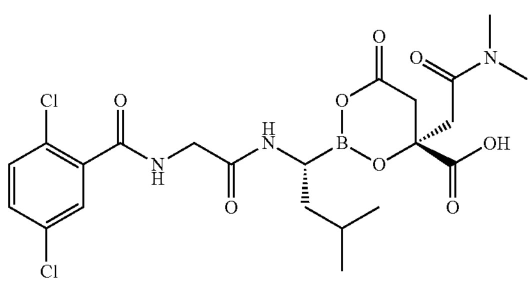 [SMILES: CC(C)C[C@H](NC(=O)CNC(=O)c1cc(Cl)ccc1Cl)B1OC(=O)C[C@@](CC(=O)N(C)C)(C(=O)O)O1] | (S)-2-((R)-1-(2-(2,5-dichlorobenzamido)acetamido)-3-methylbutyl)-4-(2-(dimethylamino)-2-oxoethyl)-6-oxo-1,3,2-dioxaborinane-4-carboxylic acid |
| HL-185 | 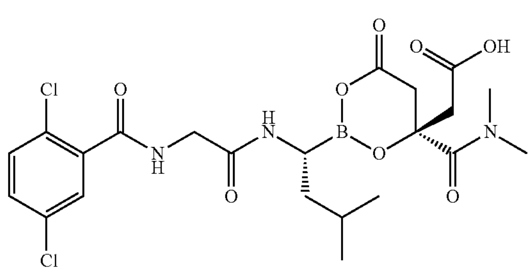 [SMILES: CC(C)C[C@H](NC(=O)CNC(=O)c1cc(Cl)ccc1Cl)B1OC(=O)C[C@](CC(=O)O)(C(=O)N(C)C)O1] | 2-((R)-2-((R)-1-(2-(2,5-dichlorobenzamido)acetamido)-3-methylbutyl)-4-(dimethylcarbamoyl)-6-oxo-1,3,2-dioxaborinan-4-yl)acetic acid |

TABLE 1-continued

| Serial # | Structure | Name |
|---|---|---|
| HL-186 | 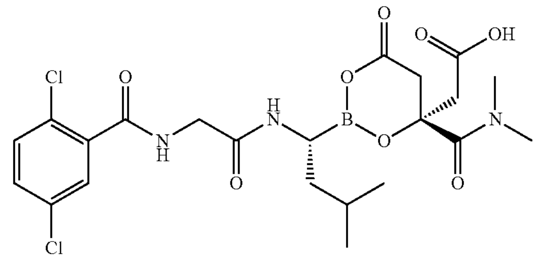 [SMILES: CC(C)C[C@H](NC(=O)CNC(=O)c1cc(Cl)ccc1Cl)B1OC(=O)C[C@@](CC(=O)O)(C(=O)N(C)C)O1] | 2-((S)-2-((R)-1-(2-(2,5-dichlorobenzamido)acetamido)-3-methylbutyl)-4-(dimethylcarbamoyl)-6-oxo-1,3,2-dioxaborinan-4-yl)acetic acid |
| HL-187 | 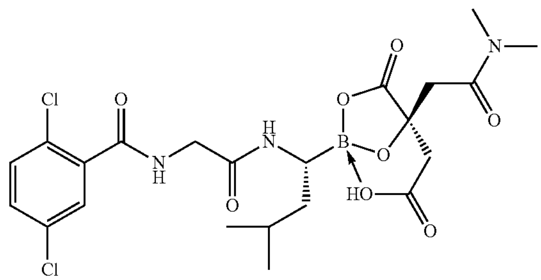 [SMILES: CC(C)C[C@H](NC(=O)CNC(=O)c1cc(Cl)ccc1Cl)[B-]12OC(=O)[C@](CC(=O)N(C)C)(CC(=O)[OH+]1)O2] | 2-((S)-2-((R)-1-(2-(2,5-dichlorobenzamido)acetamido)-3-methylbutyl)-4-(2-(dimethylamino)-2-oxoethyl)-5-oxo-1,3,2-dioxaborolan-4-yl)acetic acid |
| HL-188 | 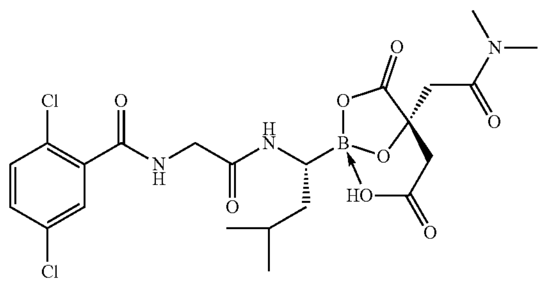 [SMILES: CC(C)C[C@H](NC(=O)CNC(=O)c1cc(Cl)ccc1Cl)[B-]12OC(=O)[C@@](CC(=O)N(C)C)(CC(=O)[OH+]1)O2] | 2-((R)-2-((R)-1-(2-(2,5-dichlorobenzamido)acetamido)-3-methylbutyl)-4-(2-(dimethylamino)-2-oxoethyl)-5-oxo-1,3,2-dioxaborolan-4-yl)acetic acid |
| HL-189 | 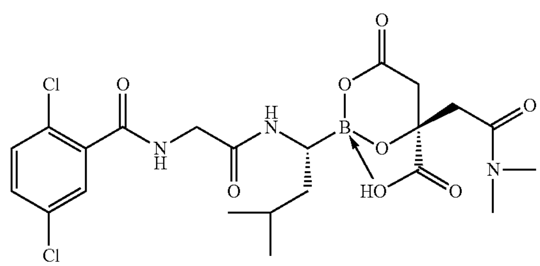 [SMILES: CC(C)C[C@H](NC(=O)CNC(=O)c1cc(Cl)ccc1Cl)[B-]12OC(=O)C[C@@](CC(=O)N(C)C)(O1)C(=O)[OH+]2] | (R)-2-((R)-1-(2-(2,5-dichlorobenzamido)acetamido)-3-methylbutyl)-4-(2-(dimethylamino)-2-oxoethyl)-6-oxo-1,3,2-dioxaborinane-4-carboxylic acid |
| HL-190 | 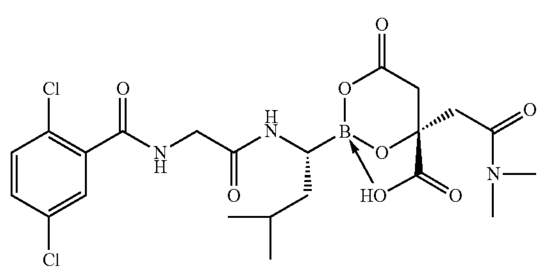 [SMILES: CC(C)C[C@H](NC(=O)CNC(=O)c1cc(Cl)ccc1Cl)[B-]12OC(=O)C[C@](CC(=O)N(C)C)(O1)C(=O)[OH+]2] | (S)-2-((R)-1-(2-(2,5-dichlorobenzamido)acetamido)-3-methylbutyl)-4-(2-(dimethylamino)-2-oxoethyl)-6-oxo-1,3,2-dioxaborinane-4-carboxylic acid |

TABLE 1-continued

| Serial # | Structure | Name |
|---|---|---|
| HL-191 | 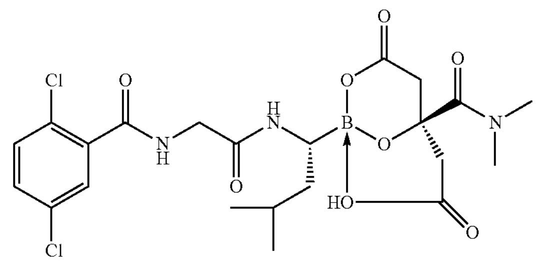 | 2-((S)-2-((R)-1-(2-(2,5-dichlorobenzamido)acetamido)-3-methylbutyl)-4-(dimethylcarbamoyl)-6-oxo-1,3,2-dioxaborinan-4-yl)acetic acid |
| HL-192 | 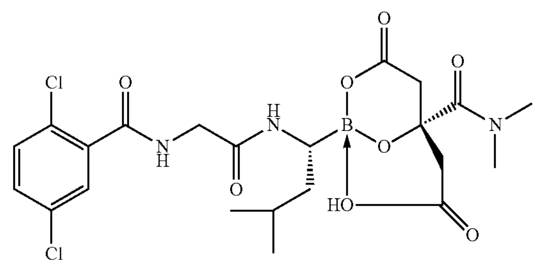 [SMILES: CC(C)C[C@H](NC(=O)CNC(=O)c1cc(Cl)ccc1Cl)[B-]12OC(=O)C[C@@](C(=O)N(C)C)(CC(=O)[OH+]1)O2] | 2-((R)-2-((R)-1-(2-(2,5-dichlorobenzamido)acetamido)-3-methylbutyl)-4-(dimethylcarbamoyl)-6-oxo-1,3,2-dioxaborinan-4-yl)acetic acid |
| HL-193 | 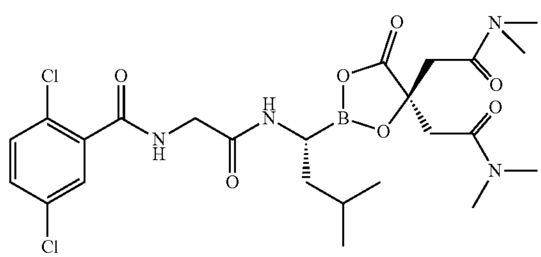 | (R)-2,2'-(2-(1-(2-(2,5-dichlorobenzamido)acetamido)-3-methylbutyl)-5-oxo-1,3,2-dioxaborolane-4,4-diyl)bis(N,N-dimethylacetamide) |
| HL-194 | 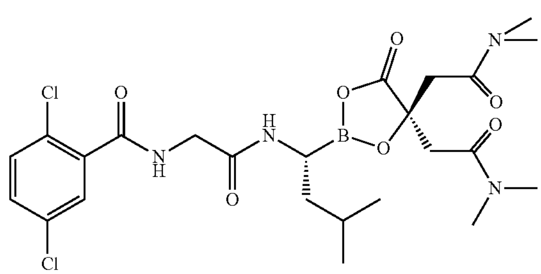 | (R)-2,2'-(2-(1-(2-(2,5-dichlorobenzamido)acetamido)-3-methylbutyl)-5-oxo-1,3,2-dioxaborolane-4,4-diyl)bis(N,N-dimethylacetamide) |
| HL-195 | 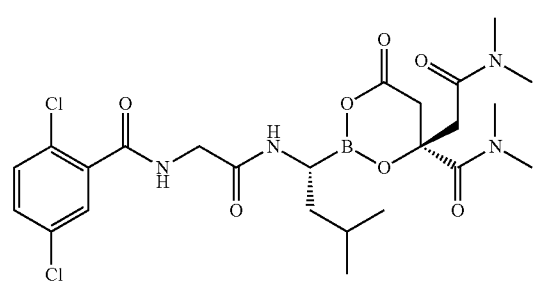 [SMILES: CC(C)C[C@H](NC(=O)CNC(=O)c1cc(Cl)ccc1Cl)B1OC(=O)C[C@](CC(=O)N(C)C)(C(=O)N(C)C)O1] | (R)-2-((R)-1-(2-(2,5-dichlorobenzamido)acetamido)-3-methylbutyl)-4-(2-(dimethylamino)-2-oxoethyl)-N,N-dimethyl-6-oxo-1,3,2-dioxaborinane-4-carboxamide |

TABLE 1-continued

| Serial # | Structure | Name |
|---|---|---|
| HL-196 | 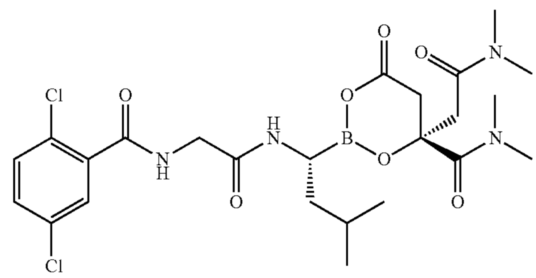 [SMILES: CC(C)C[C@H](NC(=O)CNC(=O)c1cc(Cl)ccc1Cl)B1OC(=O)C[C@@](CC(=O)N(C)C)(C(=O)N(C)C)O1] | (S)-2-((R)-1-(2-(2,5-dichlorobenzamido)acetamido)-3-methylbutyl)-4-(2-(dimethylamino)-2-oxoethyl)-N,N-dimethyl-6-oxo-1,3,2-dioxaborinane-4-carboxamide |
| HL-197 | 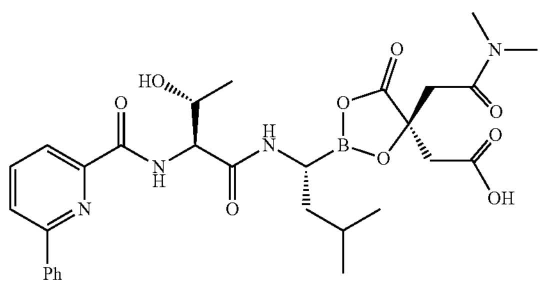 [SMILES: CC(C)C[C@H](NC(=O)[C@@H](NC(=O)c1cccc(-c2ccccc2)n1)[C@@H](C)O)B1OC(=O)[C@@](CC(=O)O)(CC(=O)N(C)C)O1] | 2-((S)-4-(2-(dimethylamino)-2-oxoethyl)-2-((R)-1-((2S,3R)-3-hydroxy-2-(6-phenylpicolinamido)butanamido)-3-methylbutyl)-5-oxo-1,3,2-dioxaborolan-4-yl)acetic acid |
| HL-198 | 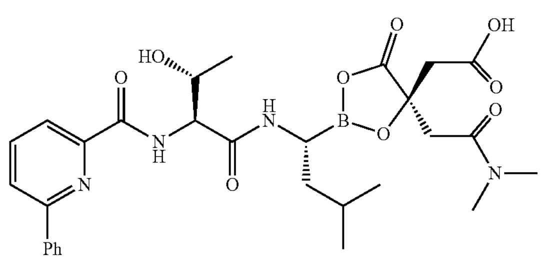 [SMILES: CC(C)C[C@H](NC(=O)[C@@H](NC(=O)c1cccc(-c2ccccc2)n1)[C@@H](C)O)B1OC(=O)[C@](CC(=O)O)(CC(=O)N(C)C)O1] | 2-((R)-4-(2-(dimethylamino)-2-oxoethyl)-2-((R)-1-((2S,3R)-3-hydroxy-2-(6-phenylpicolinamido)butanamido)-3-methylbutyl)-5-oxo-1,3,2-dioxaborolan-4-yl)acetic acid |
| HL-199 | 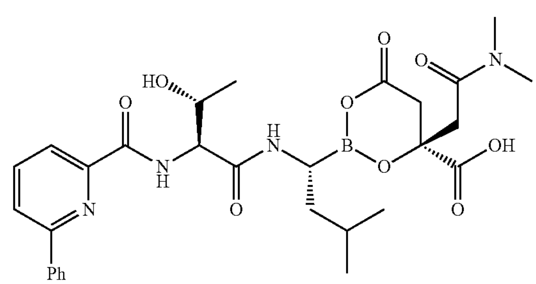 [SMILES: CC(C)C[C@H](NC(=O)[C@@H](NC(=O)c1cccc(-c2ccccc2)n1)[C@@H](C)O)B1OC(=O)C[C@](CC(=O)N(C)C)(C(=O)O)O1] | (R)-4-(2-(dimethylamino)-2-oxoethyl)-2-((R)-1-((2S,3R)-3-hydroxy-2-(6-phenylpicolinamido)butanamido)-3-methylbutyl)-6-oxo-1,3,2-dioxaborinane-4-carboxylic acid |
| HL-200 | 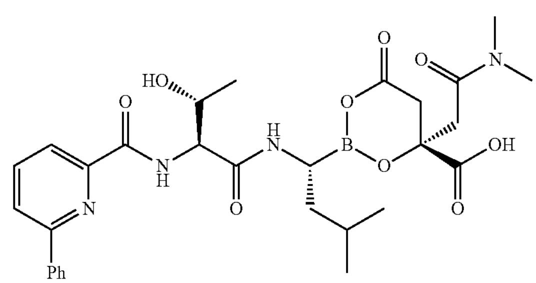 [SMILES: CC(C)C[C@H](NC(=O)[C@@H](NC(=O)c1cccc(-c2ccccc2)n1)[C@@H](C)O)B1OC(=O)C[C@@](CC(=O)N(C)C)(C(=O)O)O1] | (S)-4-(2-(dimethylamino)-2-oxoethyl)-2-((R)-1-((2S,3R)-3-hydroxy-2-(6-phenylpicolinamido)butanamido)-3-methylbutyl)-6-oxo-1,3,2-dioxaborinane-4-carboxylic acid |

TABLE 1-continued

| Serial # | Structure | Name |
|---|---|---|
| HL-201 | 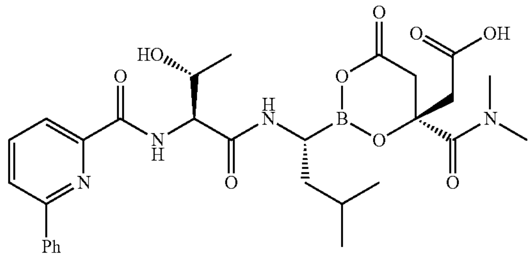 [SMILES: CC(C)C[C@H](NC(=O)[C@@H](NC(=O)c1cccc(-c2ccccc2)n1)[C@@H](C)O)B1OC(=O)C[C@](CC(=O)O)(C(=O)N(C)C)O1] | 2-((R)-4-(dimethylcarbamoyl)-2-((R)-1-((2S,3R)-3-hydroxy-2-(6-phenylpicolinamido)butanamido)-3-methylbutyl)-6-oxo-1,3,2-dioxaborinan-4-yl)acetic acid |
| HL-202 | 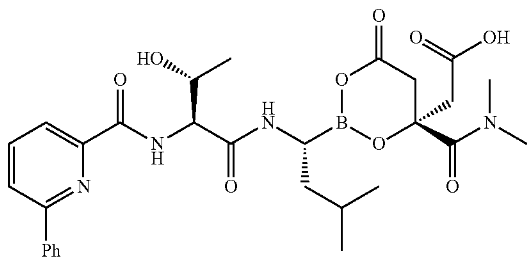 [SMILES: CC(C)C[C@H](NC(=O)[C@@H](NC(=O)c1cccc(-c2ccccc2)n1)[C@@H](C)O)B1OC(=O)C[C@@](CC(=O)O)(C(=O)N(C)C)O1] | 2-((S)-4-(dimethylcarbamoyl)-2-((R)-1-((2S,3R)-3-hydroxy-2-(6-phenylpicolinamido)butanamido)-3-methylbutyl)-6-oxo-1,3,2-dioxaborinan-4-yl)acetic acid |
| HL-203 | 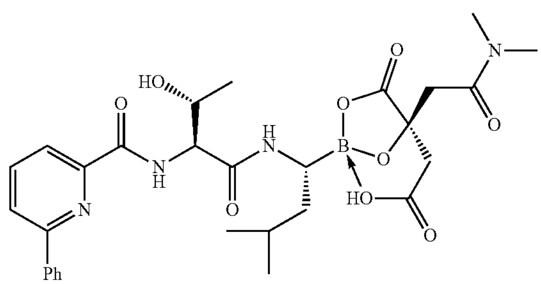 [SMILES: CC(C)C[C@H](NC(=O)[C@@H](NC(=O)c1cccc(-c2ccccc2)n1)[C@@H](C)O)[B-]12OC(=O)[C@](CC(=O)N(C)C)(CC(=O)[OH+]1)O2] | 2-((S)-4-(2-(dimethylamino)-2-oxoethyl)-2-((R)-1-((2S,3R)-3-hydroxy-2-(6-phenylpicolinamido)butanamido)-3-methylbutyl)-5-oxo-1,3,2-dioxaborolan-4-yl)acetic acid |
| HL-204 | 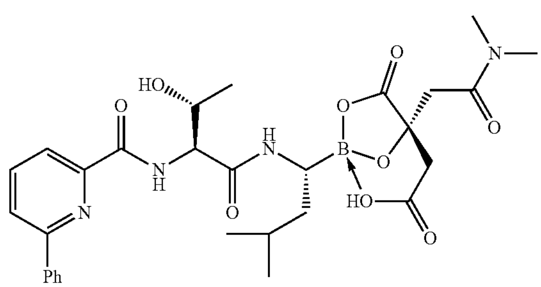 [SMILES: CC(C)C[C@H](NC(=O)[C@@H](NC(=O)c1cccc(-c2ccccc2)n1)[C@@H](C)O)[B-]12OC(=O)[C@@](CC(=O)N(C)C)(CC(=O)[OH+]1)O2] | 2-((R)-4-(2-(dimethylamino)-2-oxoethyl)-2-((R)-1-((2S,3R)-3-hydroxy-2-(6-phenylpicolinamido)butanamido)-3-methylbutyl)-5-oxo-1,3,2-dioxaborolan-4-yl)acetic acid |
| HL-205 | 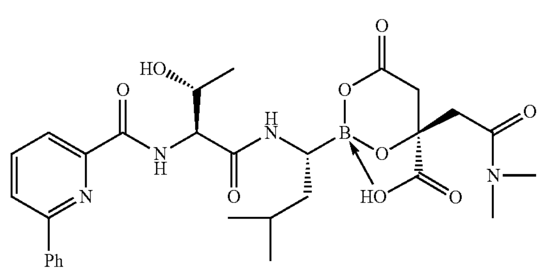 [SMILES: CC(C)C[C@H](NC(=O)[C@@H](NC(=O)c1cccc(-c2ccccc2)n1)[C@@H](C)O)[B-]12OC(=O)C[C@@](CC(=O)N(C)C)(O1)C(=O)[OH+]2] | (R)-4-(2-(dimethylamino)-2-oxoethyl)-2-((R)-1-((2S,3R)-3-hydroxy-2-(6-phenylpicolinamido)butanamido)-3-methylbutyl)-6-oxo-1,3,2-dioxaborinane-4-carboxylic acid |

TABLE 1-continued

| Serial # | Structure | Name |
|---|---|---|
| HL-206 | 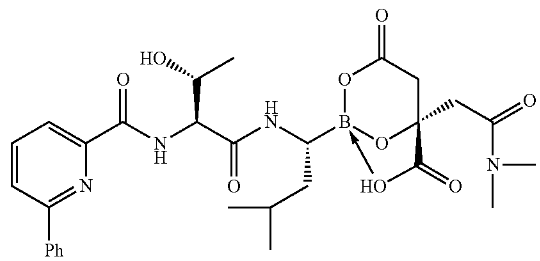 [SMILES: CC(C)C[C@H](NC(=O)[C@@H](NC(=O)c1cccc(-c2ccccc2)n1)[C@@H](C)O)[B-]12OC(=O)C[C@](CC(=O)N(C)C)(O1)C(=O)[OH+]2] | (S)-4-(2-(dimethylamino)-2-oxoethyl)-2-((R)-1-((2S,3R)-3-hydroxy-2-(6-phenylpicolinamido)butanamido)-3-methylbutyl)-6-oxo-1,3,2-dioxaborinane-4-carboxylic acid |
| HL-207 | 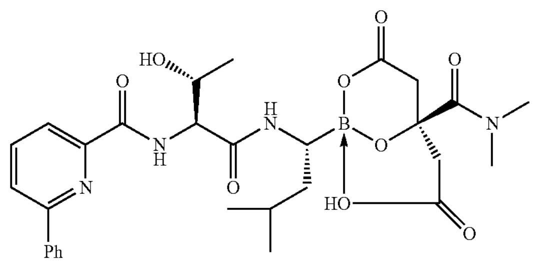 [SMILES: CC(C)C[C@H](NC(=O)[C@@H](NC(=O)c1cccc(-c2ccccc2)n1)[C@@H](C)O)[B-]12OC(=O)C[C@](C(=O)N(C)C)(CC(=O)[OH+]1)O2] | 2-((S)-4-(dimethylcarbamoyl)-2-((R)-1-((2S,3R)-3-hydroxy-2-(6-phenylpicolinamido)butanamido)-3-methylbutyl)-6-oxo-1,3,2-dioxaborinan-4-yl)acetic acid |
| HL-208 | 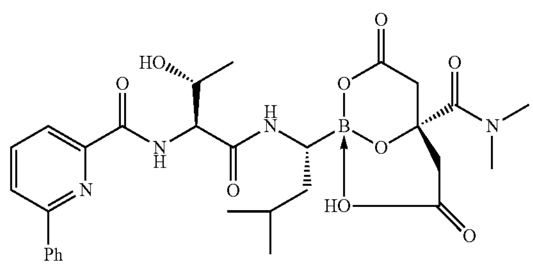 [SMILES: CC(C)C[C@H](NC(=O)[C@@H](NC(=O)c1cccc(-c2ccccc2)n1)[C@@H](C)O)[B-]12OC(=O)C[C@@](C(=O)N(C)C)(CC(=O)[OH+]1)O2] | 2-((R)-4-(dimethylcarbamoyl)-2-((R)-1-((2S,3R)-3-hydroxy-2-(6-phenylpicolinamido)butanamido)-3-methylbutyl)-6-oxo-1,3,2-dioxaborinan-4-yl)acetic acid |
| HL-209 | 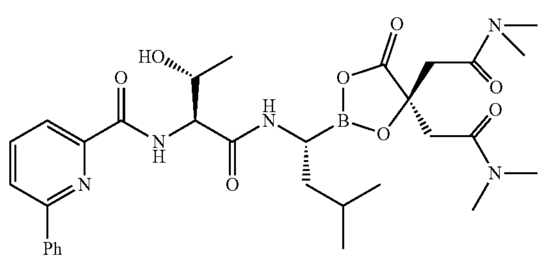 | 2,2'-(2-((R)-1-((2S,3R)-3-hydroxy-2-(6-phenylpicolinamido)butanamido)-3-methylbutyl)-5-oxo-1,3,2-dioxaborolane-4,4-diyl)bis(N,N-dimethylacetamide) |
| HL-210 | 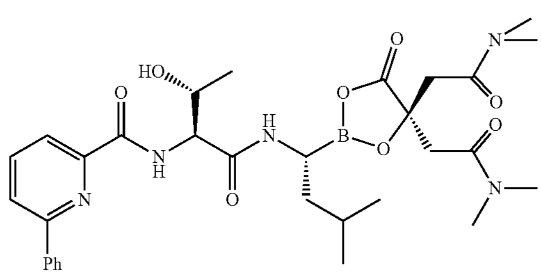 | 2,2'-(2-((R)-1-((2S,3R)-3-hydroxy-2-(6-phenylpicolinamido)butanamido)-3-methylbutyl)-5-oxo-1,3,2-dioxaborolane-4,4-diyl)bis(N,N-dimethylacetamide) |

TABLE 1-continued

| Serial # | Structure | Name |
|---|---|---|
| HL-211 | 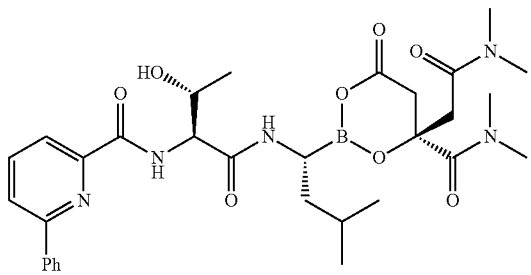 [SMILES: CC(C)C[C@H](NC(=O)[C@@H](NC(=O)c1cccc(-c2ccccc2)n1)[C@@H](C)O)B1OC(=O)C[C@](CC(=O)N(C)C)(C(=O)N(C)C)O1] | N-((2S,3R)-1-(((R)-1-((R)-4-(2-(dimethylamino)-2-oxoethyl)-4-(dimethylcarbamoyl)-6-oxo-1,3,2-dioxaborinan-2-yl)-3-methylbutyl)amino)-3-hydroxy-1-oxobutan-2-yl)-6-phenylpicolinamide |
| HL-212 | 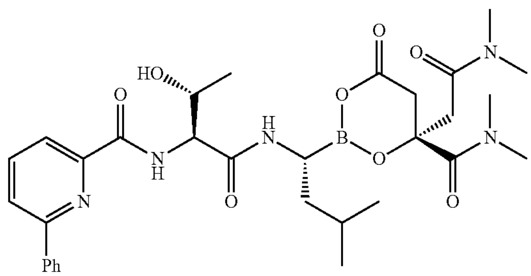 [SMILES: CC(C)C[C@H](NC(=O)[C@@H](NC(=O)c1cccc(-c2ccccc2)n1)[C@@H](C)O)B1OC(=O)C[C@@](CC(=O)N(C)C)(C(=O)N(C)C)O1] | N-((2S,3R)-1-(((R)-1-((S)-4-(2-(dimethylamino)-2-oxoethyl)-4-(dimethylcarbamoyl)-6-oxo-1,3,2-dioxaborinan-2-yl)-3-methylbutyl)amino)-3-hydroxy-1-oxobutan-2-yl)-6-phenylpicolinamide |
| HL-213 | 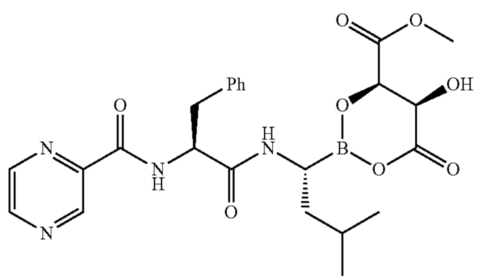 [SMILES: COC(=O)[C@@H]1OB([C@H](CC(C)C)NC(=O)[C@H](Cc2ccccc2)NC(=O)c2cnccn2)OC(=O)[C@@H]1O] | methyl (4R,5R)-5-hydroxy-2-((R)-3-methyl-1-((S)-3-phenyl-2-(pyrazine-2-carboxamido)propanamido)butyl)-6-oxo-1,3,2-dioxaborinane-4-carboxylate |
| HL-214 | 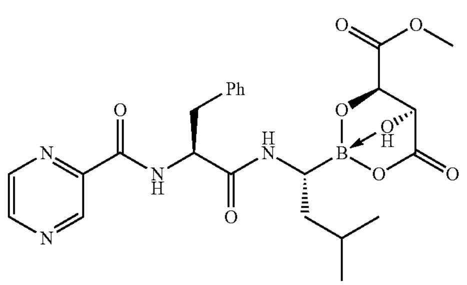 [SMILES: COC(=O)[C@@H]1O[B-]2([C@H](CC(C)C)NC(=O)[C@H](Cc3ccccc3)NC(=O)c3cnccn3)OC(=O)[C@H]1[OH+]2] | methyl (4R,5S)-5-hydroxy-2-((R)-3-methyl-1-((S)-3-phenyl-2-(pyrazine-2-carboxamido)propanamido)butyl)-6-oxo-1,3,2-dioxaborinane-4-carboxylate |
| HL-215 | 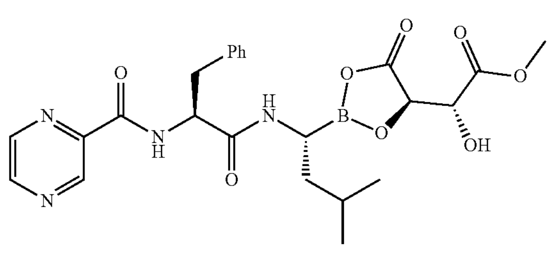 [SMILES: COC(=O)[C@H](O)[C@H]1OB([C@H](CC(C)C)NC(=O)[C@H](Cc2ccccc2)NC(=O)c2cnccn2)OC1=O] | methyl (R)-2-hydroxy-2-((R)-2-((R)-3-methyl-1-((S)-3-phenyl-2-(pyrazine-2-carboxamido)propanamido)butyl)-5-oxo-1,3,2-dioxaborolan-4-yl)acetate |

TABLE 1-continued

| Serial # | Structure | Name |
|---|---|---|
| HL-216 | 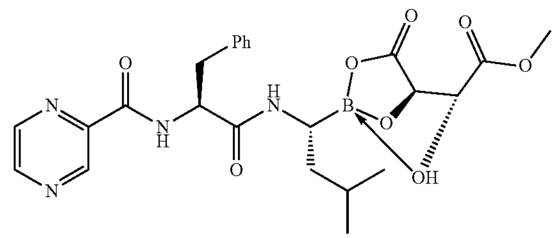 [SMILES: COC(=O)[C@@H]1[OH+][B-]2([C@H](CC(C)C)NC(=O)[C@H](Cc3ccccc3)NC(=O)c3cnccn3)OC(=O)[C@@H]1O2] | methyl (R)-2-hydroxy-2-((R)-2-((R)-3-methyl-1-((S)-3-phenyl-2-(pyrazine-2-carboxamido)propanamido)butyl)-5-oxo-1,3,2-dioxaborolan-4-yl)acetate |
| HL-217 | 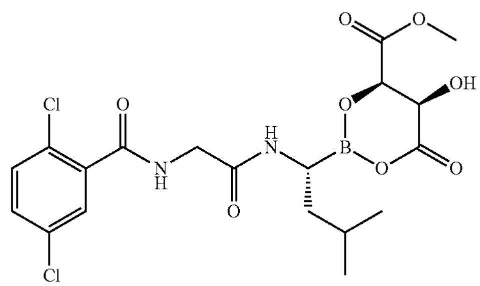 [SMILES: COC(=O)[C@@H]1OB([C@H](CC(C)C)NC(=O)CNC(=O)c2cc(Cl)ccc2Cl)OC(=O)[C@@H]1O] | methyl (4R,5R)-2-((R)-1-(2-(2,5-dichlorobenzamido)acetamido)-3-methylbutyl)-5-hydroxy-6-oxo-1,3,2-dioxaborinane-4-carboxylate |
| HL-218 | 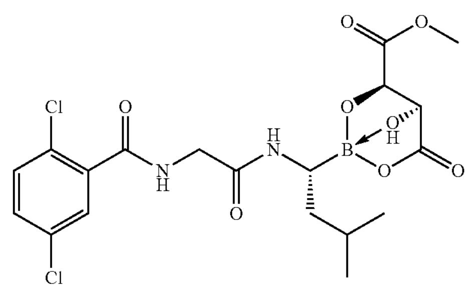 [SMILES: COC(=O)[C@@H]1O[B-]2([C@H](CC(C)C)NC(=O)CNC(=O)c3cc(Cl)ccc3Cl)OC(=O)[C@H]1[OH+]2] | methyl (4R,5S)-2-((R)-1-(2-(2,5-dichlorobenzamido)acetamido)-3-methylbutyl)-5-hydroxy-6-oxo-1,3,2-dioxaborinane-4-carboxylate |
| HL-219 | 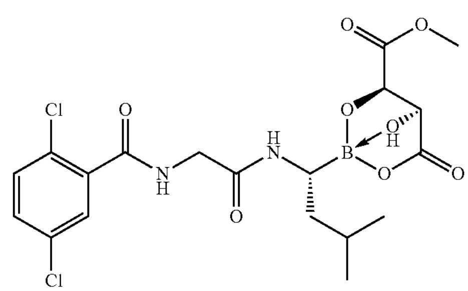 [SMILES: COC(=O)[C@@H]1O[B-]2([C@H](CC(C)C)NC(=O)CNC(=O)c3cc(Cl)ccc3Cl)OC(=O)[C@H]1[OH+]2] | methyl (4R,5S)-2-((R)-1-(2-(2,5-dichlorobenzamido)acetamido)-3-methylbutyl)-5-hydroxy-6-oxo-1,3,2-dioxaborinane-4-carboxylate |
| HL-220 | 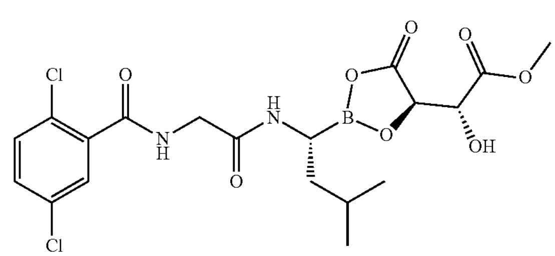 [SMILES: COC(=O)[C@H](O)[C@H]1OB([C@H](CC(C)C)NC(=O)CNC(=O)c2cc(Cl)ccc2Cl)OC1=O] | methyl (R)-2-((R)-2-((R)-1-(2-(2,5-dichlorobenzamido)acetamido)-3-methylbutyl)-5-oxo-1,3,2-dioxaborolan-4-yl)-2-hydroxyacetate |

TABLE 1-continued

| Serial # | Structure | Name |
|---|---|---|
| HL-222 | 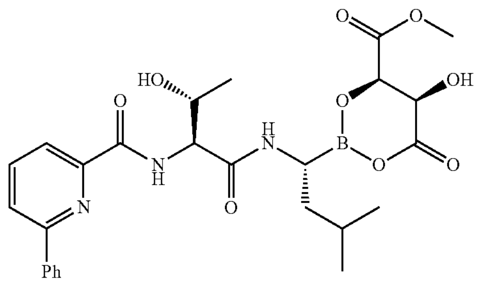 [SMILES: COC(=O)[C@@H]1OB([C@H](CC(C)C)NC(=O)[C@@H](NC(=O)c2cccc(-c3ccccc3)n2)[C@@H](C)O)OC(=O)[C@@H]1O] | methyl (4R,5R)-5-hydroxy-2-((R)-1-((2S,3R)-3-hydroxy-2-(6-phenylpicolinamido)butanamido)-3-methylbutyl)-6-oxo-1,3,2-dioxaborinane-4-carboxylate |
| HL-223 | 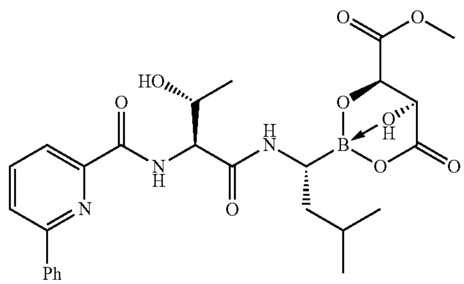 [SMILES: COC(=O)[C@@H]1O[B-]2([C@H](CC(C)C)NC(=O)[C@@H](NC(=O)c3cccc(-c4ccccc4)n3)[C@@H](C)O)OC(=O)[C@H]1[OH+]2] | methyl (4R,5S)-5-hydroxy-2-((R)-1-((2S,3R)-3-hydroxy-2-(6-phenylpicolinamido)butanamido)-3-methylbutyl)-6-oxo-1,3,2-dioxaborinane-4-carboxylate |
| HL-224 | 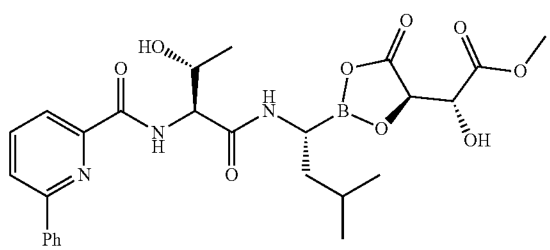 [SMILES: COC(=O)[C@H](O)[C@H]1OB([C@H](CC(C)C)NC(=O)[C@@H](NC(=O)c2cccc(-c3ccccc3)n2)[C@@H](C)O)OC1=O] | methyl (R)-2-hydroxy-2-((R)-2-((R)-1-((2S,3R)-3-hydroxy-2-(6-phenylpicolinamido)butanamido)-3-methylbutyl)-5-oxo-1,3,2-dioxaborolan-4-yl)acetate |
| HL-225 | 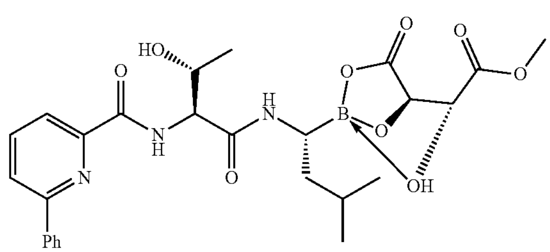 [SMILES: COC(=O)[C@@H]1[OH+][B-]2([C@H](CC(C)C)NC(=O)[C@@H](NC(=O)c3cccc(-c4ccccc4)n3)[C@@H](C)O)OC(=O)[C@@H]1O2] | methyl (R)-2-hydroxy-2-((R)-2-((R)-1-((2S,3R)-3-hydroxy-2-(6-phenylpicolinamido)butanamido)-3-methylbutyl)-5-oxo-1,3,2-dioxaborolan-4-yl)acetate |
| HL-226 | 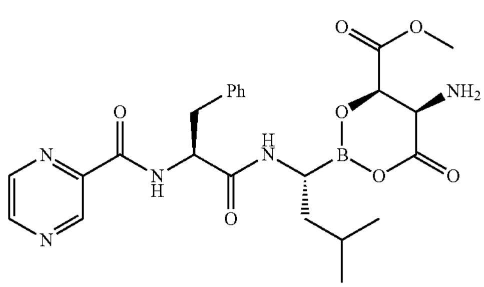 [SMILES: COC(=O)[C@@H]1OB([C@H](CC(C)C)NC(=O)[C@H](Cc2ccccc2)NC(=O)c2cnccn2)OC(=O)[C@@H]1N] | methyl (4R,5R)-5-amino-2-((R)-3-methyl-1-((S)-3-phenyl-2-(pyrazine-2-carboxamido)propanamido)butyl)-6-oxo-1,3,2-dioxaborinane-4-carboxylate |

TABLE 1-continued

| Serial # | Structure | Name |
|---|---|---|
| HL-227 | 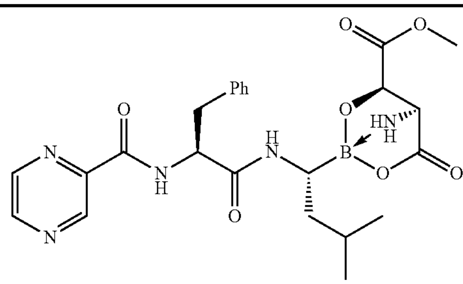 | methyl (4R,5S)-5-amino-2-((R)-3-methyl-1-((S)-3-phenyl-2-(pyrazine-2-carboxamido)propanamido)butyl)-6-oxo-1,3,2-dioxaborinane-4-carboxylate |
| HL-228 | 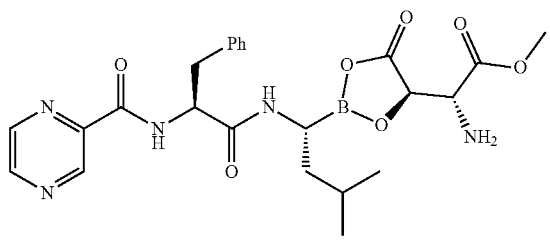 [SMILES: COC(=O)[C@H](N)[C@H]1OB([C@H](CC(C)C)NC(=O)[C@H](Cc2ccccc2)NC(=O)c2cnccn2)OC1=O] | methyl (R)-2-amino-2-((R)-2-((R)-3-methyl-1-((S)-3-phenyl-2-(pyrazine-2-carboxamido)propanamido)butyl)-5-oxo-1,3,2-dioxaborolan-4-yl)acetate |
| HL-229 | 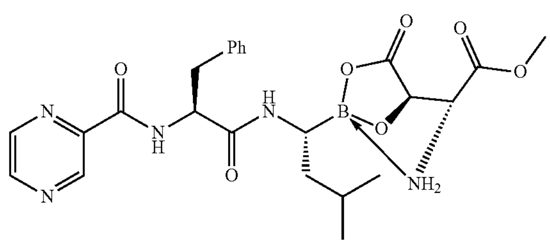 | methyl (R)-2-amino-2-((R)-2-((R)-3-methyl-1-((S)-3-phenyl-2-(pyrazine-2-carboxamido)propanamido)butyl)-5-oxo-1,3,2-dioxaborolan-4-yl)acetate |
| HL-230 | 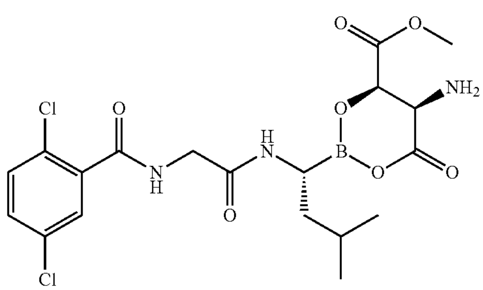 [SMILES: COC(=O)[C@@H]1OB([C@H](CC(C)C)NC(=O)CNC(=O)c2cc(Cl)ccc2Cl)OC(=O)[C@@H]1N] | methyl (4R,5R)-5-amino-2-((R)-1-(2-(2,5-dichlorobenzamido)acetamido)-3-methylbutyl)-6-oxo-1,3,2-dioxaborinane-4-carboxylate |
| HL-231 | 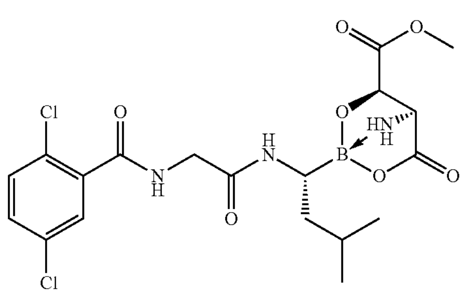 | methyl (4R,5S)-5-amino-2-((R)-1-(2-(2,5-dichlorobenzamido)acetamido)-3-methylbutyl)-6-oxo-1,3,2-dioxaborinane-4-carboxylate |
| HL-232 | 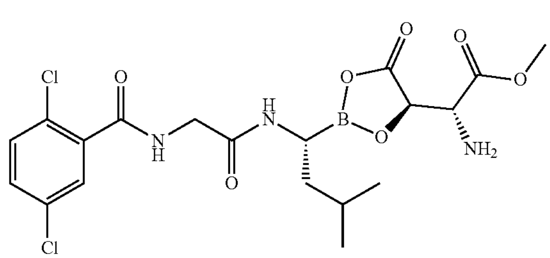 | methyl (R)-2-amino-2-((R)-2-((R)-1-(2-(2,5-dichlorobenzamido)acetamido)-3-methylbutyl)-5-oxo-1,3,2-dioxaborolan-4-yl)acetate |

TABLE 1-continued

| Serial # | Structure | Name |
|---|---|---|
| HL-233 | 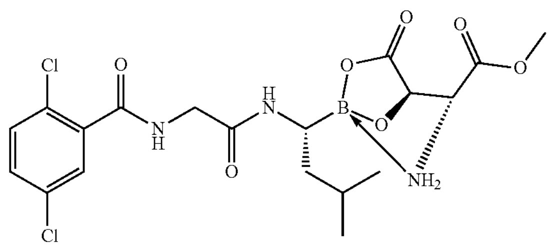 [SMILES: COC(=O)[C@@H]1[NH2+][B-]2([C@H](CC(C)C)NC(=O)CNC(=O)c3cc(Cl)ccc3Cl)OC(=O)[C@@H]1O2] | methyl (R)-2-amino-2-((R)-2-((R)-1-(2-(2,5-dichlorobenzamido)acetamido)-3-methylbutyl)-5-oxo-1,3,2-dioxaborolan-4-yl)acetate |
| HL-234 | 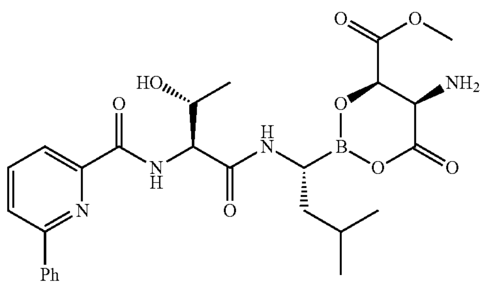 [SMILES: COC(=O)[C@@H]1OB([C@H](CC(C)C)NC(=O)[C@@H](NC(=O)c2cccc(-c3ccccc3)n2)[C@@H](C)O)OC(=O)[C@@H]1N] | methyl (4R,5R)-5-amino-2-((R)-1-((2S,3R)-3-hydroxy-2-(6-phenylpicolinamido)butanamido)-3-methylbutyl)-6-oxo-1,3,2-dioxaborinane-4-carboxylate |
| HL-235 | 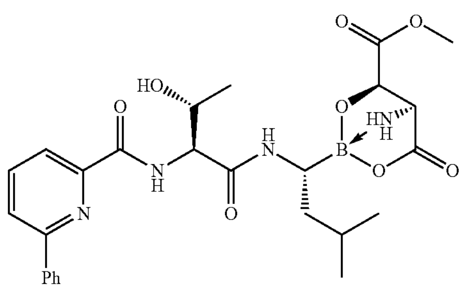 | methyl (4R,5S)-5-amino-2-((R)-1-((2S,3R)-3-hydroxy-2-(6-phenylpicolinamido)butanamido)-3-methylbutyl)-6-oxo-1,3,2-dioxaborinane-4-carboxylate |
| HL-236 | 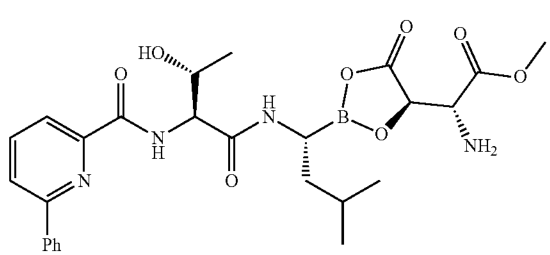 [SMILES: COC(=O)[C@H](N)[C@H]1OB([C@H](CC(C)C)NC(=O)[C@@H](NC(=O)c2cccc(-c3ccccc3)n2)[C@@H](C)O)OC1=O] | methyl (R)-2-amino-2-((R)-2-((R)-1-((2S,3R)-3-hydroxy-2-(6-phenylpicolinamido)butanamido)-3-methylbutyl)-5-oxo-1,3,2-dioxaborolan-4-yl)acetate |
| HL-237 | 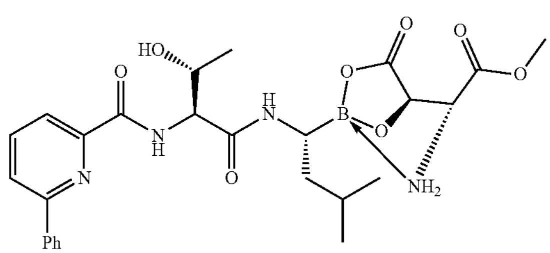 | methyl (R)-2-amino-2-((R)-2-((R)-1-((2S,3R)-3-hydroxy-2-(6-phenylpicolinamido)butanamido)-3-methylbutyl)-5-oxo-1,3,2-dioxaborolan-4-yl)acetate |

TABLE 1-continued

| Serial # | Structure | Name |
|---|---|---|
| HL-238 | 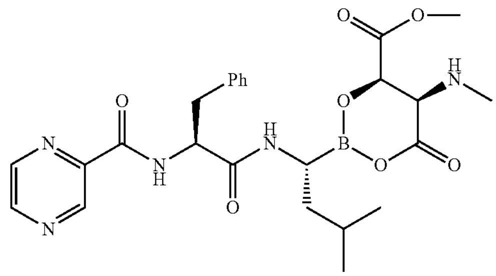 [SMILES: CN[C@H]1C(=O)OB([C@H](CC(C)C)NC(=O)[C@H](Cc2ccccc2)NC(=O)c2cnccn2)O[C@H]1C(=O)OC] | methyl (4R,5R)-2-((R)-3-methyl-1-((S)-3-phenyl-2-(pyrazine-2-carboxamido)propanamido)butyl)-5-(methylamino)-6-oxo-1,3,2-dioxaborinane-4-carboxylate |
| HL-239 | 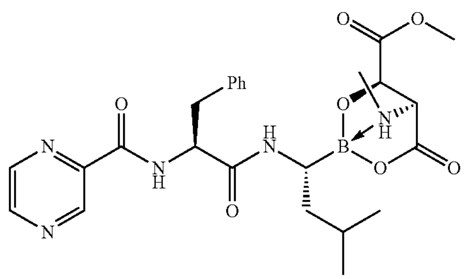 [SMILES: COC(=O)[C@@H]1O[B-]2([C@H](CC(C)C)NC(=O)[C@H](Cc3ccccc3)NC(=O)c3cnccn3)OC(=O)[C@H]1[NH+]2C] | methyl (4R,5S)-2-((R)-3-methyl-1-((S)-3-phenyl-2-(pyrazine-2-carboxamido)propanamido)butyl)-5-(methylamino)-6-oxo-1,3,2-dioxaborinane-4-carboxylate |
| HL-240 | 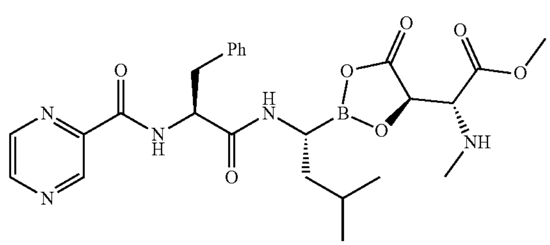 [SMILES: CN[C@@H](C(=O)OC)[C@H]1OB([C@H](CC(C)C)NC(=O)[C@H](Cc2ccccc2)NC(=O)c2cnccn2)OC1=O] | methyl (R)-2-((R)-2-((R)-3-methyl-1-((S)-3-phenyl-2-(pyrazine-2-carboxamido)propanamido)butyl)-5-oxo-1,3,2-dioxaborolan-4-yl)-2-(methylamino)acetate |
| HL-241 | 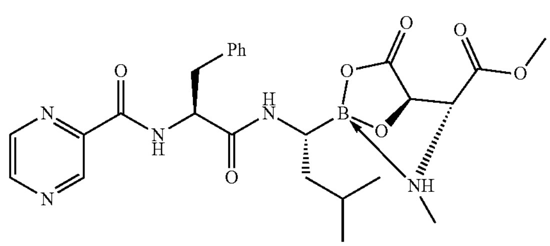 [SMILES: COC(=O)[C@H]1[C@H]2O[B-]([C@H](CC(C)C)NC(=O)[C@H](Cc3ccccc3)NC(=O)c3cnccn3)(OC2=O)[NH+]1C] | methyl (R)-2-((R)-2-((R)-3-methyl-1-((S)-3-phenyl-2-(pyrazine-2-carboxamido)propanamido)butyl)-5-oxo-1,3,2-dioxaborolan-4-yl)-2-(methylamino)acetate |
| HL-242 | 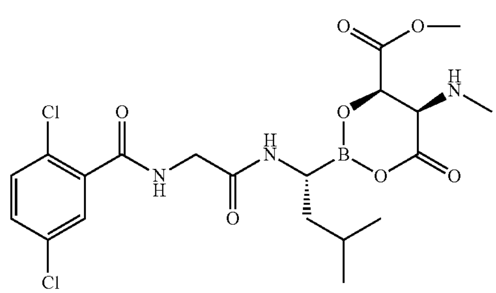 [SMILES: CN[C@H]1C(=O)OB([C@H](CC(C)C)NC(=O)CNC(=O)c2cc(Cl)ccc2Cl)O[C@H]1C(=O)OC] | methyl (4R,5R)-2-((R)-1-(2-(2,5-dichlorobenzamido)acetamido)-3-methylbutyl)-5-(methylamino)-6-oxo-1,3,2-dioxaborinane-4-carboxylate |

TABLE 1-continued

| Serial # | Structure | Name |
|---|---|---|
| HL-243 | 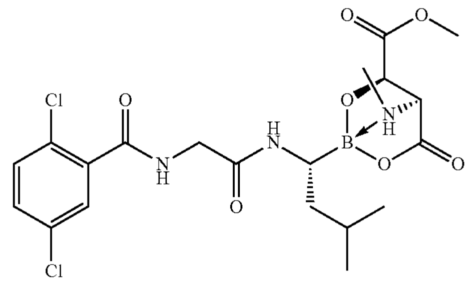 [SMILES: COC(=O)[C@@H]1O[B-]2([C@H](CC(C)C)NC(=O)CNC(=O)c3cc(Cl)ccc3Cl)OC(=O)[C@H]1[NH+]2C] | methyl (4R,5S)-2-((R)-1-(2-(2,5-dichlorobenzamido)acetamido)-3-methylbutyl)-5-(methylamino)-6-oxo-1,3,2-dioxaborinane-4-carboxylate |
| HL-244 | 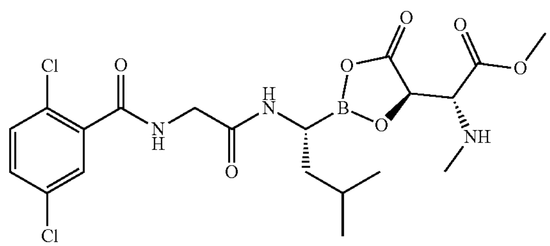 [SMILES: CN[C@@H](C(=O)OC)[C@H]1OB([C@H](CC(C)C)NC(=O)CNC(=O)c2cc(Cl)ccc2Cl)OC1=O] | methyl (R)-2-((R)-2-((R)-1-(2-(2,5-dichlorobenzamido)acetamido)-3-methylbutyl)-5-oxo-1,3,2-dioxaborolan-4-yl)-2-(methylamino)acetate |
| HL-245 | 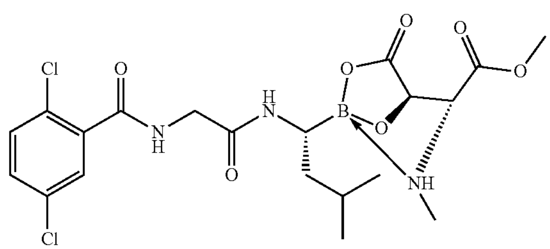 [SMILES: COC(=O)[C@H]1[C@H]2O[B-]([C@H](CC(C)C)NC(=O)CNC(=O)c3cc(Cl)ccc3Cl)(OC2=O)[NH+]1C] | methyl (R)-2-((R)-2-((R)-1-(2-(2,5-dichlorobenzamido)acetamido)-3-methylbutyl)-5-oxo-1,3,2-dioxaborolan-4-yl)-2-(methylamino)acetate |
| HL-246 | 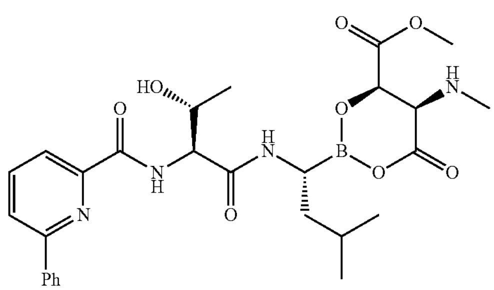 [SMILES: CN[C@H]1C(=O)OB([C@H](CC(C)C)NC(=O)[C@@H](NC(=O)c2cccc(-c3ccccc3)n2)[C@@H](C)O)O[C@H]1C(=O)OC] | methyl (4R,5R)-2-((R)-1-((2S,3R)-3-hydroxy-2-(6-phenylpicolinamido)butanamido)-3-methylbutyl)-5-(methylamino)-6-oxo-1,3,2-dioxaborinane-4-carboxylate |
| HL-247 | 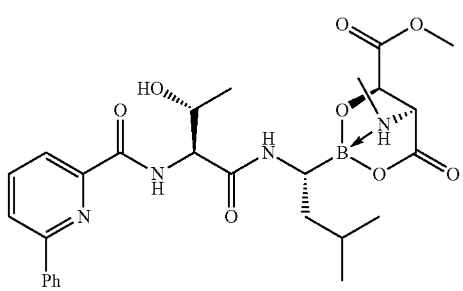 [SMILES: COC(=O)[C@@H]1O[B-]2([C@H](CC(C)C)NC(=O)[C@@H](NC(=O)c3cccc(-c4ccccc4)n3)[C@@H](C)O)OC(=O)[C@H]1[NH+]2C] | methyl (4R,5S)-2-((R)-1-((2S,3R)-3-hydroxy-2-(6-phenylpicolinamido)butanamido)-3-methylbutyl)-5-(methylamino)-6-oxo-1,3,2-dioxaborinane-4-carboxylate |

TABLE 1-continued

| Serial # | Structure | Name |
|---|---|---|
| HL-248 | 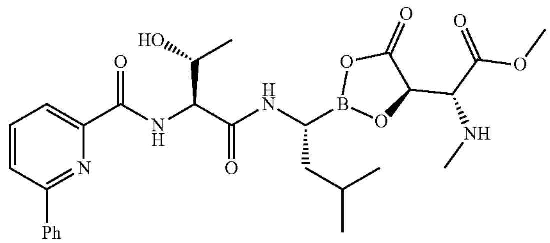 [SMILES: CN[C@@H](C(=O)OC)[C@H]1OB([C@H](CC(C)C)NC(=O)[C@@H](NC(=O)c2cccc(-c3ccccc3)n2)[C@@H](C)O)OC1=O] | methyl (R)-2-((R)-2-((R)-1-((2S,3R)-3-hydroxy-2-(6 phenylpicolinamido) butanamido)-3-methylbutyl)-5-oxo-1,3,2-dioxaborolan-4-yl)-2-(methylamino)acetate |
| HL-249 | 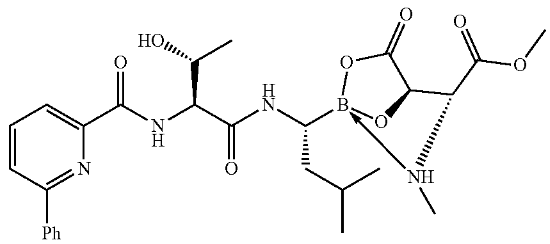 [SMILES: COC(=O)[C@H]1[C@H]2O[B-]([C@H](CC(C)C)NC(=O)[C@@H](NC(=O)c3cccc(-c4ccccc4)n3)[C@@H](C)O)(OC2=O)[NH+]1C] | methyl (R)-2-((R)-2-((R)-1-((2S,3R)-3-hydroxy-2-(6-phenylpicolinamido) butanamido)-3-methylbutyl)-5-oxo-1,3,2-dioxaborolan-4-yl)-2-(methylamino)acetate |
| HL-250 | 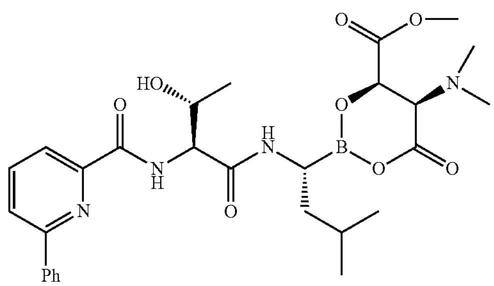 [SMILES: COC(=O)[C@@H]1OB([C@H](CC(C)C)NC(=O)[C@@H](NC(=O)c2cccc(-c3ccccc3)n2)[C@@H](C)O)OC(=O)[C@@H]1N(C)C] | methyl (4R,5R)-5-(dimethylamino)-2-((R)-1-((2S,3R)-3-hydroxy-2-(6-phenylpicolinamido) butanamido)-3-methylbutyl)-6-oxo-1,3,2-dioxaborinane-4-carboxylate |
| HL-251 | 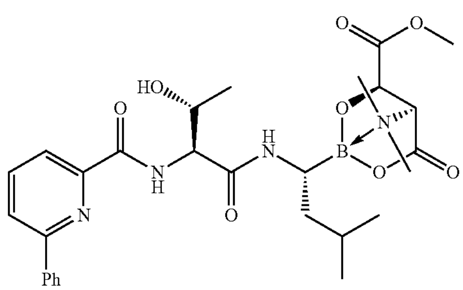 [SMILES: COC(=O)[C@@H]1O[B-]2([C@H](CC(C)C)NC(=O)[C@@H](NC(=O)c3cccc(-c4ccccc4)n3)[C@@H](C)O)OC(=O)[C@H]1[N+]2(C)C] | methyl (4R,5S)-5-(dimethylamino)-2-((R)-1-((2S,3R)-3-hydroxy-2-(6 phenylpicolinamido) butanamido)-3-methylbutyl)-6-oxo-1,3,2-dioxaborinane-4-carboxylate |
| HL-252 | 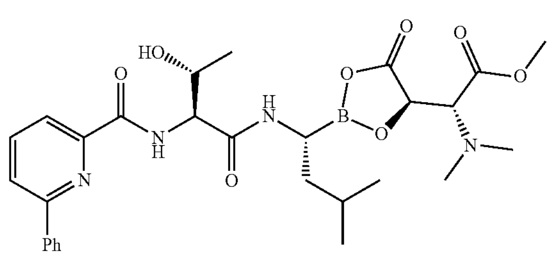 [SMILES: COC(=O)[C@@H]([C@H]1OB([C@H](CC(C)C)NC(=O)[C@@H](NC(=O)c2cccc(-c3ccccc3)n2)[C@@H](C)O)OC1=O)N(C)C] | methyl (R)-2-(dimethylamino)-2-((R)-2-((R)-1-((2S,3R)-3-hydroxy-2-(6-phenylpicolinamido) butanamido)-3-methylbutyl)-5-oxo-1,3,2-dioxaborolan-4-yl)acetate |
| HL-253 | 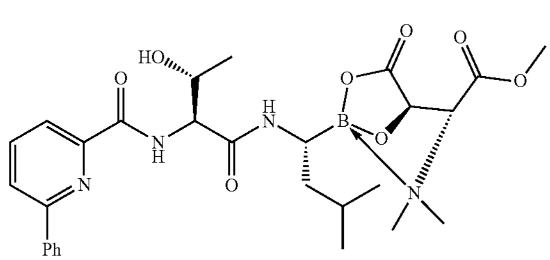 [SMILES: COC(=O)[C@H]1[C@H]2O[B-]([C@H](CC(C)C)NC(=O)[C@@H](NC(=O)c3cccc(-c4ccccc4)n3)[C@@H](C)O)(OC2=O)[N+]1(C)C] | methyl (R)-2-(dimethylamino)-2-((R)-2-((R)-1-((2S,3R)-3-hydroxy-2-(6-phenylpicolinamido) butanamido)-3-methylbutyl)-5-oxo-1,3,2-dioxaborolan-4-yl)acetate |

TABLE 1-continued

| Serial # | Structure | Name |
|---|---|---|
| HL-254 | 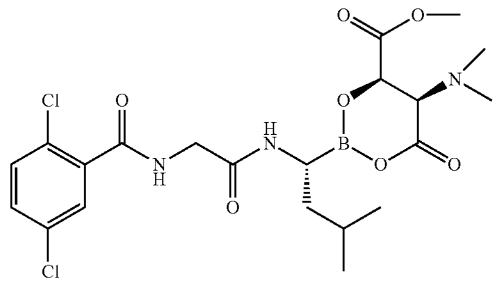 [SMILES: COC(=O)[C@@H]1OB([C@H](CC(C)C)NC(=O)CNC(=O)c2cc(Cl)ccc2Cl)OC(=O)[C@@H]1N(C)C] | methyl (4R,5R)-2-((R)-1-(2-(2,5-dichlorobenzamido)acetamido)-3-methylbutyl)-5-(dimethylamino)-6-oxo-1,3,2-dioxaborinane-4-carboxylate |
| HL-255 | 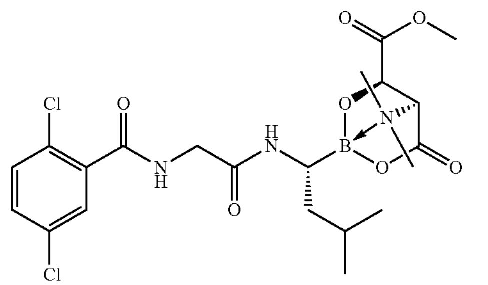 [SMILES: COC(=O)[C@@H]1O[B-]2([C@H](CC(C)C)NC(=O)CNC(=O)c3cc(Cl)ccc3Cl)OC(=O)[C@H]1[N+]2(C)C] | methyl (4R,5S)-2-((R)-1-(2-(2,5-dichlorobenzamido)acetamido)-3-methylbutyl)-5-(dimethylamino)-6-oxo-1,3,2-dioxaborinane-4-carboxylate |
| HL-256 | 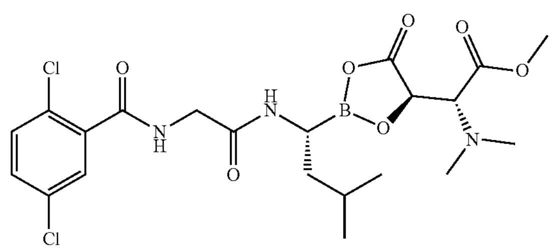 [SMILES: COC(=O)[C@@H]([C@H]1OB([C@H](CC(C)C)NC(=O)CNC(=O)c2cc(Cl)ccc2Cl)OC1=O)N(C)C] | methyl (R)-2-((R)-2-((R)-1-(2-(2,5-dichlorobenzamido)acetamido)-3-methylbutyl)-5-oxo-1,3,2-dioxaborolan-4-yl)-2-(dimethylamino)acetate |
| HL-257 | 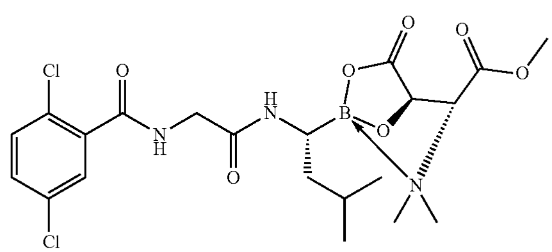 [SMILES: COC(=O)[C@H]1[C@H]2O[B-]([C@H](CC(C)C)NC(=O)CNC(=O)c3cc(Cl)ccc3Cl)(OC2=O)[N+]1(C)C] | methyl (R)-2-((R)-2-((R)-1-(2-(2,5-dichlorobenzamido)acetamido)-3-methylbutyl)-5-oxo-1,3,2-dioxaborolan-4-yl)-2-(dimethylamino)acetate |
| HL-258 | 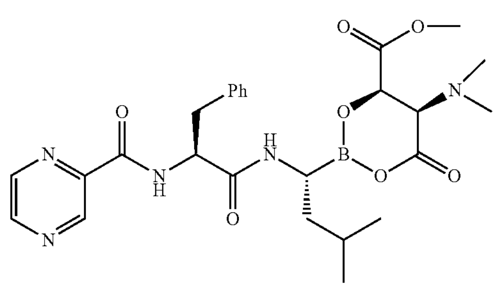 [SMILES: COC(=O)[C@@H]1OB([C@H](CC(C)C)NC(=O)[C@H](Cc2ccccc2)NC(=O)c2cnccn2)OC(=O)[C@@H]1N(C)C] | methyl (4R,5R)-5-(dimethylamino)-2-((R)-3-methyl-1-((S)-3-phenyl-2-(pyrazine-2-carboxamido)propanamido)butyl)-6-oxo-1,3,2-dioxaborinane-4-carboxylate |

TABLE 1-continued

| Serial # | Structure | Name |
|---|---|---|
| HL-259 | 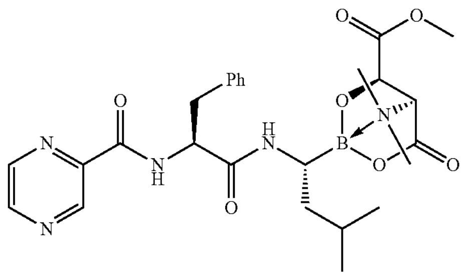 [SMILES: COC(=O)[C@@H]1O[B-]2([C@H](CC(C)C)NC(=O)[C@H](Cc3ccccc3)NC(=O)c3cnccn3)OC(=O)[C@H]1[N+]2(C)C] | methyl (4R,5S)-5-(dimethylamino)-2-((R)-3-methyl-1-((S)-3-phenyl-2-(pyrazine-2-carboxamido)propanamido)butyl)-6-oxo-1,3,2-dioxaborinane-4-carboxylate |
| HL-260 | 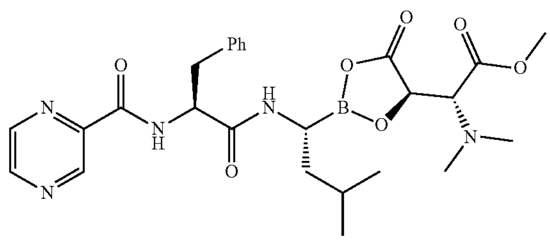 [SMILES: COC(=O)[C@@H]([C@H]1OB([C@H](CC(C)C)NC(=O)[C@H](Cc2ccccc2)NC(=O)c2cnccn2)OC1=O)N(C)C] | methyl (R)-2-(dimethylamino)-2-((R)-2-(R)-3-methyl-1-((S)-3-phenyl-2-(pyrazine-2-carboxamido)propanamido)butyl)-5-oxo-1,3,2-dioxaborolan-4-yl)acetate |
| HL-261 | 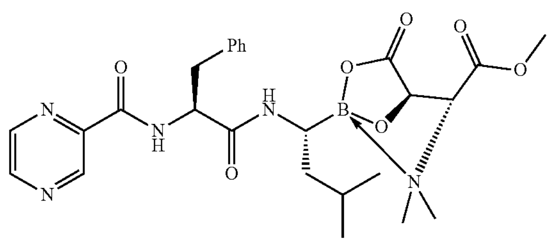 [SMILES: COC(=O)[C@H]1[C@H]2O[B-]([C@H](CC(C)C)NC(=O)[C@H](Cc3ccccc3)NC(=O)c3cnccn3)(OC2=O)[N+]1(C)C] | methyl (R)-2-(dimethylamino)-2-((R)-2-((R)-3-methyl-1-((S)-3-phenyl-2-(pyrazine-2-carboxamido)propanamido)butyl)-5-oxo-1,3,2-dioxaborolan-4-yl)acetate |
| HL-262 | 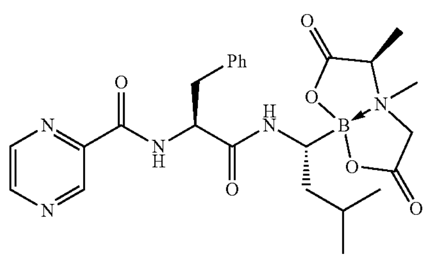 [SMILES: CC(C)C[C@H](NC(=O)[C@H](Cc1ccccc1)NC(=O)c1cnccn1)[B-]12OC(=O)C[N+]1(C)[C@H](C)C(=O)O2] | N-((S)-1-(((R)-1-((R)-5,6-dimethyl-4,8-dioxo-1,3,6,2-dioxazaborocan-2-yl)-3-methylbutyl)amino)-1-oxo-3-phenylpropan-2-yl)pyrazine-2-carboxamide |
| HL-263 | 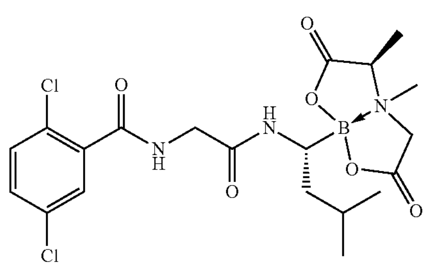 [SMILES: CC(C)C[C@H](NC(=O)CNC(=O)c1cc(Cl)ccc1Cl)[B-]12OC(=O)C[N+]1(C)[C@H](C)C(=O)O2] | 2,5-dichloro-N-(2-(((R)-1-((R)-5,6-dimethyl-4,8-dioxo-1,3,6,2-dioxazaborocan-2-yl)-3-methylbutyl)amino)-2-oxoethyl)benzamide |
| HL-264 | 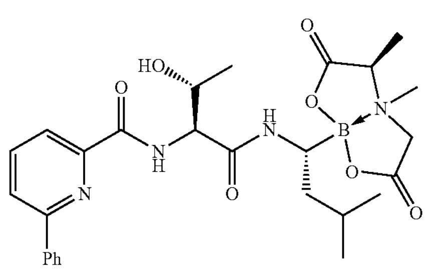 [SMILES: CC(C)C[C@H](NC(=O)[C@@H](NC(=O)c1cccc(-c2ccccc2)n1)[C@@H](C)O)[B-]12OC(=O)C[N+]1(C)[C@H](C)C(=O)O2] | N-((2S,3R)-1-(((R)-1-((R)-5,6-dimethyl-4,8-dioxo-1,3,6,2-dioxazaborocan-2-yl)-3-methylbutyl)amino)-3-hydroxy-1-oxobutan-2-yl)-6-phenylpicolinamide |

TABLE 1-continued

| Serial # | Structure | Name |
|---|---|---|
| HL-265 | 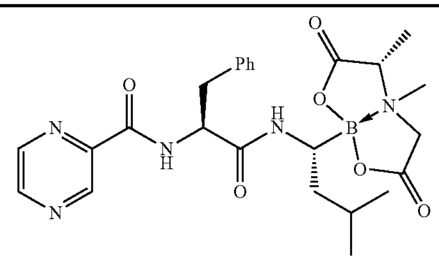 | N-((S)-1-(((R)-1-((R)-5,6-dimethyl-4,8-dioxo-1,3,6,2-dioxazaborocan-2-yl)-3-methylbutyl)amino)-1-oxo-3-phenylpropan-2-yl)pyrazine-2-carboxamide |
| HL-266 | 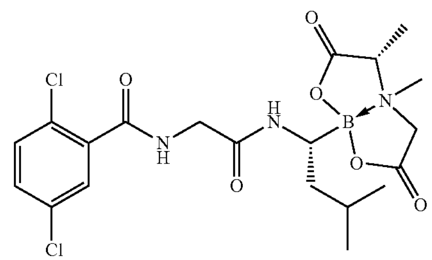 [SMILES: CC(C)C[C@H](NC(=O)CNC(=O)c1cc(Cl)ccc1Cl)[B-]12OC(=O)C[N+]1(C)[C@@H](C)C(=O)O2] | 2,5-dichloro-N-(2-(((R)-1-((R)-5,6-dimethyl-4,8-dioxo-1,3,6,2-dioxazaborocan-2-yl)-3-methylbutyl)amino)-2-oxoethyl)benzamide |
| HL-267 | 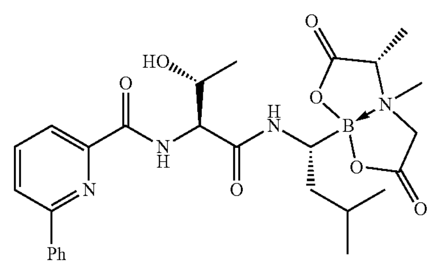 [SMILES: CC(C)C[C@H](NC(=O)[C@@H](NC(=O)c1cccc(-c2ccccc2)n1)[C@@H](C)O)[B-]12OC(=O)C[N+]1(C)[C@@H](C)C(=O)O2] | N-((2S,3R)-1-(((R)-1-((R)-5,6-dimethyl-4,8-dioxo-1,3,6,2-dioxazaborocan-2-yl)-3-methylbutyl)amino)-3-hydroxy-1-oxobutan-2-yl)-6-phenylpicolinamide |
| HL-268 | 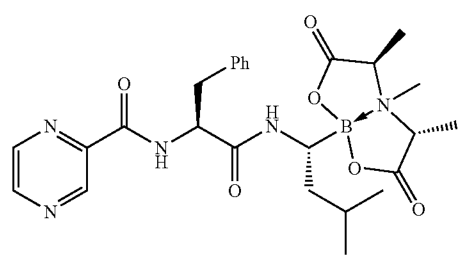 [SMILES: CC(C)C[C@H](NC(=O)[C@H](Cc1ccccc1)NC(=O)c1cnccn1)[B-]12OC(=O)[C@@H](C)[N+]1(C)[C@H](C)C(=O)O2] | N-((S)-1-(((R)-3-methyl-1-((5R,7R)-5,6,7-trimethyl-4,8-dioxo-1,3,6,2-dioxazaborocan-2-yl)butyl)amino)-1-oxo-3-phenylpropan-2-yl)pyrazine-2-carboxamide |
| HL-269 | 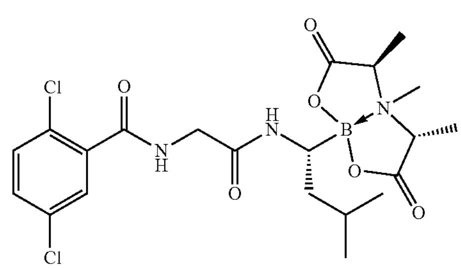 [SMILES: CC(C)C[C@H](NC(=O)CNC(=O)c1cc(Cl)ccc1Cl)[B-]12OC(=O)[C@@H](C)[N+]1(C)[C@H](C)C(=O)O2] | 2,5-dichloro-N-(2-(((R)-3-methyl-1-((5R,7R)-5,6,7-trimethyl-4,8-dioxo-1,3,6,2-dioxazaborocan-2-yl)butyl)amino)-2-oxoethyl)benzamide |
| HL-270 | 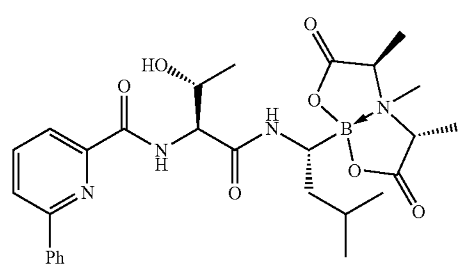 [SMILES: CC(C)C[C@H](NC(=O)[C@@H](NC(=O)c1cccc(-c2ccccc2)n1)[C@@H](C)O)[B-]12OC(=O)[C@@H](C)[N+]1(C)[C@H](C)C(=O)O2] | N-((2S,3R)-3-hydroxy-1-(((R)-3-methyl-1-((5R,7R)-5,6,7-trimethyl-4,8-dioxo-1,3,6,2-dioxazaborocan-2-yl)butyl)amino)-1-oxobutan-2-yl)-6-phenylpicolinamide |

TABLE 1-continued

| Serial # | Structure | Name |
| --- | --- | --- |
| HL-271 | 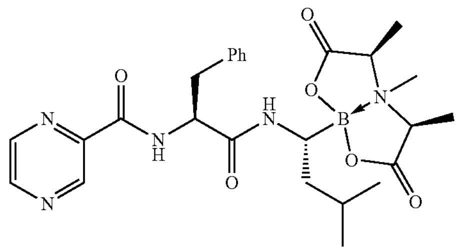 [SMILES: CC(C)C[C@H](NC(=O)[C@H](Cc1ccccc1)NC(=O)c1cnccn1)[B-]12OC(=O)[C@@H](C)[N+]1(C)[C@@H](C)C(=O)O2] | N-((S)-1-(((R)-3-methyl-1-((5R,7S)-5,6,7-trimethyl-4,8-dioxo-1,3,6,2-dioxazaborocan-2-yl)butyl)amino)-1-oxo-3-phenylpropan-2-yl)pyrazine-2-carboxamide |
| HL-272 | 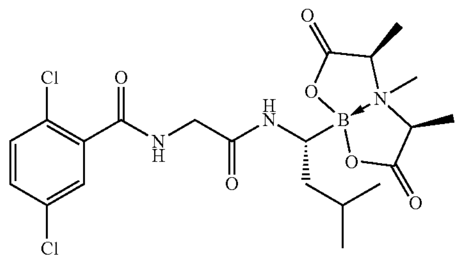 [SMILES: CC(C)C[C@H](NC(=O)CNC(=O)c1cc(Cl)ccc1Cl)[B-]12OC(=O)[C@@H](C)[N+]1(C)[C@@H](C)C(=O)O2] | 2,5-dichloro-N-(2-(((R)-3-methyl-1-((5R,7S)-5,6,7-trimethyl-4,8-dioxo-1,3,6,2-dioxazaborocan-2-yl)butyl)amino)-2-oxoethyl)benzamide |
| HL-273 | 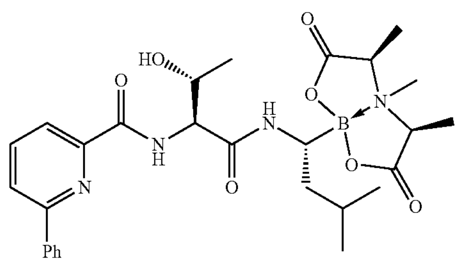 [SMILES: CC(C)C[C@H](NC(=O)[C@@H](NC(=O)c1cccc(-c2ccccc2)n1)[C@@H](C)O)[B-]12OC(=O)[C@@H](C)[N+]1(C)[C@@H](C)C(=O)O2] | N-((2S,3R)-3-hydroxy-1-(((R)-3-methyl-1-((5R,7S)-5,6,7-trimethyl-4,8-dioxo-1,3,6,2-dioxazaborocan-2-yl)butyl)amino)-1-oxobutan-2-yl)-6-phenylpicolinamide |
| HL-274 | 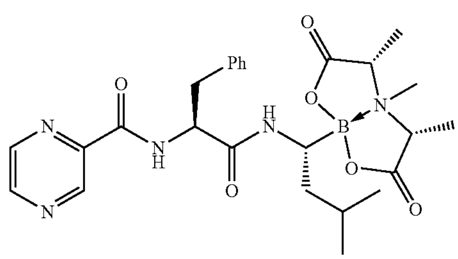 [SMILES: CC(C)C[C@H](NC(=O)[C@H](Cc1ccccc1)NC(=O)c1cnccn1)[B-]12OC(=O)[C@@H](C)[N+]1(C)[C@@H](C)C(=O)O2] | N-((S)-1-(((R)-3-methyl-1-((5R,7R)-5,6,7-trimethyl-4,8-dioxo-1,3,6,2-dioxazaborocan-2-yl)butyl)amino)-1-oxo-3-phenylpropan-2-yl)pyrazine-2-carboxamide |
| HL-275 | 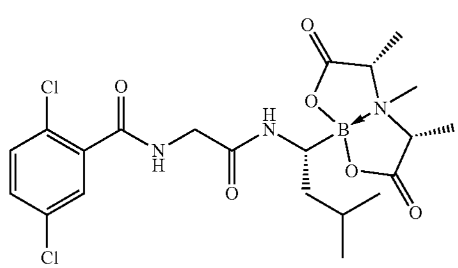 [SMILES: CC(C)C[C@H](NC(=O)CNC(=O)c1cc(Cl)ccc1Cl)[B-]12OC(=O)[C@@H](C)[N+]1(C)[C@@H](C)C(=O)O2] | 2,5-dichloro-N-(2-(((R)-3-methyl-1-((5R,7R)-5,6,7-trimethyl-4,8-dioxo-1,3,6,2-dioxazaborocan-2-yl)butyl)amino)-2-oxoethyl)benzamide |
| HL-276 | 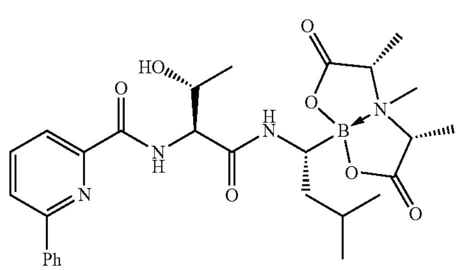 [SMILES: CC(C)C[C@H](NC(=O)[C@@H](NC(=O)c1cccc(-c2ccccc2)n1)[C@@H](C)O)[B-]12OC(=O)[C@@H](C)[N+]1(C)[C@@H](C)C(=O)O2] | N-((2S,3R)-3-hydroxy-1-(((R)-3-methyl-1-((5R,7R)-5,6,7-trimethyl-4,8-dioxo-1,3,6,2-dioxazaborocan-2-yl)butyl)amino)-1-oxobutan-2-yl)-6-phenylpicolinamide |

TABLE 1-continued

| Serial # | Structure | Name |
|---|---|---|
| HL-277 | 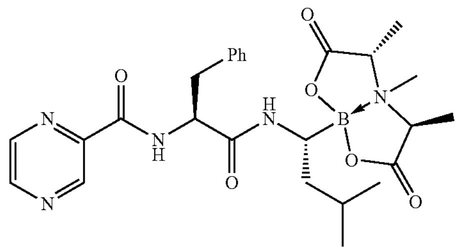 [SMILES: CC(C)C[C@H](NC(=O)[C@H](Cc1ccccc1)NC(=O)c1cnccn1)[B-]12OC(=O)[C@H](C)[N+]1(C)[C@@H](C)C(=O)O2] | N-((S)-1-(((R)-3-methyl-1-((5R,7S)-5,6,7-trimethyl-4,8-dioxo-1,3,6,2-dioxazaborocan-2-yl)butyl)amino)-1-oxo-3-phenylpropan-2-yl)pyrazine-2-carboxamide |
| HL-278 | 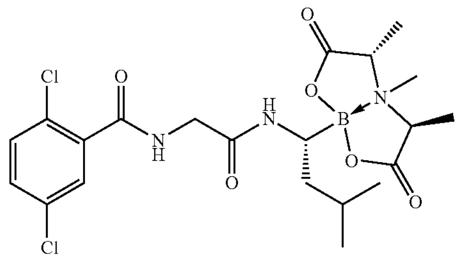 [SMILES: CC(C)C[C@H](NC(=O)CNC(=O)c1cc(Cl)ccc1Cl)[B-]12OC(=O)[C@H](C)[N+]1(C)[C@@H](C)C(=O)O2] | 2,5-dichloro-N-(2-(((R)-3-methyl-1-((5R,7S)-5,6,7-trimethyl-4,8-dioxo-1,3,6,2-dioxazaborocan-2-yl)butyl)amino)-2-oxoethyl)benzamide |
| HL-279 | 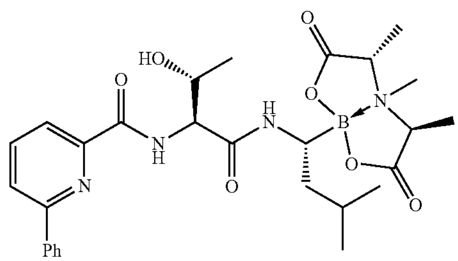 [SMILES: CC(C)C[C@H](NC(=O)[C@@H](NC(=O)c1cccc(-c2ccccc2)n1)[C@@H](C)O)[B-]12OC(=O)[C@H](C)[N+]1(C)[C@@H](C)C(=O)O2] | N-((2S,3R)-3-hydroxy-1-(((R)-3-methyl-1-((5R,7S)-5,6,7-trimethyl-4,8-dioxo-1,3,6,2-dioxazaborocan-2-yl)butyl)amino)-1-oxobutan-2-yl)-6-phenylpicolinamide |
| HL-280 | 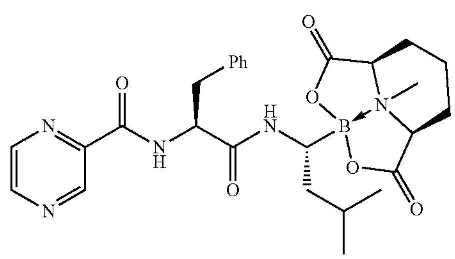 | N-((S)-1-(((R)-3-methyl-1-((1R,7S)-11-methyl-2,6-dioxo-3,5-dioxa-11-aza-4-borabicyclo[5.3.1]undecan-4-yl)butyl)amino)-1-oxo-3-phenylpropan-2-yl)pyrazine-2-carboxamide |
| HL-281 | 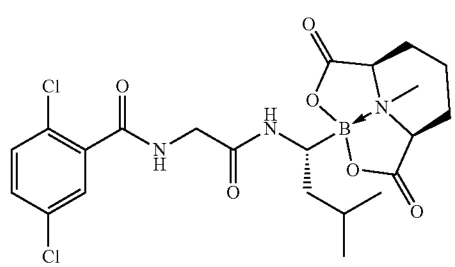 | 2,5-dichloro-N-(2-(((R)-3-methyl-1-((1R,7S)-11-methyl-2,6-dioxo-3,5-dioxa-11-aza-4-borabicyclo[5.3.1]undecan-4-yl)butyl)amino)-2-oxoethyl)benzamide |
| HL-282 | 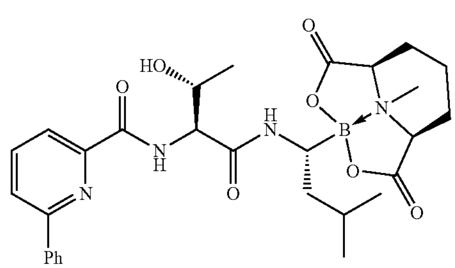 | N-((2S,3R)-3-hydroxy-1-(((R)-3-methyl-1-((1R,7S)-11-methyl-2,6-dioxo-3,5-dioxa-11-aza-4-borabicyclo[5.3.1]undecan-4-yl)butyl)amino)-1-oxobutan-2-yl)-6-phenylpicolinamide |

TABLE 1-continued

| Serial # | Structure | Name |
|---|---|---|
| HL-283 | 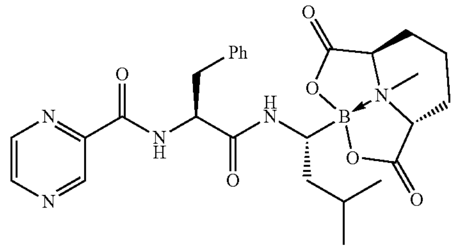 | N-((S)-1-(((R)-3-methyl-1-((1R,7R)-11-methyl-2,6-dioxo-3,5-dioxa-11-aza-4-borabicyclo[5.3.1]undecan-4-yl)butyl)amino)-1-oxo-3-phenylpropan-2-yl)pyrazine-2-carboxamide |
| HL-284 | 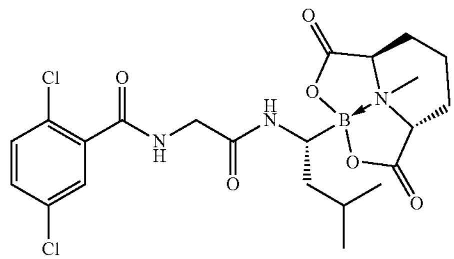 | 2,5-dichloro-N-(2-(((R)-3-methyl-1-((1R,7R)-11-methyl-2,6-dioxo-3,5-dioxa-11-aza-4-borabicyclo[5.3.1]undecan-4-yl)butyl)amino)-2-oxoethyl)benzamide |
| HL-285 | 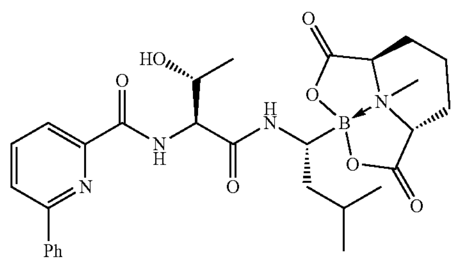 | N-((2S,3R)-3-hydroxy-1-(((R)-3-methyl-1-((1R,7R)-11-methyl-2,6-dioxo-3,5-dioxa-11-aza-4-borabicyclo[5.3.1]undecan-4-yl)butyl)amino)-1-oxobutan-2-yl)-6-phenylpicolinamide |
| HL-286 | 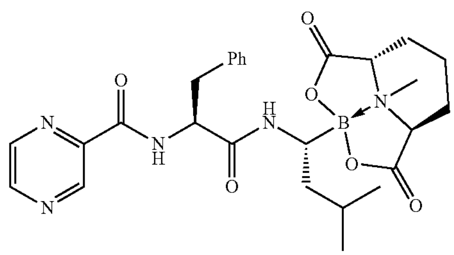 | N-((S)-1-(((R)-3-methyl-1-((1S,7S)-11-methyl-2,6-dioxo-3,5-dioxa-11-aza-4-borabicyclo[5.3.1]undecan-4-yl)butyl)amino)-1-oxo-3-phenylpropan-2-yl)pyrazine-2-carboxamide |
| HL-287 | 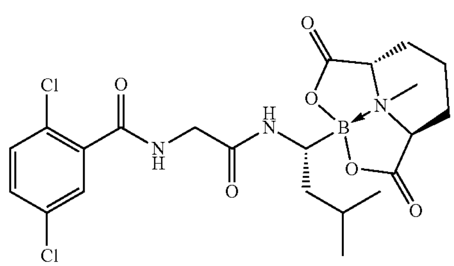 | 2,5-dichloro-N-(2-(((R)-3-methyl-1-((1S,7S)-11-methyl-2,6-dioxo-3,5-dioxa-11-aza-4-borabicyclo[5.3.1]undecan-4-yl)butyl)amino)-2-oxoethyl)benzamide |
| HL-288 | 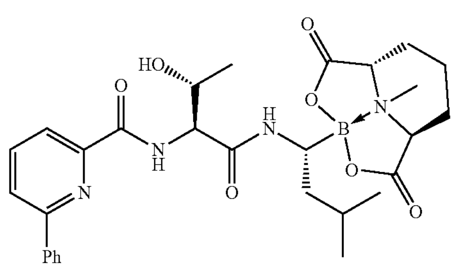 | N-((2S,3R)-3-hydroxy-1-(((R)-3-methyl-1-((1S,7S)-11-methyl-2,6-dioxo-3,5-dioxa-11-aza-4-borabicyclo[5.3.1]undecan-4-yl)butyl)amino)-1-oxobutan-2-yl)-6-phenylpicolinamide |

TABLE 1-continued

| Serial # | Structure | Name |
|---|---|---|
| HL-289 | 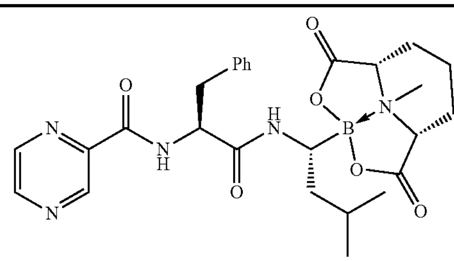 | N-((S)-1-(((R)-3-methyl-1-((1R,7S)-11-methyl-2,6-dioxo-3,5-dioxa-11-aza-4-borabicyclo[5.3.1]undecan-4-yl)butyl)amino)-1-oxo-3-phenylpropan-2-yl)pyrazine-2-carboxamide |
| HL-290 | 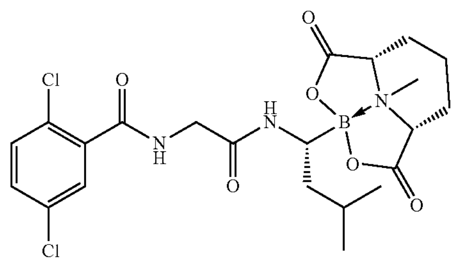 | 2,5-dichloro-N-(2-(((R)-3-methyl-1-((1R,7S)-11-methyl-2,6-dioxo-3,5-dioxa-11-aza-4-borabicyclo[5.3.1]undecan-4-yl)butyl)amino)-2-oxoethyl)benzamide |
| HL-291 | 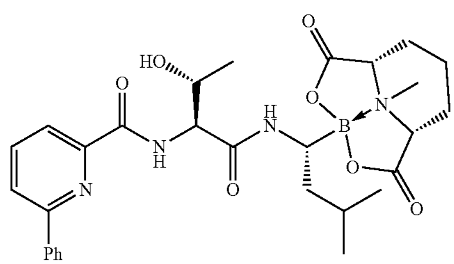 | N-((2S,3R)-3-hydroxy-1-(((R)-3-methyl-1-((1R,7S)-11-methyl-2,6-dioxo-3,5-dioxa-11-aza-4-borabicyclo[5.3.1]undecan-4-yl)butyl)amino)-1-oxobutan-2-yl)-6-phenylpicolinamide |
| HL-292 | 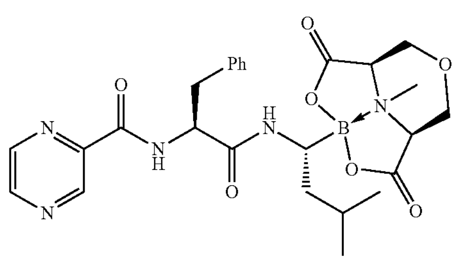 | N-((S)-1-(((R)-3-methyl-1-((1R,7S)-11-methyl-2,6-dioxo-3,5,9-trioxa-11-aza-4-borabicyclo[5.3.1]undecan-4-yl)butyl)amino)-1-oxo-3-phenylpropan-2-yl)pyrazine-2-carboxamide |
| HL-293 | 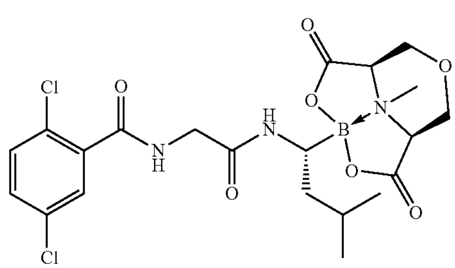 | 2,5-dichloro-N-(2-(((R)-3-methyl-1-((1R,7S)-11-methyl-2,6-dioxo-3,5,9-trioxa-11-aza-4-borabicyclo[5.3.1]undecan-4-yl)butyl)amino)-2-oxoethyl)benzamide |
| HL-294 | 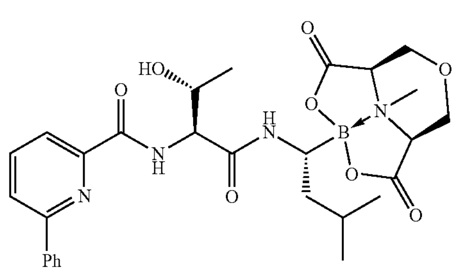 | N-((2S,3R)-3-hydroxy-1-(((R)-3-methyl-1-((1R,7S)-11-methyl-2,6-dioxo-3,5,9-trioxa-11-aza-4-borabicyclo[5.3.1]undecan-4-yl)butyl)amino)-1-oxobutan-2-yl)-6-phenylpicolinamide |

TABLE 1-continued

| Serial # | Structure | Name |
|---|---|---|
| HL-295 | 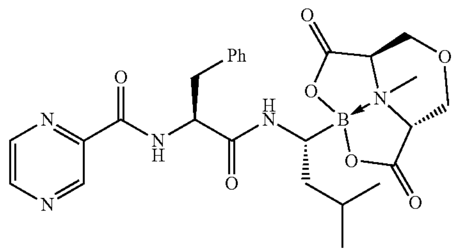 | N-((S)-1-(((R)-3-methyl-1-((1R,7R)-11-methyl-2,6-dioxo-3,5,9-trioxa-11-aza-4-borabicyclo[5.3.1]undecan-4-yl)butyl)amino)-1-oxo-3-phenylpropan-2-yl)pyrazine-2-carboxamide |
| HL-296 | 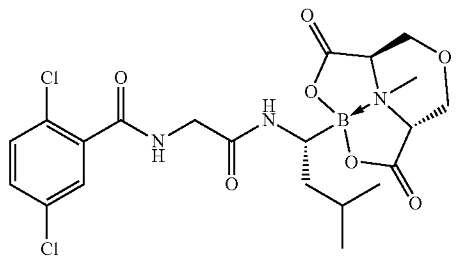 | 2,5-dichloro-N-(2-(((R)-3-methyl-1-((1R,7R)-11-methyl-2,6-dioxo-3,5,9-trioxa-11-aza-4-borabicyclo[5.3.1]undecan-4-yl)butyl)amino)-2-oxoethyl)benzamide |
| HL-297 | 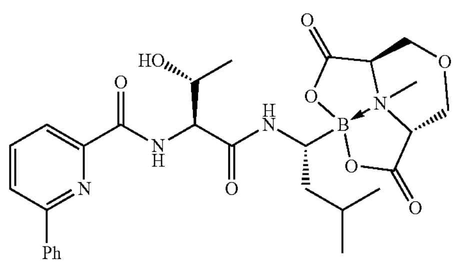 | N-((2S,3R)-3-hydroxy-1-(((R)-3-methyl-1-((1R,7R)-11-methyl-2,6-dioxo-3,5,9-trioxa-11-aza-4-borabicyclo[5.3.1]undecan-4-yl)butyl)amino)-1-oxobutan-2-yl)-6-phenylpicolinamide |
| HL-298 | 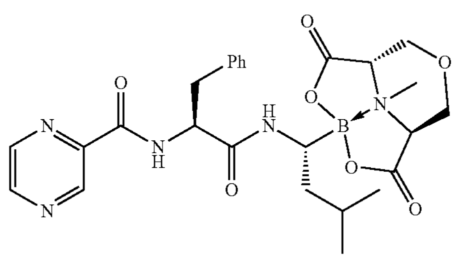 | N-((S)-1-(((R)-3-methyl-1-((1S,7S)-11-methyl-2,6-dioxo-3,5,9-trioxa-11-aza-4-borabicyclo[5.3.1]undecan-4-yl)butyl)amino)-1-oxo-3-phenylpropan-2-yl)pyrazine-2-carboxamide |
| HL-299 | 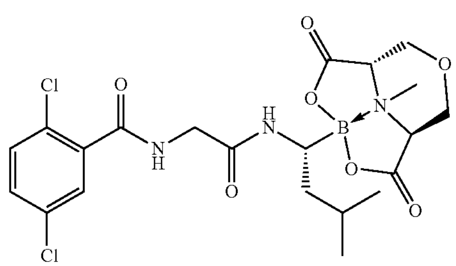 | 2,5-dichloro-N-(2-(((R)-3-methyl-1-((1S,7S)-11-methyl-2,6-dioxo-3,5,9-trioxa-11-aza-4-borabicyclo[5.3.1]undecan-4-yl)butyl)amino)-2-oxoethyl)benzamide |
| HL-300 | 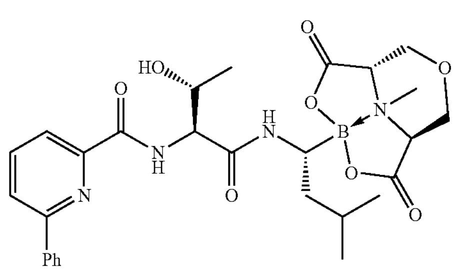 | N-((2S,3R)-3-hydroxy-1-(((R)-3-methyl-1-((1S,7S)-11-methyl-2,6-dioxo-3,5,9-trioxa-11-aza-4-borabicyclo[5.3.1]undecan-4-yl)butyl)amino)-1-oxobutan-2-yl)-6-phenylpicolinamide |

TABLE 1-continued

| Serial # | Structure | Name |
|---|---|---|
| HL-301 | 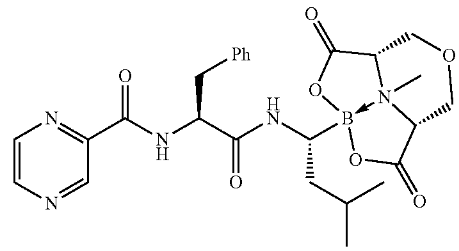 | N-((S)-1-(((R)-3-methyl-1-((1R,7S)-11-methyl-2,6-dioxo-3,5,9-trioxa-11-aza-4-borabicyclo[5.3.1]undecan-4-yl)butyl)amino)-1-oxo-3-phenylpropan-2-yl)pyrazine-2-carboxamide |
| HL-302 | 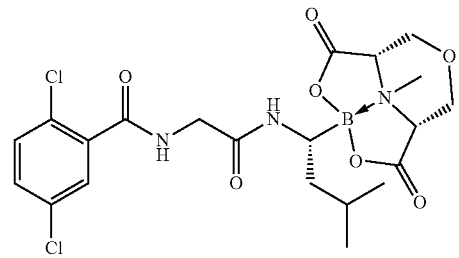 | 2,5-dichloro-N-(2-(((R)-3-methyl-1-((1R,7S)-11-methyl-2,6-dioxo-3,5,9-trioxa-11-aza-4-borabicyclo[5.3.1]undecan-4-yl)butyl)amino)-2-oxoethyl)benzamide |
| HL-303 | 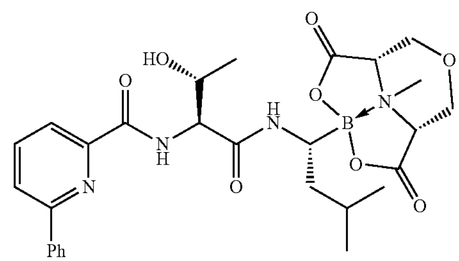 | N-((2S,3R)-3-hydroxy-1-(((R)-3-methyl-1-((1R,7S)-11-methyl-2,6-dioxo-3,5,9-trioxa-11-aza-4-borabicyclo[5.3.1]undecan-4-yl)butyl)amino)-1-oxobutan-2-yl)-6-phenylpicolinamide |
| HL-304 | 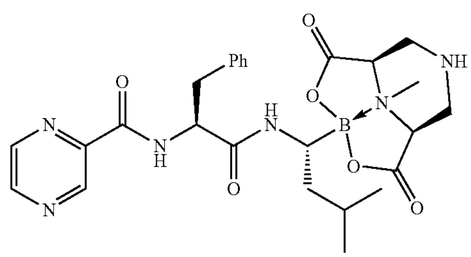 | N-((S)-1-(((R)-3-methyl-1-((1R,7S)-11-methyl-2,6-dioxo-3,5-dioxa-9,11-diaza-4-borabicyclo[5.3.1]undecan-4-yl)butyl)amino)-1-oxo-3-phenylpropan-2-yl)pyrazine-2-carboxamide |
| HL-305 | 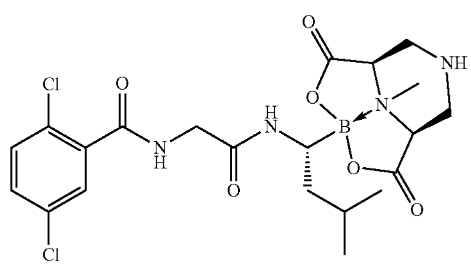 | 2,5-dichloro-N-(2-(((R)-3-methyl-1-((1R,7S)-11-methyl-2,6-dioxo-3,5-dioxa-9,11-diaza-4-borabicyclo[5.3.1]undecan-4-yl)butyl)amino)-2-oxoethyl)benzamide |
| HL-306 | 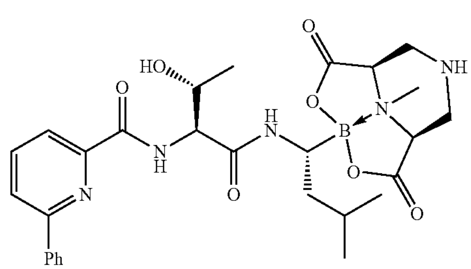 | N-((2S,3R)-3-hydroxy-1-(((R)-3-methyl-1-((1R,7S)-11-methyl-2,6-dioxo-3,5-dioxa-9,11-diaza-4-borabicyclo[5.3.1]undecan-4-yl)butyl)amino)-1-oxobutan-2-yl)-6-phenylpicolinamide |

TABLE 1-continued

| Serial # | Structure | Name |
|---|---|---|
| HL-307 | 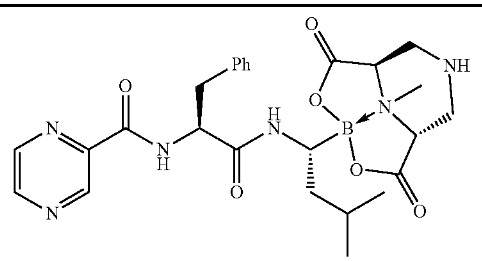 | N-((S)-1-(((R)-3-methyl-1-((1R,7R)-11-methyl-2,6-dioxo-3,5-dioxa-9,11-diaza-4-borabicyclo[5.3.1]undecan-4-yl)butyl)amino)-1-oxo-3-phenylpropan-2-yl)pyrazine-2-carboxamide |
| HL-308 | 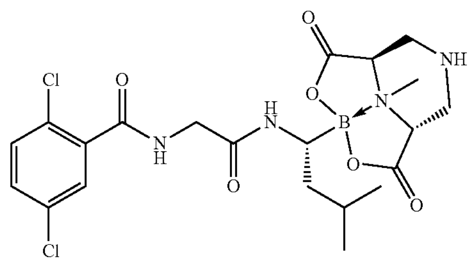 | 2,5-dichloro-N-(2-(((R)-3-methyl-1-((1R,7R)-11-methyl-2,6-dioxo-3,5-dioxa-9,11-diaza-4-borabicyclo[5.3.1]undecan-4-yl)butyl)amino)-2-oxoethyl)benzamide |
| HL-309 | 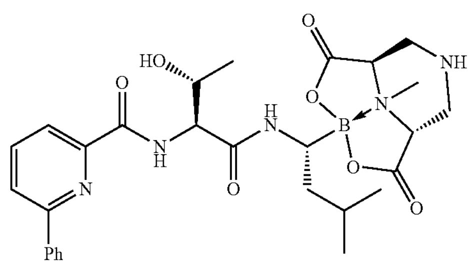 | N-((2S,3R)-3-hydroxy-1-(((R)-3-methyl-1-((1R,7R)-11-methyl-2,6-dioxo-3,5-dioxa-9,11-diaza-4-borabicyclo[5.3.1]undecan-4-yl)butyl)amino)-1-oxobutan-2-yl)-6-phenylpicolinamide |
| HL-310 | 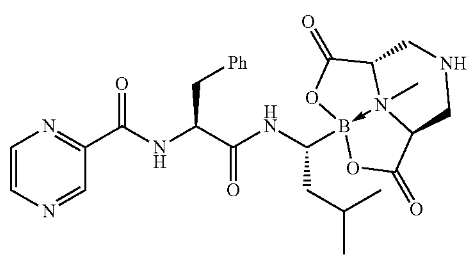 | N-((S)-1-(((R)-3-methyl-1-((1S,7S)-11-methyl-2,6-dioxo-3,5-dioxa-9,11-diaza-4-borabicyclo[5.3.1]undecan-4-yl)butyl)amino)-1-oxo-3-phenylpropan-2-yl)pyrazine-2-carboxamide |
| HL-311 | 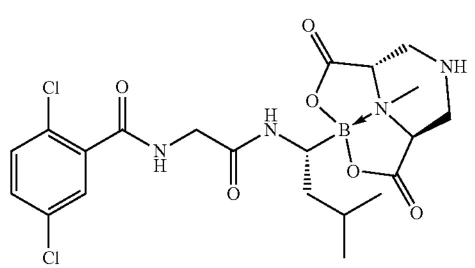 | 2,5-dichloro-N-(2-(((R)-3-methyl-1-((1S,7S)-11-methyl-2,6-dioxo-3,5-dioxa-9,11-diaza-4-borabicyclo[5.3.1]undecan-4-yl)butyl)amino)-2-oxoethyl)benzamide |
| HL-312 | 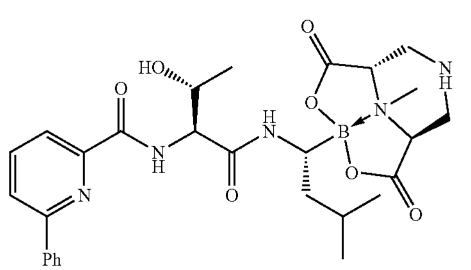 | N-((2S,3R)-3-hydroxy-1-(((R)-3-methyl-1-((1S,7S)-11-methyl-2,6-dioxo-3,5-dioxa-9,11-diaza-4-borabicyclo[5.3.1]undecan-4-yl)butyl)amino)-1-oxobutan-2-yl)-6-phenylpicolinamide |

TABLE 1-continued

| Serial # | Structure | Name |
|---|---|---|
| HL-313 | 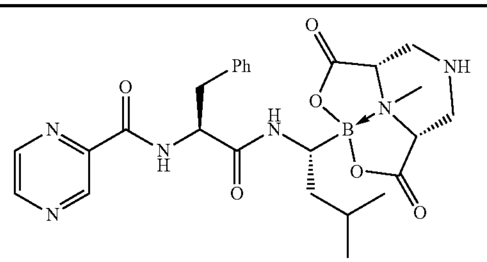 | N-((S)-1-(((R)-3-methyl-1-((1R,7S)-11-methyl-2,6-dioxo-3,5-dioxa-9,11-diaza-4-borabicyclo[5.3.1]undecan-4-yl)butyl)amino)-1-oxo-3-phenylpropan-2-yl)pyrazine-2-carboxamide |
| HL-314 | 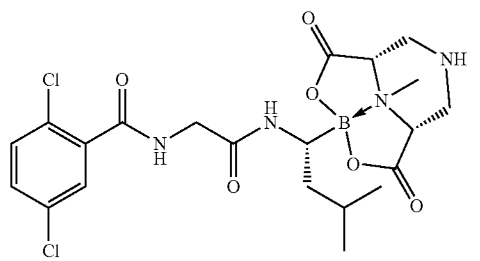 | 2,5-dichloro-N-(2-(((R)-3-methyl-1-((1R,7S)-11-methyl-2,6-dioxo-3,5-dioxa-9,11-diaza-4-borabicyclo[5.3.1]undecan-4-yl)butyl)amino)-2-oxoethyl)benzamide |
| HL-315 | 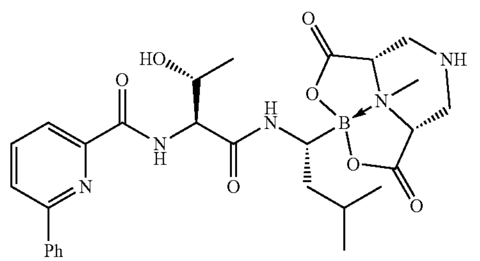 | N-((2S,3R)-3-hydroxy-1-(((R)-3-methyl-1-((1R,7S)-11-methyl-2,6-dioxo-3,5-dioxa-9,11-diaza-4-borabicyclo[5.3.1]undecan-4-yl)butyl)amino)-1-oxobutan-2-yl)-6-phenylpicolinamide |
| HL-316 | 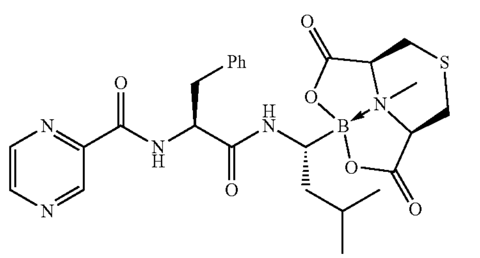 | N-((S)-1-(((R)-3-methyl-1-((1R,7S)-11-methyl-2,6-dioxo-3,5-dioxa-9-thia-11-aza-4-borabicyclo[5.3.1]undecan-4-yl)butyl)amino)-1-oxo-3-phenylpropan-2-yl)pyrazine-2-carboxamide |
| HL-317 | 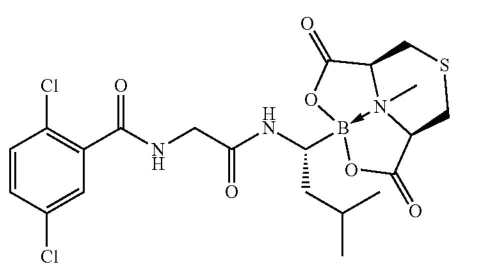 | 2,5-dichloro-N-(2-(((R)-3-methyl-1-((1R,7S)-11-methyl-2,6-dioxo-3,5-dioxa-9-thia-11-aza-4-borabicyclo[5.3.1]undecan-4-yl)butyl)amino)-2-oxoethyl)benzamide |
| HL-318 | 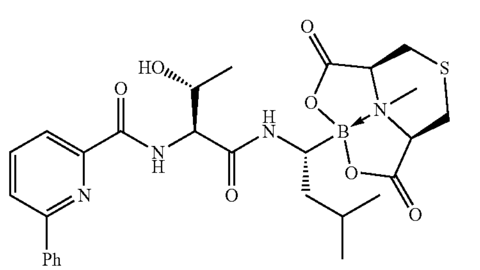 | N-((2S,3R)-3-hydroxy-1-(((R)-3-methyl-1-((1R,7S)-11-methyl-2,6-dioxo-3,5-dioxa-9-thia-11-aza-4-borabicyclo[5.3.1]undecan-4-yl)butyl)amino)-1-oxobutan-2-yl)-6-phenylpicolinamide |

TABLE 1-continued

| Serial # | Structure | Name |
|---|---|---|
| HL-319 | 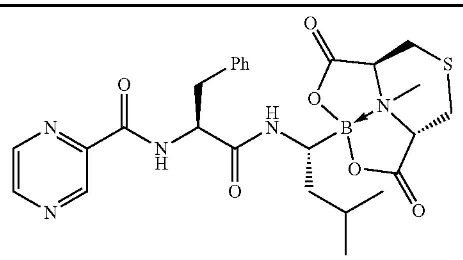 | N-((S)-1-(((R)-3-methyl-1-((1S,7S)-11-methyl-2,6-dioxo-3,5-dioxa-9-thia-11-aza-4-borabicyclo[5.3.1]undecan-4-yl)butyl)amino)-1-oxo-3-phenylpropan-2-yl)pyrazine-2-carboxamide |
| HL-320 | 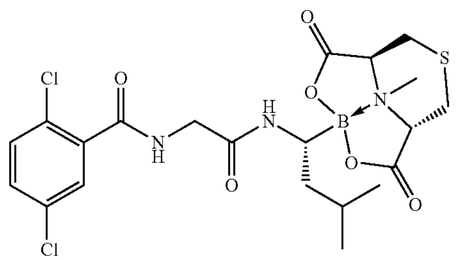 | 2,5-dichloro-N-(2-(((R)-3-methyl-1-((1S,7S)-11-methyl-2,6-dioxo-3,5-dioxa-9-thia-11-aza-4-borabicyclo[5.3.1]undecan-4-yl)butyl)amino)-2-oxoethyl)benzamide |
| HL-321 | 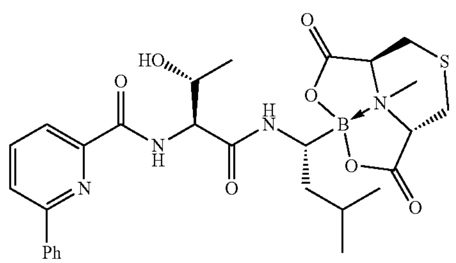 | N-((2S,3R)-3-hydroxy-1-(((R)-3-methyl-1-((1S,7S)-11-methyl-2,6-dioxo-3,5-dioxa-9-thia-11-aza-4-borabicyclo[5.3.1]undecan-4-yl)butyl)amino)-1-oxobutan-2-yl)-6-phenylpicolinamide |
| HL-322 | 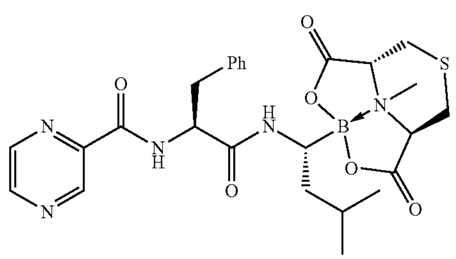 | N-((S)-1-(((R)-3-methyl-1-((1R,7R)-11-methyl-2,6-dioxo-3,5-dioxa-9-thia-11-aza-4-borabicyclo[5.3.1]undecan-4-yl)butyl)amino)-1-oxo-3-phenylpropan-2-yl)pyrazine-2-carboxamide |
| HL-323 | 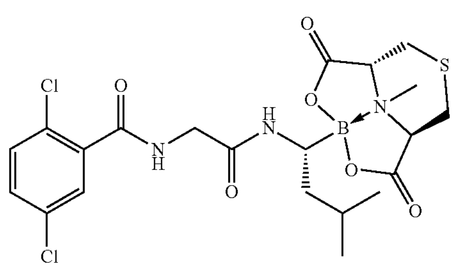 | 2,5-dichloro-N-(2-(((R)-3-methyl-1-((1R,7R)-11-methyl-2,6-dioxo-3,5-dioxa-9-thia-11-aza-4-borabicyclo[5.3.1]undecan-4-yl)butyl)amino)-2-oxoethyl)benzamide |
| HL-324 | 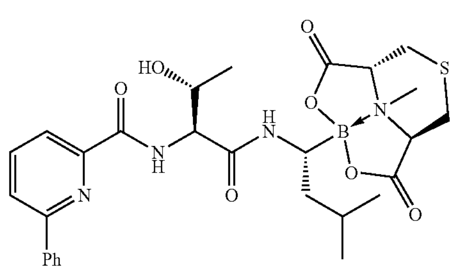 | N-((2S,3R)-3-hydroxy-1-(((R)-3-methyl-1-((1R,7R)-11-methyl-2,6-dioxo-3,5-dioxa-9-thia-11-aza-4-borabicyclo[5.3.1]undecan-4-yl)butyl)amino)-1-oxobutan-2-yl)-6-phenylpicolinamide |

TABLE 1-continued

| Serial # | Structure | Name |
|---|---|---|
| HL-325 | 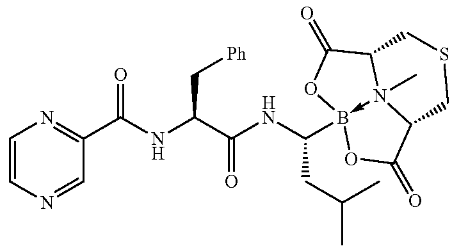 | N-((S)-1-(((R)-3-methyl-1-((1R,7S)-11-methyl-2,6-dioxo-3,5-dioxa-9-thia-11-aza-4-borabicyclo[5.3.1]undecan-4-yl)butyl)amino)-1-oxo-3-phenylpropan-2-yl)pyrazine-2-carboxamide |
| HL-326 | 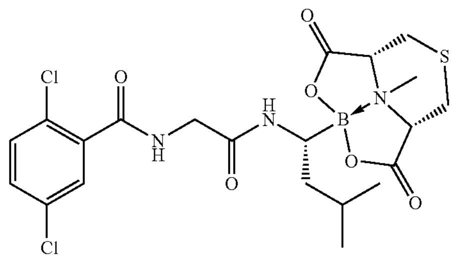 | 2,5-dichloro-N-(2-(((R)-3-methyl-1-((1R,7S)-11-methyl-2,6-dioxo-3,5-dioxa-9-thia-11-aza-4-borabicyclo[5.3.1]undecan-4-yl)butyl)amino)-2-oxoethyl)benzamide |
| HL-327 | 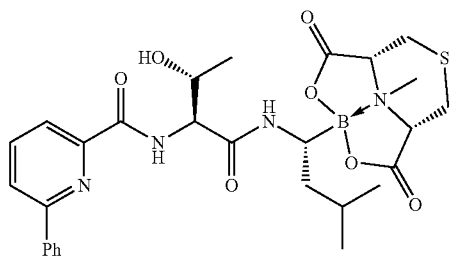 | N-((2S,3R)-3-hydroxy-1-(((R)-3-methyl-1-((1R,7S)-11-methyl-2,6-dioxo-3,5-dioxa-9-thia-11-aza-4-borabicyclo[5.3.1]undecan-4-yl)butyl)amino)-1-oxobutan-2-yl)-6-phenylpicolinamide |
| HL-328 | 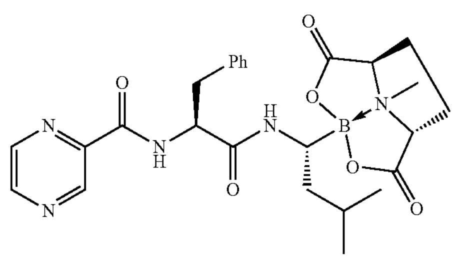 | N-((S)-1-(((R)-3-methyl-1-((1R,7R)-10-methyl-2,6-dioxo-3,5-dioxa-10-aza-4-borabicyclo[5.2.1]decan-4-yl)butyl)amino)-1-oxo-3-phenylpropan-2-yl)pyrazine-2-carboxamide |
| HL-329 | 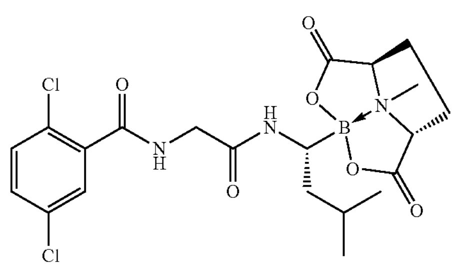 | 2,5-dichloro-N-(2-(((R)-3-methyl-1-((1R,7R)-10-methyl-2,6-dioxo-3,5-dioxa-10-aza-4-borabicyclo[5.2.1]decan-4-yl)butyl)amino)-2-oxoethyl)benzamide |
| HL-330 | 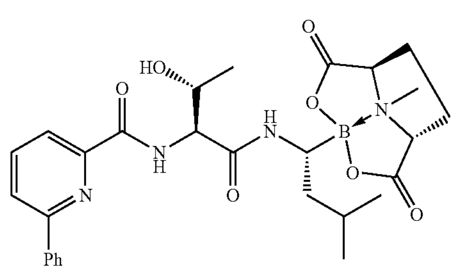 | N-((2S,3R)-3-hydroxy-1-(((R)-3-methyl-1-((1R,7R)-10-methyl-2,6-dioxo-3,5-dioxa-10-aza-4-borabicyclo[5.2.1]decan-4-yl)butyl)amino)-1-oxobutan-2-yl)-6-phenylpicolinamide |

TABLE 1-continued

| Serial # | Structure | Name |
|---|---|---|
| HL-331 | 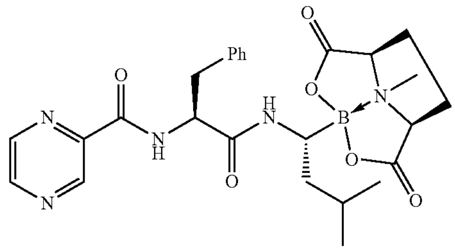 | N-((S)-1-(((R)-3-methyl-1-((1R,7S)-10-methyl-2,6-dioxo-3,5-dioxa-10-aza-4-borabicyclo[5.2.1]decan-4-yl)butyl)amino)-1-oxo-3-phenylpropan-2-yl)pyrazine-2-carboxamide |
| HL-332 | 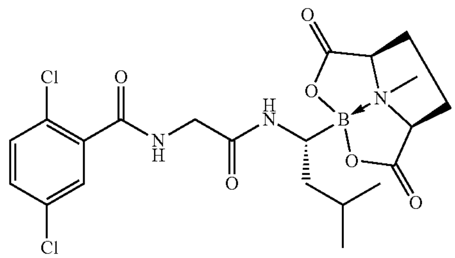 | 2,5-dichloro-N-(2-(((R)-3-methyl-1-((1R,7S)-10-methyl-2,6-dioxo-3,5-dioxa-10-aza-4-borabicyclo[5.2.1]decan-4-yl)butyl)amino)-2-oxoethyl)benzamide |
| HL-333 | 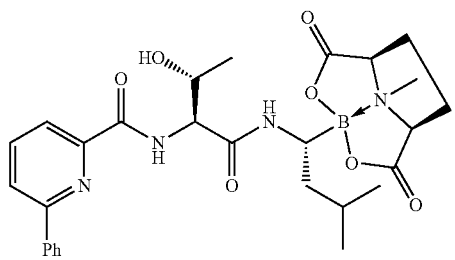 | N-((2S,3R)-3-hydroxy-1-(((R)-3-methyl-1-((1R,7S)-10-methyl-2,6-dioxo-3,5-dioxa-10-aza-4-borabicyclo[5.2.1]decan-4-yl)butyl)amino)-1-oxobutan-2-yl)-6-phenylpicolinamide |
| HL-334 | 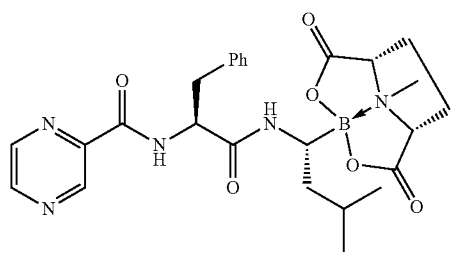 | N-((S)-1-(((R)-3-methyl-1-((1R,7S)-10-methyl-2,6-dioxo-3,5-dioxa-10-aza-4-borabicyclo[5.2.1]decan-4-yl)butyl)amino)-1-oxo-3-phenylpropan-2-yl)pyrazine-2-carboxamide |
| HL-335 | 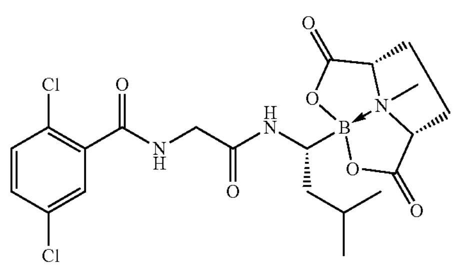 | 2,5-dichloro-N-(2-(((R)-3-methyl-1-((1R,7S)-10-methyl-2,6-dioxo-3,5-dioxa-10-aza-4-borabicyclo[5.2.1]decan-4-yl)butyl)amino)-2-oxoethyl)benzamide |
| HL-336 | 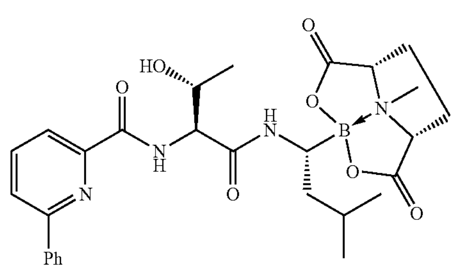 | N-((2S,3R)-3-hydroxy-1-(((R)-3-methyl-1-((1R,7S)-10-methyl-2,6-dioxo-3,5-dioxa-10-aza-4-borabicyclo[5.2.1]decan-4-yl)butyl)amino)-1-oxobutan-2-yl)-6-phenylpicolinamide |

TABLE 1-continued

| Serial # | Structure | Name |
|---|---|---|
| HL-337 | 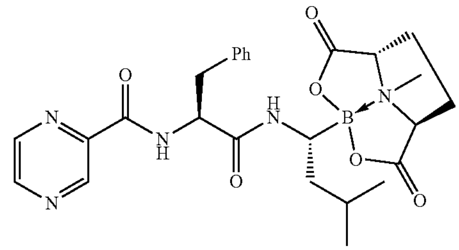 | N-((S)-1-(((R)-3-methyl-1-((1S,7S)-10-methyl-2,6-dioxo-3,5-dioxa-10-aza-4-borabicyclo[5.2.1]decan-4-yl)butyl)amino)-1-oxo-3-phenylpropan-2-yl)pyrazine-2-carboxamide |
| HL-338 | 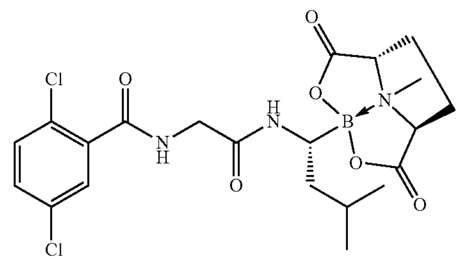 | 2,5-dichloro-N-(2-(((R)-3-methyl-1-((1S,7S)-10-methyl-2,6-dioxo-3,5-dioxa-10-aza-4-borabicyclo[5.2.1]decan-4-yl)butyl)amino)-2-oxoethyl)benzamide |
| HL-339 | 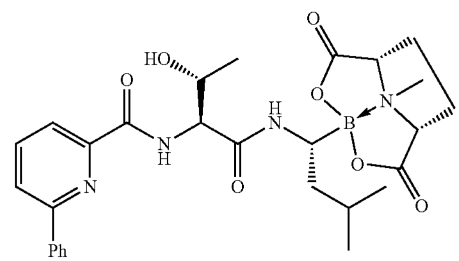 | N-((2S,3R)-3-hydroxy-1-(((R)-3-methyl-1-((1R,7S)-10-methyl-2,6-dioxo-3,5-dioxa-10-aza-4-borabicyclo[5.2.1]decan-4-yl)butyl)amino)-1-oxobutan-2-yl)-6-phenylpicolinamide |
| HL-340 | 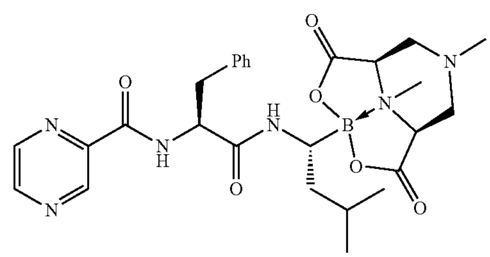 | N-((S)-1-(((R)-1-((1R,7S)-9,11-dimethyl-2,6-dioxo-3,5-dioxa-9,11-diaza-4-borabicyclo[5.3.1]undecan-4-yl)-3-methylbutyl)amino)-1-oxo-3-phenylpropan-2-yl)pyrazine-2-carboxamide |
| HL-341 | 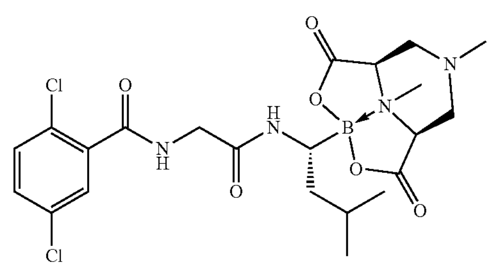 | 2,5-dichloro-N-(2-(((R)-1-((1R,7S)-9,11-dimethyl-2,6-dioxo-3,5-dioxa-9,11-diaza-4-borabicyclo[5.3.1]undecan-4-yl)-3-methylbutyl)amino)-2-oxoethyl)benzamide |
| HL-342 | 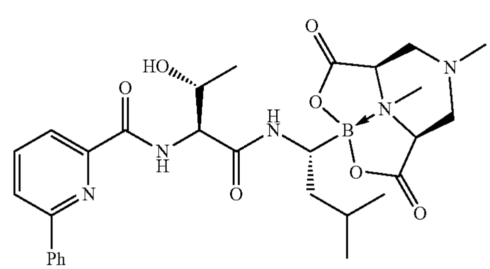 | N-((2S,3R)-1-(((R)-1-((1R,7S)-9,11-dimethyl-2,6-dioxo-3,5-dioxa-9,11-diaza-4-borabicyclo[5.3.1]undecan-4-yl)-3-methylbutyl)amino)-3-hydroxy-1-oxobutan-2-yl)-6-phenylpicolinamide |

TABLE 1-continued

| Serial # | Structure | Name |
|---|---|---|
| HL-343 | 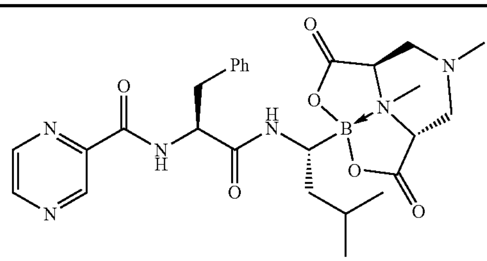 | N-((S)-1-(((R)-1-((1R,7R)-9,11-dimethyl-2,6-dioxo-3,5-dioxa-9,11-diaza-4-borabicyclo[5.3.1]undecan-4-yl)-3-methylbutyl)amino)-1-oxo-3-phenylpropan-2-yl)pyrazine-2-carboxamide |
| HL-344 | 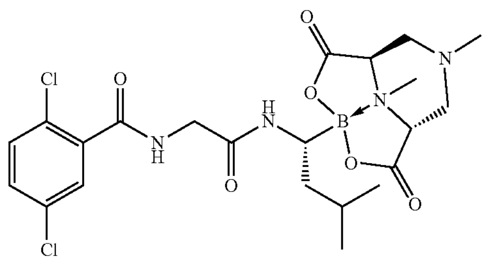 | 2,5-dichloro-N-(2-(((R)-1-((1R,7R)-9,11-dimethyl-2,6-dioxo-3,5-dioxa-9,11-diaza-4-borabicyclo[5.3.1]undecan-4-yl)-3-methylbutyl)amino)-2-oxoethyl)benzamide |
| HL-345 | 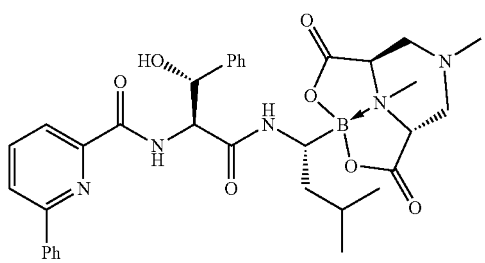 | N-((2S,3R)-1-(((R)-1-((1R,7R)-9,11-dimethyl-2,6-dioxo-3,5-dioxa-9,11-diaza-4-borabicyclo[5.3.1]undecan-4-yl)-3-methylbutyl)amino)-3-hydroxy-1-oxo-3-phenylpropan-2-yl)-6-phenylpicolinamide |
| HL-346 | 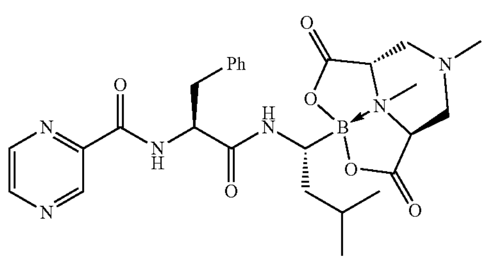 | N-((S)-1-(((R)-1-((1S,7S)-9,11-dimethyl-2,6-dioxo-3,5-dioxa-9,11-diaza-4-borabicyclo[5.3.1]undecan-4-yl)-3-methylbutyl)amino)-1-oxo-3-phenylpropan-2-yl)pyrazine-2-carboxamide |
| HL-347 | 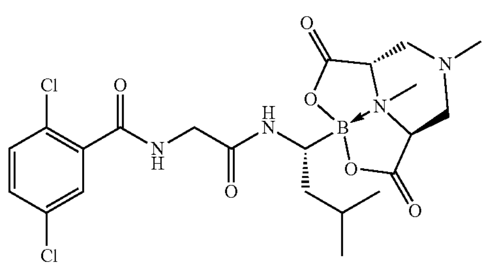 | 2,5-dichloro-N-(2-(((R)-1-((1S,7S)-9,11-dimethyl-2,6-dioxo-3,5-dioxa-9,11-diaza-4-borabicyclo[5.3.1]undecan-4-yl)-3-methylbutyl)amino)-2-oxoethyl)benzamide |
| HL-348 | 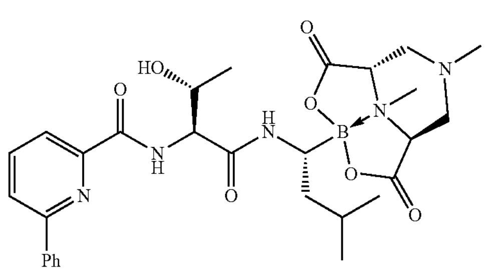 | N-((2S,3R)-1-(((R)-1-((1S,7S)-9,11-dimethyl-2,6-dioxo-3,5-dioxa-9,11-diaza-4-borabicyclo[5.3.1]undecan-4-yl)-3-methylbutyl)amino)-3-hydroxy-1-oxobutan-2-yl)-6-phenylpicolinamide |

TABLE 1-continued

| Serial # | Structure | Name |
|---|---|---|
| HL-349 | 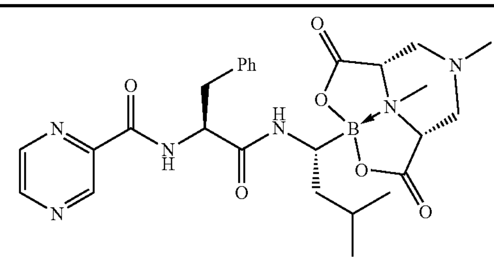 | N-((S)-1-(((R)-1-((1R,7S)-9,11-dimethyl-2,6-dioxo-3,5-dioxa-9,11-diaza-4-borabicyclo[5.3.1]undecan-4-yl)-3-methylbutyl)amino)-1-oxo-3-phenylpropan-2-yl)pyrazine-2-carboxamide |
| HL-350 | 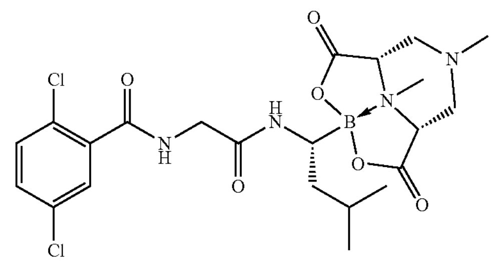 | 2,5-dichloro-N-(2-(((R)-1-((1R,7S)-9,11-dimethyl-2,6-dioxo-3,5-dioxa-9,11-diaza-4-borabicyclo[5.3.1]undecan-4-yl)-3-methylbutyl)amino)-2-oxoethyl)benzamide |
| HL-351 | 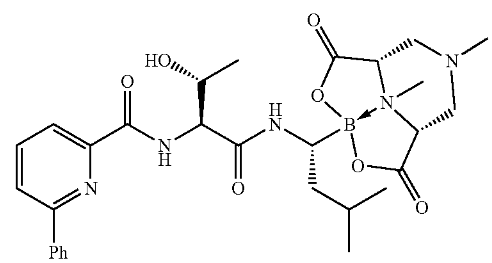 | N-((2S,3R)-1-(((R)-1-((1R,7S)-9,11-dimethyl-2,6-dioxo-3,5-dioxa-9,11-diaza-4-borabicyclo[5.3.1]undecan-4-yl)-3-methylbutyl)amino)-3-hydroxy-1-oxobutan-2-yl)-6-phenylpicolinamide |
| HL-352 | 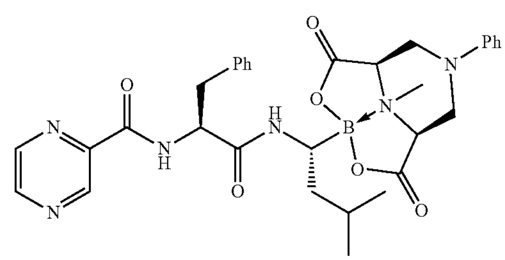 | N-((S)-1-(((R)-3-methyl-1-((1R,7S)-11-methyl-2,6-dioxo-9-phenyl-3,5-dioxa-9,11-diaza-4-borabicyclo[5.3.1]undecan-4-yl)butyl)amino)-1-oxo-3-phenylpropan-2-yl)pyrazine-2-carboxamide |
| HL-353 | 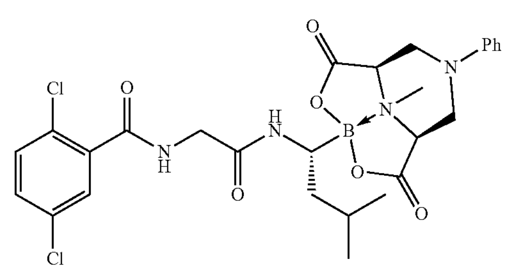 | 2,5-dichloro-N-(2-(((R)-3-methyl-1-((1R,7S)-11-methyl-2,6-dioxo-9-phenyl-3,5-dioxa-9,11-diaza-4-borabicyclo[5.3.1]undecan-4-yl)butyl)amino)-2-oxoethyl)benzamide |
| HL-354 | 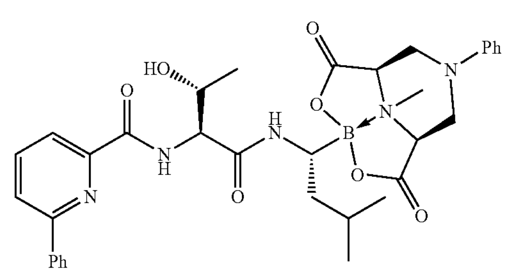 | N-((2S,3R)-3-hydroxy-1-(((R)-3-methyl-1-((1R,7S)-11-methyl-2,6-dioxo-9-phenyl-3,5-dioxa-9,11-diaza-4-borabicyclo[5.3.1]undecan-4-yl)butyl)amino)-1-oxobutan-2-yl)-6-phenylpicolinamide |

TABLE 1-continued

| Serial # | Structure | Name |
|---|---|---|
| HL-355 | 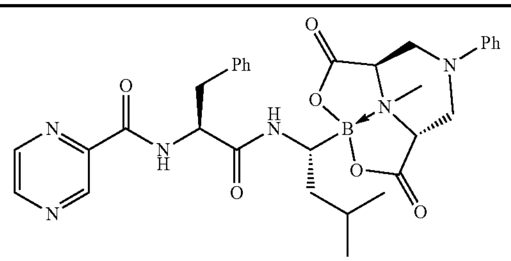 | N-((S)-1-(((R)-3-methyl-1-((1R,7R)-11-methyl-2,6-dioxo-9-phenyl-3,5-dioxa-9,11-diaza-4-borabicyclo[5.3.1]undecan-4-yl)butyl)amino)-1-oxo-3-phenylpropan-2-yl)pyrazine-2-carboxamide |
| HL-356 | 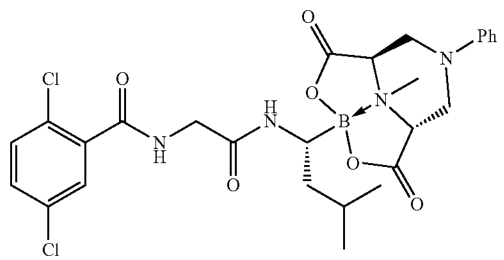 | 2,5-dichloro-N-(2-(((R)-3-methyl-1-((1R,7R)-11-methyl-2,6-dioxo-9-phenyl-3,5-dioxa-9,11-diaza-4-borabicyclo[5.3.1]undecan-4-yl)butyl)amino)-2-oxoethyl)benzamide |
| HL-357 | 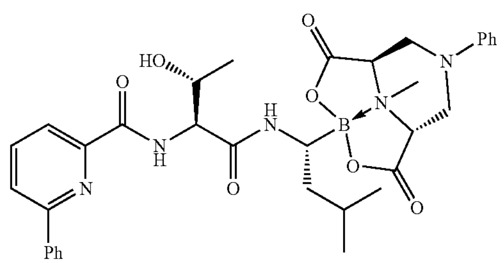 | N-((2S,3R)-3-hydroxy-1-(((R)-3-methyl-1-((1R,7R)-11-methyl-2,6-dioxo-9-phenyl-3,5-dioxa-9,11-diaza-4-borabicyclo[5.3.1]undecan-4-yl)butyl)amino)-1-oxobutan-2-yl)-6-phenylpicolinamide |
| HL-358 | 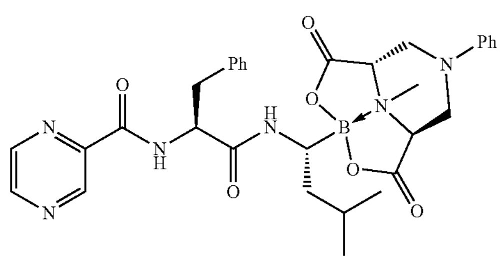 | N-((S)-1-(((R)-3-methyl-1-((1S,7S)-11-methyl-2,6-dioxo-9-phenyl-3,5-dioxa-9,11-diaza-4-borabicyclo[5.3.1]undecan-4-yl)butyl)amino)-1-oxo-3-phenylpropan-2-yl)pyrazine-2-carboxamide |
| HL-359 | 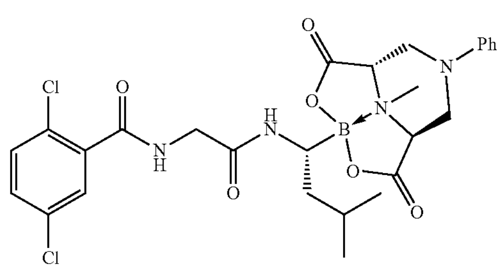 | 2,5-dichloro-N-(2-(((R)-3-methyl-1-((1S,7S)-11-methyl-2,6-dioxo-9-phenyl-3,5-dioxa-9,11-diaza-4-borabicyclo[5.3.1]undecan-4-yl)butyl)amino)-2-oxoethyl)benzamide |
| HL-360 | 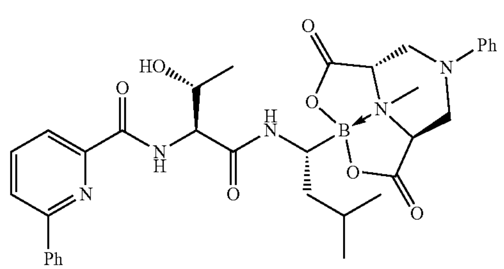 | N-((2S,3R)-3-hydroxy-1-(((R)-3-methyl-1-((1S,7S)-11-methyl-2,6-dioxo-9-phenyl-3,5-dioxa-9,11-diaza-4-borabicyclo[5.3.1]undecan-4-yl)butyl)amino)-1-oxobutan-2-yl)-6-phenylpicolinamide |

TABLE 1-continued

| Serial # | Structure | Name |
|---|---|---|
| HL-361 | 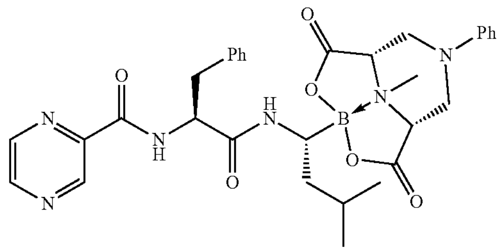 | N-((S)-1-(((R)-3-methyl-1-((1R,7S)-11-methyl-2,6-dioxo-9-phenyl-3,5-dioxa-9,11-diaza-4-borabicyclo[5.3.1]undecan-4-yl)butyl)amino)-1-oxo-3-phenylpropan-2-yl)pyrazine-2-carboxamide |
| HL-362 | 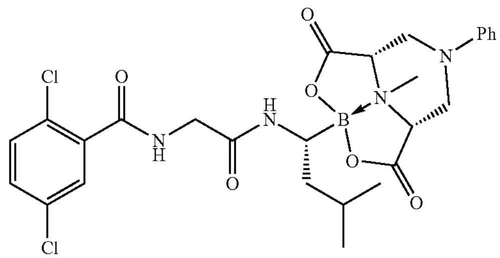 | 2,5-dichloro-N-(2-(((R)-3-methyl-1-((1R,7S)-11-methyl-2,6-dioxo-9-phenyl-3,5-dioxa-9,11-diaza-4-borabicyclo[5.3.1]undecan-4-yl)butyl)amino)-2-oxoethyl)benzamide |
| HL-363 | 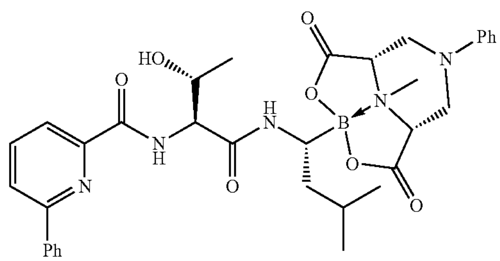 | N-((2S,3R)-3-hydroxy-1-(((R)-3-methyl-1-((1R,7S)-11-methyl-2,6-dioxo-9-phenyl-3,5-dioxa-9,11-diaza-4-borabicyclo[5.3.1]undecan-4-yl)butyl)amino)-1-oxobutan-2-yl)-6-phenylpicolinamide |
| HL-364 | 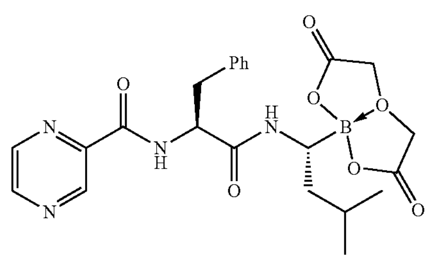 [SMILES: CC(C)C[C@H](NC(=O)[C@H](Cc1ccccc1)NC(=O)c1cnccn1)[B-]12OC(=O)C[O+]1CC(=O)O2] | N-((S)-1-(((R)-1-(4,8-dioxo-1,3,6,2-trioxaborocan-2-yl)-3-methylbutyl)amino)-1-oxo-3-phenylpropan-2-yl)pyrazine-2-carboxamide |
| HL-365 | 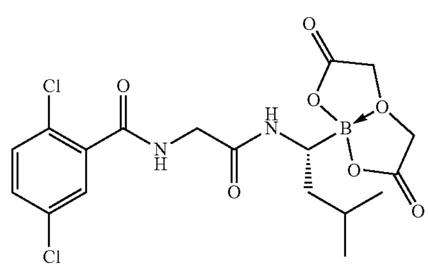 [SMILES: CC(C)C[C@H](NC(=O)CNC(=O)c1cc(Cl)ccc1Cl)[B-]12OC(=O)C[O+]1CC(=O)O2] | (R)-2,5-dichloro-N-(2-((1-(4,8-dioxo-1,3,6,2-trioxaborocan-2-yl)-3-methylbutyl)amino)-2-oxoethyl)benzamide |
| HL-366 | 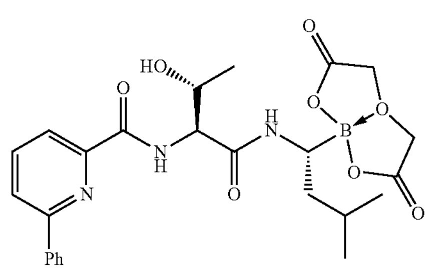 [SMILES: CC(C)C[C@H](NC(=O)[C@@H](NC(=O)c1cccc(-c2ccccc2)n1)[C@@H](C)O)[B-]12OC(=O)C[O+]1CC(=O)O2] | N-((2S,3R)-1-(((R)-1-(4,8-dioxo-1,3,6,2-trioxaborocan-2-yl)-3-methylbutyl)amino)-3-hydroxy-1-oxobutan-2-yl)-6-phenylpicolinamide |

TABLE 1-continued

| Serial # | Structure | Name |
|---|---|---|
| HL-367 | 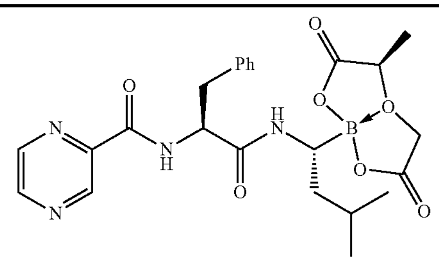 | N-((S)-1-(((R)-3-methyl-1-((R)-5-methyl-4,8-dioxo-1,3,6,2-trioxaborocan-2-yl)butyl)amino)-1-oxo-3-phenylpropan-2-yl)pyrazine-2-carboxamide |
| HL-368 | 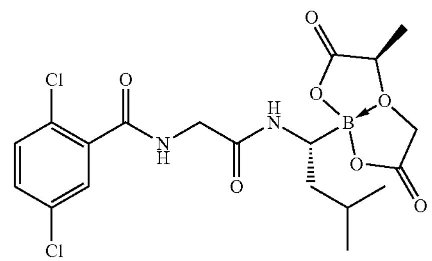 [SMILES: CC(C)C[C@H](NC(=O)CNC(=O)c1cc(Cl)ccc1Cl)[B-]12OC(=O)C[O+]1[C@H](C)C(=O)O2] | 2,5-dichloro-N-(2-(((R)-3-methyl-1-((R)-5-methyl-4,8-dioxo-1,3,6,2-trioxaborocan-2-yl)butyl)amino)-2-oxoethyl)benzamide |
| HL-369 | 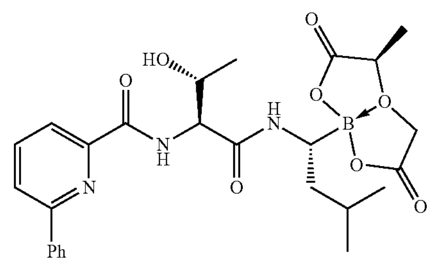 [SMILES: CC(C)C[C@H](NC(=O)[C@@H](NC(=O)c1cccc(-c2ccccc2)n1)[C@@H](C)O)[B-]12OC(=O)C[O+]1[C@H](C)C(=O)O2] | N-((2S,3R)-3-hydroxy-1-(((R)-3-methyl-1-((R)-5-methyl-4,8-dioxo-1,3,6,2-trioxaborocan-2-yl)butyl)amino)-1-oxobutan-2-yl)-6-phenylpicolinamide |
| HL-370 | 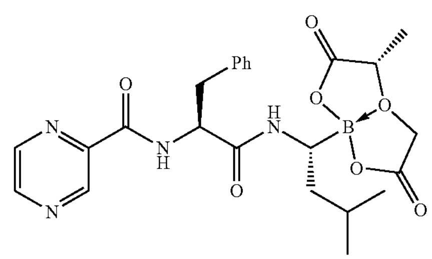 [SMILES: CC(C)C[C@H](NC(=O)[C@H](Cc1ccccc1)NC(=O)c1cnccn1)[B-]12OC(=O)C[O+]1[C@@H](C)C(=O)O2] | N-((S)-1-(((R)-3-methyl-1-((R)-5-methyl-4,8-dioxo-1,3,6,2-trioxaborocan-2-yl)butyl)amino)-1-oxo-3-phenylpropan-2-yl)pyrazine-2-carboxamide |
| HL-371 | 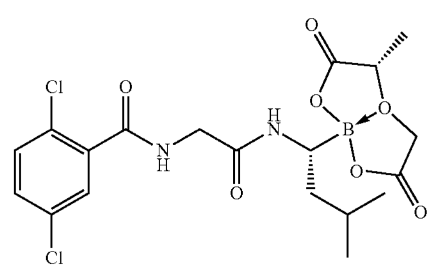 | 2,5-dichloro-N-(2-(((R)-3-methyl-1-((R)-5-methyl-4,8-dioxo-1,3,6,2-trioxaborocan-2-yl)butyl)amino)-2-oxoethyl)benzamide |
| HL-372 | 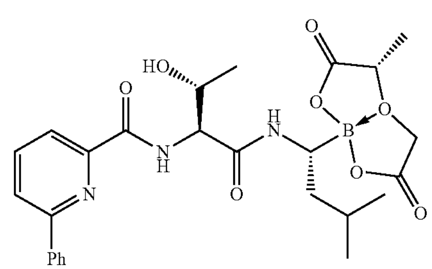 [SMILES: CC(C)C[C@H](NC(=O)[C@@H](NC(=O)c1cccc(-c2ccccc2)n1)[C@@H](C)O)[B-]12OC(=O)C[O+]1[C@@H](C)C(=O)O2] | N-((2S,3R)-3-hydroxy-1-(((R)-3-methyl-1-((R)-5-methyl-4,8-dioxo-1,3,6,2-trioxaborocan-2-yl)butyl)amino)-1-oxobutan-2-yl)-6-phenylpicolinamide |

TABLE 1-continued

| Serial # | Structure | Name |
|---|---|---|
| HL-373 | 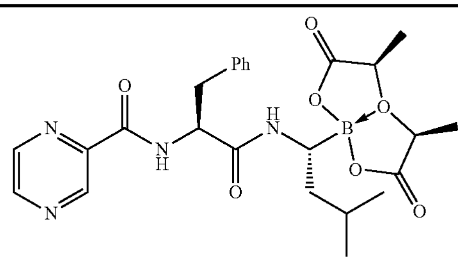 | N-((S)-1-(((R)-1-((5R,7S)-5,7-dimethyl-4,8-dioxo-1,3,6,2-trioxaborocan-2-yl)-3-methylbutyl)amino)-1-oxo-3-phenylpropan-2-yl)pyrazine-2-carboxamide |
| HL-374 | 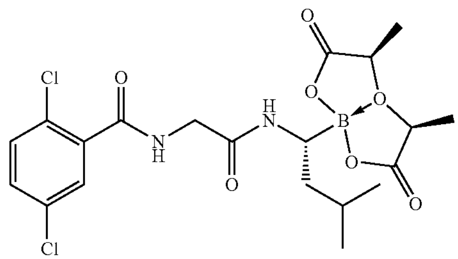 [SMILES: CC(C)C[C@H](NC(=O)CNC(=O)c1cc(Cl)ccc1Cl)[B-]12OC(=O)[C@@H](C)[O+]1[C@@H](C)C(=O)O2] | 2,5-dichloro-N-(2-(((R)-1-((5R,7S)-5,7-dimethyl-4,8-dioxo-1,3,6,2-trioxaborocan-2-yl)-3-methylbutyl)amino)-2-oxoethyl)benzamide |
| HL-375 | 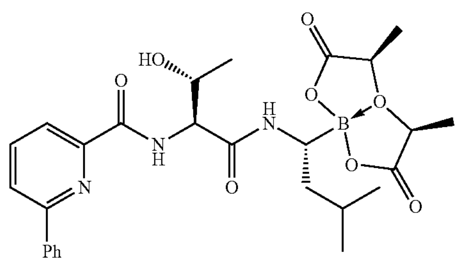 [SMILES: CC(C)C[C@H](NC(=O)[C@@H](NC(=O)c1cccc(-c2ccccc2)n1)[C@@H](C)O)[B-]12OC(=O)[C@@H](C)[O+]1[C@@H](C)C(=O)O2] | N-((2S,3R)-1-(((R)-1-((5R,7S)-5,7-dimethyl-4,8-dioxo-1,3,6,2-trioxaborocan-2-yl)-3-methylbutyl)amino)-3-hydroxy-1-oxobutan-2-yl)-6-phenylpicolinamide |
| HL-376 | 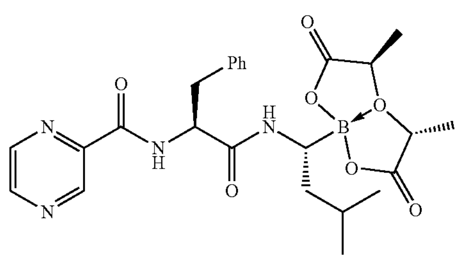 [SMILES: CC(C)C[C@H](NC(=O)[C@H](Cc1ccccc1)NC(=O)c1cnccn1)[B-]12OC(=O)[C@@H](C)[O+]1[C@H](C)C(=O)O2] | N-((S)-1-(((R)-1-((5R,7R)-5,7-dimethyl-4,8-dioxo-1,3,6,2-trioxaborocan-2-yl)-3-methylbutyl)amino)-1-oxo-3-phenylpropan-2-yl)pyrazine-2-carboxamide |
| HL-377 | 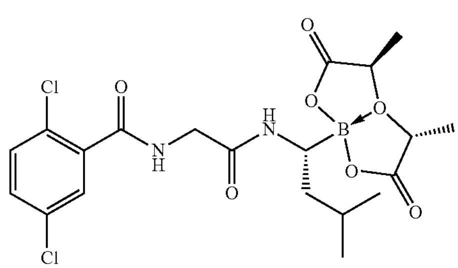 [SMILES: CC(C)C[C@H](NC(=O)CNC(=O)c1cc(Cl)ccc1Cl)[B-]12OC(=O)[C@@H](C)[O+]1[C@H](C)C(=O)O2] | 2,5-dichloro-N-(2-(((R)-1-((5R,7R)-5,7-dimethyl-4,8-dioxo-1,3,6,2-trioxaborocan-2-yl)-3-methylbutyl)amino)-2-oxoethyl)benzamide |
| HL-378 | 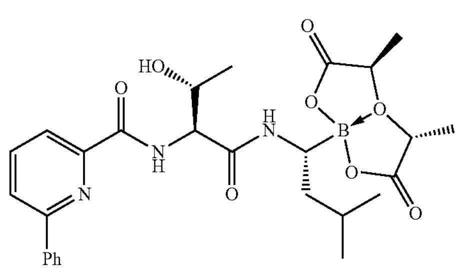 [SMILES: CC(C)C[C@H](NC(=O)[C@@H](NC(=O)c1cccc(-c2ccccc2)n1)[C@@H](C)O)[B-]12OC(=O)[C@@H](C)[O+]1[C@H](C)C(=O)O2] | N-((2S,3R)-1-(((R)-1-((5R,7R)-5,7-dimethyl-4,8-dioxo-1,3,6,2-trioxaborocan-2-yl)-3-methylbutyl)amino)-3-hydroxy-1-oxobutan-2-yl)-6-phenylpicolinamide |

TABLE 1-continued

| Serial # | Structure | Name |
|---|---|---|
| HL-379 | 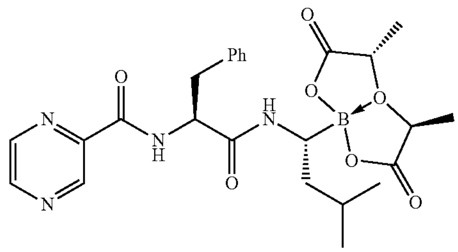 | N-((S)-1-(((R)-1-((5R,7S)-5,7-dimethyl-4,8-dioxo-1,3,6,2-trioxaborocan-2-yl)-3-methylbutyl)amino)-1-oxo-3-phenylpropan-2-yl)pyrazine-2-carboxamide |
| HL-380 | 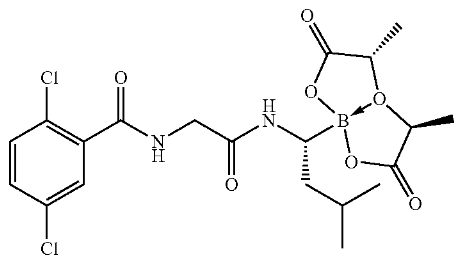 [SMILES: CC(C)C[C@H](NC(=O)CNC(=O)c1cc(Cl)ccc1Cl)[B-]12OC(=O)[C@H](C)[O+]1[C@@H](C)C(=O)O2] | 2,5-dichloro-N-(2-(((R)-1-((5R,7S)-5,7-dimethyl-4,8-dioxo-1,3,6,2-trioxaborocan-2-yl)-3-methylbutyl)amino)-2-oxoethyl)benzamide |
| HL-381 | 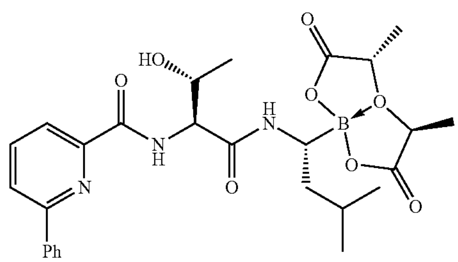 [SMILES: CC(C)C[C@H](NC(=O)[C@@H](NC(=O)c1cccc(-c2ccccc2)n1)[C@@H](C)O)[B-]12OC(=O)[C@H](C)[O+]1[C@@H](C)C(=O)O2] | N-((2S,3R)-1-(((R)-1-((5R,7S)-5,7-dimethyl-4,8-dioxo-1,3,6,2-trioxaborocan-2-yl)-3-methylbutyl)amino)-3-hydroxy-1-oxobutan-2-yl)-6-phenylpicolinamide |
| HL-382 | 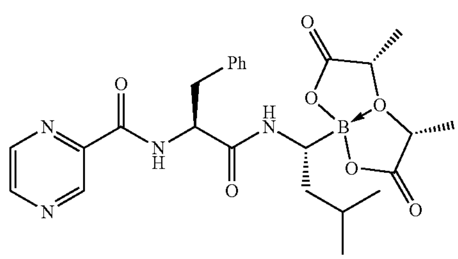 [SMILES: CC(C)C[C@H](NC(=O)[C@H](Cc1ccccc1)NC(=O)c1cnccn1)[B-]12OC(=O)[C@@H](C)[O+]1[C@@H](C)C(=O)O2] | N-((S)-1-(((R)-1-((5R,7R)-5,7-dimethyl-4,8-dioxo-1,3,6,2-trioxaborocan-2-yl)-3-methylbutyl)amino)-1-oxo-3-phenylpropan-2-yl)pyrazine-2-carboxamide |
| HL-383 | 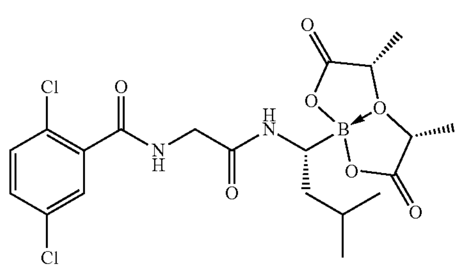 [SMILES: CC(C)C[C@H](NC(=O)CNC(=O)c1cc(Cl)ccc1Cl)[B-]12OC(=O)[C@@H](C)[O+]1[C@@H](C)C(=O)O2] | 2,5-dichloro-N-(2-(((R)-1-((5R,7R)-5,7-dimethyl-4,8-dioxo-1,3,6,2-trioxaborocan-2-yl)-3-methylbutyl)amino)-2-oxoethyl)benzamide |
| HL-384 | 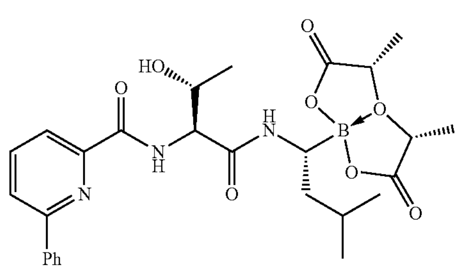 [SMILES: CC(C)C[C@H](NC(=O)[C@@H](NC(=O)c1cccc(-c2ccccc2)n1)[C@@H](C)O)[B-]12OC(=O)[C@@H](C)[O+]1[C@@H](C)C(=O)O2] | N-((2S,3R)-1-(((R)-1-((5R,7R)-5,7-dimethyl-4,8-dioxo-1,3,6,2-trioxaborocan-2-yl)-3-methylbutyl)amino)-3-hydroxy-1-oxobutan-2-yl)-6-phenylpicolinamide |

TABLE 1-continued

| Serial # | Structure | Name |
|---|---|---|
| HL-385 | 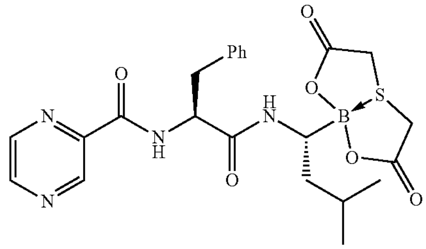 | N-((S)-1-(((R)-1-(4,8-dioxo-1,3,6,2-dioxathiaborocan-2-yl)-3-methylbutyl)amino)-1-oxo-3-phenylpropan-2-yl)pyrazine-2-carboxamide |
| HL-386 | 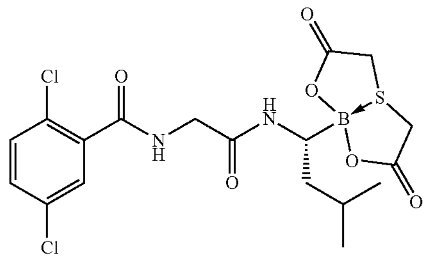 | (R)-2,5-dichloro-N-(2-((1-(4,8-dioxo-1,3,6,2-dioxathiaborocan-2-yl)-3-methylbutyl)amino)-2-oxoethyl)benzamide |
| HL-387 | 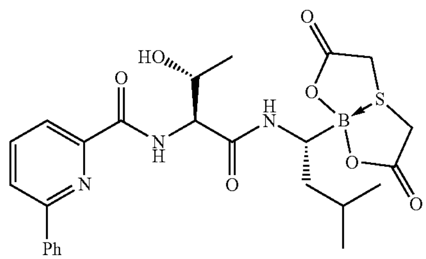 | N-((2S,3R)-1-(((R)-1-(4,8-dioxo-1,3,6,2-dioxathiaborocan-2-yl)-3-methylbutyl)amino)-3-hydroxy-1-oxobutan-2-yl)-6-phenylpicolinamide |
| HL-388 | 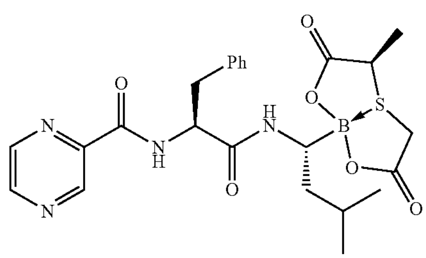 | N-((S)-1-(((R)-3-methyl-1-((R)-5-methyl-4,8-dioxo-1,3,6,2-dioxathiaborocan-2-yl)butyl)amino)-1-oxo-3-phenylpropan-2-yl)pyrazine-2-carboxamide |
| HL-389 | 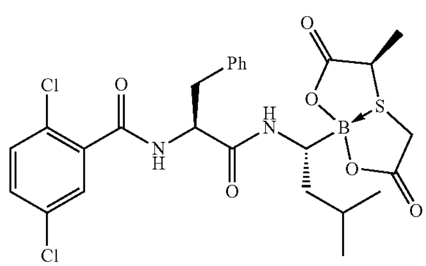 | 2,5-dichloro-N-((S)-1-(((R)-3-methyl-1-((R)-5-methyl-4,8-dioxo-1,3,6,2-dioxathiaborocan-2-yl)butyl)amino)-1-oxo-3-phenylpropan-2-yl)benzamide |
| HL-390 | 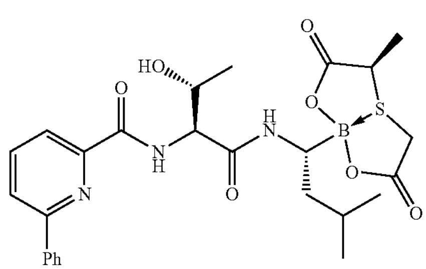 | N-((2S,3R)-3-hydroxy-1-(((R)-3-methyl-1-((R)-5-methyl-4,8-dioxo-1,3,6,2-dioxathiaborocan-2-yl)butyl)amino)-1-oxobutan-2-yl)-6-phenylpicolinamide |

TABLE 1-continued

| Serial # | Structure | Name |
|---|---|---|
| HL-391 | 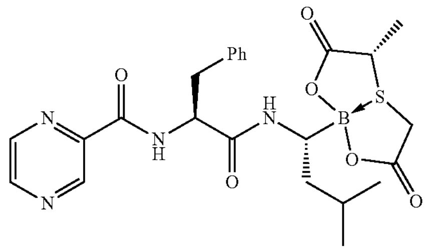 | N-((S)-1-(((R)-3-methyl-1-((R)-5-methyl-4,8-dioxo-1,3,6,2-dioxathiaborocan-2-yl)butyl)amino)-1-oxo-3-phenylpropan-2-yl)pyrazine-2-carboxamide |
| HL-392 | 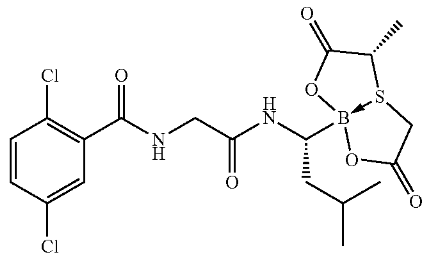 | 2,5-dichloro-N-(2-(((R)-3-methyl-1-((R)-5-methyl-4,8-dioxo-1,3,6,2-dioxathiaborocan-2-yl)butyl)amino)-2-oxoethyl)benzamide |
| HL-393 | 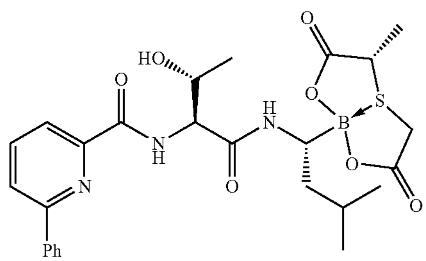 | N-((2S,3R)-3-hydroxy-1-(((R)-3-methyl-1-((R)-5-methyl-4,8-dioxo-1,3,6,2-dioxathiaborocan-2-yl)butyl)amino)-1-oxobutan-2-yl)-6-phenylpicolinamide |
| HL-394 | 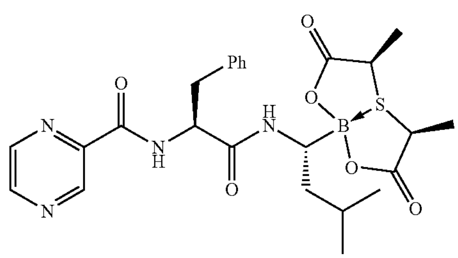 | N-((S)-1-(((R)-1-((5R,7S)-5,7-dimethyl-4,8-dioxo-1,3,6,2-dioxathiaborocan-2-yl)-3-methylbutyl)amino)-1-oxo-3-phenylpropan-2-yl)pyrazine-2-carboxamide |
| HL-395 | 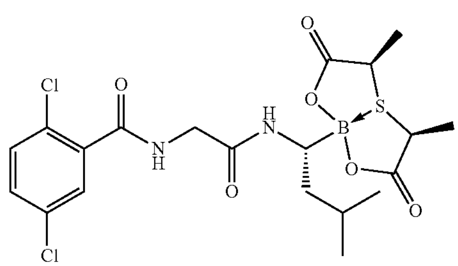 | 2,5-dichloro-N-(2-(((R)-1-((5R,7S)-5,7-dimethyl-4,8-dioxo-1,3,6,2-dioxathiaborocan-2-yl)-3-methylbutyl)amino)-2-oxoethyl)benzamide |
| HL-396 | 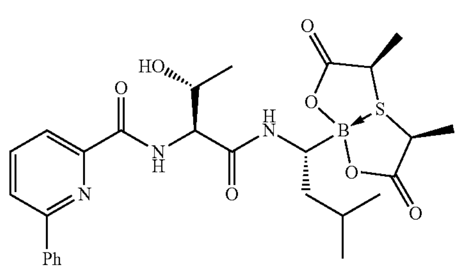 | N-((2S,3R)-1-(((R)-1-((5R,7S)-5,7-dimethyl-4,8-dioxo-1,3,6,2-dioxathiaborocan-2-yl)-3-methylbutyl)amino)-3-hydroxy-1-oxobutan-2-yl)-6-phenylpicolinamide |

TABLE 1-continued

| Serial # | Structure | Name |
|---|---|---|
| HL-397 | 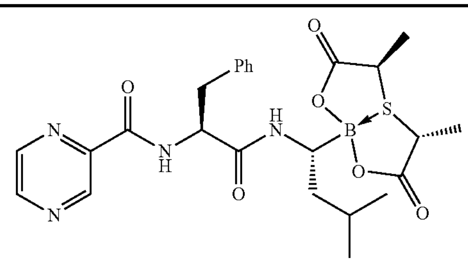 | N-((S)-1-(((R)-1-((5R,7R)-5,7-dimethyl-4,8-dioxo-1,3,6,2-dioxathiaborocan-2-yl)-3-methylbutyl)amino)-1-oxo-3-phenylpropan-2-yl)pyrazine-2-carboxamide |
| HL-398 | 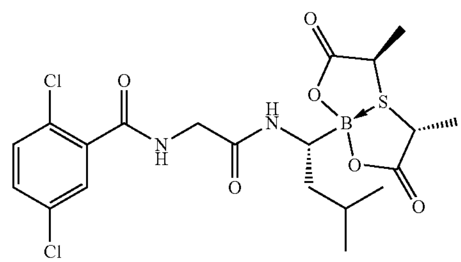 | 2,5-dichloro-N-(2-(((R)-1-((5R,7R)-5,7-dimethyl-4,8-dioxo-1,3,6,2-dioxathiaborocan-2-yl)-3-methylbutyl)amino)-2-oxoethyl)benzamide |
| HL-399 | 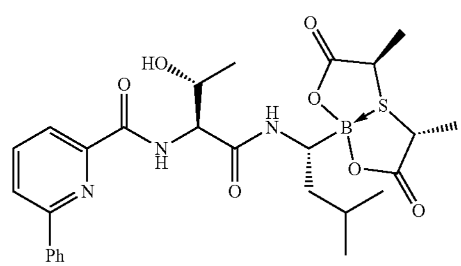 | N-((2S,3R)-1-(((R)-1-((5R,7R)-5,7-dimethyl-4,8-dioxo-1,3,6,2-dioxathiaborocan-2-yl)-3-methylbutyl)amino)-3-hydroxy-1-oxobutan-2-yl)-6-phenylpicolinamide |
| HL-400 | 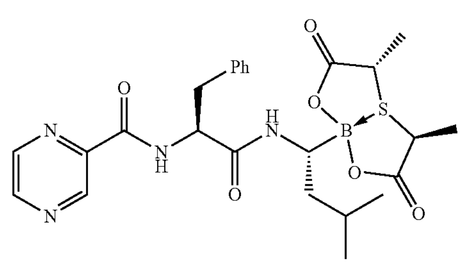 | N-((S)-1-(((R)-1-((5R,7S)-5,7-dimethyl-4,8-dioxo-1,3,6,2-dioxathiaborocan-2-yl)-3-methylbutyl)amino)-1-oxo-3-phenylpropan-2-yl)pyrazine-2-carboxamide |
| HL-401 | 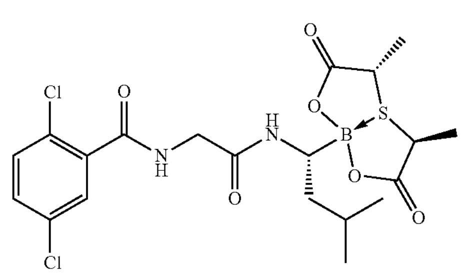 | 2,5-dichloro-N-(2-(((R)-1-((5R,7S)-5,7-dimethyl-4,8-dioxo-1,3,6,2-dioxathiaborocan-2-yl)-3-methylbutyl)amino)-2-oxoethyl)benzamide |
| HL-402 | 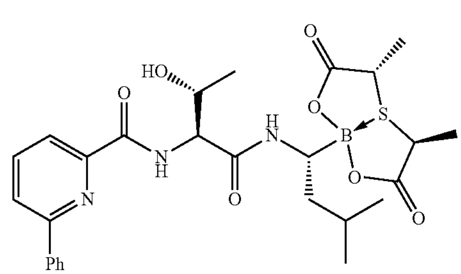 | N-((2S,3R)-1-(((R)-1-((5R,7S)-5,7-dimethyl-4,8-dioxo-1,3,6,2-dioxathiaborocan-2-yl)-3-methylbutyl)amino)-3-hydroxy-1-oxobutan-2-yl)-6-phenylpicolinamide |

TABLE 1-continued

| Serial # | Structure | Name |
| --- | --- | --- |
| HL-403 | 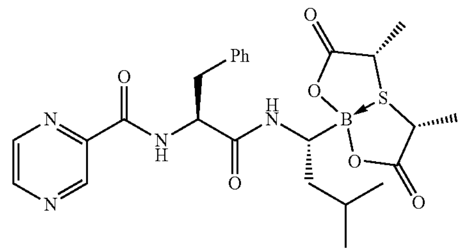 | N-((S)-1-(((R)-1-((5R,7R)-5,7-dimethyl-4,8-dioxo-1,3,6,2-dioxathiaborocan-2-yl)-3-methylbutyl)amino)-1-oxo-3-phenylpropan-2-yl)pyrazine-2-carboxamide |
| HL-404 | 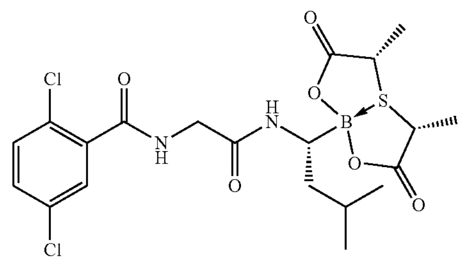 | 2,5-dichloro-N-(2-(((R)-1-((5R,7R)-5,7-dimethyl-4,8-dioxo-1,3,6,2-dioxathiaborocan-2-yl)-3-methylbutyl)amino)-2-oxoethyl)benzamide |
| HL-405 | 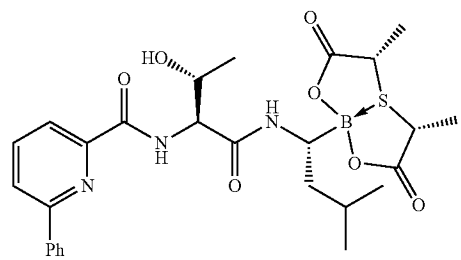 | N-((2S,3R)-1-(((R)-1-((5R,7R)-5,7-dimethyl-4,8-dioxo-1,3,6,2-dioxathiaborocan-2-yl)-3-methylbutyl)amino)-3-hydroxy-1-oxobutan-2-yl)-6-phenylpicolinamide |
| HL-406 | 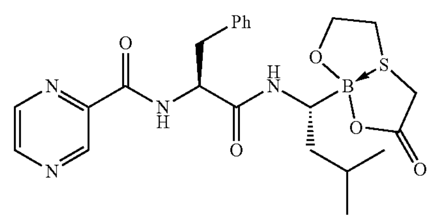 | N-((S)-1-(((R)-3-methyl-1-(4-oxo-1,3,6,2-dioxathiaborocan-2-yl)butyl)amino)-1-oxo-3-phenylpropan-2-yl)pyrazine-2-carboxamide |
| HL-407 | 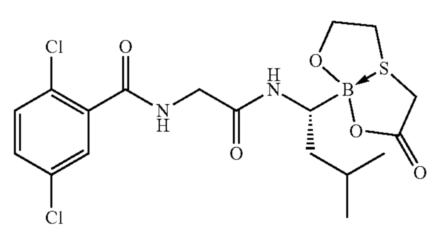 | (R)-2,5-dichloro-N-(2-((3-methyl-1-(4-oxo-1,3,6,2-dioxathiaborocan-2-yl)butyl)amino)-2-oxoethyl)benzamide |
| HL-408 | 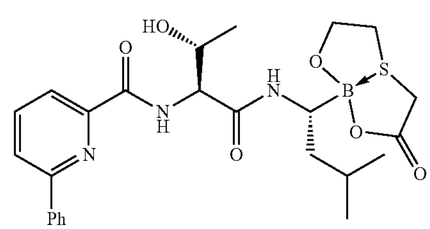 | N-((2S,3R)-3-hydroxy-1-(((R)-3-methyl-1-(4-oxo-1,3,6,2-dioxathiaborocan-2-yl)butyl)amino)-1-oxobutan-2-yl)-6-phenylpicolinamide |

TABLE 1-continued

| Serial # | Structure | Name |
|---|---|---|
| HL-409 | 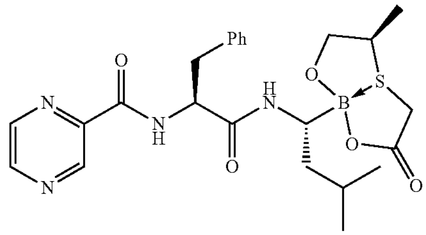 | N-((S)-1-(((R)-3-methyl-1-((R)-7-methyl-4-oxo-1,3,6,2-dioxathiaborocan-2-yl)butyl)amino)-1-oxo-3-phenylpropan-2-yl)pyrazine-2-carboxamide |
| HL-410 | 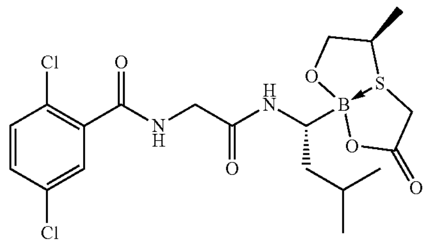 | 2,5-dichloro-N-(2-(((R)-3-methyl-1-((R)-7-methyl-4-oxo-1,3,6,2-dioxathiaborocan-2-yl)butyl)amino)-2-oxoethyl)benzamide |
| HL-411 | 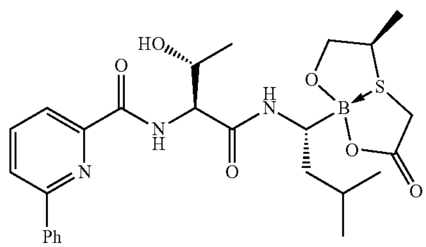 | N-((2S,3R)-3-hydroxy-1-(((R)-3-methyl-1-((R)-7-methyl-4-oxo-1,3,6,2-dioxathiaborocan-2-yl)butyl)amino)-1-oxobutan-2-yl)-6-phenylpicolinamide |
| HL-412 | 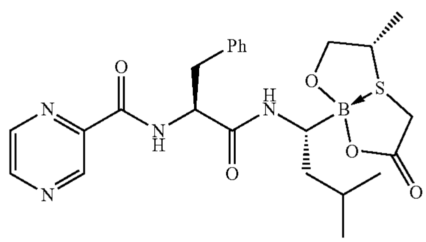 | N-((S)-1-(((R)-3-methyl-1-((R)-7-methyl-4-oxo-1,3,6,2-dioxathiaborocan-2-yl)butyl)amino)-1-oxo-3-phenylpropan-2-yl)pyrazine-2-carboxamide |
| HL-413 | 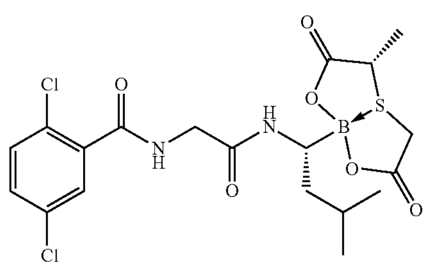 | 2,5-dichloro-N-(2-(((R)-3-methyl-1-((R)-5-methyl-4,8-dioxo-1,3,6,2-dioxathiaborocan-2-yl)butyl)amino)-2-oxoethyl)benzamide |
| HL-414 | 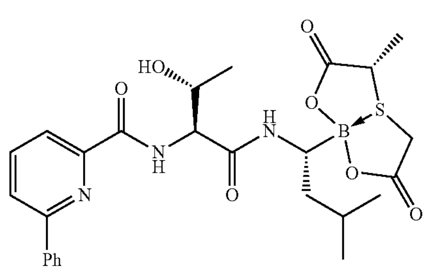 | N-((2S,3R)-3-hydroxy-1-(((R)-3-methyl-1-((R)-5-methyl-4,8-dioxo-1,3,6,2-dioxathiaborocan-2-yl)butyl)amino)-1-oxobutan-2-yl)-6-phenylpicolinamide |

TABLE 1-continued

| Serial # | Structure | Name |
|---|---|---|
| HL-415 | 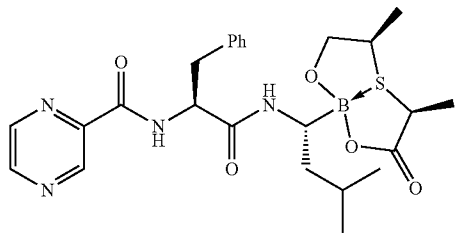 | N-((S)-1-(((R)-1-((5S,7R)-5,7-dimethyl-4-oxo-1,3,6,2-dioxathiaborocan-2-yl)-3-methylbutyl)amino)-1-oxo-3-phenylpropan-2-yl)pyrazine-2-carboxamide |
| HL-416 | 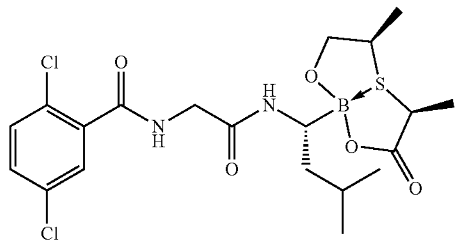 | 2,5-dichloro-N-(2-(((R)-1-((5S,7R)-5,7-dimethyl-4-oxo-1,3,6,2-dioxathiaborocan-2-yl)-3-methylbutyl)amino)-2-oxoethyl)benzamide |
| HL-417 | 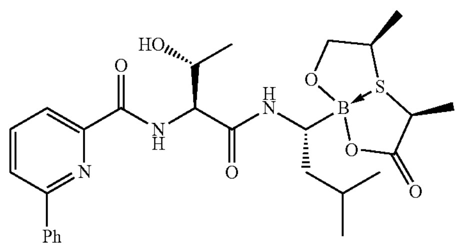 | N-((2S,3R)-1-(((R)-1-((5S,7R)-5,7-dimethyl-4-oxo-1,3,6,2-dioxathiaborocan-2-yl)-3-methylbutyl)amino)-3-hydroxy-1-oxobutan-2-yl)-6-phenylpicolinamide |
| HL-418 | 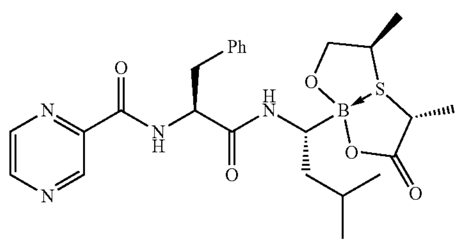 | N-((S)-1-(((R)-1-((5R,7R)-5,7-dimethyl-4-oxo-1,3,6,2-dioxathiaborocan-2-yl)-3-methylbutyl)amino)-1-oxo-3-phenylpropan-2-yl)pyrazine-2-carboxamide |
| HL-419 | 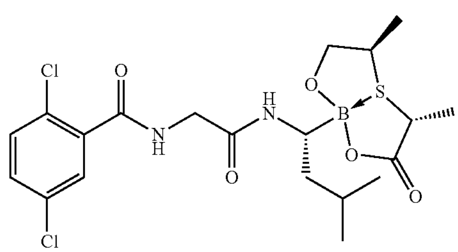 | 2,5-dichloro-N-(2-(((R)-1-((5R,7R)-5,7-dimethyl-4-oxo-1,3,6,2-dioxathiaborocan-2-yl)-3-methylbutyl)amino)-2-oxoethyl)benzamide |
| HL-420 | 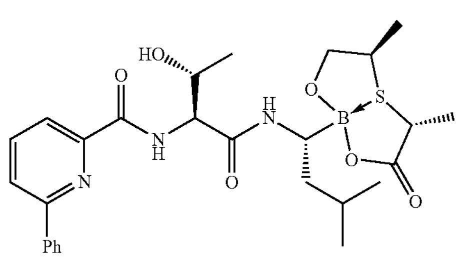 | N-((2S,3R)-1-(((R)-1-((5R,7R)-5,7-dimethyl-4-oxo-1,3,6,2-dioxathiaborocan-2-yl)-3-methylbutyl)amino)-3-hydroxy-1-oxobutan-2-yl)-6-phenylpicolinamide |

TABLE 1-continued

| Serial # | Structure | Name |
|---|---|---|
| HL-421 | 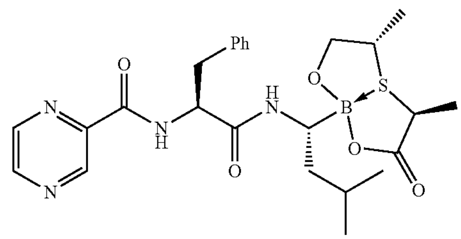 | N-((S)-1-(((R)-1-((5S,7R)-5,7-dimethyl-4-oxo-1,3,6,2-dioxathiaborocan-2-yl)-3-methylbutyl)amino)-1-oxo-3-phenylpropan-2-yl)pyrazine-2-carboxamide |
| HL-422 | 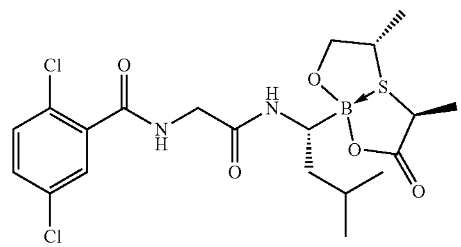 | 2,5-dichloro-N-(2-(((R)-1-((5S,7R)-5,7-dimethyl-4-oxo-1,3,6,2-dioxathiaborocan-2-yl)-3-methylbutyl)amino)-2-oxoethyl)benzamide |
| HL-423 | 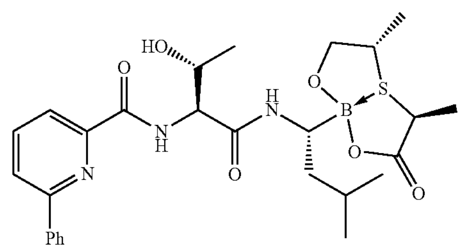 | N-((2S,3R)-1-(((R)-1-((5S,7R)-5,7-dimethyl-4-oxo-1,3,6,2-dioxathiaborocan-2-yl)-3-methylbutyl)amino)-3-hydroxy-1-oxobutan-2-yl)-6-phenylpicolinamide |
| HL-424 | 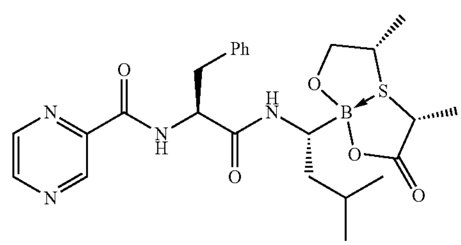 | N-((S)-1-(((R)-1-((5R,7R)-5,7-dimethyl-4-oxo-1,3,6,2-dioxathiaborocan-2-yl)-3-methylbutyl)amino)-1-oxo-3-phenylpropan-2-yl)pyrazine-2-carboxamide |
| HL-425 | 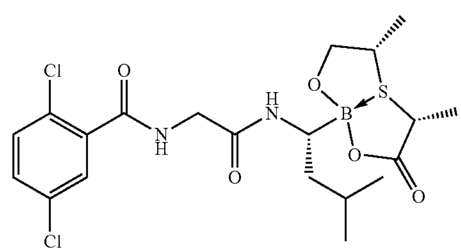 | 2,5-dichloro-N-(2-(((R)-1-((5R,7R)-5,7-dimethyl-4-oxo-1,3,6,2-dioxathiaborocan-2-yl)-3-methylbutyl)amino)-2-oxoethyl)benzamide |
| HL-426 | 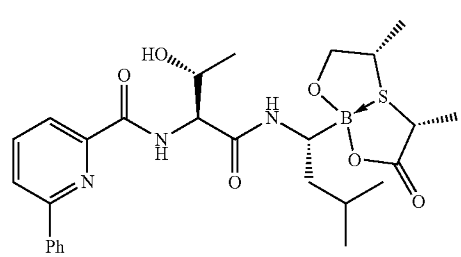 | N-((2S,3R)-1-(((R)-1-((5R,7R)-5,7-dimethyl-4-oxo-1,3,6,2-dioxathiaborocan-2-yl)-3-methylbutyl)amino)-3-hydroxy-1-oxobutan-2-yl)-6-phenylpicolinamide |

TABLE 1-continued

| Serial # | Structure | Name |
|---|---|---|
| HL-427 | 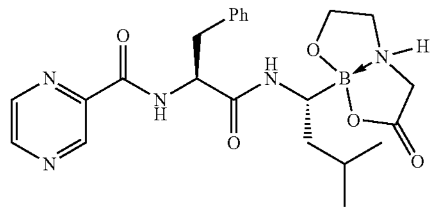 [SMILES: CC(C)C[C@H](NC(=O)[C@H](Cc1ccccc1)NC(=O)c1cnccn1)[B-]12OCC[NH+]1CC(=O)O2] | N-((S)-1-(((R)-3-methyl-1-(4-oxo-1,3,6,2-dioxazaborocan-2-yl)butyl)amino)-1-oxo-3-phenylpropan-2-yl)pyrazine-2-carboxamide |
| HL-428 | 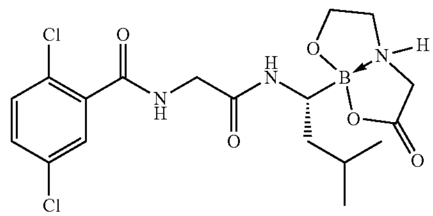 [SMILES: CC(C)C[C@H](NC(=O)CNC(=O)c1cc(Cl)ccc1Cl)[B-]12OCC[NH+]1CC(=O)O2] | (R)-2,5-dichloro-N-(2-((3-methyl-1-(4-oxo-1,3,6,2-dioxazaborocan-2-yl)butyl)amino)-2-oxoethyl)benzamide |
| HL-429 | 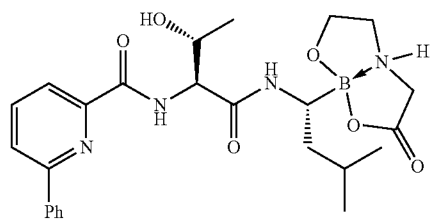 [SMILES: CC(C)C[C@H](NC(=O)[C@@H](NC(=O)c1cccc(-c2ccccc2)n1)[C@@H](C)O)[B-]12OCC[NH+]1CC(=O)O2] | N-((2S,3R)-3-hydroxy-1-(((R)-3-methyl-1-(4-oxo-1,3,6,2-dioxazaborocan-2-yl)butyl)amino)-1-oxobutan-2-yl)-6-phenylpicolinamide |
| HL-430 | 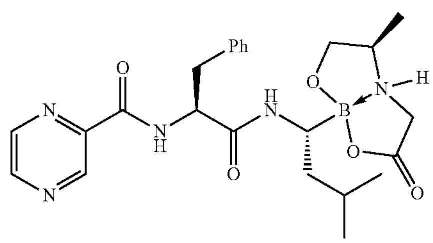 [SMILES: CC(C)C[C@H](NC(=O)[C@H](Cc1ccccc1)NC(=O)c1cnccn1)[B-]12OC[C@@H](C)[NH+]1CC(=O)O2] | N-((S)-1-(((R)-3-methyl-1-((R)-7-methyl-4-oxo-1,3,6,2-dioxazaborocan-2-yl)butyl)amino)-1-oxo-3-phenylpropan-2-yl)pyrazine-2-carboxamide |
| HL-431 | 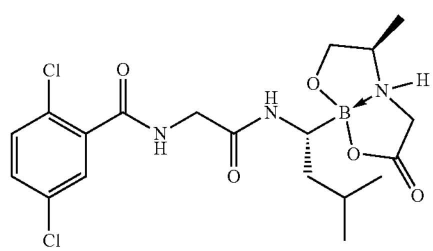 [SMILES: CC(C)C[C@H](NC(=O)CNC(=O)c1cc(Cl)ccc1Cl)[B-]12OC[C@@H](C)[NH+]1CC(=O)O2] | 2,5-dichloro-N-(2-(((R)-3-methyl-1-((R)-7-methyl-4-oxo-1,3,6,2-dioxazaborocan-2-yl)butyl)amino)-2-oxoethyl)benzamide |
| HL-432 | 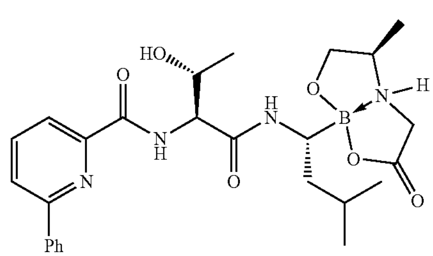 [SMILES: CC(C)C[C@H](NC(=O)[C@@H](NC(=O)c1cccc(-c2ccccc2)n1)[C@@H](C)O)[B-]12OC[C@@H](C)[NH+]1CC(=O)O2] | N-((2S,3R)-3-hydroxy-1-(((R)-3-methyl-1-((R)-7-methyl-4-oxo-1,3,6,2-dioxazaborocan-2-yl)butyl)amino)-1-oxobutan-2-yl)-6-phenylpicolinamide |

TABLE 1-continued

| Serial # | Structure | Name |
|---|---|---|
| HL-433 | 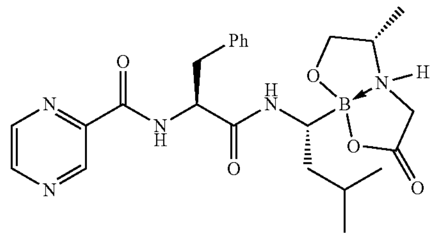 [SMILES: CC(C)C[C@H](NC(=O)[C@H](Cc1ccccc1)NC(=O)c1cnccn1)[B-]12OC[C@H](C)[NH+]1CC(=O)O2] | N-((S)-1-(((R)-3-methyl-1-((R)-7-methyl-4-oxo-1,3,6,2-dioxazaborocan-2-yl)butyl)amino)-1-oxo-3-phenylpropan-2-yl)pyrazine-2-carboxamide |
| HL-434 | 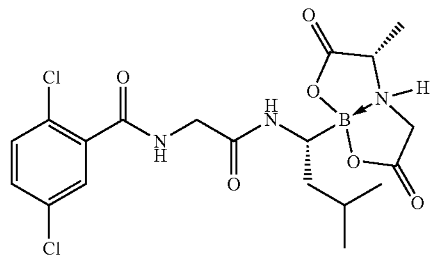 [SMILES: CC(C)C[C@H](NC(=O)CNC(=O)c1cc(Cl)ccc1Cl)[B-]12OC(=O)C[NH+]1[C@@H](C)C(=O)O2] | 2,5-dichloro-N-(2-(((R)-3-methyl-1-((R)-5-methyl-4,8-dioxo-1,3,6,2-dioxazaborocan-2-yl)butyl)amino)-2-oxoethyl)benzamide |
| HL-435 | 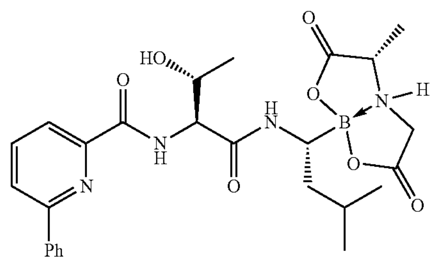 [SMILES: CC(C)C[C@H](NC(=O)[C@@H](NC(=O)c1cccc(-c2ccccc2)n1)[C@@H](C)O)[B-]12OC(=O)C[NH+]1[C@@H](C)C(=O)O2] | N-((2S,3R)-3-hydroxy-1-(((R)-3-methyl-1-((R)-5-methyl-4,8-dioxo-1,3,6,2-dioxazaborocan-2-yl)butyl)amino)-1-oxobutan-2-yl)-6-phenylpicolinamide |
| HL-436 | 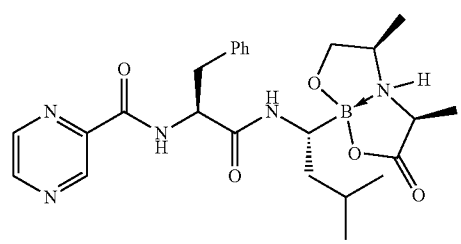 [SMILES: CC(C)C[C@H](NC(=O)[C@H](Cc1ccccc1)NC(=O)c1cnccn1)[B-]12OC[C@@H](C)[NH+]1[C@@H](C)C(=O)O2] | N-((S)-1-(((R)-1-((5S,7R)-5,7-dimethyl-4-oxo-1,3,6,2-dioxazaborocan-2-yl)-3-methylbutyl)amino)-1-oxo-3-phenylpropan-2-yl)pyrazine-2-carboxamide |
| HL-437 | 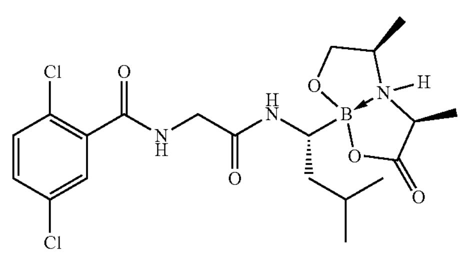 [SMILES: CC(C)C[C@H](NC(=O)CNC(=O)c1cc(Cl)ccc1Cl)[B-]12OC[C@@H](C)[NH+]1[C@@H](C)C(=O)O2] | 2,5-dichloro-N-(2-(((R)-1-((5S,7R)-5,7-dimethyl-4-oxo-1,3,6,2-dioxazaborocan-2-yl)-3-methylbutyl)amino)-2-oxoethyl)benzamide |
| HL-438 | 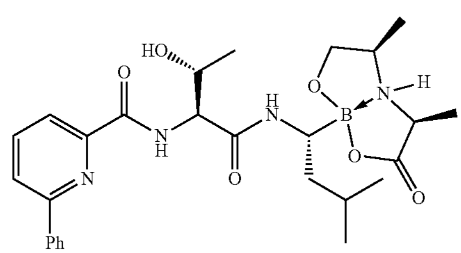 [SMILES: CC(C)C[C@H](NC(=O)[C@@H](NC(=O)c1cccc(-c2ccccc2)n1)[C@@H](C)O)[B-]12OC[C@@H](C)[NH+]1[C@@H](C)C(=O)O2] | N-((2S,3R)-1-(((R)-1-((5S,7R)-5,7-dimethyl-4-oxo-1,3,6,2-dioxazaborocan-2-yl)-3-methylbutyl)amino)-3-hydroxy-1-oxobutan-2-yl)-6-phenylpicolinamide |

TABLE 1-continued

| Serial # | Structure | Name |
|---|---|---|
| HL-439 | 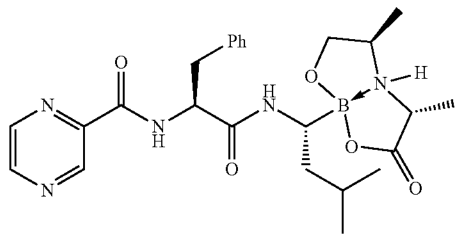 [SMILES: CC(C)C[C@H](NC(=O)[C@H](Cc1ccccc1)NC(=O)c1cnccn1)[B-]12OC[C@@H](C)[NH+]1[C@H](C)C(=O)O2] | N-((S)-1-(((R)-1-((5R,7R)-5,7-dimethyl-4-oxo-1,3,6,2-dioxazaborocan-2-yl)-3-methylbutyl)amino)-1-oxo-3-phenylpropan-2-yl)pyrazine-2-carboxamide |
| HL-440 | 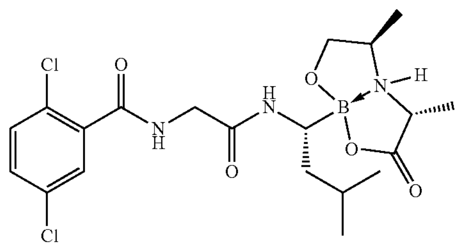 [SMILES: CC(C)C[C@H](NC(=O)CNC(=O)c1cc(Cl)ccc1Cl)[B-]12OC[C@@H](C)[NH+]1[C@H](C)C(=O)O2] | 2,5-dichloro-N-(2-(((R)-1-((5R,7R)-5,7-dimethyl-4-oxo-1,3,6,2-dioxazaborocan-2-yl)-3-methylbutyl)amino)-2-oxoethyl)benzamide |
| HL-441 | 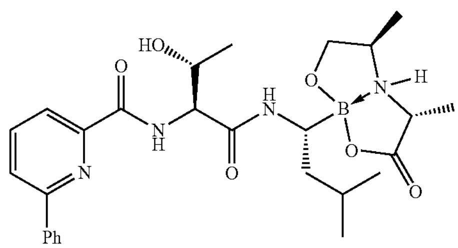 [SMILES: CC(C)C[C@H](NC(=O)[C@@H](NC(=O)c1cccc(-c2ccccc2)n1)[C@@H](C)O)[B-]12OC[C@@H](C)[NH+]1[C@H](C)C(=O)O2] | N-((2S,3R)-1-(((R)-1-((5R,7R)-5,7-dimethyl-4-oxo-1,3,6,2-dioxazaborocan-2-yl)-3-methylbutyl)amino)-3-hydroxy-1-oxobutan-2-yl)-6-phenylpicolinamide |
| HL-442 | 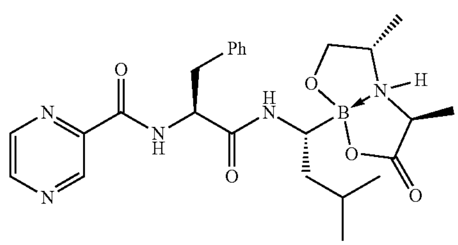 [SMILES: CC(C)C[C@H](NC(=O)[C@H](Cc1ccccc1)NC(=O)c1cnccn1)[B-]12OC[C@H](C)[NH+]1[C@@H](C)C(=O)O2] | N-((S)-1-(((R)-1-((5S,7R)-5,7-dimethyl-4-oxo-1,3,6,2-dioxazaborocan-2-yl)-3-methylbutyl)amino)-1-oxo-3-phenylpropan-2-yl)pyrazine-2-carboxamide |
| HL-443 | 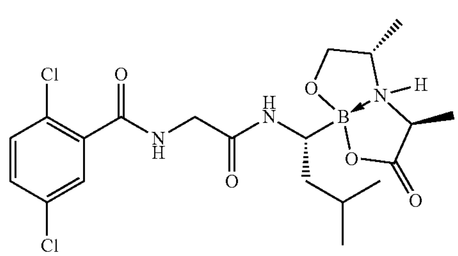 [SMILES: CC(C)C[C@H](NC(=O)CNC(=O)c1cc(Cl)ccc1Cl)[B-]12OC[C@H](C)[NH+]1[C@@H](C)C(=O)O2] | 2,5-dichloro-N-(2-(((R)-1-((5S,7R)-5,7-dimethyl-4-oxo-1,3,6,2-dioxazaborocan-2-yl)-3-methylbutyl)amino)-2-oxoethyl)benzamide |
| HL-444 | 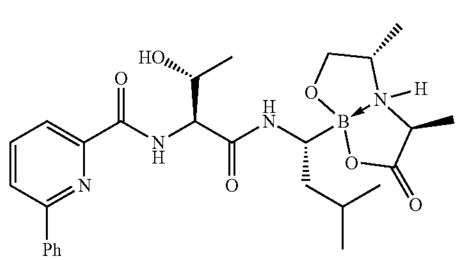 [SMILES: CC(C)C[C@H](NC(=O)[C@@H](NC(=O)c1cccc(-c2ccccc2)n1)[C@@H](C)O)[B-]12OC[C@H](C)[NH+]1[C@@H](C)C(=O)O2] | N-((2S,3R)-1-(((R)-1-((5S,7R)-5,7-dimethyl-4-oxo-1,3,6,2-dioxazaborocan-2-yl)-3-methylbutyl)amino)-3-hydroxy-1-oxobutan-2-yl)-6-phenylpicolinamide |

TABLE 1-continued

| Serial # | Structure | Name |
|---|---|---|
| HL-445 | 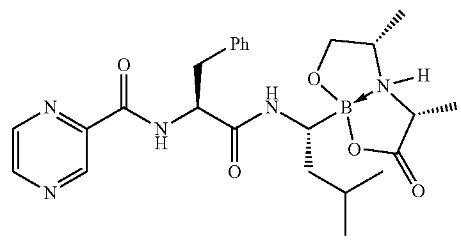 [SMILES: CC(C)C[C@H](NC(=O)[C@H](Cc1ccccc1)NC(=O)c1cnccn1)[B-]12OC[C@H](C)[NH+]1[C@H](C)C(=O)O2] | N-((S)-1-(((R)-1-((5R,7R)-5,7-dimethyl-4-oxo-1,3,6,2-dioxazaborocan-2-yl)-3-methylbutyl)amino)-1-oxo-3-phenylpropan-2-yl)pyrazine-2-carboxamide |
| HL-446 | 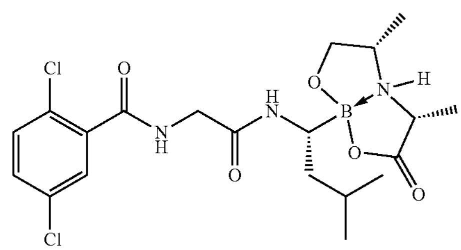 [SMILES: CC(C)C[C@H](NC(=O)CNC(=O)c1cc(Cl)ccc1Cl)[B-]12OC[C@H](C)[NH+]1[C@H](C)C(=O)O2] | 2,5-dichloro-N-(2-(((R)-1-((5R,7R)-5,7-dimethyl-4-oxo-1,3,6,2-dioxazaborocan-2-yl)-3-methylbutyl)amino)-2-oxoethyl)benzamide |
| HL-447 | 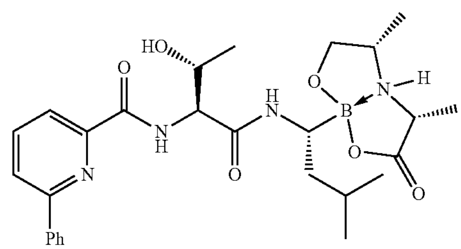 [SMILES: CC(C)C[C@H](NC(=O)[C@@H](NC(=O)c1cccc(-c2ccccc2)n1)[C@@H](C)O)[B-]12OC[C@H](C)[NH+]1[C@H](C)C(=O)O2] | N-((2S,3R)-1-(((R)-1-((5R,7R)-5,7-dimethyl-4-oxo-1,3,6,2-dioxazaborocan-2-yl)-3-methylbutyl)amino)-3-hydroxy-1-oxobutan-2-yl)-6-phenylpicolinamide |
| HL-448 | 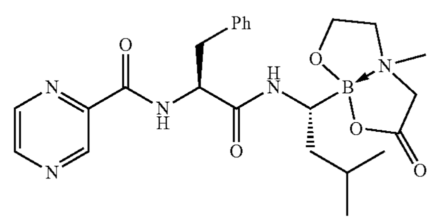 [SMILES: CC(C)C[C@H](NC(=O)[C@H](Cc1ccccc1)NC(=O)c1cnccn1)[B-]12OCC[N+]1(C)CC(=O)O2] | N-((S)-1-(((R)-3-methyl-1-(6-methyl-4-oxo-1,3,6,2-dioxazaborocan-2-yl)butyl)amino)-1-oxo-3-phenylpropan-2-yl)pyrazine-2-carboxamide |
| HL-449 | 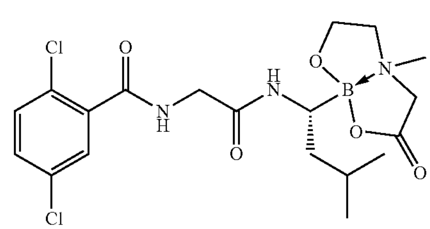 [SMILES: CC(C)C[C@H](NC(=O)CNC(=O)c1cc(Cl)ccc1Cl)[B-]12OCC[N+]1(C)CC(=O)O2] | (R)-2,5-dichloro-N-(2-((3-methyl-1-(6-methyl-4-oxo-1,3,6,2-dioxazaborocan-2-yl)butyl)amino)-2-oxoethyl)benzamide |
| HL-450 | 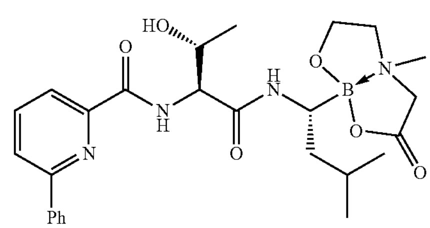 [SMILES: CC(C)C[C@H](NC(=O)[C@@H](NC(=O)c1cccc(-c2ccccc2)n1)[C@@H](C)O)[B-]12OCC[N+]1(C)CC(=O)O2] | N-((2S,3R)-3-hydroxy-1-(((R)-3-methyl-1-(6-methyl-4-oxo-1,3,6,2-dioxazaborocan-2-yl)butyl)amino)-1-oxobutan-2-yl)-6-phenylpicolinamide |

TABLE 1-continued

| Serial # | Structure | Name |
|---|---|---|
| HL-451 | 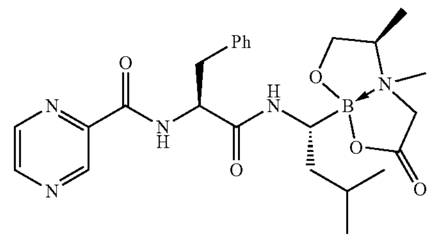 [SMILES: CC(C)C[C@H](NC(=O)[C@H](Cc1ccccc1)NC(=O)c1cnccn1)[B-]12OC[C@@H](C)[N+]1(C)CC(=O)O2] | N-((S)-1-(((R)-1-((R)-6,7-dimethyl-4-oxo-1,3,6,2-dioxazaborocan-2-yl)-3-methylbutyl)amino)-1-oxo-3-phenylpropan-2-yl)pyrazine-2-carboxamide |
| HL-452 | 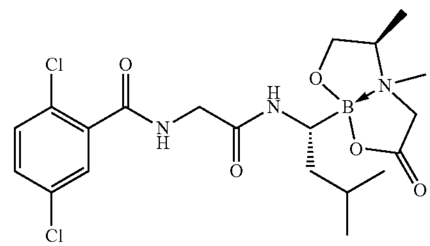 [SMILES: CC(C)C[C@H](NC(=O)CNC(=O)c1cc(Cl)ccc1Cl)[B-]12OC[C@@H](C)[N+]1(C)CC(=O)O2] | 2,5-dichloro-N-(2-(((R)-1-((R)-6,7-dimethyl-4-oxo-1,3,6,2-dioxazaborocan-2-yl)-3-methylbutyl)amino)-2-oxoethyl)benzamide |
| HL-453 | 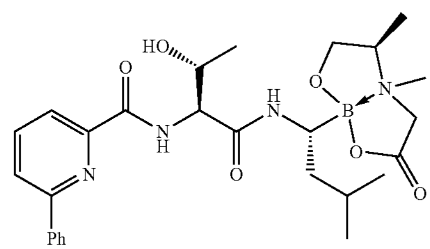 [SMILES: CC(C)C[C@H](NC(=O)[C@@H](NC(=O)c1cccc(-c2ccccc2)n1)[C@@H](C)O)[B-]12OC[C@@H](C)[N+]1(C)CC(=O)O2] | N-((2S,3R)-1-(((R)-1-((R)-6,7-dimethyl-4-oxo-1,3,6,2-dioxazaborocan-2-yl)-3-methylbutyl)amino)-3-hydroxy-1-oxobutan-2-yl)-6-phenylpicolinamide |
| HL-454 | 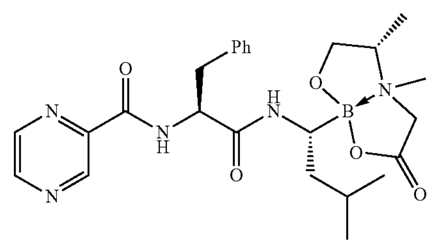 [SMILES: CC(C)C[C@H](NC(=O)[C@H](Cc1ccccc1)NC(=O)c1cnccn1)[B-]12OC[C@H](C)[N+]1(C)CC(=O)O2] | N-((S)-1-(((R)-1-((R)-6,7-dimethyl-4-oxo-1,3,6,2-dioxazaborocan-2-yl)-3-methylbutyl)amino)-1-oxo-3-phenylpropan-2-yl)pyrazine-2-carboxamide |
| HL-455 | 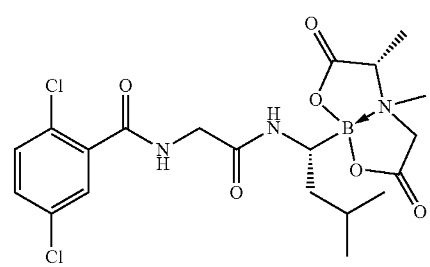 [SMILES: CC(C)C[C@H](NC(=O)CNC(=O)c1cc(Cl)ccc1Cl)[B-]12OC(=O)C[N+]1(C)[C@@H](C)C(=O)O2] | 2,5-dichloro-N-(2-(((R)-1-((R)-5,6-dimethyl-4,8-dioxo-1,3,6,2-dioxazaborocan-2-yl)-3-methylbutyl)amino)-2-oxoethyl)benzamide |
| HL-456 | 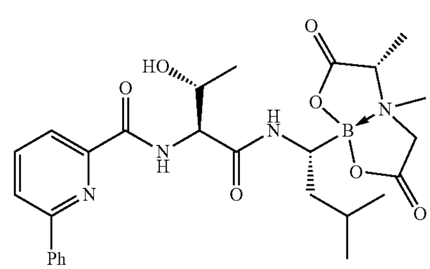 [SMILES: CC(C)C[C@H](NC(=O)[C@@H](NC(=O)c1cccc(-c2ccccc2)n1)[C@@H](C)O)[B-]12OC(=O)C[N+]1(C)[C@@H](C)C(=O)O2] | N-((2S,3R)-1-(((R)-1-((R)-5,6-dimethyl-4,8-dioxo-1,3,6,2-dioxazaborocan-2-yl)-3-methylbutyl)amino)-3-hydroxy-1-oxobutan-2-yl)-6-phenylpicolinamide |

TABLE 1-continued

| Serial # | Structure | Name |
|---|---|---|
| HL-457 | 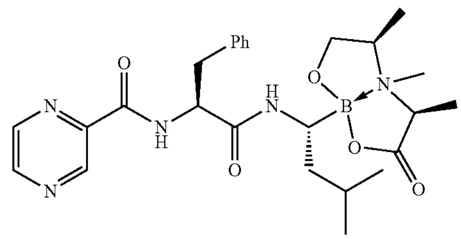 [SMILES: CC(C)C[C@H](NC(=O)[C@H](Cc1ccccc1)NC(=O)c1cnccn1)[B-]12OC[C@@H](C)[N+]1(C)[C@@H](C)C(=O)O2] | N-((S)-1-(((R)-3-methyl-1-((5S,7R)-5,6,7-trimethyl-4-oxo-1,3,6,2-dioxazaborocan-2-yl)butyl)amino)-1-oxo-3-phenylpropan-2-yl)pyrazine-2-carboxamide |
| HL-458 | 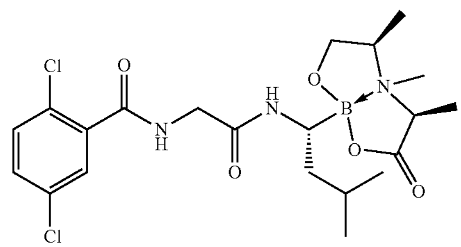 | 2,5-dichloro-N-(2-(((R)-3-methyl-1-((5S,7R)-5,6,7-trimethyl-4-oxo-1,3,6,2-dioxazaborocan-2-yl)butyl)amino)-2-oxoethyl)benzamide |
| HL-459 | 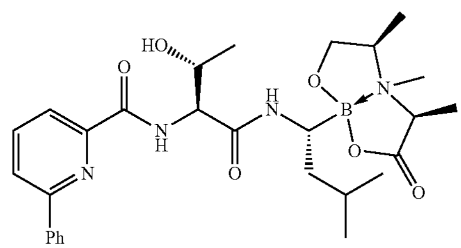 [SMILES: CC(C)C[C@H](NC(=O)[C@@H](NC(=O)c1cccc(-c2ccccc2)n1)[C@@H](C)O)[B-]12OC[C@@H](C)[N+]1(C)[C@@H](C)C(=O)O2] | N-((2S,3R)-3-hydroxy-1-(((R)-3-methyl-1-((5S,7R)-5,6,7-trimethyl-4-oxo-1,3,6,2-dioxazaborocan-2-yl)butyl)amino)-1-oxobutan-2-yl)-6-phenylpicolinamide |
| HL-460 | 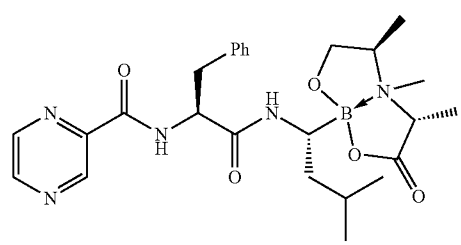 [SMILES: CC(C)C[C@H](NC(=O)[C@H](Cc1ccccc1)NC(=O)c1cnccn1)[B-]12OC[C@@H](C)[N+]1(C)[C@H](C)C(=O)O2] | N-((S)-1-(((R)-3-methyl-1-((5R,7R)-5,6,7-trimethyl-4-oxo-1,3,6,2-dioxazaborocan-2-yl)butyl)amino)-1-oxo-3-phenylpropan-2-yl)pyrazine-2-carboxamide |
| HL-461 | 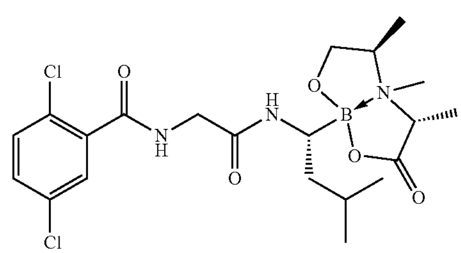 [SMILES: CC(C)C[C@H](NC(=O)CNC(=O)c1cc(Cl)ccc1Cl)[B-]12OC[C@@H](C)[N+]1(C)[C@H](C)C(=O)O2] | 2,5-dichloro-N-(2-(((R)-3-methyl-1-((5R,7R)-5,6,7-trimethyl-4-oxo-1,3,6,2-dioxazaborocan-2-yl)butyl)amino)-2-oxoethyl)benzamide |
| HL-462 | 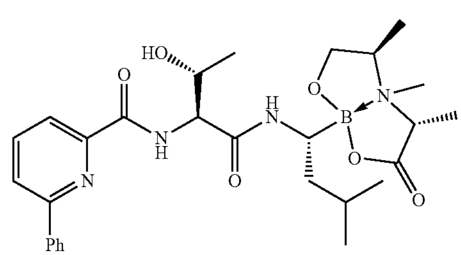 [SMILES: CC(C)C[C@H](NC(=O)[C@@H](NC(=O)c1cccc(-c2ccccc2)n1)[C@@H](C)O)[B-]12OC[C@@H](C)[N+]1(C)[C@H](C)C(=O)O2] | N-((2S,3R)-3-hydroxy-1-(((R)-3-methyl-1-((5R,7R)-5,6,7-trimethyl-4-oxo-1,3,6,2-dioxazaborocan-2-yl)butyl)amino)-1-oxobutan-2-yl)-6-phenylpicolinamide |

TABLE 1-continued

| Serial # | Structure | Name |
|---|---|---|
| HL-463 | 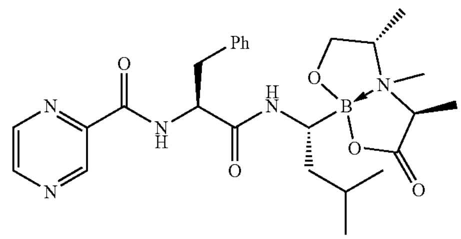 [SMILES: CC(C)C[C@H](NC(=O)[C@H](Cc1ccccc1)NC(=O)c1cnccn1)[B-]12OC[C@H](C)[N+]1(C)[C@@H](C)C(=O)O2] | N-((S)-1-(((R)-3-methyl-1-((5S,7R)-5,6,7-trimethyl-4-oxo-1,3,6,2-dioxazaborocan-2-yl)butyl)amino)-1-oxo-3-phenylpropan-2-yl)pyrazine-2-carboxamide |
| HL-464 | 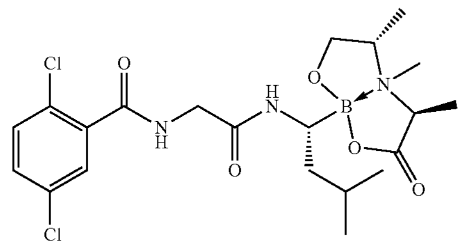 [SMILES: CC(C)C[C@H](NC(=O)CNC(=O)c1cc(Cl)ccc1Cl)[B-]12OC[C@H](C)[N+]1(C)[C@@H](C)C(=O)O2] | 2,5-dichloro-N-(2-(((R)-3-methyl-1-((5S,7R)-5,6,7-trimethyl-4-oxo-1,3,6,2-dioxazaborocan-2-yl)butyl)amino)-2-oxoethyl)benzamide |
| HL-465 | 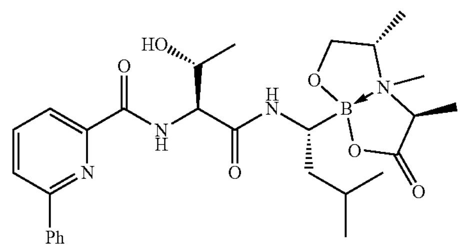 [SMILES: CC(C)C[C@H](NC(=O)[C@@H](NC(=O)c1cccc(-c2ccccc2)n1)[C@@H](C)O)[B-]12OC[C@H](C)[N+]1(C)[C@@H](C)C(=O)O2] | N-((2S,3R)-3-hydroxy-1-(((R)-3-methyl-1-((5S,7R)-5,6,7-trimethyl-4-oxo-1,3,6,2-dioxazaborocan-2-yl)butyl)amino)-1-oxobutan-2-yl)-6-phenylpicolinamide |
| HL-466 | 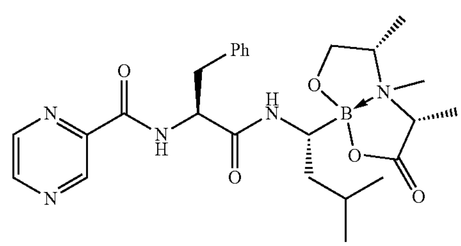 [SMILES: CC(C)C[C@H](NC(=O)[C@H](Cc1ccccc1)NC(=O)c1cnccn1)[B-]12OC[C@H](C)[N+]1(C)[C@H](C)C(=O)O2] | N-((S)-1-(((R)-3-methyl-1-((5R,7R)-5,6,7-trimethyl-4-oxo-1,3,6,2-dioxazaborocan-2-yl)butyl)amino)-1-oxo-3-phenylpropan-2-yl)pyrazine-2-carboxamide |
| HL-467 | 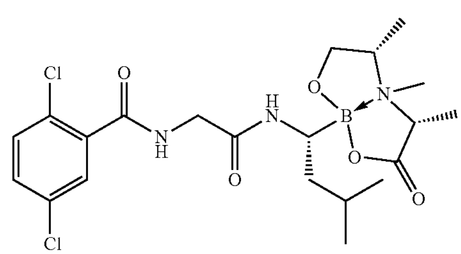 [SMILES: CC(C)C[C@H](NC(=O)CNC(=O)c1cc(Cl)ccc1Cl)[B-]12OC[C@H](C)[N+]1(C)[C@H](C)C(=O)O2] | 2,5-dichloro-N-(2-(((R)-3-methyl-1-((5R,7R)-5,6,7-trimethyl-4-oxo-1,3,6,2-dioxazaborocan-2-yl)butyl)amino)-2-oxoethyl)benzamide |
| HL-468 | 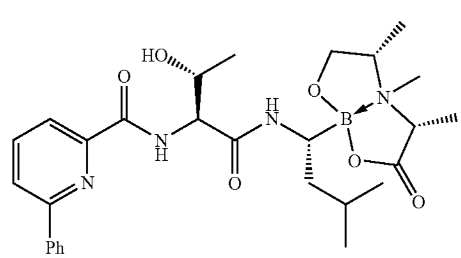 [SMILES: CC(C)C[C@H](NC(=O)[C@@H](NC(=O)c1cccc(-c2ccccc2)n1)[C@@H](C)O)[B-]12OC[C@H](C)[N+]1(C)[C@H](C)C(=O)O2] | N-((2S,3R)-3-hydroxy-1-(((R)-3-methyl-1-((5R,7R)-5,6,7-trimethyl-4-oxo-1,3,6,2-dioxazaborocan-2-yl)butyl)amino)-1-oxobutan-2-yl)-6-phenylpicolinamide |

TABLE 1-continued

| Serial # | Structure | Name |
|---|---|---|
| HL-469 | 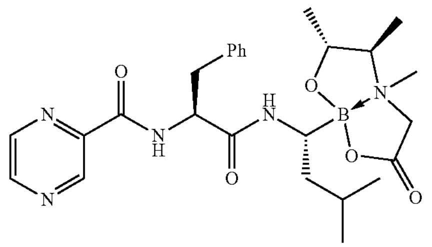 [SMILES: CC(C)C[C@H](NC(=O)[C@H](Cc1ccccc1)NC(=O)c1cnccn1)[B-]12OC(=O)C[N+]1(C)[C@H](C)[C@@H](C)O2] | N-((S)-1-(((R)-3-methyl-1-((2R,3R)-2,3,4-trimethyl-6-oxotetrahydro-2H-4l4,8l4-[1,3,2]oxazaborolo[2,3-b][1,3,2]oxazaborol-8-yl)butyl)amino)-1-oxo-3-phenylpropan-2-yl)pyrazine-2-carboxamide |
| HL-470 | 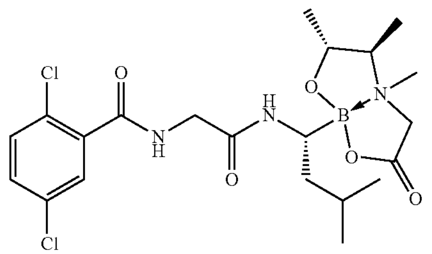 [SMILES: CC(C)C[C@H](NC(=O)CNC(=O)c1cc(Cl)ccc1Cl)[B-]12OC(=O)C[N+]1(C)[C@H](C)[C@@H](C)O2] | 2,5-dichloro-N-(2-(((R)-3-methyl-1-((2R,3R)-2,3,4-trimethyl-6-oxotetrahydro-2H-4l4,8l4-[1,3,2]oxazaborolo[2,3-b][1,3,2]oxazaborol-8-yl)butyl)amino)-2-oxoethyl)benzamide |
| HL-471 | 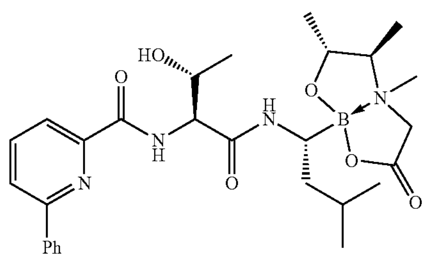 [SMILES: CC(C)C[C@H](NC(=O)[C@@H](NC(=O)c1cccc(-c2ccccc2)n1)[C@@H](C)O)[B-]12OC(=O)C[N+]1(C)[C@H](C)[C@@H](C)O2] | N-((2S,3R)-3-hydroxy-1-(((R)-3-methyl-1-((2R,3R)-2,3,4-trimethyl-6-oxotetrahydro-2H-4l4,8l4-[1,3,2]oxazaborolo[2,3-b][1,3,2]oxazaborol-8-yl)butyl)amino)-1-oxobutan-2-yl)-6-phenylpicolinamide |
| HL-472 | 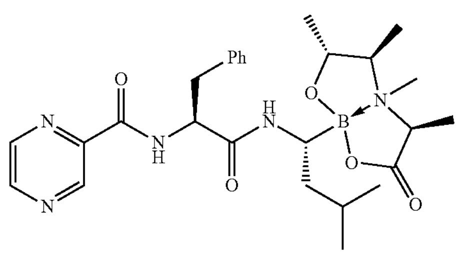 [SMILES: CC(C)C[C@H](NC(=O)[C@H](Cc1ccccc1)NC(=O)c1cnccn1)[B-]12OC(=O)[C@H](C)[N+]1(C)[C@H](C)[C@@H](C)O2] | N-((S)-1-(((R)-3-methyl-1-((2R,3R,5S)-2,3,4,5-tetramethyl-6-oxotetrahydro-2H-4l4,8l4-[1,3,2]oxazaborolo[2,3-b][1,3,2]oxazaborol-8-yl)butyl)amino)-1-oxo-3-phenylpropan-2-yl)pyrazine-2-carboxamide |
| HL-473 | 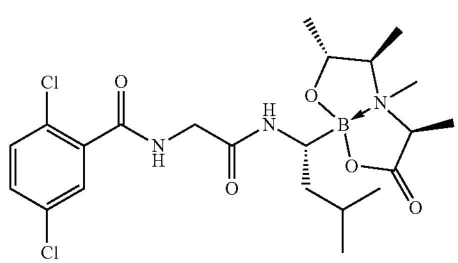 [SMILES: CC(C)C[C@H](NC(=O)CNC(=O)c1cc(Cl)ccc1Cl)[B-]12OC(=O)[C@H](C)[N+]1(C)[C@H](C)[C@@H](C)O2] | 2,5-dichloro-N-(2-(((R)-3-methyl-1-((2R,3R,5S)-2,3,4,5-tetramethyl-6-oxotetrahydro-2H-4l4,8l4-[1,3,2]oxazaborolo[2,3-b][1,3,2]oxazaborol-8-yl)butyl)amino)-2-oxoethyl)benzamide |
| HL-474 | 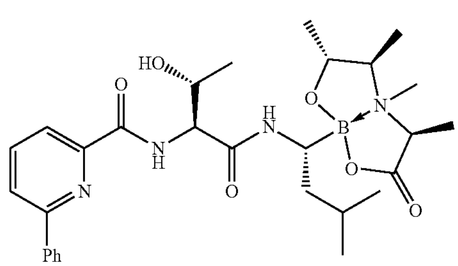 [SMILES: CC(C)C[C@H](NC(=O)[C@@H](NC(=O)c1cccc(-c2ccccc2)n1)[C@@H](C)O)[B-]12OC(=O)[C@H](C)[N+]1(C)[C@H](C)[C@@H](C)O2] | N-((2S,3R)-3-hydroxy-1-(((R)-3-methyl-1-((2R,3R,5S)-2,3,4,5-tetramethyl-6-oxotetrahydro-2H-4l4,8l4-[1,3,2]oxazaborolo[2,3-b][1,3,2]oxazaborol-8-yl)butyl)amino)-1-oxobutan-2-yl)-6-phenylpicolinamide |

TABLE 1-continued

| Serial # | Structure | Name |
|---|---|---|
| HL-475 | 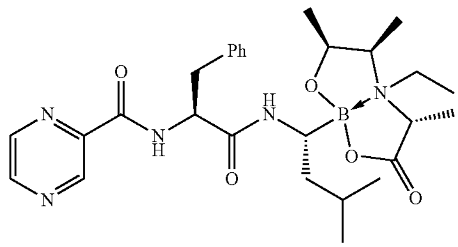 [SMILES: CC[N+]12[C@H](C)C(=O)O[B-]1([C@H](CC(C)C)NC(=O)[C@H](Cc1ccccc1)NC(=O)c1cnccn1)O[C@@H](C)[C@H]2C] | N-((S)-1-(((R)-1-((2S,3R,5R)-4-ethyl-2,3,5-trimethyl-6-oxotetrahydro-2H-4l4,8l4-[1,3,2]oxazaborolo[2,3-b][1,3,2]oxazaborol-8-yl)-3-methylbutyl)amino)-1-oxo-3-phenylpropan-2-yl)pyrazine-2-carboxamide |
| HL-476 | 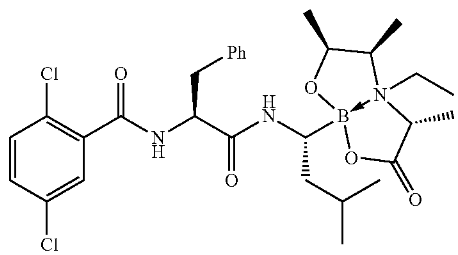 [SMILES: CC[N+]12[C@H](C)C(=O)O[B-]1([C@H](CC(C)C)NC(=O)[C@H](Cc1ccccc1)NC(=O)c1cc(Cl)ccc1Cl)O[C@@H](C)[C@H]2C] | 2,5-dichloro-N-((S)-1-(((R)-1-((2S,3R,5R)-4-ethyl-2,3,5-trimethyl-6-oxotetrahydro-2H-4l4,8l4-[1,3,2]oxazaborolo[2,3-b][1,3,2]oxazaborol-8-yl)-3-methylbutyl)amino)-1-oxo-3-phenylpropan-2-yl)benzamide |
| HL-477 | 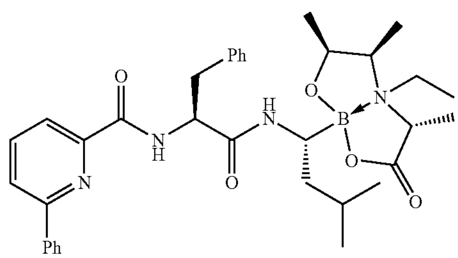 [SMILES: CC[N+]12[C@H](C)C(=O)O[B-]1([C@H](CC(C)C)NC(=O)[C@H](Cc1ccccc1)NC(=O)c1cccc(-c3ccccc3)n1)O[C@@H](C)[C@H]2C] | N-((S)-1-(((R)-1-((2S,3R,5R)-4-ethyl-2,3,5-trimethyl-6-oxotetrahydro-2H-4l4,8l4-[1,3,2]oxazaborolo[2,3-b][1,3,2]oxazaborol-8-yl)-3-methylbutyl)amino)-1-oxo-3-phenylpropan-2-yl)-6-phenylpicolinamide |
| HL-478 | 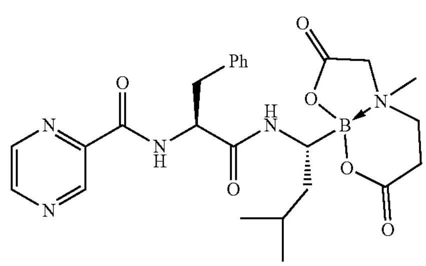 [SMILES: CC(C)C[C@H](NC(=O)[C@H](Cc1ccccc1)NC(=O)c1cnccn1)[B-]12OC(=O)CC[N+]1(C)CC(=O)O2] | N-((S)-1-(((R)-3-methyl-1-(6-methyl-4,9-dioxo-1,3,6,2-dioxazaboronan-2-yl)butyl)amino)-1-oxo-3-phenylpropan-2-yl)pyrazine-2-carboxamide |
| HL-479 | 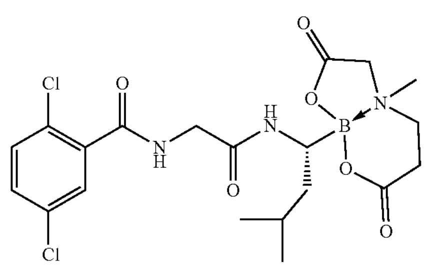 [SMILES: CC(C)C[C@H](NC(=O)CNC(=O)c1cc(Cl)ccc1Cl)[B-]12OC(=O)CC[N+]1(C)CC(=O)O2] | (R)-2,5-dichloro-N-(2-((3-methyl-1-(6-methyl-4,9-dioxo-1,3,6,2-dioxazaboronan-2-yl)butyl)amino)-2-oxoethyl)benzamide |
| HL-480 | 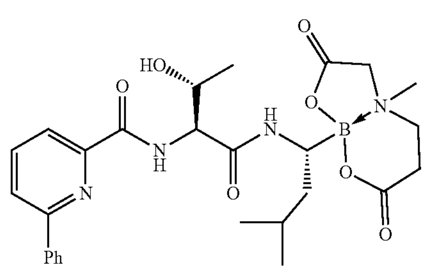 [SMILES: CC(C)C[C@H](NC(=O)[C@@H](NC(=O)c1cccc(-c2ccccc2)n1)[C@@H](C)O)[B-]12OC(=O)CC[N+]1(C)CC(=O)O2] | N-((2S,3R)-3-hydroxy-1-(((R)-3-methyl-1-(6-methyl-4,9-dioxo-1,3,6,2-dioxazaboronan-2-yl)butyl)amino)-1-oxobutan-2-yl)-6-phenylpicolinamide |

TABLE 1-continued

| Serial # | Structure | Name |
|---|---|---|
| HL-481 | 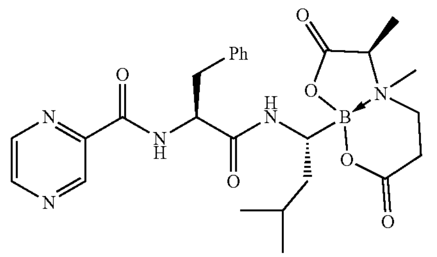 [SMILES: CC(C)C[C@H](NC(=O)[C@H](Cc1ccccc1)NC(=O)c1cnccn1)[B-]12OC(=O)CC[N+]1(C)[C@H](C)C(=O)O2] | N-((S)-1-(((R)-1-((R)-5,6-dimethyl-4,9-dioxo-1,3,6,2-dioxazaboronan-2-yl)-3-methylbutyl)amino)-1-oxo-3-phenylpropan-2-yl)pyrazine-2-carboxamide |
| HL-482 | 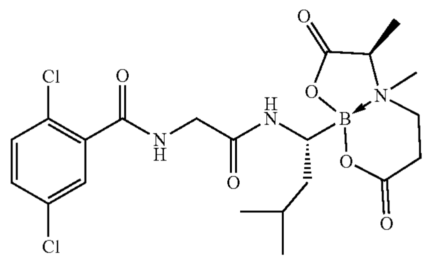 [SMILES: CC(C)C[C@H](NC(=O)CNC(=O)c1cc(Cl)ccc1Cl)[B-]12OC(=O)CC[N+]1(C)[C@H](C)C(=O)O2] | 2,5-dichloro-N-(2-(((R)-1-((R)-5,6-dimethyl-4,9-dioxo-1,3,6,2-dioxazaboronan-2-yl)-3-methylbutyl)amino)-2-oxoethyl)benzamide |
| HL-483 | 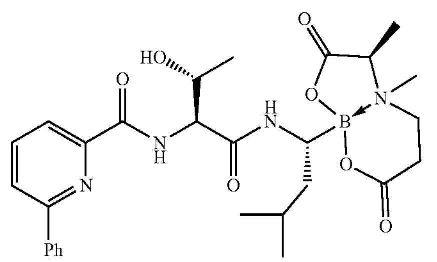 [SMILES: CC(C)C[C@H](NC(=O)[C@@H](NC(=O)c1cccc(-c2ccccc2)n1)[C@@H](C)O)[B-]12OC(=O)CC[N+]1(C)[C@H](C)C(=O)O2] | N-((2S,3R)-1-(((R)-1-((R)-5,6-dimethyl-4,9-dioxo-1,3,6,2-dioxazaboronan-2-yl)-3-methylbutyl)amino)-3-hydroxy-1-oxobutan-2-yl)-6-phenylpicolinamide |
| HL-484 | 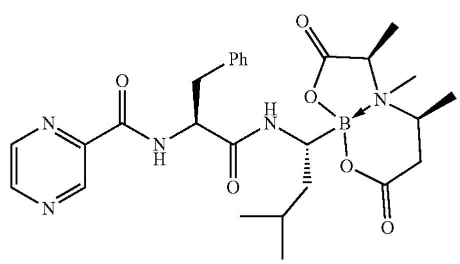 [SMILES: CC(C)C[C@H](NC(=O)[C@H](Cc1ccccc1)NC(=O)c1cnccn1)[B-]12OC(=O)C[C@H](C)[N+]1(C)[C@H](C)C(=O)O2] | N-((S)-1-(((R)-3-methyl-1-((5R,7S)-5,6,7-trimethyl-4,9-dioxo-1,3,6,2-dioxazaboronan-2-yl)butyl)amino)-1-oxo-3-phenylpropan-2-yl)pyrazine-2-carboxamide |
| HL-485 | 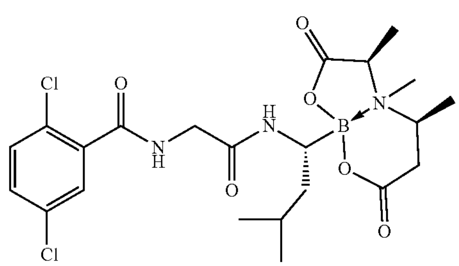 [SMILES: CC(C)C[C@H](NC(=O)CNC(=O)c1cc(Cl)ccc1Cl)[B-]12OC(=O)C[C@H](C)[N+]1(C)[C@H](C)C(=O)O2] | 2,5-dichloro-N-(2-(((R)-3-methyl-1-((5R,7S)-5,6,7-trimethyl-4,9-dioxo-1,3,6,2-dioxazaboronan-2-yl)butyl)amino)-2-oxoethyl)benzamide |
| HL-486 | 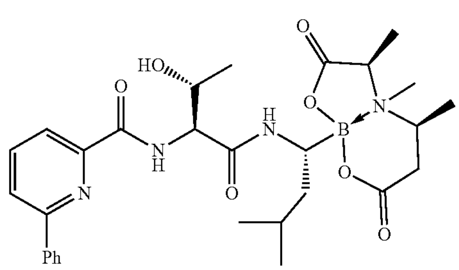 [SMILES: CC(C)C[C@H](NC(=O)[C@@H](NC(=O)c1cccc(-c2ccccc2)n1)[C@@H](C)O)[B-]12OC(=O)C[C@H](C)[N+]1(C)[C@H](C)C(=O)O2] | N-((2S,3R)-3-hydroxy-1-(((R)-3-methyl-1-((5R,7S)-5,6,7-trimethyl-4,9-dioxo-1,3,6,2-dioxazaboronan-2-yl)butyl)amino)-1-oxobutan-2-yl)-6-phenylpicolinamide |

TABLE 1-continued

| Serial # | Structure | Name |
|---|---|---|
| HL-487 | 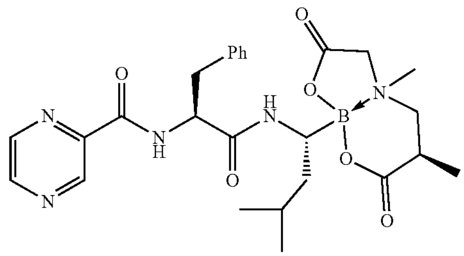 [SMILES: CC(C)C[C@H](NC(=O)[C@H](Cc1ccccc1)NC(=O)c1cnccn1)[B-]12OC(=O)C[N+]1(C)C[C@@H](C)C(=O)O2] | N-((S)-1-(((R)-1-((R)-6,8-dimethyl-4,9-dioxo-1,3,6,2-dioxazaboronan-2-yl)-3-methylbutyl)amino)-1-oxo-3-phenylpropan-2-yl)pyrazine-2-carboxamide |
| HL-488 | 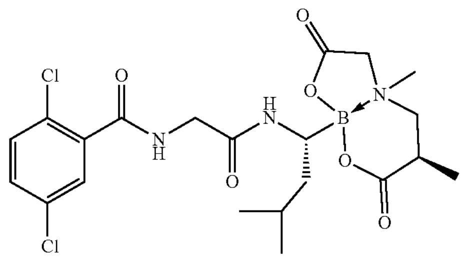 [SMILES: CC(C)C[C@H](NC(=O)CNC(=O)c1cc(Cl)ccc1Cl)[B-]12OC(=O)C[N+]1(C)C[C@@H](C)C(=O)O2] | 2,5-dichloro-N-(2-(((R)-1-((R)-6,8-dimethyl-4,9-dioxo-1,3,6,2-dioxazaboronan-2-yl)-3-methylbutyl)amino)-2-oxoethyl)benzamide |
| HL-489 | 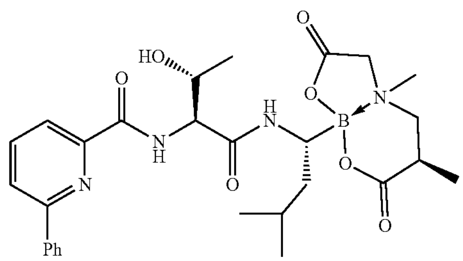 [SMILES: CC(C)C[C@H](NC(=O)[C@@H](NC(=O)c1cccc(-c2ccccc2)n1)[C@@H](C)O)[B-]12OC(=O)C[N+]1(C)C[C@@H](C)C(=O)O2] | N-((2S,3R)-1-(((R)-1-((R)-6,8-dimethyl-4,9-dioxo-1,3,6,2-dioxazaboronan-2-yl)-3-methylbutyl)amino)-3-hydroxy-1-oxobutan-2-yl)-6-phenylpicolinamide |
| HL-490 | 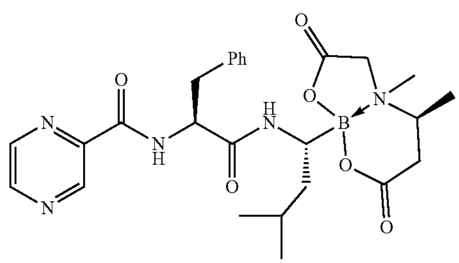 [SMILES: CC(C)C[C@H](NC(=O)[C@H](Cc1ccccc1)NC(=O)c1cnccn1)[B-]12OC(=O)C[C@H](C)[N+]1(C)CC(=O)O2] | N-((S)-1-(((R)-1-((S)-6,7-dimethyl-4,9-dioxo-1,3,6,2-dioxazaboronan-2-yl)-3-methylbutyl)amino)-1-oxo-3-phenylpropan-2-yl)pyrazine-2-carboxamide |
| HL-491 | 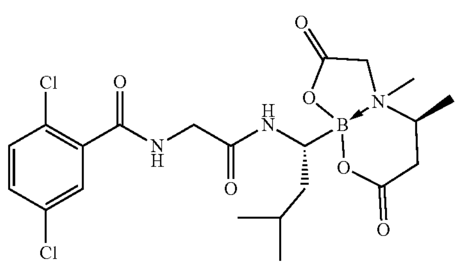 [SMILES: CC(C)C[C@H](NC(=O)CNC(=O)c1cc(Cl)ccc1Cl)[B-]12OC(=O)C[C@H](C)[N+]1(C)CC(=O)O2] | 2,5-dichloro-N-(2-(((R)-1-((S)-6,7-dimethyl-4,9-dioxo-1,3,6,2-dioxazaboronan-2-yl)-3-methylbutyl)amino)-2-oxoethyl)benzamide |
| HL-492 | 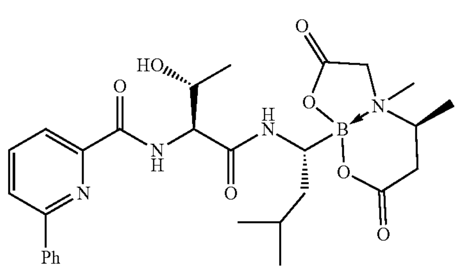 [SMILES: CC(C)C[C@H](NC(=O)[C@@H](NC(=O)c1cccc(-c2ccccc2)n1)[C@@H](C)O)[B-]12OC(=O)C[C@H](C)[N+]1(C)CC(=O)O2] | N-((2S,3R)-1-(((R)-1-((S)-6,7-dimethyl-4,9-dioxo-1,3,6,2-dioxazaboronan-2-yl)-3-methylbutyl)amino)-3-hydroxy-1-oxobutan-2-yl)-6-phenylpicolinamide |

TABLE 1-continued

| Serial # | Structure | Name |
|---|---|---|
| HL-493 | 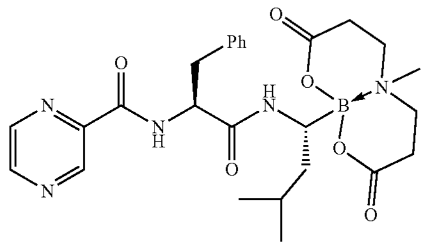 [SMILES: CC(C)C[C@H](NC(=O)[C@H](Cc1ccccc1)NC(=O)c1cnccn1)[B-]12OC(=O)CC[N+]1(C)CCC(=O)O2] | N-((S)-1-(((R)-3-methyl-1-(7-methyl-4,10-dioxo-1,3,7,2-dioxazaborecan-2-yl)butyl)amino)-1-oxo-3-phenylpropan-2-yl)pyrazine-2-carboxamide |
| HL-494 | 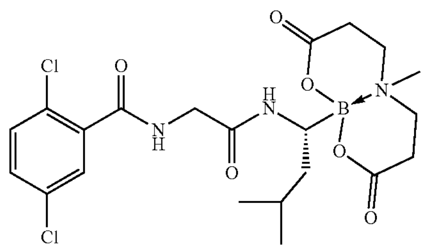 [SMILES: CC(C)C[C@H](NC(=O)CNC(=O)c1cc(Cl)ccc1Cl)[B-]12OC(=O)CC[N+]1(C)CCC(=O)O2] | (R)-2,5-dichloro-N-(2-((3-methyl-1-(7-methyl-4,10-dioxo-1,3,7,2-dioxazaborecan-2-yl)butyl)amino)-2-oxoethyl)benzamide |
| HL-495 | 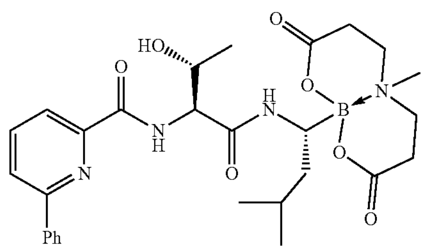 [SMILES: CC(C)C[C@H](NC(=O)[C@@H](NC(=O)c1cccc(-c2ccccc2)n1)[C@@H](C)O)[B-]12OC(=O)CC[N+]1(C)CCC(=O)O2] | N-((2S,3R)-3-hydroxy-1-(((R)-3-methyl-1-(7-methyl-4,10-dioxo-1,3,7,2-dioxazaborecan-2-yl)butyl)amino)-1-oxobutan-2-yl)-6-phenylpicolinamide |
| HL-496 | 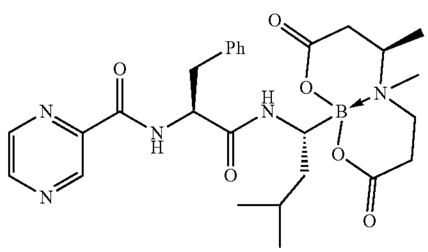 [SMILES: CC(C)C[C@H](NC(=O)[C@H](Cc1ccccc1)NC(=O)c1cnccn1)[B-]12OC(=O)CC[N+]1(C)[C@H](C)CC(=O)O2] | N-((S)-1-(((R)-1-((R)-6,7-dimethyl-4,10-dioxo-1,3,7,2-dioxazaborecan-2-yl)-3-methylbutyl)amino)-1-oxo-3-phenylpropan-2-yl)pyrazine-2-carboxamide |
| HL-497 | 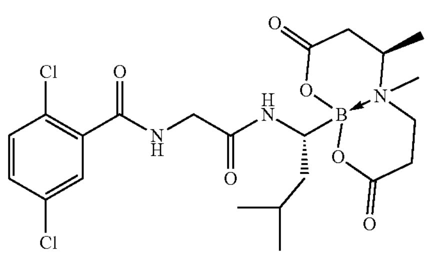 [SMILES: CC(C)C[C@H](NC(=O)CNC(=O)c1cc(Cl)ccc1Cl)[B-]12OC(=O)CC[N+]1(C)[C@H](C)CC(=O)O2] | 2,5-dichloro-N-(2-(((R)-1-((R)-6,7-dimethyl-4,10-dioxo-1,3,7,2-dioxazaborecan-2-yl)-3-methylbutyl)amino)-2-oxoethyl)benzamide |
| HL-498 | 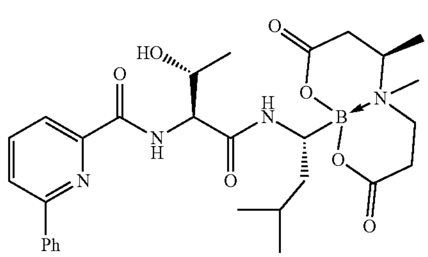 [SMILES: CC(C)C[C@H](NC(=O)[C@@H](NC(=O)c1cccc(-c2ccccc2)n1)[C@@H](C)O)[B-]12OC(=O)CC[N+]1(C)[C@H](C)CC(=O)O2] | N-((2S,3R)-1-(((R)-1-((R)-6,7-dimethyl-4,10-dioxo-1,3,7,2-dioxazaborecan-2-yl)-3-methylbutyl)amino)-3-hydroxy-1-oxobutan-2-yl)-6-phenylpicolinamide |

TABLE 1-continued

| Serial # | Structure | Name |
|---|---|---|
| HL-499 | 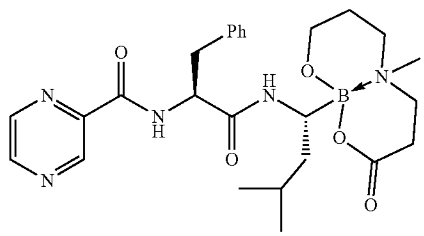 [SMILES: CC(C)C[C@H](NC(=O)[C@H](Cc1ccccc1)NC(=O)c1cnccn1)[B-]12OCCC[N+]1(C)CCC(=O)O2] | N-((S)-1-(((R)-3-methyl-1-(7-methyl-4-oxo-1,3,7,2-dioxazaborecan-2-yl)butyl)amino)-1-oxo-3-phenylpropan-2-yl)pyrazine-2-carboxamide |
| HL-500 | 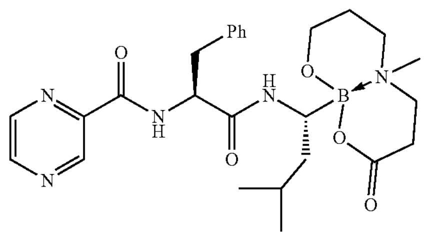 [SMILES: CC(C)C[C@H](NC(=O)[C@H](Cc1ccccc1)NC(=O)c1cnccn1)[B-]12OCCC[N+]1(C)CCC(=O)O2] | (R)-2,5-dichloro-N-(2-((3-methyl-1-(7-methyl-4-oxo-1,3,7,2-dioxazaborecan-2-yl)butyl)amino)-2-oxoethyl)benzamide |
| HL-501 | 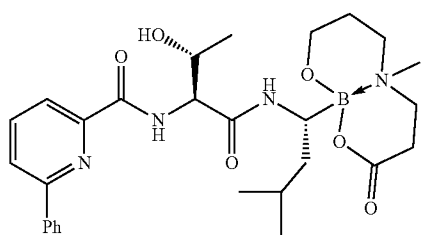 [SMILES: CC(C)C[C@H](NC(=O)[C@@H](NC(=O)c1cccc(-c2ccccc2)n1)[C@@H](C)O)[B-]12OCCC[N+]1(C)CCC(=O)O2] | N-((2S,3R)-3-hydroxy-1-(((R)-3-methyl-1-(7-methyl-4-oxo-1,3,7,2-dioxazaborecan-2-yl)butyl)amino)-1-oxobutan-2-yl)-6-phenylpicolinamide |
| HL-502 | 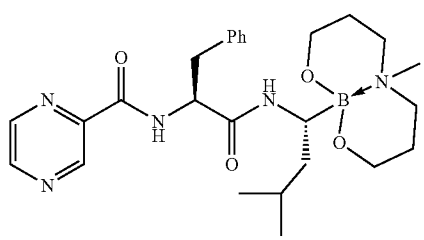 [SMILES: CC(C)C[C@H](NC(=O)[C@H](Cc1ccccc1)NC(=O)c1cnccn1)[B-]12OCCC[N+]1(C)CCCO2] | N-((S)-1-(((R)-3-methyl-1-(7-methyl-1,3,7,2-dioxazaborecan-2-yl)butyl)amino)-1-oxo-3-phenylpropan-2-yl)pyrazine-2-carboxamide |
| HL-503 | 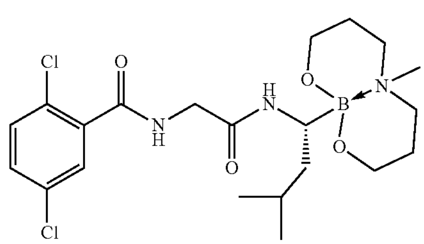 [SMILES: CC(C)C[C@H](NC(=O)CNC(=O)c1cc(Cl)ccc1Cl)[B-]12OCCC[N+]1(C)CCCO2] | (R)-2,5-dichloro-N-(2-((3-methyl-1-(7-methyl-1,3,7,2-dioxazaborecan-2-yl)butyl)amino)-2-oxoethyl)benzamide |
| HL-504 | 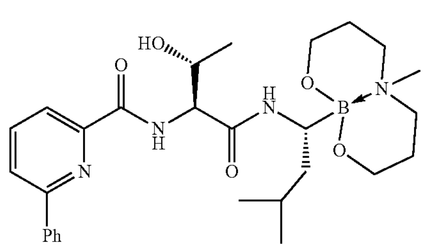 [SMILES: CC(C)C[C@H](NC(=O)[C@@H](NC(=O)c1cccc(-c2ccccc2)n1)[C@@H](C)O)[B-]12OCCC[N+]1(C)CCCO2] | N-((2S,3R)-3-hydroxy-1-(((R)-3-methyl-1-(7-methyl-1,3,7,2-dioxazaborecan-2-yl)butyl)amino)-1-oxobutan-2-yl)-6-phenylpicolinamide |

TABLE 1-continued

| Serial # | Structure | Name |
|---|---|---|
| HL-505 | 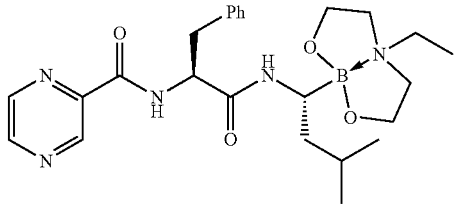 [SMILES: CC[N+]12CCO[B-]1([C@H](CC(C)C)NC(=O)[C@H](Cc1ccccc1)NC(=O)c1cnccn1)OCC2] | N-((S)-1-(((R)-1-(4-ethyltetrahydro-2H-4l4,8l4-[1,3,2]oxazaborolo[2,3-b][1,3,2]oxazaborol-8-yl)-3-methylbutyl)amino)-1-oxo-3-phenylpropan-2-yl)pyrazine-2-carboxamide |
| HL-506 | 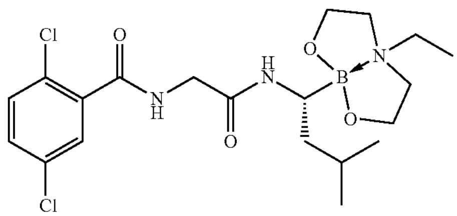 [SMILES: CC[N+]12CCO[B-]1([C@H](CC(C)C)NC(=O)CNC(=O)c1cc(Cl)ccc1Cl)OCC2] | (R)-2,5-dichloro-N-(2-((1-(4-ethyltetrahydro-2H-4l4,8l4-[1,3,2]oxazaborolo[2,3-b][1,3,2]oxazaborol-8-yl)-3-methylbutyl)amino)-2-oxoethyl)benzamide |
| HL-507 | 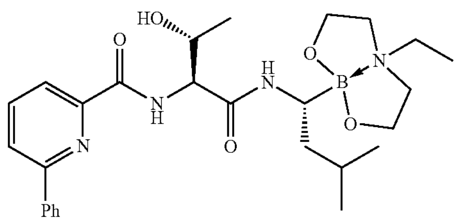 [SMILES: CC[N+]12CCO[B-]1([C@H](CC(C)C)NC(=O)[C@@H](NC(=O)c1cccc(-c3ccccc3)n1)[C@@H](C)O)OCC2] | N-((2S,3R)-1-(((R)-1-(4-ethyltetrahydro-2H-4l4,8l4-[1,3,2]oxazaborolo[2,3-b][1,3,2]oxazaborol-8-yl)-3-methylbutyl)amino)-3-hydroxy-1-oxobutan-2-yl)-6-phenylpicolinamide |

Stability Study

Compounds were tested for their stability, under three different conditions (see Table 2), by the following procedures:

1. Room Temperature and Dry: compounds were left at the room temperature (20° C.) under inert dry gas;
2. 30° C. and 65% Humidity: compounds sealed with double bags were put into a stability chamber. Temperature was set at 30° C. while the humidity was controlled at 65%.
3. 37° C. pH=7.4 solution: compounds were dissolved in PBS solution and then the entire solution was submerged under a 37° C. water bath.

TABLE 2

Stability study of designed chiral specific boron derivatives.

| Compound | Room Temp Dry | 30° C./ 65% Humidity | 37° C. H₂O/ pH 7.4 |
|---|---|---|---|
| HL01-0 | − | | |
| HL01-11 | + | + | + |
| HL01-15 | + | + | + |
| HL01-17 | + | − | Decompose Instant |

Note:
"+" meaning stable, "−" meaning quickly degradable, as determined by RP-HPLC.

Cell Viability Assay

1. Cell Line

The multiple myeloma cell line MM1.S was obtained from the ATCC. Cells were cultured in standard RPMI-1640 media (Hyclone) supplemented with 10% heat-inactivated fetal bovine serum (Gibco), 1% penicillin/streptomycin (Gibco) and grown in a humidified incubator with 5% $CO_2$ at 37° C.

Eight thousand MM1.S cells per well were seeded in tissue culture-treated 96-well plate (Nunc) and incubated overnight.

2. Compound Treatment

Eighteen hours after seeding, MM1.S cells were treated with a series of concentrations of five different compounds (Bortezomib, HL01-01, HL01-11, HL01-15, HL1-147) or DMSO vehicle control for 72 hrs in a humidified incubator with 5% $CO_2$, at 37° C. The concentrations of five different compounds were 0.3, 1, 3.16, 10, 31.6, 100, 316, and 1000 nM. Each well had the same DMSO concentration of 0.05%.

3. Cell Viability Assay (MTS Assay)

The effects of compounds on cell viability were assessed using CellTiter 96®A Queous One solution Reagent (Promega; G3580).

After being treated with various compounds for 72 hrs, cells in the 96-well plate were centrifuged 1000 rpm for 3 minutes, and 180 ul supernatant were removed from each well. Cells were incubated with 20 ul CellTiter 96®A Queous One solution Reagent and put into incubator with 5% CO₂, at 37° C. for an additional 4 hrs. The absorbance was measured at 490 nm with Automatic Microplate reader (Infinite M1000 pro, Tecan). There was a liner relationship ($r^2=0.99$) between absorbance and cell number in each plate format. Four sets of experiments for each drug combinations were carried out. Cell viability (Percentage of Cell Survival) was calculated by the following formula: cell viability (%)=(average absorbance of treated group-average absorbance of blank)/(average absorbance of untreated group-average absorbance of blank)×100%. IC50 values were calculated using Prism software.

Results

The cytotoxic effects of compounds including Bortezomib, HL01-11, and HL01-15 on MM1.S cell were assessed using the MTS assay. It was found that all compounds could dose-dependently decrease the cell viability in MM1.S cell. As represented by the cell line assay shown in FIG. 1. Bortezomib and HL01-11 exhibited strong cytotoxic effects on MM1.S cells and both compounds had similar $IC_{50}$ values nearly 2 nM. The effect of HL01-15 was weaker than the other compounds. The $IC_{50}$ value of HL01-15 was 6.85 nM, as set forth in Table 3:

TABLE 3

| Compound | $IC_{50}$ (nM) |
| --- | --- |
| Bortezomib | 1.76 |
| HL01-01 | 1.96 |
| HL01-11 | 1.62 |
| HL01-15 | 6.85 |
| HL01-17 (Ixazomib) | 9.45 |

Five compounds exhibited cytotoxicity in MM1.S cells. MM1.S cells were treated with various concentrations of Bortezomib, HL01-11, and HL01-15 for 72 h. Cell viability was assessed using the MTS assay. Mean SEM (n=4).

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A compound represented by the following formula:

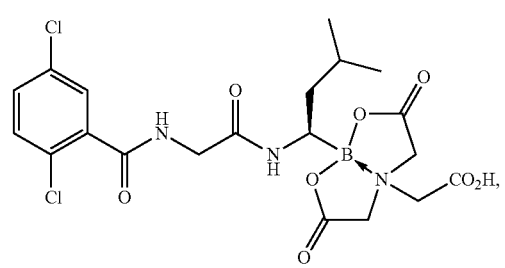

HL01-29 or a pharmaceutically acceptable salt thereof.

2. A pharmaceutical composition comprising a compound of claim 1 or a pharmaceutically acceptable salt thereof, in combination with a pharmaceutically acceptable carrier, a diluent, or an excipient.

3. A method of treating multiple myeloma in a human in need thereof, comprising administering to said human an effective amount of a compound of claim 1 or a pharmaceutically acceptable acid addition salt thereof.

4. A compound represented by the following formula:

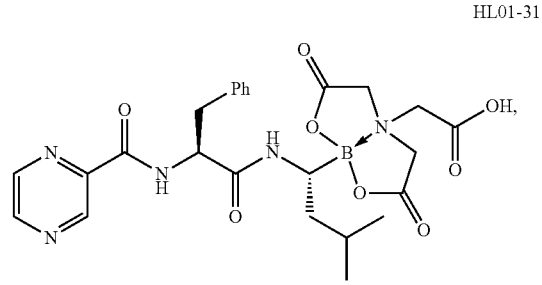 [SMILES: CC(C)C[C@H](NC(=O)[C@H](Cc1ccccc1)NC(=O)c1cnccn1)[B-]12OC(=O)C[N+]1(CC(=O)O)CC(=O)O2]

HL01-31 or a pharmaceutically acceptable salt thereof.

5. A pharmaceutical composition comprising a compound of claim 4 or a pharmaceutically acceptable salt thereof, in combination with a pharmaceutically acceptable carrier, a diluent, or an excipient.

6. A method of treating multiple myeloma in a human in need thereof, comprising administering to said human an effective amount of a compound of claim 4 or a pharmaceutically acceptable acid addition salt thereof.

* * * * *